US012187662B2

(12) United States Patent
Katzenellenbogen et al.

(10) Patent No.: US 12,187,662 B2
(45) Date of Patent: Jan. 7, 2025

(54) FOXM1 INHIBITOR COMPOSITIONS AND METHODS OF USING THE SAME

(71) Applicant: The Board of Trustees of the University of Illinois, Urbana, IL (US)

(72) Inventors: John A. Katzenellenbogen, Urbana, IL (US); Benita Katzenellenbogen, Urbana, IL (US); Sung Hoon Kim, Champaign, IL (US); Noah Bindman, Seattle, WA (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 1007 days.

(21) Appl. No.: 17/046,161

(22) PCT Filed: Apr. 9, 2019

(86) PCT No.: PCT/US2019/026633
§ 371 (c)(1),
(2) Date: Oct. 8, 2020

(87) PCT Pub. No.: WO2019/199863
PCT Pub. Date: Oct. 17, 2019

(65) Prior Publication Data
US 2021/0032193 A1 Feb. 4, 2021

Related U.S. Application Data

(60) Provisional application No. 62/655,470, filed on Apr. 10, 2018.

(51) Int. Cl.
C07C 217/18 (2006.01)
A61P 35/00 (2006.01)
G01N 33/574 (2006.01)

(52) U.S. Cl.
CPC ............ C07C 217/18 (2013.01); A61P 35/00 (2018.01); G01N 33/57415 (2013.01)

(58) Field of Classification Search
None
See application file for complete search history.

(56) References Cited

U.S. PATENT DOCUMENTS 3,636,166 A * 1/1972 Lednicer ............... C07C 43/215
568/721
3,711,556 A 1/1973 Lee
2013/0142784 A1 6/2013 Raychaudhuri et al.
2015/0353935 A1 12/2015 Huang et al.
2016/0346236 A1 12/2016 Su et al.

FOREIGN PATENT DOCUMENTS

CN 113476608 A 10/2021
WO WO2018026776 A2 2/2018
WO WO2018175965 A1 9/2018

OTHER PUBLICATIONS

Australian Patent Office Action for Application No. 2019251359 dated Aug. 16, 2023 (3 pages).
Nettles et al., "Supplemental Information, NFKB selectivity of estrogen receptor ligands revealed by comparative crystallographic analyses", Nature Chemical Biology, 2008, 24 pages.
European Patent Office Office Action for U.S. Appl. No. 19/785,430 dated Mar. 7, 2023 (3 pages).
Japanese Office Action for application 2020-555415, dated Mar. 13, 2023, 7 pages with machine translation.
Chinese Patent Office Action for application 201980036124.6, dated Dec. 29, 2022 (11 pages with translation).
Alvarez-Fernandez et al., "Protein phosphatase 2A (B55alpha) prevents premature activation of forkhead transcription factor FoxM1 by antagonizing cyclin A/cyclin dependent kinase-mediated phosphorylation", The Journal of Biological Chemistry, vol. 286, 2011, pp. 33029-36.
Anders et al., "A systematic screen for CDK4/6 substrates links FOXM1 phosphorylation to senescence suppression in cancer cells", Cancer Cell, vol. 20, 2011, pp. 620-634.
Aytes et al., "Cross-species regulatory network analysis identifies a synergistic interaction between FOXM1 and CENPF that drives prostate cancer malignancy", Cancer Cell, vol. 25, 2014, pp. 638-651.
Bergamaschi et al., "The forkhead transcription factor FOXM1 promotes endocrine resistance and invasiveness in estrogen receptor-positive breast cancer by expansion of stem-like cancer cells", Breast Cancer Res, vol. 16, No. 436, 2014, pp. 1-18.
Bhat et al., "Thiazole antibiotics target FoxM1 and induce apoptosis in human cancer cells", PLoS ONE, vol. 4, 2009, p. e5592.
Carr et al., "FoxM1 mediates resistance to herceptin and paclitaxel", Cancer Research, vol. 70, 2010, pp. 5054-5063.
Chirila et al., "Comparison of palbociclib in combination with letrozole or fulvestrant with endocrine therapies for advanced/metastatic breast cancer: network meta-analysis", Curr Med Res Opin, vol. 33, 2017, pp. 1457-1466.
Costa, "FoxM1 Dances with Mitosis", Nat Cell Biol, vol. 7, 2005, pp. 108-110.
Cui et al., "FOXM1 promotes the warburg effect and pancreatic cancer progression via transactivation of LDHA expression", Clin Cancer Res, vol. 20, 2014, pp. 2595-2606.
De Olano et al., "The p38 MAPK-MK2 axis regulates E2F1 and FOXM1 expression after epirubicin treatment" Mol Cancer Res, vol. 10, 2012, pp. 1189-1202.

(Continued)

Primary Examiner — Kamal A Saeed
Assistant Examiner — Karen Cheng
(74) Attorney, Agent, or Firm — Michael Best & Friedrich LLP

(57) ABSTRACT

Provided are compounds, or pharmaceutically acceptable salts thereof, which are useful for inhibiting FOXM1, inhibiting cancer growth, and/or treating cancer. In particular, these compounds and their corresponding quaternary ammonium salts may be used to treat various forms of breast cancer.

37 Claims, 27 Drawing Sheets

(56) References Cited

OTHER PUBLICATIONS

Drews-Elger et al., "Primary breast tumor-derived cellular models: characterization of tumorigenic, metastatic, and cancer-associated fibroblasts in dissociated tumor (DT) cultures", Breast Cancer Research and Treatment, vol. 144, 2014, pp. 503-517.

Duan et al., "MicroRNA-370 directly targets FOXM1 to inhibit cell growth and metastasis in osteosarcoma cells", International Journal of Clinical and Experimental Pathology, vol. 8, 2015, pp. 10250-60.

Fu et al., "Plk1-dependent phosphorylation of FoxM1 regulates a transcriptional programme required for mitotic progression", Nat Cell Biol, vol. 10, 2008, pp. 1076-1082.

Gartel, "FOXM1 in Cancer: Interactions and Vulnerabilities", Cancer Research 2017, vol. 77, No. 12, pp. 3135-3139.

Gartel, "Suppression of the Oncogenic Transcription Factor FOXM1 by Proteasome Inhibitors", Scientifica, 2014, Article ID: 596528, 5 pages.

Gong et al., "Estrogen receptor-alpha and aryl hydrocarbon receptor involvement in the actions of botanical estrogens in target cells", Mol Cell Endocrinol, vol. 437, 2016, pp. 190-200.

Gormally et al., "Suppression of the FOXM1 transcriptional programme via novel small molecule inhibition", Nature Communications, vol. 5, 2014, 11 pages.

Gusarova et al., "A cell-penetrating ARF peptide inhibitor of FoxM1 in mouse hepatocellular carcinoma treatment", The Journal of Clinical Investigation, vol. 117, 2007, pp. 99-111.

He et al., "MiR-216b inhibits cell proliferation by targeting FOXM1 in cervical cancer cells and is associated with better prognosis", BMC Cancer, vol. 17, No. 673, 2017, 12 pages.

Hegde et al., "The transcription factor FOXM1 is a cellular target of the natural product thiostrepton", Nature Chemistry, vol. 3, 2011, pp. 725-731.

Hou et al., "miR-361-5p suppresses lung cancer cell lines progression by targeting FOXM1", Neoplasma, vol. 64, 2017, pp. 526-534.

Joshi et al., "MELK-dependent FOXM1 phosphorylation is essential for proliferation of glioma stem cells", Stem Cells, vol. 31, 2013, pp. 1051-1063.

Kalinichenko et al., "Foxm1b transcription factor is essential for development of hepatocellular carcinomas and is negatively regulated by the p19ARF tumor suppressor", Genes & Development, vol. 18, 2004, pp. 830-850.

Kambach et al., "ErbB2, FoxM1 and 14-3-3zeta prime breast cancer cells for invasion in response to ionizing radiation", Oncogene, vol. 33, 2014, pp. 589-598.

Karunarathna et al., "OTUB1 inhibits the ubiquitination and degradation of FOXM1 in breast cancer and epirubicin resistance", Oncogene, vol. 35, 2016, pp. 1433-1444.

Ke et al., "miR-149 Inhibits Non-Small-Cell Lung Cancer Cells EMT by Targeting FOXM1", Biochemistry Research International, 2013, Article ID: 506731, 8 pages.

Ketola et al., "Targeting Prostate Cancer Subtype 1 by Forkhead Box M1 Pathway Inhibition", Clin Cancer Res, vol. 23, 2017, pp. 6923-6933.

Kongsema et al., "RNF168 cooperates with RNF8 to mediate FOXM1 ubiquitination and degradation in breast cancer epirubicin treatment", Oncogenesis, vol. 5, 2016, p. e252, 16 pages.

Koo et al., "FOXM1: From cancer initiation to progression and treatment", Biochimica et biophysica acta, vol. 1819, 2012, pp. 28-37.

Li et al., "MicroRNA-134 reverses multidrug resistance in human lung adenocarcinoma cells by targeting FOXM1", Oncology Letters, vol. 13, 2017, pp. 1451-1455.

Lu et al., "FoxM1 is a promising candidate target in the treatment of breast cancer", Oncotarget, vol. 9, 2018, pp. 842-852.

Lv et al., "Acetylation of FOXM1 is essential for its transactivation and tumor growth stimulation", Oncotarget, vol. 7, 2016, pp. 60366-82.

Ma et al., "Raf/MEK/MAPK signaling stimulates the nuclear translocation and transactivating activity of FOXM1c", Journal of Cell Science, vol. 118, 2005, pp. 795-806.

Madak-Erdogan et al., "Integrative genomics of gene and metabolic regulation by estrogen receptors alpha and beta, and their coregulators", Mol Syst Biol, vol. 9, No. 676, 2013, 19 pages.

Millour et al., "FOXM1 is a transcriptional target of ERalpha and has a critical role in breast cancer endocrine sensitivity and resistance", Oncogene, vol. 29, 2010, pp. 2983-2995.

Nettles et al., "NFκB selectivity of estrogen receptor ligands revealed by comparative crystallographic analyses", Nature Chemical Biology, vol. 4, Mar. 2008, pp. 241-247.

O'Leary et al., "Treating cancer with selective CDK4/6 inhibitors", Nature Reviews Clinical Oncology, vol. 13, 2016, pp. 417-430.

Pai et al., "Drug affinity responsive target stability (DARTS) for small-molecule target identification", Methods Mol Biol, vol. 1263, 2015, pp. 287-298.

Peake et al., "Resistance to HER2-targeted therapies: a potential role for FOXM1", Breast Cancer Manag, vol. 3, 2014, pp. 423-431.

Rajamanickam et al., "Inhibition of FoxM1-Mediated DNA Repair by Imipramine Blue Suppresses Breast Cancer Growth and Metastasis", Clin Cancer Res, vol. 22, 2016, pp. 3524-3536.

Raychaudhuri et al., "FoxM1: a master regulator of tumor metastasis", Cancer Research, vol. 71, 2011, pp. 4329-4333.

Salhia et al., "Integrated genomic and epigenomic analysis of breast cancer brain metastasis", PLoS ONE, vol. 9, 2014, p. 85448.

Sanders et al., "FOXM1 binds directly to non-consensus sequences in the human genome", Genome Biology, vol. 16, No. 130, 2015, pp. 1-23.

Sanders et al., "Genome-wide mapping of FOXM1 binding reveals co-binding with estrogen receptor alpha in breast cancer cells", Genome Biology, vol. 14, R6, 2013, pp. 1-16.

Sun et al., "The FOXM1 inhibitor RCM-1 suppresses goblet cell metaplasia and prevents IL-13 and STAT6 signaling in allergen-exposed mice", Sci Signal, vol. 10, 2017, pp. 1-10.

Tan et al., "Chk2 mediates stabilization of the FoxM1 transcription factor to stimulate expression of DNA repair genes", Molecular and Cellular Biology, vol. 27, 2007, pp. 1007-1016.

Tassi et al., "FOXM1 expression is significantly associated with chemotherapy resistance and adverse prognosis in non-serous epithelial ovarian cancer patients.", Journal of Experimental & Clinical Cancer Research, vol. 36, No. 63, 2017, 18 pages.

Wang et al., "Forkhead Box M1 Regulates the Transcriptional Network of Genes Essential for Mitotic Progression and Genes Encoding the SCF (Skp2-Cks1) Ubiquitin Ligase", Mol Cell Biol, vol. 25, 2005, pp. 10875-94.

Wang et al., "FoxM1 expression is significantly associated with cisplatin-based chemotherapy resistance and poor prognosis in advanced non-small cell lung cancer patients", Lung Cancer, vol. 79, 2013, pp. 173-179.

Wang et al., "Glioblastoma multiforme formation and EMT: role of FoxM1 transcription factor", Current Pharmaceutical Design, vol. 21, 2015, pp. 1268-1271.

Xia et al., "Overexpression of FOXM1 is associated with poor prognosis and clinicopathologic stage of pancreatic ductal adenocarcinoma", Pancreas, vol. 41, 2012, pp. 629-635.

Yao et al., "The FOXO3-FOXM1 axis: A key cancer drug target and a modulator of cancer drug resistance", Seminars in Cancer Biol, 2018, vol. 50, pp. 77-89.

Zhang et al., "Akt/FoxM1 signaling pathway-mediated upregulation of MYBL2 promotes progression of human glioma", Journal of Experimental & Clinical Cancer Research, vol. 36, No. 105, 2017, pp. 1-18.

Zhao et al., "Structurally Novel Antiestrogens Elicit Differential Responses from Constitutively Active Mutant Estrogen Receptors in Breast Cancer Cells and Tumors", Cancer Res, vol. 77, 2017, pp. 5602-5613.

Zona et al., "FOXM1: an emerging master regulator of DNA damage response and genotoxic agent resistance", Biochimica et biophysica acta, 2014, vol. 1839, pp. 1316-1322.

International Preliminary Report on Patentability for Application No. PCT/US2019/026633 dated Oct. 13, 2020 (7 pages).

International Search Report and Written Opinion for Application No. PCT/US2019/026633 dated Jul. 9, 2019 (9 pages).

European Patent Office Extended Search Report for Application No. 19785430.0 dated Dec. 1, 2021 (9 pages).

(56) References Cited

OTHER PUBLICATIONS

Wang et al., "New Class of Selective Estrogen Receptor Degraders (SERDs): Expanding the Toolbox of PROTAC Degrons", ACS Medicinal Chemistry Letters, 2018, vol. 9, No. 8, pp. 803-808.
Wang et al., "Supporting Information New Class of Selective Estrogen Receptor Degraders (SERDs): Expanding the Toolbox of PROTAC Degrons", ACS Medicinal Chemistry Letters, Supplement, 2018, 52 pages.

* cited by examiner

FOXM1 INHIBITOR COMPOSITIONS AND METHODS OF USING THE SAME

CROSS-REFERENCE TO RELATED APPLICATION

This patent application is the U.S. national stage entry, under 35 U.S.C. § 371, of International Application Number PCT/US2019/026633, filed Apr. 9, 2019, which claims priority to U.S. Provisional Application No. 62/655,470, filed on Apr. 10, 2018, the entire contents of each of which are hereby incorporated by reference.

STATEMENT REGARDING FEDERALLY SPONSORED RESEARCH OR DEVELOPMENT

This invention was made with government support under DK015556 awarded by the National Institutes of Health. The government has certain rights in the invention.

BACKGROUND

The transcription factor FOXM1 is overexpressed and amplified in many types of cancers and is a master regulator of cancer cell division, aggressiveness, and metastasis. FOXM1 promotes all of the hallmarks of cancer, stimulating cell proliferation, genome instability, angiogenesis, and suppressing cell senescence. High expression of FOXM1 is also associated with resistance to endocrine therapies in estrogen receptor-positive breast cancers and with resistance to radiation and many chemotherapies in several subtypes of breast cancer, and in many other cancers as well. Reports have shown that FOXM1 increases the cancer stem cell population, drives proliferation, motility and invasiveness, and therapy resistance, and found that knockdown of FOXM1 in breast cancer cells could restore sensitivity to endocrine therapy. Hence, targeting FOXM1 is of great importance and may benefit many patients with tumors high in FOXM1. The development of FOXM1 inhibitors is needed to meet this clinical need.

SUMMARY

The present disclosure relates to compounds or a pharmaceutically acceptable salt thereof, which may be useful for inhibiting FOXM1 or treating cancer. In one aspect, the invention provides compounds or compositions of formula (I), or a pharmaceutically acceptable salt thereof,

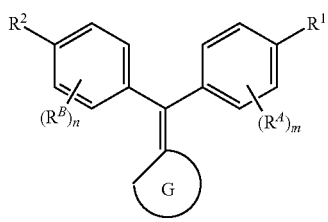

(I)

wherein
G is an optionally substituted polycycloalkylidene;
$R^A$ and $R^B$ at each occurrence are independently halogen, $C_{1-4}$alkyl, or $C_{1-4}$halolakyl;
$R^1$ and $R^2$ are independently —OH, halogen, —CN, —OC$_{2-8}$alkylene-L-T, or —OR$^3$, and at least one of $R^1$ and $R^2$ is —OR$^3$;
L is a linker;
T is a fluorescence acceptor or a fluorescence donor;
$R^3$ is —(CH$_2$CH$_2$O)$_p$—C$_{2-8}$alkylene-NR$^x$R$^y$;
$R^x$ and $R^y$ at each occurrence are independently hydrogen, $C_{1-4}$alkyl, —C$_{2-4}$alkylene-OH, or
$R^x$ and $R^y$ together with the nitrogen to which they are attached form a 4- to 8-membered heterocycle or heteroaryl, wherein the heterocycle and heteroaryl are optionally substituted with 1, 2, 3, or 4 substituents independently selected from the group consisting of $C_{1-4}$alkyl, halogen, —OH, $C_{1-4}$halolakyl, and —C$_{1-4}$alkylene-OH;
m is 0, 1, 2, 3, or 4;
n is 0, 1, 2, 3, or 4; and
p is 0, 1, 2, 3, 4, or 5.

In some embodiments, the present disclosure provides a quaternary ammonium salt of compounds disclosed herein, in which
$R^3$ is —(CH$_2$CH$_2$O)$_p$—C$_{2-8}$alkylene-[NR$^x$R$^y$R$^z$]$^+$·X$^-$;
$R^x$ and $R^y$ at each occurrence are independently $C_{1-4}$alkyl or —C$_{2-4}$alkylene-OH, or
$R^x$ and $R^y$ together with the nitrogen to which they are attached form a 4- to 8-membered heterocycle or heteroaryl, wherein the heterocycle and heteroaryl are optionally substituted with 1, 2, 3, or 4 substituents independently selected from the group consisting of $C_{1-4}$alkyl, halogen, —OH, $C_{1-4}$halolakyl, and —C$_{1-4}$alkylene-OH;
$R^z$ is $C_{1-4}$alkyl or —C$_{2-4}$alkylene-OH; and
$X^-$ is a counterion.

In another aspect, the present disclosure provides a method of inhibiting FOXM1 comprising administering to a subject in need thereof a therapeutically effective amount of a compound disclosed herein, or a pharmaceutically acceptable salt thereof.

In another aspect, the present disclosure provides a method of inhibiting cancer growth comprising administering to a subject in need thereof a therapeutically effective amount of a compound disclosed herein, or a pharmaceutically acceptable salt thereof.

In another aspect, the present disclosure provides a method of treating cancer comprising administering to a subject in need thereof a therapeutically effective amount of a compound disclosed herein, or a pharmaceutically acceptable salt thereof.

In another aspect, the present disclosure provides an assay method, comprising: incubating
  i) a FOXM1 that is fused with an amino acid sequence that allows covalent attachment of biotin,
  ii) a streptavidin that is labeled with a fluorescent donor moiety or a fluorescent acceptor moiety, and
  iii) a compound as disclosed herein, or a salt thereof, wherein one of $R^1$ and $R^2$ is —OC$_{2-8}$alkylene-L-T, and the other is —OR$^3$, wherein T is a fluorescent acceptor moiety if the streptavidin is labeled with a fluorescent donor moiety, or wherein T is a fluorescent donor moiety if the streptavidin is labeled with a fluorescent acceptor moiety in a reaction mixture in either the presence or absence of the substance;
exposing the reaction mixture to light that allows fluorescence resonance energy transfer to take place; and
measuring fluorescence emission from the reaction mixture;
wherein if the fluorescence emission measurement from the reaction mixture in the presence of the substance is different than the fluorescent emission measurement from the mixture in the absence of the substance, the substance is acting as a FOXM1 inhibitor.

Other aspects will become apparent by consideration of the detailed description and accompanying drawings.

BRIEF DESCRIPTION OF THE DRAWINGS

The features, objects and advantages other than those set forth above will become more readily apparent when consideration is given to the detailed description below. Such detailed description makes reference to the following drawings.

FIG. 2A shows Western blot analysis results showing that the cell lines differ in their relative content of FOXM1 protein, being lowest in MCF10A cells and highest in DT22 cells. FIG. 2B shows results of inhibition of cell proliferation by NB-55 examined in dose-response studies in these cell lines. Proliferation was monitored over 6 days, with addition of compound on day 0, 2, and 4 with cell harvest on day 6. Values are mean±SD with assays done in triplicate.

FIG. 6A shows the results of parent compounds and corresponding salt (pairs): NB-55 and NB-63; NB-65 and NB-68; and NB-70 and NB-71. FIG. 6B shows the results of parent compounds and corresponding salt (pairs): NB-72 and NB-73; and NB-51 and NB-115. PK was studied after single dose administration via s.c. injection or oral gavage at the doses indicated. Multiple plasma samples were collected from each mouse (n=4 mice for each experiment) over the course of 48 h after compound was administered at time zero. Compounds were quantified using LC-MS/MS. The data were fitted to a non-compartment PK model.

FIG. 7A shows tumor growth in mice dosed daily for 7 days, and then every other day from day 7 on, with 100 mg/kg of NB-55 or control vehicle by oral gavage. FIG. 7B shows tumor growth in mice dosed at 40 mg/kg with NB-68, NB-71, or NB-73 by s.c. injection at 40 mg/kg daily for 4 days and then 20 mg/kg every third day until day 13 and then 10 mg/kg every third day, or with control vehicle. Tumor volumes in Veh and compound treated animals were monitored (2-way ANOVA, Dunnett's post-test, , $P<0.01$). FIG. 7C shows the result of tumor growth in mice treated with low doses of NB-73 (5 or 10 mg/kg s.c. daily until day 21 and then every other day). In FIGS. 7A-7C, volumes of tumors in Veh and compound treated animals were monitored (2-way ANOVA, Bonferroni post-test, **, $P<0.0001$, n=8 per group). At the end of treatments, tumors from FIG. 7C were processed for gene expression analysis by q-PCR, and the results are shown in FIG. 7D. (T-test, *, $p<0.05$; , $p<0.01$; *, $p<0.001$; ****, $P<0.0001$, n=8 per group).

FIG. 10A shows the structure of fluorophore probe Fl-NB-72. FIG. 10B shows the result of direct binding of Fl-NB-72 to FOXM1 by tr-FRET. FIG. 10C shows representative results of competitive binding assays of FOXM1 inhibitors using Fl-NB-72 as the tr-FRET probe.

FIG. 17A shows regulation of FOXM1 signature genes by NB-73 (4 μM) in MCF7 cells at 9 h and 24 h, and by NB-73 treatment (1.5 μM, 24 h) in MDA-MB-231 cells. FIG. 17B shows Venn diagram showing overlap of genes with $p<0.05$ and regulated more than 2-fold by NB-73, NB-55 and FDI-6 (20 μM) in MCF7 cells, 24 h treatment. FIG. 17C shows Gene Set Enrichment Analysis (GSEA) showing Enrichment Scores. MDA-MB-231 cells treated with NB-73 (1.5 μM, 24 h) or siFOXM1 (25 nM, 72 h). Gene sets used FOXM1 genes derived from 4 independent data sets of FOXM1 cistromes. NES, normalized enrichment score.

DETAILED DESCRIPTION

1. Definitions

Figure 1:
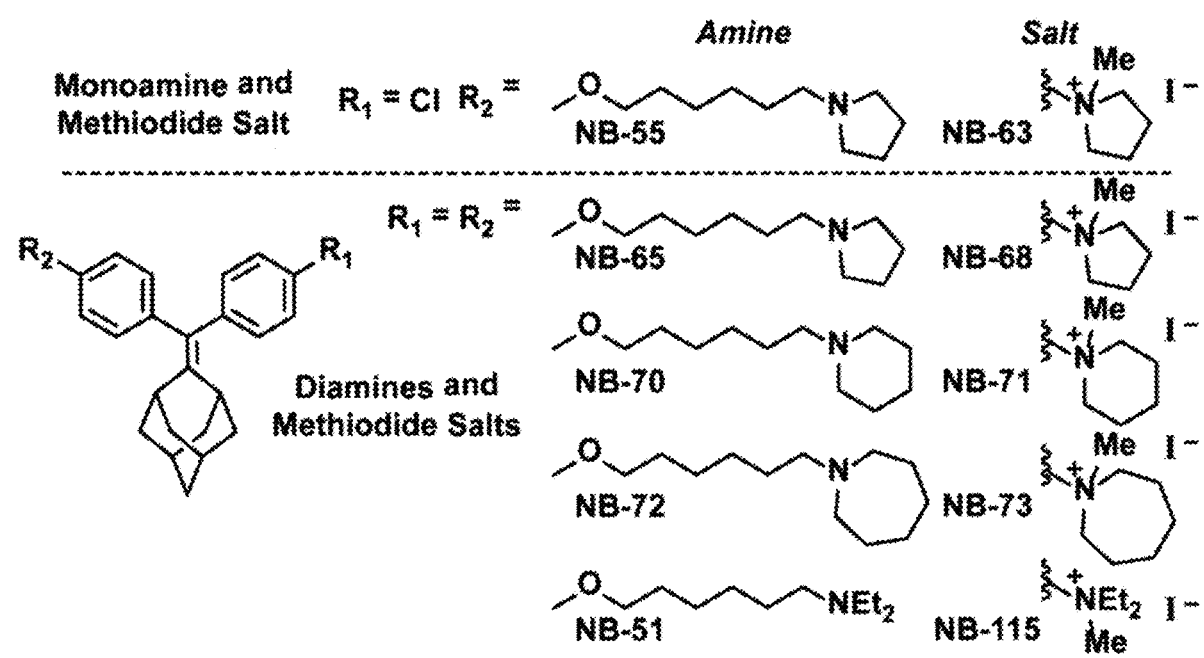
FIG. 1 shows structures of representative FOXM1 inhibitors, such as 1,1-diarylethylene monoamine, diamines, and their methiodide, or pharmaceutically acceptable methylammonium salts.

As described herein, compounds of the invention can optionally be substituted with one or more substituents, such as are illustrated generally above, or as exemplified by particular classes, subclasses, and species of the invention. As described herein, the variables in formula I encompass specific groups, such as, for example, alkyl and cycloalkyl. As one of ordinary skill in the art will recognize, combinations of substituents envisioned by this invention are those combinations that result in the formation of stable or chemically feasible compounds. The term "stable," as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

Unless otherwise defined, all technical and scientific terms used herein have the same meaning as commonly understood by one of ordinary skill in the art. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

The term "alkoxy" as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy and tert-butoxy.

The term "alkyl" as used herein, means a straight or branched chain saturated hydrocarbon. Representative examples of alkyl include, but are not limited to, methyl, ethyl, n-propyl, isopropyl, n-butyl, sec-butyl, isobutyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylene," as used herein, means a divalent group derived from a straight or branched chain saturated hydrocarbon. Representative examples of alkylene include, but are not limited to, —CH$_2$—, —CH$_2$CH$_2$—, —CH$_2$CH$_2$CH$_2$—, —CH$_2$CH(CH$_3$)CH$_2$—, and CH$_2$CH(CH$_3$)CH(CH$_3$)CH$_2$—.

The term "aryl," as used herein, means phenyl or a bicyclic aryl. The bicyclic aryl is naphthyl, dihydronaphthalenyl, tetrahydronaphthalenyl, indanyl, or indenyl. The phenyl and bicyclic aryls are attached to the parent molecular moiety through any carbon atom contained within the phenyl or bicyclic aryl.

The term "cycloalkyl" as used herein, means a monovalent group derived from an all-carbon ring system containing zero heteroatoms as ring atoms, and zero double bonds. The all-carbon ring system can be a monocyclic, bicylic, or tricyclic ring system, and can be a fused ring system, a bridged ring system, or a Spiro ring system, or combinations thereof. Examples of cycloalkyls include, but are not limited to, cyclopropyl, cyclobutyl, cyclopentyl, cyclohexyl, cycloheptyl, cyclooctyl, and

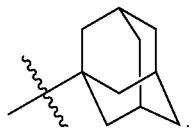 [SMILES: *C12CC3CC(CC(C3)C1)C2]

The cycloalkyl groups described herein can be appended to the parent molecular moiety through any substitutable carbon atom.

The term "cycloalkylene" as used herein, means a divalent group derived from an all-carbon ring system containing zero heteroatoms as ring atoms and zero double bonds, which attaches to the parent molecule at two different ring carbons atoms. The all-carbon ring system can be a monocyclic, bicylic, or tricyclic ring system, and can be a fused ring system, a bridged ring system, or a Spiro ring system. Representative examples of cycloalkylene include, but are not limited to those derived from C$_{3-10}$ rings, such as

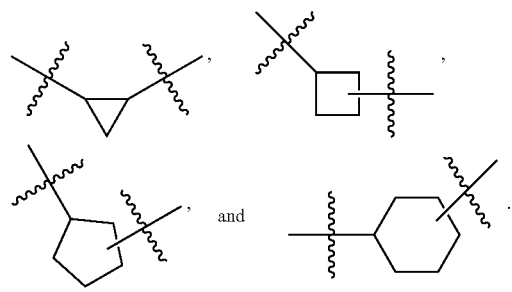

The term "halogen" means a chlorine, bromine, iodine, or fluorine atom.

The term "haloalkyl," as used herein, means an alkyl, as defined herein, in which one, two, three, four, five, six, or seven hydrogen atoms are replaced by halogen. For example, representative examples of haloalkyl include, but are not limited to, 2-fluoroethyl, difluoromethyl, trifluoromethyl, 2,2,2-trifluoroethyl, 2,2,2-trifluoro-1, 1-dimethylethyl, and the like.

The term "heteroaryl," as used herein, means an aromatic heterocycle, i.e., an aromatic ring that contains at least one heteroatom selected from O, N, or S. A heteroaryl may contain from 5 to 12 ring atoms. A heteroaryl may be a 5- to 6-membered monocyclic heteroaryl or an 8- to 12-membered bicyclic heteroaryl. A 5-membered monocyclic heteroaryl ring contains two double bonds, and one, two, three, or four heteroatoms as ring atoms. Representative examples of 5-membered monocyclic heteroaryls include, but are not limited to, furanyl, imidazolyl, isoxazolyl, isothiazolyl, oxadiazolyl, oxazolyl, pyrazolyl, pyrrolyl, tetrazolyl, thiadiazolyl, thiazolyl, thienyl, and triazolyl. A 6-membered heteroaryl ring contains three double bonds, and one, two, three or four heteroatoms as ring atoms. Representative examples of 6-membered monocyclic heteroaryls include, but are not limited to, pyridinyl, pyridazinyl, pyrimidinyl, pyrazinyl, and triazinyl. The bicyclic heteroaryl is an 8- to 12-membered ring system having a monocyclic heteroaryl fused to an aromatic, saturated, or partially saturated carbocyclic ring, or fused to a second monocyclic heteroaryl ring. Representative examples of bicyclic heteroaryl include, but are not limited to, benzofuranyl, benzoxadiazolyl, 1,3-benzothiazolyl, benzimidazolyl, benzothienyl, indolyl, indazolyl, isoquinolinyl, naphthyridinyl, oxazolopyridine, quinolinyl, thienopyridinyl, 5,6, 7,8-tetrahydroquinolinyl, and 6, 7-dihydro-5H-cyclopenta[b Jpyridinyl. The heteroaryl groups are connected to the parent molecular moiety through any substitutable carbon atom or any substitutable nitrogen atom contained within the groups.

The terms "heterocycle" or "heterocyclic" refer generally to ring systems containing at least one heteroatom as a ring atom where the heteroatom is selected from oxygen, nitrogen, and sulfur. In some embodiments, a nitrogen or sulfur atom of the heterocycle is optionally substituted with oxo. Heterocycles may be a monocyclic heterocycle, a fused bicyclic heterocycle, or a spiro heterocycle. The monocyclic heterocycle is generally a 4, 5, 6, 7, or 8-membered non-aromatic ring containing at least one heteroatom selected from O, N, or S. The 4-membered ring contains one heteroatom and optionally one double bond. The 5-membered ring contains zero or one double bond and one, two or three heteroatoms. The 6, 7, or 8-membered ring contains zero, one, or two double bonds, and one, two, or three heteroatoms. Representative examples of monocyclic heterocycle include, but are not limited to, azetidinyl, azepanyl, diazepanyl, 1,3-dioxanyl, 1,4-dioxanyl, 1,3-dioxolanyl, 4,5-dihydroisoxazol-5-yl, 3,4-dihydropyranyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydrothienyl, thiadiazolinyl, thiadiazolidinyl, thiazolinyl, thiazolidinyl, thiomorpholinyl, 1,1-dioxidothiomorpholinyl, thiopyranyl, and trithianyl. The fused bicyclic heterocycle is a 7-12-membered ring system having a monocyclic heterocycle fused to a phenyl, to a saturated or partially saturated carbocyclic ring, or to another monocyclic heterocyclic ring, or to a monocyclic heteroaryl ring. Representative examples of fused bicyclic heterocycle include, but are not limited to, 1,3-benzodioxol-4-yl, 1,3-benzodithiolyl, 3-azabicyclo[3.1.0]hexanyl, hexahydro-1H-furo[3,4-c]pyrrolyl, 2,3-dihydro-1,4-benzodioxinyl, 2,3-dihydro-1-benzofuranyl, 2,3-dihydro-1-benzothienyl, 2,3-dihydro-1H-indolyl, 5,6,7,8-tetrahydroimidazo[1,2-a]pyrazinyl, and 1,2,3,4-tetrahydroquinolinyl. Spiro heterocycle means a 4-, 5-, 6-, 7-, or 8-membered monocyclic heterocycle ring wherein two of the substituents on the same carbon atom form a second ring having 3, 4, 5, 6, 7, or 8 members. Examples of a Spiro heterocycle include, but are not limited to, 1,4-dioxa-8-azaspiro[4.5]decanyl, 2-oxa-7-azaspiro[3.5]nonanyl, 2-oxa-6-azaspiro[3.3]heptanyl, and 8-azaspiro[4.5]decane. The monocyclic heterocycle groups of the present invention may contain an alkylene bridge of 1, 2, or 3 carbon atoms, linking two nonadjacent atoms of the group. Examples of such a bridged heterocycle include, but are not limited to, 2,5-diazabicyclo[2.2.1]heptanyl, 2-azabicyclo[2.2.1]heptanyl, 2-azabicyclo[2.2.2]octanyl, and oxabicyclo[2.2.1]heptanyl. The monocyclic, fused bicyclic, and Spiro heterocycle groups are connected to the parent molecular moiety through any substitutable carbon atom or any substitutable nitrogen atom contained within the group.

The term "hydroxy" as used herein, means an —OH group.

The term hydroxyalkyl as used herein means an alkyl, as defined herein, in which a hydrogen atom is replaced by —OH. For example, representative examples of hydroxyalkyl include, but are not limited to those derived from $C_{1-6}$ alkyls, such as —CH$_2$OH, —CH$_2$CH$_2$OH, —CH$_2$CH$_2$CH$_2$OH, and the like.

The term "oxo" as used herein refers to an oxygen atom bonded to the parent molecular moiety. An oxo may be attached to a carbon atom or a sulfur atom by a double bond. Alternatively, an oxo may be attached to a nitrogen atom by a single bond, i.e., an N-oxide.

The term "polycycloalkylidene" as used herein refers to an all-carbon ring system having a divalent ring carbon atom that bonds to the parent molecular moiety through a carbon-carbon double bond. The divalent ring carbon atom is formed by removal of two hydrogen atoms from the same ring carbon atom of a corresponding polycycloalkane. A polycycloalkane refers to an all-carbon ring system having at least one alkylene bridge (i.e., an alkylene that connects two non-adjacent carbon atoms) and optionally having a fused ring (i.e., an alkylene connecting two adjacent carbon atoms) and/or a spirocyclic ring (i.e., an alkylene connected at either end to the same carbon atom). Representative structures of the polycycloalkane include, but are not limited to adamantane, noradamantane, norbornane, (3aR,4R,7S,7aS)-octahydro-1H-4,7-methanoindene, bicyclo[2.2.2]octane, and (2R,3S,4S,5R)-pentacyclo[4.3.0.0$^{2,5}$.0$^{3,8}$.0$^{4,7}$] nonane (alternatively named homocubane).

Terms such as "alkyl," "cycloalkyl," "alkylene," "cycloalkylene," "polycycloalkylidene" etc. may be preceded by a designation indicating the number of atoms present in the group in a particular instance (e.g., "$C_1$-$C_4$alkyl," "$C_{1-4}$alkyl," "$C_{3-6}$cycloalkyl," "$C_{1-4}$alkylene"). These designations are used as generally understood by those skilled in the art. For example, the representation "C" followed by a subscripted number indicates the number of carbon atoms present in the group that follows. Thus, "$C_3$alkyl" is an alkyl group with three carbon atoms (i.e., n-propyl, isopropyl). Where a range is given, as in "$C_1$-$C_4$" or "$C_{1-4}$," the members of the group that follows may have any number of carbon atoms falling within the recited range. A "$C_1$-$C_4$alkyl" or "$C_{1-4}$alkyl," for example, is an alkyl group having from 1 to 4 carbon atoms, however arranged (i.e., straight chain or branched).

If a group is described as being "substituted", a non-hydrogen substituent group is in the place of hydrogen radical on a carbon or nitrogen of that group. Thus, for example, a substituted alkyl is an alkyl in which at least one non-hydrogen radical is in the place of a hydrogen radical on the alkyl. To illustrate, monofluoroalkyl is alkyl substituted with a fluoro radical, and difluoroalkyl is alkyl substituted with two fluoro radicals. It should be recognized that if there is more than one substitution on a substituent, each non-hydrogen radical may be identical or different (unless otherwise stated). Substituent groups include, but are not limited to, halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, aryl alkyl, hydroxy, hydroxyalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, aryl sulfonyl, aminosulfonyl, sulfinyl, —COOH, ketone, amide, carbamate, and acyl.

When a group is referred to as "unsubstituted" or not referred to as "substituted" or "optionally substituted", it means that the group does not have any substituents. If a group is described as being "optionally substituted", the group may be either (1) not substituted or (2) substituted. If a group is described as being optionally substituted with up to a particular number of non-hydrogen radicals, that group may be either (1) not substituted; or (2) substituted by up to that particular number of substituent groups or by up to the maximum number of substitutable positions on that group, whichever is less.

If substituents are described as being independently selected from a group, each substituent is selected independent of the other. Each substituent, therefore, may be identical to or different from the other substituent(s).

As used herein, the term "E2" refers to estradiol.

The term "administering" and/or "administer" as used herein refer to any route for delivering a pharmaceutical composition to a patient. Routes of delivery may include non invasive peroral (through the mouth), topical (skin), transmucosal (nasal, buccal/sublingual, vaginal, ocular and rectal) and inhalation routes, as well as parenteral routes, and other methods know in the art. Parenteral refers to a route of administration that is generally associated with injection, including intraorbital, infusion, intraarterial, intracarotid, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders. In one embodiment, the composition is administered subcutaneously. In another embodiment, the composition is administered orally.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an ""effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

The term "prevent," or "preventing" means an application that involves a slowing, stopping or reversing of progression of a disease or disorder, or the application or administration of a pharmaceutical composition comprising at least one of any of the compounds described herein, where the subject has a disease or a symptom of a disease, where the purpose is to cure, heal, alleviate, relieve, alter, remedy, ameliorate, improve or affect the disease or symptoms of the disease. Although there can be overlap between "treating" and "preventing," it is intended that the latter is a more drastic (i.e., less subtle) reduction in the disease or disorder than would be observed during the former. Likewise, it is intended that "treating" can occur in an individual having a disease or disorder, whereas "preventing" can occur in an individual merely susceptible to or not yet exhibiting overt signs and symptoms of a disease or disorder. As used herein, "prevent," "preventing," and the like are compared to an appropriate control subject.

The term "subject" or "patient" encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

The terms "treat," "treating," or "treatment," as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

The term "FRET" means "fluorescence resonance energy transfer" or "Forster resonance energy transfer", and refers to the radiationless transmission of an energy quantum from its site of absorption (the donor) to the site of its utilization (the acceptor) in a molecule, or system of molecules, by resonance interaction between donor and acceptor species, over distances considerably greater than interatomic, without substantial conversion to thermal energy, and without the donor and acceptor coming into kinetic collision. A donor is a moiety that initially absorbs energy (e.g., optical energy or electronic energy).

2. Compounds

A first aspect of the invention provides compounds or compositions of formula (I), or a pharmaceutically acceptable salt thereof,

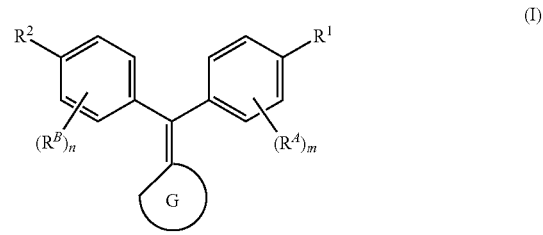

(I)

wherein

G is an optionally substituted polycycloalkylidene;

$R^A$ and $R^B$ at each occurrence are independently halogen, $C_{1-4}$alkyl, or $C_{1-4}$halolakyl;

$R^1$ and $R^2$ are independently —OH, halogen, —CN, —OC$_{2-8}$alkylene-L-T, or —OR$^3$, and at least one of $R^1$ and $R^2$ is —OR$^3$;

T is a fluorescence acceptor or a fluorescence donor;

$R^3$ is —(CH$_2$CH$_2$O)$_p$—C$_{2-8}$alkylene-NR$^x$R$^y$;

$R^x$ and $R^y$ at each occurrence are independently hydrogen, $C_{1-4}$alkyl, —C$_{2-4}$alkylene-OH, or $R^x$ and $R^y$ together with the nitrogen to which they are attached form a 4- to 8-membered heterocycle or heteroaryl, wherein the heterocycle and heteroaryl are optionally substituted with 1, 2, 3, or 4 substituents independently selected from the group consisting of $C_{1-4}$alkyl, halogen, —OH, $C_{1-4}$halolakyl, and —C$_{1-4}$alkylene-OH;

m is 0, 1, 2, 3, or 4;

n is 0, 1, 2, 3, or 4; and p is 0, 1, 2, 3, 4, or 5.

G is a polycycloalkylidene group as defined herein. In some embodiments, G is a $C_{6-30}$ bicyclic or tricyclic ring system, or a ring system with an even higher number of rings. In some embodiments, G is a fused ring system, a bridged ring system, or a Spiro ring systems. In some embodiments, G is a $C_{6-25}$, a $C_{6-20}$, a $C_{8-20}$, or a $C_{10-20}$ ring system. In some embodiments, G is a $C_6$, $C_7$, $C_8$, $C_9$, $C_{10}$, $C_{11}$, $C_{12}$, $C_{13}$, $C_{14}$, $C_{15}$, or $C_{16}$ polycycloalkylidene group as disclosed herein. G may be substituted or unsubstituted. In some embodiments, G is substituted with $C_{1-10}$alkyl, halogen, $C_{1-10}$haloalkyl, $C_{1-10}$hydroxyalkyl, cyano, nitro, amino, or other substituent groups as disclosed herein. In some embodiments, G is unsubstituted.

In some embodiments, G is

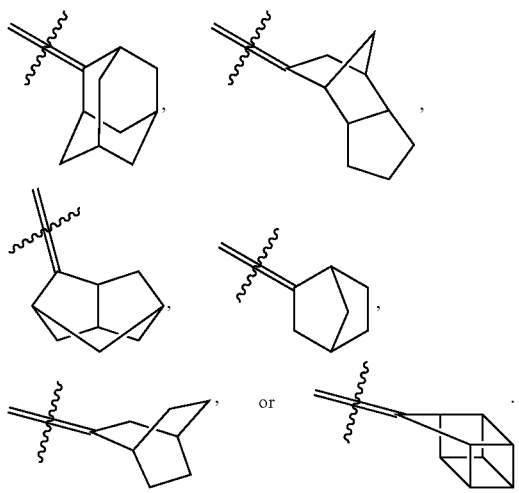

In particular embodiments, G is

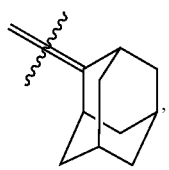 [SMILES: *=C1C2CC3CC(C2)CC1C3]

In some embodiments, m is 0. In some embodiments, n is 0. In some embodiments, both m and n are 0.

In some embodiment, the compound of formula (I) has a structure of formula (I-a)

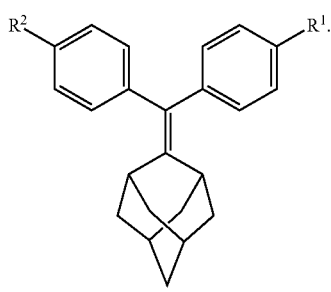

wherein $R^1$ and $R^2$ are as defined above.

In some embodiments, one of $R^1$ and $R^2$ is —OH, halogen, or —CN, and the other is —$OR^3$. In some embodiments, one of $R^1$ and $R^2$ is halogen (such as chloro), and the other is —$OR^3$. In some embodiments, both $R^1$ and $R^2$ are independently —$OR^3$. In some embodiments, both $R^1$ and $R^2$ are independently —$OR^3$, and $R^1$ and $R^2$ are different. In some embodiments, both $R^1$ and $R^2$ are independently —$OR^3$, and $R^1$ and $R^2$ are the same.

In some embodiments, one of $R^1$ and $R^2$ is —$OC_{2-8}$alkylene-L-T, and the other is —$OR^3$. In some embodiments, one of $R^1$ and $R^2$ is —$OC_{4-8}$alkylene-L-T, and the other is —$OR^3$. In particular embodiments, one of $R^1$ and $R^2$ is —$O(CH_2)_6$-L-T, and the other is —$OR^3$.

T may be a fluorescence acceptor or a fluorescence donor. The terms "fluorescence acceptor" or a "fluorescence donor" may include any moieties or groups suitable for Fluorescence Resonance Energy Transfer (FRET). In some embodiments, the fluorescence acceptor and fluorescence donor are moieties or function groups derived from a fluorophore. Suitable fluorophores include, but are not limited to: xanthene derivatives (e.g., fluorescein, rhodamine, Oregon green, eosin, Texas red, etc.), cyanine derivatives (e.g., cyanine, indocarbocyanine, oxacarbocyanine, thiacarbocyanine, merocyanine, etc.), naphthalene derivatives (e.g., dansyl and prodan derivatives), oxadiazole derivatives (e.g., pyridyloxazole, nitrobenzoxadiazole, benzoxadiazole, etc.), pyrene derivatives (e.g., cascade blue), oxazine derivatives (e.g., Nile red, Nile blue, cresyl violet, oxazine 170, etc.), acridine derivatives (e.g., proflavin, acridine orange, acridine yellow, etc.), arylmethine derivatives (e.g., auramine, crystal violet, malachite green, etc.), tetrapyrrole derivatives (e.g., porphin, phtalocyanine, bilirubin, etc.), CF dye (Biotium), BODIPY (Invitrogen), ALEXA FLuoR (Invitrogen), DYLIGHT FLUOR (Thermo Scientific, Pierce), ATTO and TRACY (Sigma Aldrich), FluoProbes (Interchim), DY and MEGASTOKES (Dyomics), SULFO CY dyes (CYANDYE, LLC), SETAU AND SQUARE DYES (SETA BioMedicals), QUASAR and CAL FLUOR dyes (Biosearch Technologies), SURELIGHT DYES (APC, RPE, PerCP, Phycobilisomes)(Columbia Biosciences), APC, APCXL, RPE, BPE (Phyco-Biotech), autofluorescent proteins (e.g., YFP, RFP, mCherry, mKate), quantum dot nanocrystals, etc. For FRET assays, the compounds having a T group as disclosed herein may be used as fluorescence acceptor or a fluorescence donor molecule, corresponding to a fluorescence donor or a fluorescence acceptor, respectively, in another molecule. The donor-acceptor pair may be selected using known methods. In some embodiments, T is derived from a fluorescein or rhodamine analog. In some embodiments, T is derived from fluorescein.

L may be any suitable linker connecting T to the parent molecule, which does not interfere a FRET experiment. In some embodiments, L is —$(CR^{a1}R^{a2})_{m1}$—, wherein m1 is 1 to 100, optionally wherein one or more $CR^{a1}R^{a2}$ groups are replaced by a heteroatom or heteroatom group selected from the group consisting of O, N(R), S(=O), and S(=O)$_2$, optionally wherein one or more $CR^{a1}R^{a2}$ groups are replaced by C(=O), optionally wherein two adjacent $CR^{a1}R^{a2}$ groups form $CR^{a1}$=$CR^{a1}$, and optionally wherein one or more $CR^{a1}R^{a2}$ groups are replaced by a -Cy- group, wherein each Cy is independently selected from the group consisting of aryl, heteroaryl, cycloalkyl, cycloalkenyl, and heterocycle; wherein $R^{a1}$, $R^{a2}$, and $R^{a3}$ are independently selected from the group consisting of hydrogen and $C_1$-$C_4$-alkyl. In some embodiments of formula (I) or formula (I-a), the -L-T group is —NHC(O)-T. In particular embodiments, the -L-T group is

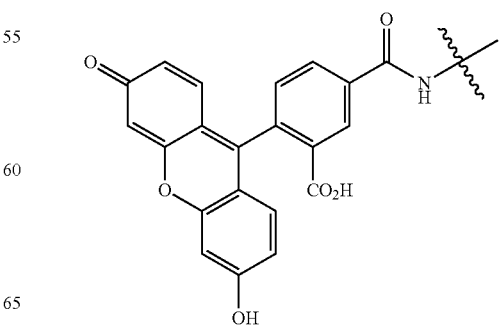

or

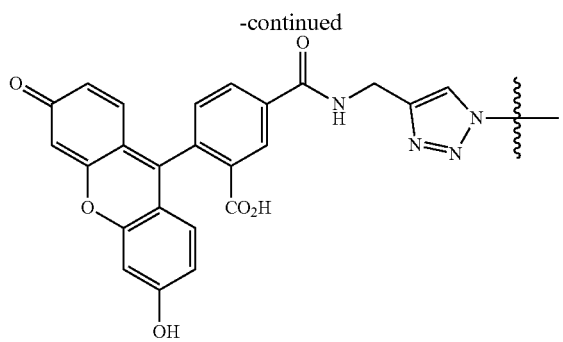

In some embodiments, disclosed is a compound having a structure of

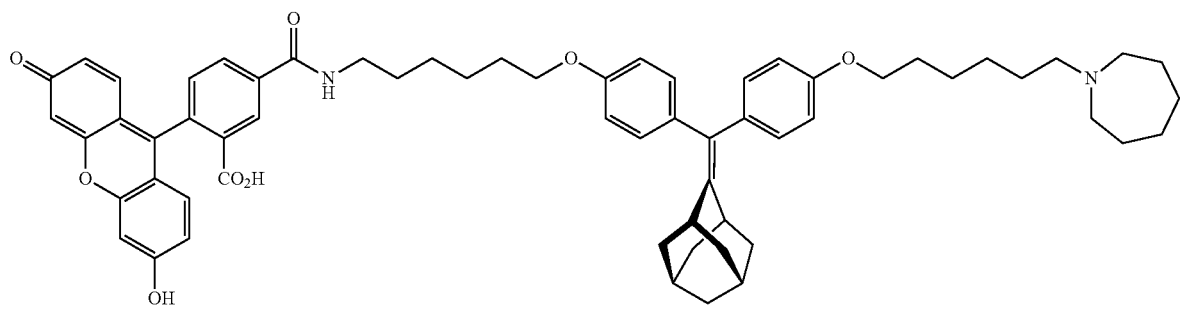

or a salt thereof, such as a pharmaceutically acceptable salt thereof.

In some embodiments, p is 0, 1, or 2. In some embodiments, $R^3$ is $—(CH_2CH_2O)_p—C_{4-8}$alkylene-$NR^xR^y$ or $—(CH_2CH_2O)_p—C_{2-4}$alkylene-$NR^xR^y$, wherein p is 0, 1, or 2. In some embodiments, $R^3$ is $—C_{4-8}$alkylene-$NR^xR^y$. In some embodiments, $R^3$ is $—CH_2CH_2O—CH_2CH_2—NR^xR^y$ or $—(CH_2CH_2O)_2—CH_2CH_2—NR^xR^y$. In some embodiments, $R^3$ is $—(CH_2)_4—NR^xR^y$, $—(CH_2)_6—NR^xR^y$, or $—(CH_2)_8—NR^xR^y$. In particular embodiments, $R^3$ is $—(CH_2)_6—NR^xR^y$.

In some embodiments, $R^x$ and $R^y$ at each occurrence are independently $C_{1-4}$alkyl or $—C_{2-4}$alkylene-OH. In some embodiments, $R^x$ and $R^y$ at each occurrence are independently $C_{1-4}$alkyl, such as methyl or ethyl. In some embodiments, $R^x$ is $C_{1-4}$alkyl and $R^y$ is $—C_{2-4}$alkylene-OH. In some embodiments, $R^x$ and $R^y$ at each occurrence are independently $—C_{2-4}$alkylene-OH, such as $—(CH_2)_2OH$. In some embodiments, both $R^x$ and $R^y$ are ethyl. In some embodiments, $R^x$ is ethyl and $R^y$ is $—(CH_2)_2OH$. In some embodiments, both $R^x$ and $R^y$ are $—(CH_2)_2OH$.

In some embodiments, $R^x$ and $R^y$ together with the nitrogen to which they are attached form 4- to 8-membered heterocycle or heteroaryl, wherein the heterocycle and heteroaryl are optionally substituted with 1, 2, 3, or 4 substituents independently selected from the group consisting of $C_{1-4}$alkyl, halogen, —OH, $C_{1-4}$haloalkyl, and $—C_{1-4}$alkylene-OH. As defined herein, the heterocycle may have as few as 4 ring atoms (such as a 4-, 5-, 6-, 7-, or 8-membered heterocycle), and the heteraryl may have at least 5 ring atoms (such as a 5-, 6-, 7-, or 8-membered heteroaryl). In some embodiments, $—NR^xR^y$ is a heteroaryl, such as

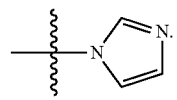 [SMILES: *n1ccnc1]

In some embodiments, $—NR^xR^y$ is

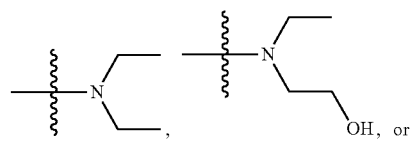

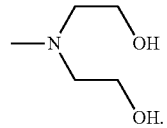

In some embodiments, $—NR^xR^y$ is

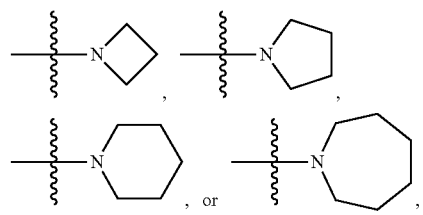

each of which is optionally substituted. In some embodiments, $—NR^xR^y$ is

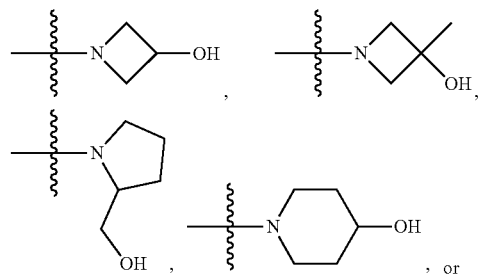

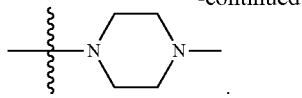

In some embodiments, —NR$^x$R$^y$ is

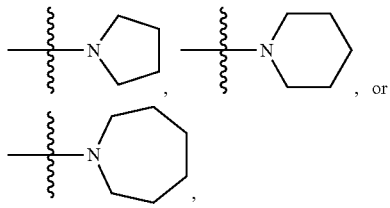

each of which is optionally substituted.

The compounds or compositions disclosed herein may be in the form of a salt, such as a pharmaceutically acceptable salt. As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in J Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N(C$_{1-4}$alkyl)$_4$ salts. The present disclosure also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed with counterions such as halide, hydroxide, carboxylate, sulfate, phosphate, nitrate, lower alkyl sulfonate and aryl (e.g., phenyl/substituted phenyl) sulfonate.

In some embodiments, the compounds or compositions disclosed herein are in the form of a pharmaceutically acceptable, quaternary ammonium salt. For example, one N atom of the R$^3$ group of the compounds of formula (I) or (I-a) may be quaternized, such that R$^3$ is in a salt form of —(CH$_2$CH$_2$O)$_p$—C$_{2-8}$alkylene-[NR$^x$R$^y$R$^z$]$^+$·X$^-$, wherein R$^x$ and R$^y$ at each occurrence are independently C$_{1-4}$alkyl or —C$_{2-4}$alkylene-OH, or R$^x$ and R$^y$ together with the nitrogen to which they are attached form a 4- to 8-membered heterocycle or heteroaryl, wherein the heterocycle and heteroaryl are optionally substituted with 1, 2, 3, or 4 substituents independently selected from the group consisting of C$_{1-4}$alkyl, halogen, —OH, C$_{1-4}$haloalkyl, and —C$_{1-4}$alkylene-OH;

R$^z$ is C$_{1-4}$alkyl or —C$_{2-4}$alkylene-OH; and

X$^-$ is a counterion, with G, R$^A$, R$^B$, R$^1$, R$^2$, n, m, p, L, and T, when present, being as defined above.

In some embodiments of formula (I) or formula (I-a), one of R$^1$ and R$^2$ is —OR$^3$, in which R$^3$ is —(CH$_2$CH$_2$O)$_r$—C$_{2-8}$alkylene-[NR$^x$R$^y$R$^z$]$^+$·X$^-$. In some embodiments of formula (I) or formula (I-a), both R$^1$ and R$^2$ are —OR$^3$, in which each R$^3$ group is independently —(CH$_2$CH$_2$O)$_p$—C$_{2-8}$ alkylene-[NR$^x$R$^y$R$^z$]$^+$·X$^-$. In some embodiments of formula (I) or formula (I-a), one or both of R$^1$ and R$^2$ are —OR$^3$, in which each R$^3$ is independently —C$_{4-8}$alkylene-[NR$^x$R$^y$R$^z$]$^+$·X$^-$. In some embodiments of formula (I) or formula (I-a), one or both of R$^1$ and R$^2$ are —OR$^3$, in which each R$^3$ is —(CH$_2$)$_4$—[NR$^x$R$^y$R$^z$]$^+$·X$^-$, —(CH$_2$)$_6$—[NR$^x$R$^y$R$^z$]$^+$·X$^-$, or —(CH$_2$)$_8$—[NR$^x$R$^y$R$^z$]$^+$·X$^-$. In some embodiments of formula (I) or formula (I-a), one or both of R$^1$ and R$^2$ are —OR$^3$, in which each R$^3$ is —(CH$_2$)$_6$—[NR$^x$R$^y$R$^z$]$^+$·X$^-$.

In some embodiments, in the —[NR$^x$R$^y$R$^z$]$^+$·X$^-$ group, R$^x$ and R$^y$ at each occurrence are independently C$_{1-4}$alkyl or —C$_{2-4}$alkylene-OH. For example, in each —[NR$^x$R$^y$R$^z$]$^+$·X$^-$ group, R$^x$ and R$^y$ each may be independently C$_{1-4}$alkyl, such as methyl or ethyl; or R$^x$ may be a C$_{1-4}$alkyl and R$^y$ may be —C$_{2-4}$alkylene-OH, or R$^x$ and R$^y$ each may be independently —C$_{2-4}$alkylene-OH, such as —(CH$_2$)$_2$OH. In some embodiments, both R$^x$ and R$^y$ are ethyl in the —[NR$^x$R$^y$R$^z$]$^+$·X$^-$ group. In some embodiments, R$^x$ is ethyl and R$^y$ is —(CH$_2$)$_2$OH in the —[NR$^x$R$^y$R$^z$]$^+$·X$^-$ group. In some embodiments, both R$^x$ and R$^y$ are —(CH$_2$)$_2$OH in the —[NR$^x$R$^y$R$^z$]$^+$·X$^-$ group.

In some embodiments, in the —[NR$^x$R$^y$R$^z$]$^+$·X$^-$ group, R$^x$ and R$^y$ together with the nitrogen to which they are attached form a 4- to 8-membered heterocycle or heteroaryl, wherein the heterocycle and heteroaryl are optionally substituted with 1, 2, 3, or 4 substituents independently selected from the group consisting of C$_{1-4}$alkyl, halogen, —OH, C$_{1-4}$haloalkyl, and —C$_{1-4}$alkylene-OH. In some embodiments, in the —[NR$^x$R$^y$R$^z$]$^+$·X$^-$ group, —NR$^x$R$^y$ is

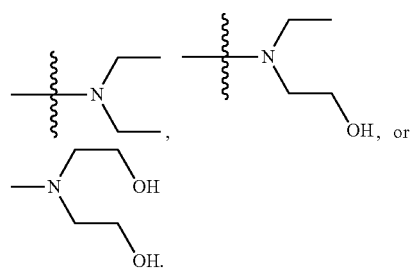

In some embodiments, in the —[N$R^xR^yR^z$]$^+$·X$^-$ group, —N$R^xR^y$ is a heteroaryl, such as

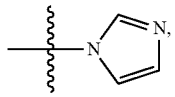

with one N atom in the heteraryl being quaternized. In some embodiments in the —[N$R^xR^yR^z$]$^+$·X$^-$ group, —N$R^xR^y$ is

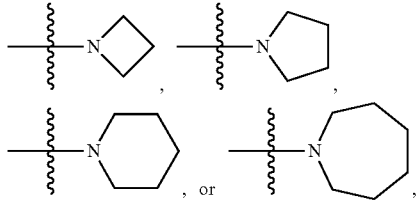

each of which is optionally substituted, with the N atom being quaternized. In some embodiments, in the [N$R^xR^yR^z$]$^+$· X$^-$ group, —N$R^xR^y$ is

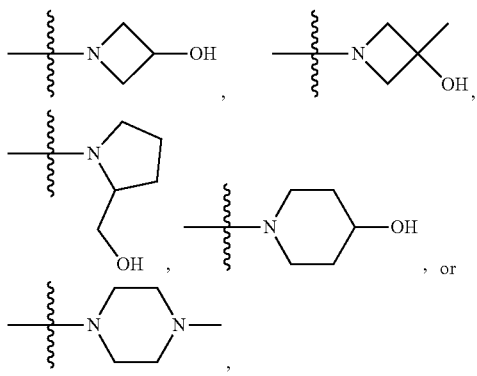

with one N atom being quaternized. In some embodiments, —[N$R^xR^yR^z$]$^+$·X$^-$ group, —N$R^xR^y$ is

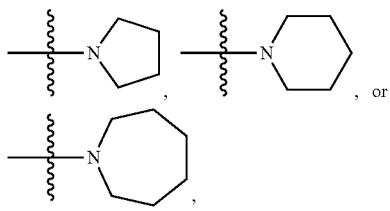

each of which is optionally substituted, with the N atom being quaternized.

In some embodiments, the —[N$R^xR^yR^z$]$^+$·X$^-$ group is

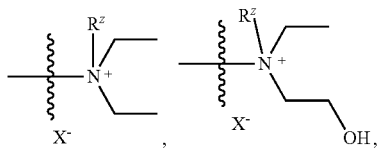

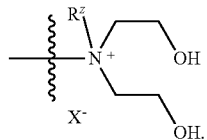

In some embodiments, the —[N$R^xR^yR^z$]$^+$·X$^-$ group is

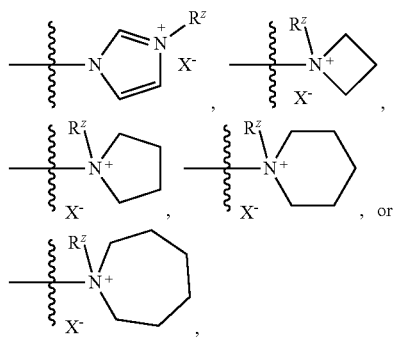

each of which is optionally substituted with 1, 2, 3, or 4 substituents independently selected from the group consisting of $C_{1-4}$alkyl, halogen, —OH, $C_{1-4}$halolakyl, and —$C_{1-4}$ alkylene-OH. In some embodiments, the —[N$R^xR^yR^z$]$^+$·X$^-$ group is

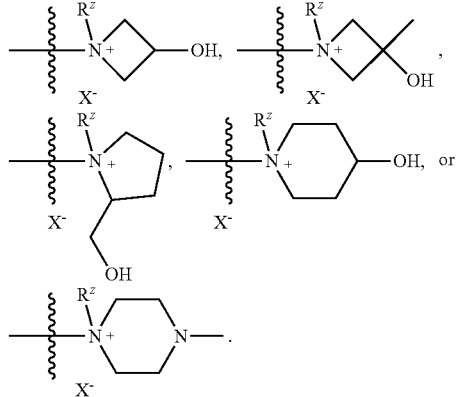

In some embodiments, the —[N$R^xR^yR^z$]$^+$·X$^-$ group is

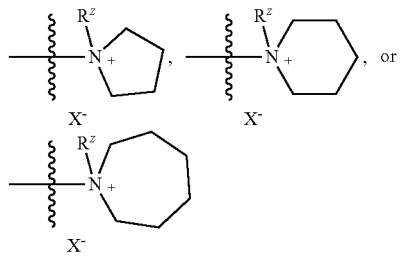

each of which is optionally substituted.

In some embodiments, $R^z$ is methyl or ethyl. In some embodiments, $R^z$ is methyl. In some embodiments, $R^z$ is —$C_{2-4}$alkylene-OH, such as —$(CH_2)_2$OH.

X⁻ may include any suitable negatively charged counterion known in the art. In some embodiments, X⁻ is halides, sulfonate (such as $CH_3SO_3^-$), phosphonate (such as $H_2PO_4^-$), acetate, oxalate, fumarate, tartarate, or lactate salt. In some embodiments, X⁻ is I⁻, Br⁻, Cl⁻, or $CH_3SO_3^-$. In particular embodiments, X is I⁻ or $CH_3SO_3^-$.

Suitable —[NR$^x$R$^y$R$^z$]·X⁻ groups include, for example,

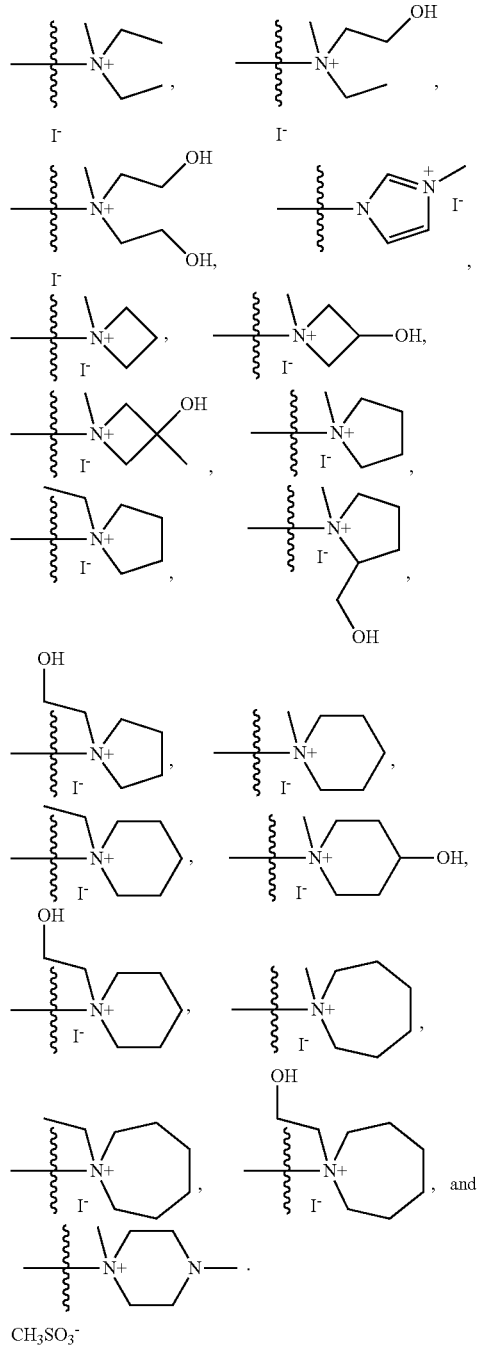

Representative compounds disclosed herein and their corresponding quaternary ammonium salts are shown in FIG. 1, which includes one monoamine and four diamine compounds, in each case with the corresponding methiodide salt, or pharmaceutically acceptable methylammonium salt.

Disclosed is a compound selected from the group consisting of:
1-(6-(4-((Z)-((5S,7S)-adamantan-2-ylidene)(4-chlorophenyl)methyl)phenoxy)hexyl)pyrrolidine;
1-(6-(4-((Z)-((5S,7S)-Adamantan-2-ylidene)(4-chlorophenyl)methyl)phenoxy)hexyl)piperidine;
1-(6-(4-((Z)-((5S,7S)-adamantan-2-ylidene)(4-chlorophenyl)methyl)phenoxy)hexyl)azepane;
1,1'-((((((5r,7r)-adamantan-2-ylidene)methylene)bis(4,1-phenylene))bis(oxy))bis(hexane-6,1-diyl))dipyrrolidine;
1,1'-((((((5r,7r)-Adamantan-2-ylidene)methylene)bis(4,1-phenylene))bis(oxy))bis(hexane-6,1-diyl))dipiperidine;
1,1'-((((((5r,7r)-Adamantan-2-ylidene)methylene)bis(4,1-phenylene))bis(oxy))bis(hexane-6,1-diyl))bis(azepane);
6,6'-(((((5r,7r)-adamantan-2-ylidene)methylene)bis(4,1-phenylene))bis(oxy))bis(N,N-diethylhexan-1-amine);
2,2'-((((((5r,7r)-adamantan-2-ylidene)methylene)bis(4,1-phenylene))bis(oxy))bis(hexane-6,1-diyl))bis(ethylazanediyl))bis(ethan-1-ol);
2,2',2'',2'''-((((((5r,7r)-adamantan-2-ylidene)methylene)bis(4,1-phenylene))bis(oxy))bis(hexane-6,1-diyl))bis(azanetriyl))tetrakis(ethan-1-ol);
1,1'-((((((5r,7r)-adamantan-2-ylidene)methylene)bis(4,1-phenylene))bis(oxy))bis(hexane-6,1-diyl))bis(azetidine);
1,1'-((((((5r,7r)-adamantan-2-ylidene)methyl ene)bis(4,1-phenylene))bis(oxy))bis(hexane-6,1-diyl))bis(azetidin-3-ol);
1,1'-((((((5r,7r)-adamantan-2-ylidene)methylene)bis(4,1-phenylene))bis(oxy))bis(hexane-6,1-diyl))bis(3-methylazetidin-3-ol);
((2S,2'S)-((((((5r,7r)-adamantan-2-ylidene)methylene)bis(4,1-phenylene))bis(oxy))bis(hexane-6,1-diyl))bis(pyrrolidine-1,2-diyl))dimethanol;
1,1'-((((((5r,7r)-adamantan-2-ylidene)methylene)bis(4,1-phenylene))bis(oxy))bis(hexane-6,1-diyl))bis(piperidin-4-ol);
5-((6-(4-((E)-((5r,7r)-adamantan-2-ylidene)(4-((6-(azepan-1-yl)hexyl)oxy)phenyl)methyl)phenoxy)hexyl)carbamoyl)-2-(6-hydroxy-3-oxo-3H-xanthen-9-yl)benzoic acid;
1-(6-(4-((Z)-((5r,7r)-adamantan-2-ylidene)(4-((6-(4-((3-carboxy-4-(6-hydroxy-3-oxo-3H-xanthen-9-yl)benzamido)methyl)-1H-1,2,3-triazol-1-yl)hexyl)oxy)phenyl)methyl)phenoxy)hexyl)-1-methylazepan-1-ium iodide;
4-((E)-((5R,7R)-adamantan-2-ylidene)(4-((6-(diethylamino)hexyl)oxy)phenyl)methyl)phenol;
6-(4-((Z)-((5S,7S)-adamantan-2-ylidene)(4-chlorophenyl)methyl)phenoxy)-N,N-diethylhexan-1-amine;
1-(6-(4-((Z)-((5S,7S)-adamantan-2-ylidene)(4-chlorophenyl)methyl)phenoxy)hexyl)-1H-imidazole;
1-(6-(4-((Z)-((5S,7S)-adamantan-2-ylidene)(4-chlorophenyl)methyl)phenoxy)hexyl)-4-methylpiperazine;
1,1'-((((((5r,7r)-adamantan-2-ylidene)methylene)bis(4,1-phenylene))bis(oxy))bis(butane-4,1-diyl))dipiperidine;
1,1'-((((((5r,7r)-adamantan-2-ylidene)methyl ene)bis(4,1-phenyl ene))bis(oxy))bis(butane-4,1-diyl))bis(azepane);
1,1'-((((((5r,7r)-adamantan-2-ylidene)methylene)bis(4,1-phenylene))bis(oxy))bis(pentane-5,1-diyl))dipiperidine;
1,1'-((((((5r,7r)-adamantan-2-ylidene)methylene)bis(4,1-phenylene))bis(oxy))bis(pentane-5,1-diyl))bis(azepane);
1,1'-((((((5r,7r)-adamantan-2-ylidene)methyl ene)bis(4,1-phenylene))bis(oxy))bis(octane-8,1-diyl))bis(azepane);
2,2'-(((((((5r,7r)-adamantan-2-ylidene)methylene)bis(4,1-phenylene))bis(oxy))bis(ethane-2,1-diyl))bis(oxy))bis(ethane-2,1-diyl))bis(oxy))bis(N,N-diethyl ethan-1-amine);

4,4'-((((((5r,7r)-adamantan-2-ylidene)methylene)bis(4,1-phenylene))bis(oxy))bis(hexane-6,1-diyl))bis(1-methylpiperazine); and 1,1'-((((((5r,7r)-adamantan-2-ylidene)methylene)bis(4,1-phenylene))bis(oxy))bis(hexane-6,1-diyl))bis(1H-imidazole), or a pharmaceutically acceptable salt thereof.

Also disclosed is a quaternary ammonium salt selected from the group consisting of, 1-(6-(4-((Z)-((5S,7S)-adamantan-2-ylidene)(4-chlorophenyl)methyl)phenoxy)hexyl)-1-methylpyrrolidin-1-ium iodide;

1,1'-((((((5r,7r)-adamantan-2-ylidene)methyl ene)bis(4,1-phenyl ene))bis(oxy))bis(hexane-6,1-diyl))bis(1-methylpyrrolidin-1-ium) diiodide;

1,1'-((((((5r,7r)-adamantan-2-ylidene)methylene)bis(4,1-phenylene))bis(oxy))bis(hexane-6,1-diyl))bis(1-methylpiperidin-1-ium) diodide;

1,1'-((((((5r,7r)-adamantan-2-ylidene)methylene)bis(4,1-phenylene))bis(oxy))bis(hexane-6,1-diyl))bis(1-methylazepan-1-ium) diiodide;

6-(4-(((5r,7r)-adamantan-2-ylidene)(4-((6-(diethyl(methyl)-λ⁴-azaneyl)hexyl)oxy)phenyl)methyl)phenoxy)-N,N-diethyl-N-methylhexan-1-aminium diiodide;

6,6'-(((((5r,7r)-adamantan-2-ylidene)methylene)bis(4,1-phenylene))bis(oxy))bis(N-ethyl-N-(2-hydroxyethyl)-N-methylhexan-1-aminium) diiodide;

6,6'-(((((5r,7r)-adamantan-2-ylidene)methylene)bis(4,1-phenylene))bis(oxy))bis(N,N-bis(2-hydroxyethyl)-N-methylhexan-1-aminium) diiodide;

1,1'-((((((5r,7r)-adamantan-2-ylidene)methylene)bis(4,1-phenyl ene))bis(oxy))bis(hexane-6,1-diyl))bis(1-methylazetidin-1-ium) diiodide;

1,1'-((((((5r,7r)-adamantan-2-ylidene)methylene)bis(4,1-phenylene))bis(oxy))bis(hexane-6,1-diyl))bis(3-hydroxy-1,3-dimethylazetidin-1-ium) diiodide;

(1R,1'R,2S,2'S)-1,1'-(((((5r,7r)-adamantan-2-ylidene) methyl ene)bis(4,1-phenylene))bis(oxy))bis(hexane-6,1-diyl))bis(2-(hydroxymethyl)-1-methylpyrrolidin-1-ium) diiodide;

1,1'-((((((5r,7r)-adamantan-2-ylidene)methylene)bis(4,1-phenylene))bis(oxy))bis(hexane-6,1-diyl))bis(4-hydroxy-1-methylpiperidin-1-ium) diiodide;

1,1'-(((((5r,7r)-adamantan-2-ylidene)methylene)bis(4,1-phenylene))bis(oxy))bis(hexane-6,1-diyl))bis(1-(2-hydroxyethyl)pyrrolidin-1-ium) diiodide;

1,1'-(((((5r,7r)-adamantan-2-ylidene)methylene)bis(4,1-phenylene))bis(oxy))bis(hexane-6,1-diyl))bis(1-(2-hydroxyethyl)piperidin-1-ium) diiodide;

1,1'-(((((5r,7r)-adamantan-2-ylidene)methylene)bis(4,1-phenylene))bis(oxy))bis(hexane-6,1-diyl))bis(1-(2-hydroxyethyl)azepan-1-ium) diiodide;

1-(6-(4-((Z)-((5S,7S)-adamantan-2-ylidene)(4-chlorophenyl)methyl)phenoxy)hexyl)-3-methyl-1H-imidazol-3-ium iodide;

(S)-1-(6-(4-((Z)-((5S,7S)-adamantan-2-ylidene)(4-chlorophenyl)methyl)phenoxy)hexyl)-1-methyl-1λ⁴-piperidin-2-ylium iodide;

1-(6-(4-((Z)-((5 S,7S)-adamantan-2-ylidene)(4-chlorophenyl)methyl)phenoxy)hexyl)-1-methylazepan-1-ium iodide;

1-(4-(4-((E)-((5R,7R)-adamantan-2-ylidene)(4-(4-(1-metheyliumylpiperidin-1-ium-1-yl)butoxy)phenyl) methyl)phenoxy)butyl)-1-methylpiperidin-1-ium diiodide;

1,1'-(((((5r,7r)-adamantan-2-ylidene)methylene)bis(4,1-phenylene))bis(oxy))bis(butane-4,1-diyl))bis(1-methylazepan-1-ium) diiodide;

1,1'-(((((5r,7r)-adamantan-2-ylidene)methylene)bis(4,1-phenylene))bis(oxy))bis(pentane-5,1-diyl))bis(1-methylpiperidin-1-ium) diiodide;

1,1'-(((((5r,7r)-adamantan-2-ylidene)methylene)bis(4,1-phenylene))bis(oxy))bis(pentane-5,1-diyl))bis(1-methylazepan-1-ium) diiodide;

1,1'-(((((5r,7r)-adamantan-2-ylidene)methylene)bis(4,1-phenylene))bis(oxy))bis(octane-8,1-diyl))bis(1-methylazepan-1-ium) diiodide; and 1,1'-(((((5r,7r)-adamantan-2-ylidene)methylene)bis(4,1-phenylene))bis(oxy))bis(hexane-6,1-diyl))bis(1,4-dimethylpiperazin-1-ium) dimethanesulfonate.

In another embodiment, the compounds include isotope-labelled forms. An isotope-labelled form of a compound is identical to the compound apart from the fact that one or more atoms of the compound have been replaced by an atom or atoms having an atomic mass or mass number which differs from the atomic mass or mass number of the atom which usually occurs in greater natural abundance. Examples of isotopes which are readily commercially available and which can be incorporated into a compound by well-known methods include isotopes of hydrogen, carbon, nitrogen, oxygen, fluorine and chlorine, for example $^{2}H$, $^{3}H$, $^{13}C$, $^{14}C$, $^{15}N$, $^{18}O$, $^{17}O$, $^{18}F$ and $^{36}Cl$.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Thus, included within the scope of the invention are tautomers of compounds of the compounds disclosed herein.

3. Methods of Use

In the search for new and more optimal FOXM1 inhibitors, a high throughput screen of commercial, in-house compound libraries, and NCI inventory was conducted using a time-resolved Forster energy resonance transfer assay (FRET) of FOXM1-DNA binding. From this screen, a number of initial hits were obtained that were further studied in cell-free and cell-based assays. Unlike these initial hits having relatively low potency, the present disclosure provides a new family of 1,1-diarylethylene mono and diamines, and their corresponding quaternary ammonium salts (such as methiodide salts). Remarkably, the compounds or compositions disclosed herein, or salts thereof, may contain greatly improved potencies and good tumor suppressive activity in vivo.

The compounds or compositions disclosed herein, or salt thereof, may have FOXM1 inhibitory activities in cell-free and cell-based assays, and on in vivo preclinical breast tumor models. The present compounds or compositions may bind directly to FOXM1, effectively suppressing the proliferation of FOXM1-containing human breast cancer cells, and decreasing the cellular levels of FOXM1 and the expression of FOXM1-regulated genes. The present compounds or compositions may have improved potency and more favorable pharmacokinetic properties in vivo when compared to previously reported inhibitors (e.g., FDI-6, thiostrepton). In some embodiments, the inhibitor compounds disclosed herein demonstrated good oral efficacy in suppressing the growth of FOXM1-containing breast tumors in NOD-SCID-gamma (NSG) mice, as well as good efficacy in tumor suppression by subcutaneous administration. The present disclosure identifies and characterizes a new class of compounds that effectively antagonizes FOXM1 actions and tumor growth and are suitable for further clinical evaluation in targeting aggressive breast cancers driven by FOXM1.

The present disclosure provides 1,1-diarylethylene compounds (e.g., FIG. 1) distinctive from initial hits obtained from a high throughput screen for inhibitors of FOXM1-DNA binding. The compounds and salts disclosed herein are a new class of 1,1-diarylethylene mono- and diamine compounds that function as effective inhibitors of FOXM1. These compounds and corresponding salts (e.g., methiodide salts) may suppress cell proliferation, FOXM1-regulated gene expression, and growth of breast xenograft tumors in an experimental preclinical mouse model where FOXM1-mediated gene expression is suppressed in these growth-inhibited tumors.

As shown in the examples herein, of the amine compounds studied that showed good potency ($IC_{50}$ values less than 0.5 µM) and efficacies in cells in culture, several had good in vivo PK properties. Although NB-55 and NB-65 showed good PK properties (half-lives and blood levels achieved) after s.c. administration, only NB-55 showed good PK properties after oral administration. Notably, the salts of all of the amine compounds had greatly (5-50×) elevated blood levels and retained long half-lives (t ½=24 to 39 h) by s.c. route, with NB-115 being most ideal (e.g., FIGS. 6A-6B). However, these salts showed very low bioavailability (blood levels) by oral route. Because of the high and prolonged blood levels of NB-63, NB-68, NB-71, NB-73 and NB-115, these were able to greatly suppress tumor growth in vivo using low doses (5 or 10 mg/kg) administered s.c. every second or third day. By contrast, NB-55 required daily s.c. or oral treatment at 100 mg/kg for effective tumor suppression whereas 20 or 40 mg/kg doses were found to be only marginally effective (data not shown), consistent with its good but not outstanding blood levels achieved and with its 5-fold reduced potency in suppression of cell proliferation, as seen in dose-response studies in cells in culture. Of note, it was observed that the previously reported FOXM1 inhibitor, FDI-6 that showed potency similar to NB-55 in cells in culture, had very poor pharmacokinetic properties after s.c. or oral administration (FIG. 12), suggesting that it would likely not prove to be useful clinically due to low bioavailability as seen in the very low blood levels achieved.

Although FDI-6 has been shown to have FOXM1 inhibitory activity on cells in culture, no in vivo data with it has been published. Another FOXM1 inhibitor, thiostrepton, which promotes proteasomal degradation of FOXM1, lacks optimal selectivity in that many other proteins are also marked for proteasomal degradation with thiostrepton exposure of cells. Related to FDI-6, RCM-1, was characterized as a FOXM1 inhibitor, but was tested in vivo only over a 3-day period in an asthma model, where it was delivered by aerosol directly into the lungs. Other previously reported FOXM1 inhibitors also have limitations likely to preclude their clinical use. These include p19Arf, a peptide that has low stability but is effective in cells in culture and able to suppress liver tumor growth when administered intraperitoneally in mice. Also, the dye Imipramine Blue has a very short half-life ($t_{1/2}$=11 min after IV administration), but has been reported to have inhibitory activity against FOXM1 when delivered IV in a nanoparticle preparation.

Of interest, the FOXM1 inhibitors described herein were able to function as breast cancer cell proliferation suppressors in a broad range of breast cancer subtypes, both hormone receptor positive (such as MCF7 and tamoxifen-resistant MCF7) and triple negative (such as DT22, and MDA-MB-231), as well as in BT474 (ER-positive, HER2-positive), where similar $IC_{50}$ concentrations for inhibition of cell proliferation and FOXM1-regulated gene expressions were observed. Indeed, there is considerable evidence for the deleterious impact of high tumor FOXM1 on patient clinical outcome in ER-positive breast cancers, in HER2-positive breast cancers, and in triple negative breast cancers. FOXM1 is also a key player in a particularly aggressive subtype of prostate cancer (PCS1), and in many other cancers, including glioblastoma, ovarian, gastrointestinal, non-small cell lung cancers, and pancreatic ductal adenocarcinoma, where there are currently few optimal treatments. Hence, FOXM1 inhibitors may be useful in a variety of tumors with high FOXM1.

Several lines of evidence indicate that our compounds are targeting FOXM1. Our studies show that the FOXM1 inhibitors bind directly to FOXM1 and decrease the intracellular level of FOXM1 protein. Of note, FOXM1 inhibitor exposure increased FOXM1 degradation by pronase as observed in the DARTS protease sensitivity assay, implying that the compound perturbs the structure of FOXM1 to make it more readily proteolyzed. The higher activity of the compounds in FOXM1-rich cell lines (such as DT22), and its reduced activity in cells with low FOXM1 (such as MCF10A), is again supportive of FOXM1 being the target of these compounds. Likewise, the greater effectiveness of FOXM1 inhibitors in suppression of DT22 vs MCF7 tumor xenografts, is consistent with FOXM1 being the target of these compounds. Changes in cellular FOXM1 protein level might also involve posttranslational modifications of FOXM1, such as phosphorylation or acetylation that are known to affect FOXM1 stability and/or activity. However, because the inhibitors decreased the expression of FOXM1-regulated genes, including FOXM1 itself, the reduced intracellular FOXM1 protein level could also result from diminished FOXM1 gene transcription, increased mRNA degradation, or changes in FOXM1 RNA translation, possibly involving miRNAs known to target FOXM1.

Of interest, the compounds showed good inhibitory activity in ER-negative and ER positive cells, and also in Tamoxifen-resistant breast cancer cells. Since these inhibitors were effective antitumor agents when administered alone at low submicromolar doses in several breast cancer subtypes, they could be used in combination treatments targeting ER-positive recurrent metastatic endocrine therapy resistant breast cancers and aggressive triple negative breast cancers, when administered with other current standard-of-care treatments. For example, combinations of these FOXM1 inhibitors with Fulvestrant, Letrozole, PI3K inhibitors, or CDK4/6 inhibitors might enable improved tumor sensitivity and response, since we and others have shown that knockdown of FOXM1 or inhibition of FOXM1 activity with an ARF inhibitory peptide in cells in culture could restore sensitivity to tamoxifen in tamoxifen-resistant breast cancer cells. Inhibition of FOXM1 in triple negative breast cancers could likewise reduce the amounts of chemotherapy drugs or radiation needed, since high levels of FOXM1 have been found to reduce cancer responsiveness to chemotherapeutic agents and to radiation, thereby improving cancer treatment and perhaps reducing undesirable side effects of many current drug therapies.

FOXM1 Inhibition and Cancer

In another aspect, the present disclosure provides a method of inhibiting FOXM1 in a subject, the method comprising administering to a subject in need thereof a therapeutically effective amount of the a compound as disclosed herein, or a pharmaceutically acceptable salt thereof, or a pharmaceutical composition as described herein. In some embodiments, the pharmaceutically acceptable salt for the method of inhibiting FOXM1 is a quaternary ammonium salt as disclosed herein.

In another aspect, the present disclosure provides a method of increasing proteolysis of FOXM1 in a subject, the method comprising administering to a subject in need thereof a therapeutically effective amount of a compound as disclosed herein, or a pharmaceutically acceptable salt thereof, or a pharmaceutical composition as described herein. In some embodiments, the pharmaceutically acceptable salt for the method of increasing proteolysis of FOXM1 is a quaternary ammonium salt as disclosed herein.

In additional aspect, the present disclosure provides a method of inhibiting cancer growth in a subject, the method comprising administering to a subject in need thereof a therapeutically effective amount of a compound as disclosed herein, or a pharmaceutically acceptable salt thereof, or a pharmaceutical composition as described herein. In some embodiments, the pharmaceutically acceptable salt for the method of inhibiting cancer growth is a quaternary ammonium salt as disclosed herein. In some embodiments, the subject has or is suspected of having cancer.

In another aspect, the present disclosure provides a method of treating cancer in a subject, the method comprising administering to a subject in need thereof a therapeutically effective amount of a compound as disclosed herein, or a pharmaceutically acceptable salt thereof, or a pharmaceutical composition as described herein. In some embodiments, the pharmaceutically acceptable salt for the method of treating cancer is a quaternary ammonium salt as disclosed herein. In some embodiments, the subject being treated has or is suspected of having cancer. In some embodiments, the method of treating cancer is a method of therapeutically treating cancer as described herein. As non-limiting examples, the treatment may result in alleviation of cancer symptoms, reduction of pain or suffering, inhibition of cancer development, regression of cancer, and improved survival rate.

In another aspect, disclosed are compounds, or pharmaceutically acceptable salts thereof, as disclosed herein for use in inhibiting FOXM1. In some embodiments, the pharmaceutically acceptable salt for use in inhibiting FOXM1 is a quaternary ammonium salt as disclosed herein.

In another aspect, disclosed are compounds, or pharmaceutically acceptable salts thereof, as disclosed herein for use in inhibiting cancer growth. In some embodiments, the pharmaceutically acceptable salt for use in inhibiting cancer growth is a quaternary ammonium salt as disclosed herein.

In another aspect, disclosed are compounds, or pharmaceutically acceptable salts thereof, as disclosed herein for use in treating cancer. In some embodiments, the pharmaceutically acceptable salt for use in treating cancer is a quaternary ammonium salt as disclosed herein.

In another aspect, disclosed is use of compounds, or pharmaceutically acceptable salts thereof, as disclosed herein for manufacturing a medicament for inhibiting FOXM1. In some embodiments, the pharmaceutically acceptable salt used for manufacturing a medicament for inhibiting FOXM1 is a quaternary ammonium salt as disclosed herein.

In another aspect, disclosed is use of compounds, or pharmaceutically acceptable salts thereof, as disclosed herein for manufacturing a medicament for inhibiting cancer growth. In some embodiments, the pharmaceutically acceptable salt used for manufacturing a medicament for inhibiting cancer growth is a quaternary ammonium salt as disclosed herein.

In another aspect, disclosed is use of compounds, or pharmaceutically acceptable salts thereof, as disclosed herein for manufacturing a medicament for treating cancer. In some embodiments, the pharmaceutically acceptable salt used for manufacturing a medicament for treating cancer is a quaternary ammonium salt as disclosed herein.

In some embodiments, the cancer is breast cancer, prostate cancer, glioblastoma, ovarian cancer, gastrointestinal cancer, non-small cell lung cancer, pancreatic ductal adenocarcinoma, or a combination thereof.

In some embodiments, the cancer is breast cancer. In embodiments, the breast cancer is hormone receptor-positive breast cancer, ER-positive breast cancer, HER2-positive breast cancer, triple negative breast cancer, tamoxifen-resistant breast cancer, or a combination thereof.

In another embodiment, the method can further comprise administering to a subject an additional cancer treatment. The additional cancer treatments may include, but are not limited to, chemotherapy, radiation, Fulvestrant, Letrozole, PI3K inhibitors, CDK4/6 inhibitors, ARF inhibitory peptides, or a combination thereof. Other suitable additional anti-cancer therapeutic agents or treatments may also used. Administering the compositions described above may reduce the doses of the anti-cancer therapeutic while maintaining efficacy and reducing the deleterious effects caused by such treatments.

FOXM1 Binding Assays

The compounds and compositions disclosed herein may be used for FOXM1 binding assays. The compounds described herein, or salts thereof, suitable for the FOXM1 binding assays may have one of the amine appendages of the diamine compound replaced with a fluorescence donor or a fluorescence acceptor. For example, the compound may be a compound of formula (I) or formula (I-a), or a salt thereof, wherein one of $R^1$ and $R^2$ is —$OC_{2-8}$alkylene-L-T, and the other is —$OR^3$ as disclosed herein. The salts of the present compounds useful for the FOXM1 binding assays may include pharmaceutically acceptable salts or other salts suitable for various in vitro or in vivo experiments. In some embodiments, the binding assays includes a Fluorescence Resonance Energy Transfer (FRET) measurement, in which a compound, or a salt thereof, as disclosed herein having a T group is used as fluorescence acceptor or a fluorescence donor molecule, corresponding to a fluorescence donor or a fluorescence acceptor, respectively, in another molecule. Selection of donor-acceptor pairs and the FRET measurement may be carried out according to known methods.

In another aspect, provided is an assay method of screening for a substance that may be acting as a FOXM1 inhibitor, the method comprising
incubating
i) a FOXM1 that is fused with an amino acid sequence that allows covalent attachment of biotin,
ii) a streptavidin that is labeled with a fluorescent donor moiety or a fluorescent acceptor moiety, and
iii) a compound of formula (I) or formula (I-a), or a salt thereof, wherein one of $R^1$ and $R^2$ is —$OC_{2-8}$alkylene-L-T, and the other is —$OR^3$, wherein T is a fluorescent acceptor moiety if the streptavidin is labeled with a fluorescent donor moiety, or wherein T is a fluorescent donor moiety if the streptavidin is labeled with a fluorescent acceptor moiety in a reaction mixture in either the presence or absence of the substance;

exposing the reaction mixture to light that allows fluorescence resonance energy transfer to take place; and measuring fluorescence emission from the reaction mixture;

wherein if the fluorescence emission measurement from the reaction mixture in the presence of the substance is different than the fluorescence emission measurement from the mixture in the absence of the substance, the substance is acting as a FOXM1 inhibitor.

In some embodiment, the assay method further includes providing a compound of formula (I) or formula (I-a), or a salt thereof, wherein one of $R^1$ and $R^2$ is —$OC_{2-8}$alkylene-L-T, and the other is —$OR^3$, wherein T is a fluorescent acceptor moiety if the streptavidin is labeled with a fluorescent donor moiety, or wherein T is a fluorescent donor moiety if the streptavidin is labeled with a fluorescent acceptor moiety.

In some embodiments, the assay method further includes providing a streptavidin that is labeled with a fluorescent donor moiety or a fluorescent acceptor moiety.

In some embodiments, the assay method further includes providing a FOXM1 that is fused with an amino acid sequence that allows covalent attachment of biotin.

In some embodiments, the incubation is carried out by mixing i), ii), iii), and the tested substance together to form a reaction mixture, which is allowed to incubate.

In some embodiments, a method of screening for a substance that may be acting as a FOXM1 inhibitor is provided, the method comprising the steps of a) providing a FOXM1 that is fused with an amino acid sequence that allows covalent attachment of biotin, b) providing streptavidin that is labeled with a fluorescent donor moiety or a fluorescent acceptor moiety, c) providing a composition described above having one of the amine appendages of the diamine compound replaced with a fluorescent acceptor moiety if the streptavidin in step b) is labeled with a fluorescent donor moiety, and wherein the composition described above having one of the amine appendages of the diamine compound replaced with a fluorescent donor moiety if said streptavidin in step b) is labeled with a fluorescent acceptor moiety, d) incubating the FOXM1, the streptavidin and the composition described above in a reaction mixture in either the presence or absence of the substance, and e) exposing the reaction mixture to light that allows fluorescence resonance energy transfer to take place and measuring fluorescence emission from the reaction mixture; wherein if the fluorescence emission measurement from the reaction mixture in the presence of the substance is different than the fluorescence emission measurement from the mixture in the absence of the substance, the substance is acting as a FOXM1 inhibitor.

In some embodiments, the compound in step c) is a compound of formula (I) or formula (I-a), or a pharmaceutically acceptable salt thereof, wherein one of $R^1$ and $R^2$ is —$OC_{2-8}$alkylene-L-T, and the other is —$OR^3$ as disclosed herein. The -L-T may be —NHC(O)-T, as an example. In some embodiments, T is a fluorescent acceptor moiety and the streptavidin in step b) is labeled with a fluorescent donor moiety. In some embodiments, T is a fluorescent donor moiety and said streptavidin in step b) is labeled with a fluorescent acceptor moiety.

In some embodiments, the present disclosure provides a method of screening, comprising:

mixing (a) FOXM1 fused with an amino acid sequence that allows covalent attachment of biotin, (b) streptavidin labeled with a fluorescent donor moiety or a fluorescent acceptor moiety, (c) a compound as disclosed herein, in which one of $R^1$ and $R^2$ is —$OC_{2-8}$alkylene-L-T, and the other is —$OR^3$, or a salt thereof, wherein T is a fluorescent acceptor moiety if the streptavidin is labeled with a fluorescent donor moiety, and wherein T is a fluorescent donor moiety if the streptavidin is labeled with a fluorescent acceptor moiety; and (d) a test sample containing a substance, or a blank sample that does not contain the substance to form a reaction mixture;

exposing the reaction mixture to light, thereby producing a fluorescence signal; and measuring the fluorescence signal;

wherein a difference between the fluorescence signal from the reaction mixture having the test sample and the fluorescent signal from the reaction mixture having the blank sample indicates that the substance is a FOXM1 inhibitor.

In a particular embodiment, the compound or composition useful for FOXM1 binding assays is:

(FI-NB-72)

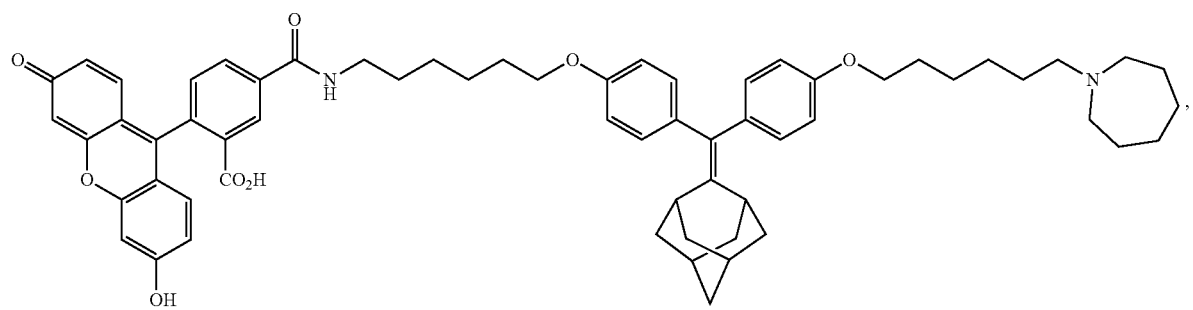 [SMILES: O=C(NCCCCCCOc1ccc(C(=C2C3CC4CC(C3)CC2C4)c2ccc(OCCCCCCN3CCCCCC3)cc2)cc1)c1ccc(-c2c3ccc(=O)cc-3oc3cc(O)ccc23)c(C(=O)O)c1 ; ","]

or a salt thereof.

In another aspect, a kit for the screening of a substance that may be acting as a FOXM1 inhibitor is provided. The kit may comprise a solution comprising FOXM1 that is fused at its C-terminus with an amino acid sequence that allows covalent attachment of biotin, a solution comprising streptavidin that is labeled with a fluorescent donor moiety or a fluorescent acceptor moiety, a solution comprising a compound or composition described herein labeled with a fluorescence donor moiety if the streptavidin is labeled with a fluorescence acceptor moiety, or a compound or composition described herein labeled with a fluorescence acceptor moiety if the streptavidin is labeled with a fluorescence donor moiety, and at least one buffer.

In some embodiments, the kit includes a compound of formula (I) or formula (I-a), or a pharmaceutically acceptable salt thereof, wherein one of R¹ and R² is —OC₂₋ₛalkylene-L-T, and the other is —OR³. The -L-T may be NHC(O)-T, as an example. In some embodiments, T is a fluorescent acceptor moiety and the streptavidin is labeled with a fluorescent donor moiety. In some embodiments, T is a fluorescent donor moiety and the streptavidin is labeled with a fluorescent acceptor moiety. In some embodiments, the kid includes fer Microscopy, in Fluorescence Microscopy of Living Cells in Culture, Part B, Methods in Cell Biology, vol. 30, ed. Taylor, D. L. & Wang, Y.-L., San Diego: Academic Press (1989), pp. 219-243; Turro, N.J., Modern Molecular Photochemistry, Menlo Park: Benjamin/Cummings Publishing Col, Inc. (1978), pp. 296-361; and Bernard Valeur, "Molecular Fluorescence: Principles and Applications" Wiley VCH, 2002. Guidance in the selection and use of specific resonance acceptor moieties is available at, for example, Berlman, I. B., Energy transfer parameters of aromatic compounds, Academic Press, New York and London (1973), which contains tables of spectral overlap integrals for the selection of resonance energy transfer pairs. Additional information sources include the Molecular Probes Catalog (2003) and website; and Tsien et al., 1990 Handbook of Biological Confocal Microscopy, pp. 169-178. Instruments useful for performing FP and/or RET and TR-RET applications are available from Tecan Group Ltd. (Switzerland)

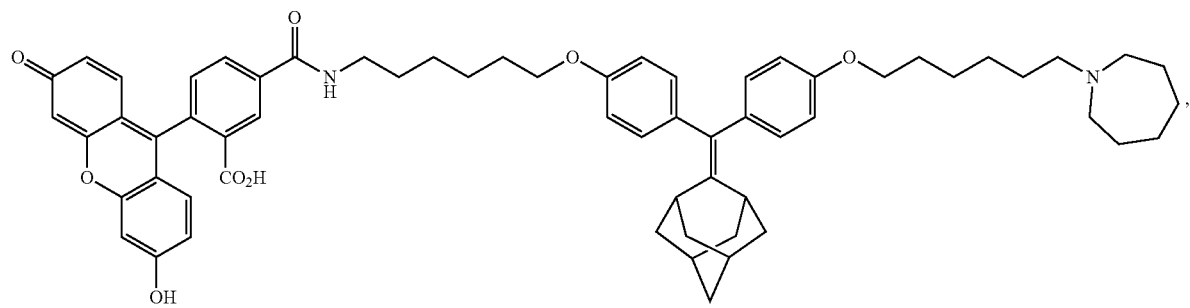

or a salt thereof. The kit may also contain positive and negative controls as well as instruction on performing the assay.

Generally, the nomenclature used herein and many of the fluorescence, luminescence, computer, detection, chemistry, and laboratory procedures described herein are commonly employed in the art. Standard techniques are generally used for chemical synthesis, fluorescence or luminescence monitoring and detection, optics, molecular biology, and computer software and integration. Chemical reactions, cell assays, and enzymatic reactions are typically performed according to the manufacturer's specifications where appropriate. See, generally, Lakowicz, J. R. *Topics in Fluorescence Spectroscopy*, (3 volumes) New York: Plenum Press (1991), and Lakowicz, J. R. *Emerging applications of florescence spectroscopy to cellular imaging: lifetime imaging, metal-ligand probes, multi photon excitation and light quenching*, Scanning Microsc. Suppl. Vol. 10 (1996) pages 213-24, for fluorescence techniques; Sambrook et al., *Molecular Cloning: A Laboratory Manual,* 2ed. (1989) Cold Spring Harbor Laboratory Press, Cold Spring Harbor, N.Y., for molecular biology methods; *Cells: A Laboratory Manual,* 1ˢᵗ edition (1998) Cold Spring Harbor Laboratory Press, Cold Spring Harbor, N.Y., for cell biology methods; and *Optics Guide* 5 Melles Griot® Irvine Calif., and Optical Waveguide Theory, Snyder & Love (published by Chapman & Hall) for general optical methods, all of which are incorporated herein by reference.

General methods for performing a variety of fluorescent or luminescent assays on luminescent materials are known in the art and are described in, e.g., Lakowicz, J. R., Topics in Fluorescence Spectroscopy, volumes 1 to 3, New York: Plenum Press (1991); Herman, B., Resonance Energy Trans- (Ultra, Ultra 384, Ultra Evolution); Perkin-Elmer (Boston, Mass.) (Fusion, EnVision, Victor V, and ViewLux), Amersham Bioscience (Piscataway, N.J.) (LeadSeeker); and Molecular Devices Corporation (Sunnyvale, Calif.) (Analyst AD, GT, and HT).

Administration

As described herein, compounds of the present invention, or a pharmaceutically acceptable salt thereof, or a pharmaceutical composition as described elsewhere herein, can be administered to such subjects by a variety of methods. In any of the uses or methods described herein, administration can be by various routes known to those skilled in the art, including without limitation oral, inhalation, intravenous, intramuscular, topical, subcutaneous, systemic, and/or intraperitoneal administration to a subject in need thereof.

The amount of the compound of the present invention, or a pharmaceutically acceptable salt thereof, required for use in treatment will vary not only with the particular compound or salt selected but also with the route of administration, the nature and/or symptoms of the estrogen receptor dependent and/or estrogen receptor mediated disease or condition being treated and the age and condition of the patient and will be ultimately at the discretion of the attendant physician or clinician. In cases of administration of a pharmaceutically acceptable salt, dosages may be calculated as the free base. As will be understood by those of skill in the art, in certain situations it may be necessary to administer the compounds disclosed herein in amounts that exceed, or even far exceed, the dosage ranges described herein in order to effectively and aggressively treat particularly aggressive estrogen receptor dependent and/or estrogen receptor mediated diseases or conditions.

In some embodiments, the compounds, or pharmaceutically acceptable salts thereof, or pharmaceutical compositions as disclosed herein may be administered by inhalation, oral administration, or intravenous administration. In general, however, a suitable dose will often be in the range of from about 0.01 mg/kg to about 100 mg/kg, such as from about 0.05 mg/kg to about 10 mg/kg. For example, a suitable dose may be in the range from about 0.10 mg/kg to about 7.5 mg/kg of body weight per day, such as about 0.10 mg/kg to about 0.50 mg/kg of body weight of the recipient per day, about 0.10 mg/kg to about 1.0 mg/kg of body weight of the recipient per day, about 0.15 mg/kg to about 5.0 mg/kg of body weight of the recipient per day, about 0.2 mg/kg to 4.0 mg/kg of body weight of the recipient per day. The compound may be administered in unit dosage form; for example, containing 1 to 100 mg, 10 to 100 mg or 5 to 50 mg of active ingredient per unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

As will be readily apparent to one skilled in the art, the useful in vivo dosage to be administered and the particular mode of administration will vary depending upon the age, weight, the severity of the affliction, and mammalian species treated, the particular compounds employed, and the specific use for which these compounds are employed. The determination of effective dosage levels, that is the dosage levels necessary to achieve the desired result, can be accomplished by one skilled in the art using routine methods, for example, human clinical trials, in vivo studies and in vitro studies. For example, useful dosages of a compound of the present invention, or pharmaceutically acceptable salts thereof, can be determined by comparing their in vitro activity, and in vivo activity in animal models. Such comparison can be done by comparison against an established drug, such as fulvestrant.

Dosage amount and interval may be adjusted individually to provide plasma levels of the active moiety which are sufficient to maintain the modulating effects, or minimal effective concentration (MEC). The MEC will vary for each compound but can be estimated from in vivo and/or in vitro data. Dosages necessary to achieve the MEC will depend on individual characteristics and route of administration. However, HPLC assays or bioassays can be used to determine plasma concentrations. Dosage intervals can also be determined using MEC value. Compositions should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the estrogen receptor dependent and/or estrogen receptor mediated disease or condition to be treated and to the route of administration. The severity of the estrogen receptor dependent and/or estrogen receptor mediated disease or condition may, for example, be evaluated, in part, by standard prognostic evaluation methods. Further, the dose, and perhaps dose frequency, will also vary according to the age, body weight, and response of the individual patient. A program comparable to that discussed above may be used in veterinary medicine.

Compounds, salts and compositions disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, dogs or monkeys, may be determined using known methods. The efficacy of a particular compound may be established using several recognized methods, such as in vitro methods, animal models, or human clinical trials. When selecting a model to determine efficacy, the skilled artisan can be guided by the state of the art to choose an appropriate model, dose, route of administration and/or regime.

A therapeutically effective amount of a compound disclosed herein, or a pharmaceutically acceptable salt thereof, or a pharmaceutical composition as disclosed herein may be administered alone or in combination with a therapeutically effective amount of at least one additional anti-cancer therapeutic agents. In some embodiments, the compounds or pharmaceutical compositions as disclosed herein are administered in combination with at least one additional anti-cancer therapeutic agents. In some embodiments, the at least one additional anti-cancer therapeutic is administered prior to or following administration of the compounds or pharmaceutical compositions as disclosed herein.

4. Pharmaceutical Compositions

In another aspect of the invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents. In one embodiment, the pharmaceutical composition comprises a therapeutically effective amount of a compound of the present disclosure, or a pharmaceutically acceptable salt thereof as disclosed herein, and one or more pharmaceutically acceptable carriers or vehicles.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

As described herein, the pharmaceutically acceptable compositions of the invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, poly ethylenepolyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutically acceptable compositions of this invention can be administered to humans and other animals orally, rectally, parenterally, intracistemally, intravaginally, intraperitoneally, topically (as by powders, ointments, or drops), bucally, as an oral or nasal spray, or the like, depending on the severity of the disease being treated.

Pharmaceutical compositions for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions can also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It can also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the compound or composition, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, can depend upon crystal size and crystalline form. Alternatively, delayed absorption of a parenterally administered drug form is accomplished by dissolving or suspending the drug in an oil vehicle.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Solid dosage forms for oral administration include capsules, tablets, pills, powders, cement, putty, and granules. In such solid dosage forms, the active compound can be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form can also comprise buffering agents.

Solid compositions of a similar type may also be employed as fillers in soft and hardfilled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Dosage forms for topical or trans dermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Compounds described herein can be administered as a pharmaceutical composition comprising the compounds of interest in combination with one or more pharmaceutically acceptable carriers. It is understood, however, that the total daily dosage of the compounds and compositions can be decided by the attending physician within the scope of sound medical judgment. The specific therapeutically effective dose level for any particular patient can depend upon a variety of factors including the disorder being treated and the severity of the disorder; activity of the specific compound employed; the specific composition employed; the age, body weight, general health and prior medical history, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved. Actual dosage levels of active ingredients in the pharmaceutical compositions can be varied so as to obtain an amount of the active compound(s) that is effective to achieve the desired therapeutic response for a particular patient and a particular mode of administration. In the treatment of certain medical conditions, repeated or chronic administration of compounds can be required to achieve the desired therapeutic response. "Repeated or chronic administration" refers to the administration of compounds daily (i.e., every day) or intermittently (i.e., not every day) over a period of days, weeks, months, or longer.

The compositions described herein may be administered with additional compositions to prolong stability, delivery, and/or activity of the compositions, or combined with additional therapeutic agents, or provided before or after the administration of additional therapeutic agents.

Combination therapy includes administration of a single pharmaceutical dosage formulation containing one or more of the compounds described herein and one or more additional pharmaceutical agents, as well as administration of the compounds and each additional pharmaceutical agent, in its own separate pharmaceutical dosage formulation. For example, a compound described herein and one or more additional pharmaceutical agents, can be administered to the patient together, in a single oral dosage composition having a fixed ratio of each active ingredient, such as a tablet or capsule; or each agent can be administered in separate oral dosage formulations. Where separate dosage formulations are used, the present compounds and one or more additional pharmaceutical agents can be administered at essentially the same time (e.g., concurrently) or at separately staggered times (e.g., sequentially).

For adults, the doses are generally from about 0.01 to about 100 mg/kg, desirably about 0.1 to about 1 mg/kg body weight per day by inhalation, from about 0.01 to about 100 mg/kg, desirably 0.1 to 70 mg/kg, more desirably 0.5 to 10 mg/kg body weight per day by oral administration, and from about 0.01 to about 50 mg/kg, desirably 0.1 to 1 mg/kg body weight per day by intravenous administration.

The compositions and methods will be described more fully hereinafter with reference to the accompanying drawings, in which some, but not all embodiments of the invention are shown. Indeed, the invention may be embodied in many different forms and should not be construed as limited to the embodiments set forth herein.

Likewise, many modifications and other embodiments of the compositions and methods described herein will come to mind to one of skill in the art to which the invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the invention pertains. Although any methods and materials similar to or equivalent to those described herein can be used in the practice or testing of the present invention, the preferred methods and materials are described herein.

5. EXAMPLES

Materials and Methods

Chemical synthesis Compounds and materials were supplied from the sources indicated: Pyrrolidine, piperidine, piperidine-4-ol, 2-(S)-hydroxymethypyrrolidine, azepane, cesium carbonate, 2-adamantanone, 4,4'-dihydroxybenzophenone, $TiCl_4$, zinc, and 6-bromohexanol (Aldrich, Milwaukee WI), azetidine, 3-hydroxyazetidine, and 3-hydroxy-3-methylazetidine (Combi-block, CA). DMF, methanol, diethyl ether, dichloromethane, methyl iodide, n-hexane, and ethyle acetate were purchased from Fisher science. All solvent were used without further purification. Yields refer to chromatographically and spectroscopically ($^1$H NMR) homogeneous materials, unless otherwise stated. Reactions were monitored by thin layer chromatography (TLC) carried out on Merck silica gel 60 F254 precoated plates (0.25 mm) using UV light as the visualizing agent and ceric ammonium molybdate and heat as developing agents. Preparative TLC plate (silicagel GF, 20×20 cm, 1000 micron) was purchased from Analtech Co. Ltd. Flash column chromatography was performed on Silica P Flash silica gel (40-64 µM, 60 Å) from SiliCycle. $^1$H NMR spectra were recorded at 23° C. on a Varian Unity-400, Varian Inova-500 or Varian Unity-500 spectrometers and are reported in ppm using residual proton as the internal standard (CHCl$_3$, δ=7.26, center line). The following abbreviations were used to explain the multiplicities: s=singlet, d=doublet, dd=doublet of doublets, t=triplet, q=quartet, m=multiplet, hep=heptet, and br=broad. Proton-decoupled $^{13}$C NMR spectra were recorded on a Varian Unity-500 (126 MHz) spectrometer and are reported in ppm using solvent as an internal standard (CDCl$_3$, δ=77.16, center line). High and low resolution mass spectra were obtained at the University of Illinois Mass Spectrometry Laboratory (a Q-TOF Ultima API, Waters Co. Ltd.).

Cell lines and cell culture methods MCF7 and other breast cancer cell lines were obtained from the ATCC and were maintained and cultured as described (Bergamaschi et al., Breast Cancer Res., 2014, 16:436; Madak-Erdogan et al., Mol. Syst. Biol., 2013, 9:676; Zhao et al., Cancer Res., 2017, 77:5602-13). DT22 cells were derived from a human triple negative invasive ductal breast carcinoma and were grown in culture as described (Drews-Elger et al., Breast cancer research and treatment, 2014, 144:503-17). All cells were tested for mycoplasma using Real-Time PCR Mycoplasma Detection Kit (Akron Biotech, Boca Raton, FL).

Cell proliferation assay WST-1 assay (Roche, Basel, Switzerland) was used to quantify cell viability as described (Gong et al., Mol. Cell Endocrinol., 2016, 437:190-200). Absorbance was measured at 450 nm using a VICTOR X5 PerkinElmer 2030 Multilabel Plate Reader. All assays were performed in triplicate.

In-cell Western and Western blot assays Cells were cultured in 96-well plates at 3000 cells/well, and treated with compounds for the times indicated. Cells were washed twice in PBS, fixed with 4% formaldehyde (Fisher Scientific) solution in PBS, permeabilized in 0.1% Triton X-100 in PBS, blocked with Odyssey Blocking Buffer (LI-COR), and incubated with FOXM1 antibody (GeneTex, 102170) rabbit HC-20 ERa antibody (Santa Cruz, Cat #SC-543) or mouse F10 ERa antibody (Santa Cruz, Cat #SC8002) at 4 C overnight. Both IRDye 800 CW goat anti-rabbit secondary antibody (LI-COR, Cat #926-32211) and Cell Tag 700 (LI-COR, Cat #926-41090) were diluted (1:600) for incubation with cells. Plates were washed and staining signals were quantified and normalized with Cell Tag signals (to control for any differences in cell number per well) using LI-COR Odyssey infrared imaging system. Fold changes in protein levels were calculated relative to the vehicle treated WT samples. Results are the average±SD from at least three independent experiments, each performed with 4 wells per treatment condition.

For Western blot analysis, whole-cell extracts were prepared using 1×RIPA lysis buffer (Upstate/Chemicon) supplemented with 1× complete protease inhibitor mixture (Roche). Proteins were separated on 4-20% SDS-PAGE gels and transferred to nitrocellulose membranes. Western blotting used antibodies against FOXM1 (Abcam 184637), ERa (Santa Cruz) and β-actin (Sigma-Aldrich), as internal loading control.

RNA isolation and real-time PCR Total RNA was isolated using TRIzol (Invitrogen) and reverse transcribed using MMTV reverse transcriptase (New England BioLabs). Real-time PCR was performed using SYBRgreen PCR Master Mix (Roche) as described (Bergamaschi et al., Breast Cancer Res., 2014, 16:436). Relative mRNA levels of genes were normalized to the housekeeping gene 36B4, and fold change calculated relative to the vehicle treated samples. Results are the average±SD from at least two independent experiments carried out in triplicate. Primer sequences for the genes studied were obtained from the Harvard Primer Bank. Sequences are available on their website.

Drug affinity responsive target stability (DARTS) assay The DARTS assay was performed as described (Pai et al., Methods Mol. Biol., 2015, 1263:287-98) to examine the effect of inhibitors on the stability of FOXM1 to proteolysis by exogenous pronase. DT22 cell lysates were incubated without or with 10 µM NB-73 for 1 h at room temperature, and with varying concentrations of pronase (none, 1:10$^3$: 1:10$^4$; 1:10$^5$; and 1:10$^6$) for an additional 30 min at room temperature. Proteins were then separated on a 4-20% SDS-PAGE gel and gels were exposed to FOXM1 antibody (Abcam rabbit polyclonal 1:750) and β-actin antibody (1:500, mouse monoclonal).

Pharmacokinetic studies All experiments involving animals were conducted in accordance with National Institutes of Health (NIH) standards for the care and use of animals, with protocols approved by the University of Illinois IACUC. The pharmacokinetics of compounds were monitored after single dose administration into female CD 1 mice (7-9 weeks of age) via s.c. injection or oral gavage as described (Zhao et al., Cancer Res., 2017, 77:5602-13). For s.c. injection, each compound was dissolved in DMSO and then mixed with corn oil for a total injection volume of 100 µL (10% DSMO+90% corn oil) per mouse. For oral gavage, compounds were administered in a 200 µL formulation of 9/0.5/0.5/90 parts of PEG400/Tween80/Povidone/0.5% Carboxymethylcellulose. Multiple plasma samples were collected from each mouse (n=4 for each experiment) over the course of 48 h after compound administration. Compounds were quantified by LC-MS/MS at the University of Illinois Metabolomics Core Facility. The data were fitted to a non-compartment model.

In vivo breast cancer xenograft studies For examination of the growth of triple-negative DT22 breast tumors, intact female NOD/SCID-gamma (NSG) mice were used. DT-22 cells (1×10$^6$ cells/mouse) were injected s.c. into the right axial mammary gland. Mice received s.c. injection or oral gavage daily or every second or third day, as indicated, with vehicle or FOXM1 inhibitor compound, and tumor growth was monitored over time.

For examination of the growth of ER-positive MCF7 xenograft tumors, female NSG mice were ovariectomized, and 2 weeks after ovariectomy, animals were supplemented with 0.36 mg E2-pellets (60-day release, Innovative Research of America) to support ER+ tumor growth. Cell suspensions of wild type MCF7 cells (1×10$^6$ cells/mouse) were injected subcutaneously (sc) in the right axial mammary gland and when tumors reached 100-150 mm$^3$ in size, mice were randomized and received compound or control vehicle (corn oil) by s.c. injection or oral gavage (PEG400/PVP/Tween/CMC as Veh) at the frequency indicated and tumor volume (length×width 2/2) was monitored over time.

RNA-Seq transcriptional profiling and gene ontology analysis For gene expression analysis, total RNA was extracted from cells using Trizol reagent and further cleaned using the Turbo DNase and RNAqueous kits (ThermoFisher). Cells were treated with Veh (0.1% EtOH), or with the compounds indicated for 9 h or 24 h. Once the sample quality and replicate reproducibility were verified, samples from each group were subjected to sequencing. RNA at a concentration of 100 ng/μL in nuclease-free water was used for library construction. cDNA libraries were prepared with the mRNA-TruSeq Kit (Illumina, Inc.). In brief, the poly-A containing mRNA was purified from total RNA, the RNA was fragmented, double-stranded cDNA was generated from fragmented RNA, and adapters were ligated to the ends.

The paired-end read data from the HiSeq 4000 were processed and analyzed through a series of steps. Base calling and de-multiplexing of samples within each lane were done with Casava 1.8.2. The RNA sequences were prepared with Illumina's TruSeq Stranded mRNAseq Sample Prep kit. Reads were trimmed of adapters and low expression data using Trimmomatic version 0.38. The star alignment tool version 2.5.3a was used to align the sequenced reads to the GRCh37 human genome from Ensembl. Gene counts were calculated using subread version 1.5.2. The edgeR Bioconductor package in R was used for normalization and differential expression analysis. Default normalization methods were used, specifically trimmed mean of M values or TMM was used to calculate the normalized expression values. This method calculates the weighted trimmed mean of the log expression ratios in a gene-wise fashion. Genes with fold-change >2 and p-value<0.05 were considered as statistically significant, differentially expressed.

Gene Set Enrichment Analysis (GSEA) was used for examination of the genome-wide expression profiles. Over-represented GO biological processes were determined by the web-based DAVID Bioinformatics Resources database.

Example 1 Compound Synthesis

The compounds used in this study were prepared according to the two synthetic schemes below. Monoamine compounds and the corresponding quaternary ammonium salts in Tables 1 may be prepared according to the synthetic process of Scheme 1. Diamine compounds and the corresponding quaternary ammonium salts in Tables 2-4 may be prepared according to the synthetic process of Scheme 2. Abbreviations used in the schemes and examples that follow are: DCM is dichloromethane; DMF is dimethylformamide; DMSO is dimethylsulfoxide; LAH is lithium aluminum hydride; MeOH is methanol; MsCl is methanesulfonyl chloride; PBS is phosphate buffered saline; SaTb is streptavidin-terbium chelate; THF is tetrahydrofuran.

Scheme 1. Preparation for NB-55, 118, and 119 and their quaternary ammonium salts

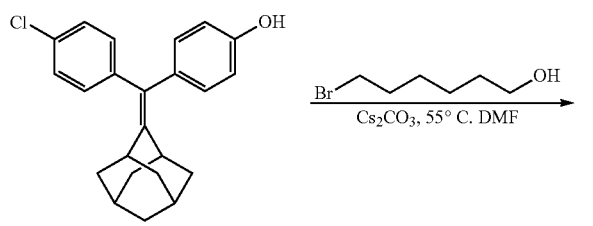

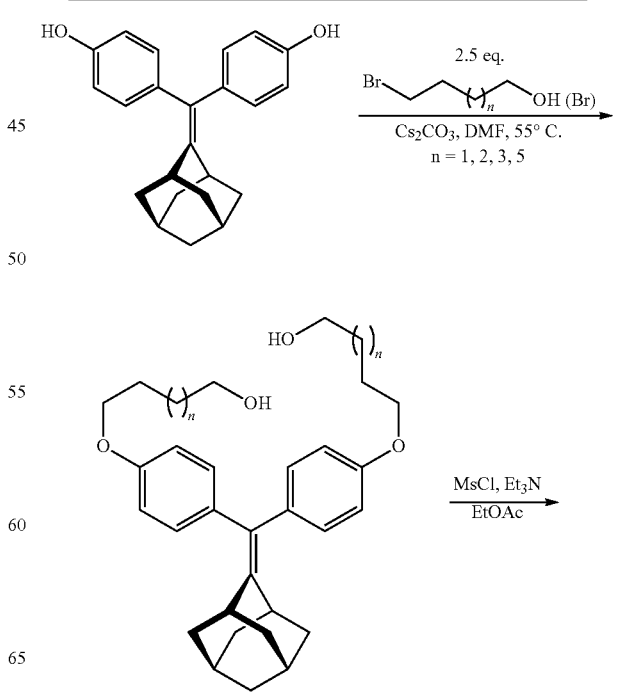

Scheme 2. Preparation for NB-51, 65, 70, and 72 and their quaternary ammonium salts

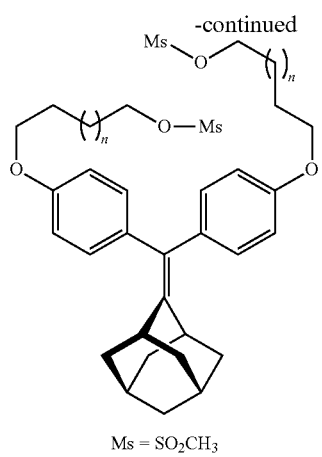
Ms = SO₂CH₃
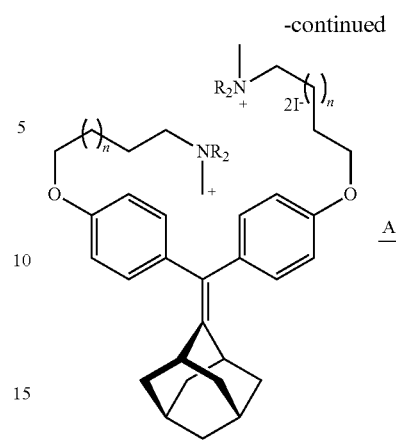
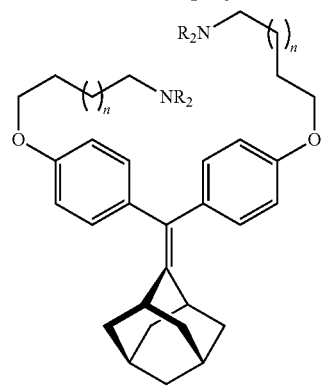
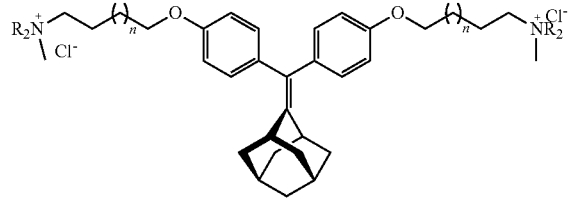
4-((E)-((5R,7R)-adamantan-2-ylidene)(4-((6-(diethylamino)hexyl)oxy)phenyl)methyl)phenol (NB-41)
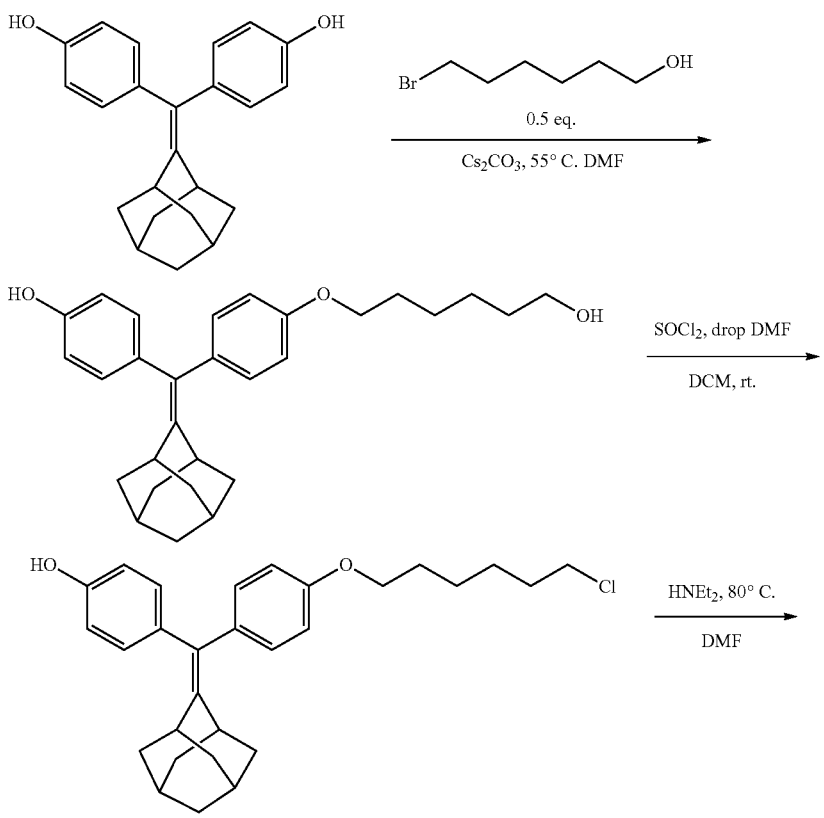

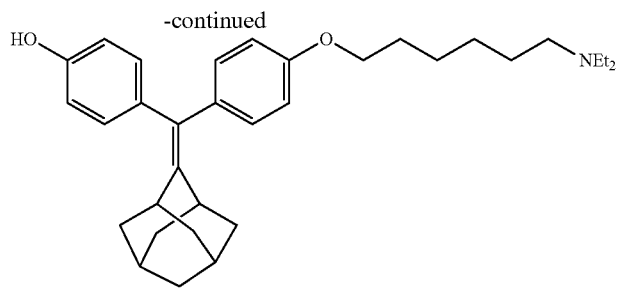

NB-41

4-((E)-((5R,7R)-adamantan-2-ylidene)(4-((6-hydroxyhexyl)oxy)phenyl)methyl)phenol

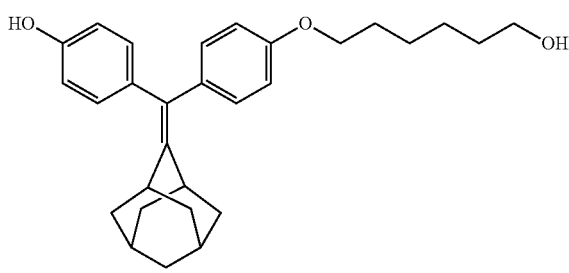 [SMILES: OCCCCCCOc1ccc(C(=C2C3CC4CC(C3)CC2C4)c2ccc(O)cc2)cc1]

The mixture of 4,4'-((((5r,7r)-adamantan-2-ylidene)methylene)diphenol (166 mg, 0.5 mmol), 6-bromohexanol (45 mg, 0.25 mmol), and cesium carbonate (326 mg, 1.00 mmol) was dissolved and suspended in dried DMF (2 mL) and was heated up and stirred at 55° C. for 5 hr. Once the starting material (bisphenol) disappeared completely on SiO2 TLC, the reaction was quenched by adding water (20 mL), followed by extraction with ethyl acetate (20 mL×3), dry under sodium sulfate, concentration under vacuum to load on silicagel column for purification. Elution with a mixture of ethyl acetate and n-hexane (50:50, v/v) provide a sticky semi-solid product (86 mg, 80%). $^1$H NMR (500 MHz, Chloroform-cl) δ 1.37-1.55 (m, 4H), 1.62 (quintet, J=6.7 Hz, 2H), 1.79 (quintet, J=6.8 Hz, 2H), 1.86 (s, 10H), 2.01 (s, 2H), 2.80 (s, 2H), 3.68 (t, J=6.6 Hz, 2H), 3.95 (t, J=6.3 Hz, 2H), 6.75 (d, J=8.5 Hz, 2H), 6.81 (6.75 (d, J=8.5 Hz, 2H), 6.91-7.11 (m, 4H).

4-((E)-((5R,7R)-adamantan-2-ylidene)(4-((6-chlorohexyl)oxy)phenyl)methyl)phenol

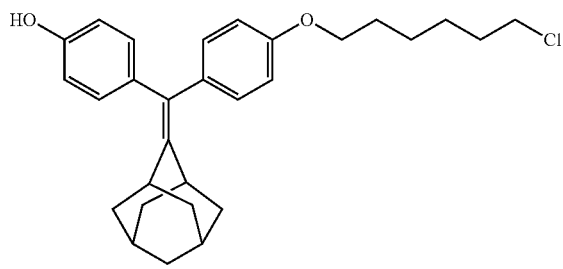 [SMILES: Oc1ccc(C(=C2C3CC4CC(C3)CC2C4)c2ccc(OCCCCCCCl)cc2)cc1]

The treatment of 4-((E)-((5R,7R)-adamantan-2-ylidene)(4-((6-hydroxyhexyl)oxy)phenyl)methyl)phenol (22 mg, 0.12 mmol) with thionyl chloride (100 μL) and one drop of DMF in dichloromethane (5 mL) at rt for 1 hr and the evaporation of solution afforded title compound quantitatively. $^1$H NMR (500 MHz, Chloroform-cl) δ 1.44-1.58 (m, 4H), 1.74-1.95 (m, 16H), 2.01 (s, 2H), 2.80 (s, 2H), 3.57 (t, J=6.7 Hz, 2H), 3.95 (t, J=6.4 Hz, 2H), 6.75 (d, J=8.0 Hz, 2H), 6.81 (d, J=8.1 Hz, 2H), 7.00 (d, J=8.0 Hz, 2H), 7.04 (d, J=8.1 Hz, 2H).

4-((E)-((5R,7R)-adamantan-2-ylidene)(4-((6-(diethylamino)hexyl)oxy)phenyl)methyl)phenol (NB-41)

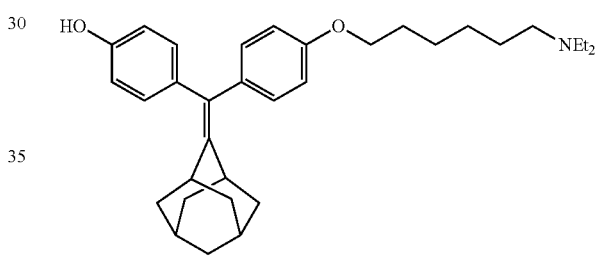

NB-41 was obtained from the reaction of 4-((E)-((5R,7R)-adamantan-2-ylidene)(4-((6-chlorohexyl)oxy)phenyl)methyl)phenol with 6 eq. excess of diethyl amine in DMF at 80° C. in 89% yield, following the same procedure described for the preparation of NB-54.

$^1$HNMR (500 MHz, CDCl$_3$) δ 1.02 (t, J=7.0 Hz, 6H), 1.33 (quintet, J=7.0 Hz, 2H), 1.40~1.51 (m, 2H), 1.73~1.92 (m, 14H), 2.00 (brs, 2H), 2.43 (t, J=7.5 Hz, 2H), 2.53 (q, J 7.0 Hz, 4H), 2.81 (brs, 2H), 3.93 (t, J=6.0 Hz, 2H), 6.76 (d, J=8.0 Hz, 2H), 6.80 (d, J=8.1 Hz, 2H), 7.01 (d, J=8.0 Hz, 2H), 7.03 (d, J=8.1 Hz, 2H).

6,6'-(((((5r,7r)-Adamantan-2-ylidene)methylene)bis (4,1-phenylene))bis(oxy))bis(hexan-1-ol) (1)

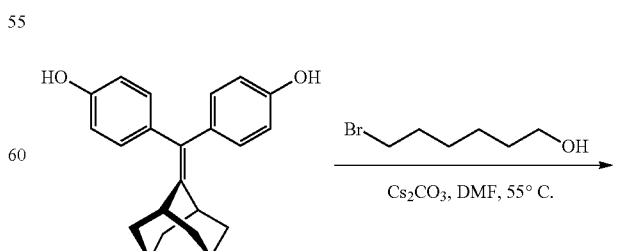

1A

-continued

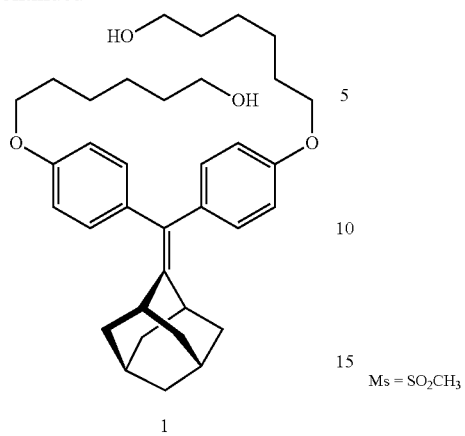

1

The mixture of 4,4'-(((5r,7r)-adamantan-2-ylidene)methylene)diphenol (332 mg, 1.00 mmol), 6-bromohexanol (434 mg, 2.40 mmol), and cesium carbonate (652 mg, 2.00 mmol) was dissolved and suspended in dried DMF (5 mL) and was heated up and stirred at 55° C. for 5 hr. Once the starting material (bisphenol) disappeared completely on $SiO_2$ TLC, the reaction was quenched by adding water (50 mL), followed by extraction with ethyl acetate (20 mL×3), dry under sodium sulfate, concentration under vacuum to load on silica gel column for purification. Elution with a mixture of ethyl acetate and n-hexane (50:50, v/v) provide a sticky semi-solid product (480 mg, 90%).

$^1$H NMR (500 MHz, $CDCl_3$) δ 1.38-1.59 (m, 8H), 1.62 (quintet, J=6.5 Hz, 4H), 1.80 (quintet, J=6.5 Hz, 4H), 1.87 (brs, 10H), 2.01 (s, 2H), 2.81 (s, 2H), 3.67 (t, J=6.5 Hz, 4H), 3.94 (t, J=6.5 Hz, 4H), 6.80 (d, J=8.5 Hz, 4H), 7.03 (d, J=8.5 Hz, 4H). $^{13}$C NMR (126 MHz, $CDCl_3$) δ 25.78, 26.19, 28.47, 29.56, 32.94, 34.67, 37.45, 39.85, 63.18, 67.90, 113.99, 129.89, 130.83, 135.92, 145.88, 157.51. HRMS (ESI, $M^++1$) $C_{35}H_{49}O_4$ Calcd. 533.3631, found 533.3636.

((((((5r,7r)-Adamantan-2-ylidene)methylene)bis(4,1-phenylene))bis(oxy))bis(hexane-6,1-diyl))dimethanesulfonate (2)

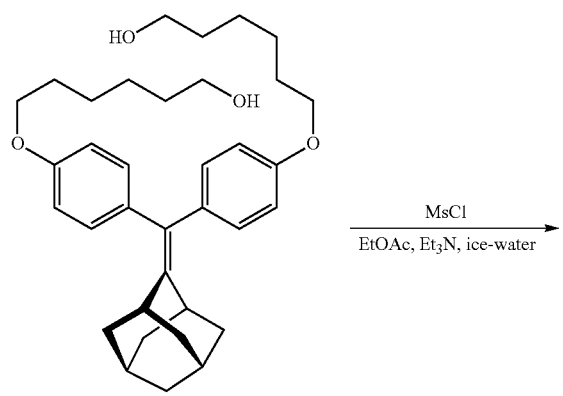

$\xrightarrow{\text{MsCl}}$
EtOAc, $Et_3N$, ice-water

-continued

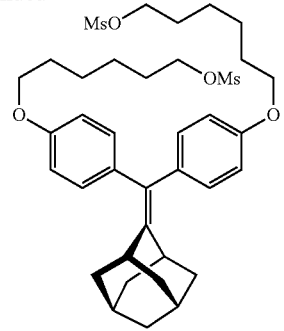

2

Ms = $SO_2CH_3$

To the mixture of 1 (266 mg, 0.50 mmol) and trimethylamine (303 mg, 0.30 mmol) in ethyl acetate (5 mL) was added dropwise methane sulfonyl chloride (172 mg, 1.50 mmol) at ice-water cooling bath. Once the diol 1 was vanished from $SiO_2$ TLC, the mixture was washed by water (5 mL×3). Ethyl acetate solution was treated with the mixture of $NaHCO_3$ (1 g) and water (5 mL) and continuously stirred for 1 hr. The ethyl acetate was separated, dried under sodium sulfate, and concentrated under vacuum to afford the title 2 compound as a colorless sticky liquid form (320 mg, 93%). This product was pure enough to be used without further purification.

$^1$H NMR (500 MHz, $CDCl_3$) δ 1.45-1.57 (m, 8H), 1.76~1.83 (m, 8H), 1.87 (brs, 10H), 2.01 (s, 2H), 2.80 (s, 2H), 3.02 (s, 6H), 3.95 (t, J=6.5 Hz, 4H), 4.26 (t, J=6.5 Hz, 4H), 6.80 (d, J=8.5 Hz, 4H), 7.03 (d, J=8.5 Hz, 4H). $^{13}$C NMR (126 MHz, $CDCl_3$) δ 25.49, 25.87, 28.47, 29.33, 29.38, 34.67, 37.44, 37.62, 39.85, 67.68, 70. 22, 113.98, 130.00, 130.84, 135.97, 145.96, 157.44. HRMS (ESI, $M^++Na$) $C_{37}H_{52}O_8S_2Na$ Calcd. 711.3001, found 711.3008.

4-((-((7_)-((5S,7S)-Adamantan-2-ylidene)(4-chlorophenyl)methyl)phenol (3)

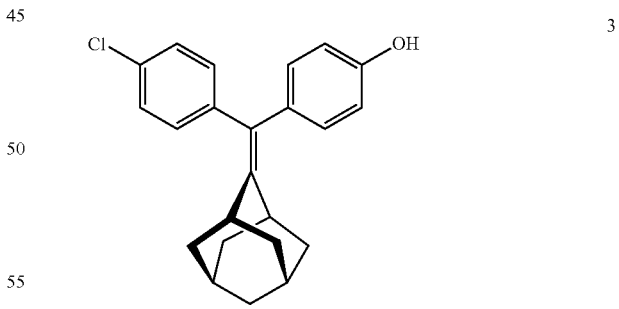

3

To the suspension of zinc powder (392 mg, 6.00 mmol) in THF (20 mL) was added dropwise $TiCl_4$ (567 mg, 3.00 mmol) at −78° C. (dry ice-Acetone) and subsequently the reaction mixture was refluxed for 2 hr and cooled down to room temperature to add the mixture of 2-adamantanone (155 mg, 1.03 mmol) and (4-chlorophenyl)(4-hydroxyphenyl)methanone (233 mg, 1.00 mmol) in THF (10 mL). The reaction mixture was refluxed for 3 hr again. The reaction mixture was cooled down to room temperature, was poured into a sat. $NaHCO_3$ aqueous solution, and stirred until the suspension color was changed from black to white. The mixture was extracted with EtOAc (20 mL×3), washed with brine, dried over $Na_2SO_4$. The solvent was evaporated under vacuum, followed by a column chromatography on $SiO_2$ using 10% EtOAc/n-Hexane as an eluent to afford title compound (280 mg, 80%).

$^1$H NMR (500 MHz, $CDCl_3$) δ 1.80~1.97 (m, 10H), 2.02 (s, 2H), 2.74 (s, 1H), 2.82 (s, 1H), 6.76 (d, J=8.5 Hz, 2H), 6.99 (d, J=8.5 Hz, 2H), 7.06 (d, J=8.5 Hz, 2H), 7.27 (d, J=8.5 Hz, 2H). $^{13}$C NMR (126 MHz, $CDCl_3$) δ 28.36, 31.26, 34.65, 34.74, 36.75, 37.32, 39.79, 115.14, 128.35, 129.14, 131.06, 131.15, 131.94, 135.38, 141.91, 147.36, 154.18. HRMS (EI, M$^+$) $C_{23}H_{23}OCl$ Calcd. 350.14375, found 350.14366.

6-(4-((-((Z)-((5S,7S)-Adamantan-2-ylidene)(4-chlorophenyl)methyl)phenoxy)hexan-1-ol (4)

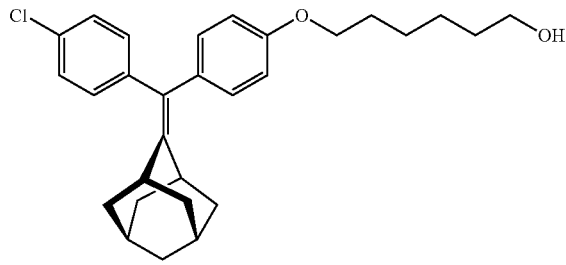

The title compound (4) was prepared from the reaction of the compound 3 (175 mg, 0.50 mmol) with 6-bromohexanol (271 mg, 1.50 mmol), and cesium carbonate (326 mg, 1.00 mmol) in 93% yield, following the same procedure described for the preparation of the compound 1 (Bisphenoxyhexanol).

$^1$H NMR (500 MHz, $CDCl_3$) δ 1.40-1.55 (m, 4H), 1.62 (quintet, J=7.0 Hz, 2H), 1.80 (quintet, J=7.0 Hz, 2H), 1.85~1.92 (m, 10H), 2.02 (s, 2H), 2.74 (s, 1H), 2.82 (s, 1H), 3.68 (t, J=7.0 Hz, 2H), 3.95 (t, J=7.0 Hz, 2H), 6.81 (d, J=8.5 Hz, 2H), 7.02 (d, J=8.5 Hz, 2H), 7.06 (d, J=8.5 Hz, 2H), 7.24 (d, J=8.5 Hz, 2H). $^{13}$C NMR (126 MHz, $CDCl_3$) δ 25.78, 26.18, 28.36, 29.54, 32.94, 34.65, 37.33, 39.80, 55.13, 63.18, 67.94, 114.15, 128.32, 129.26, 130.84, 131.16, 131.89, 135.06, 141.98, 147.21, 157.74. HRMS (EI, M$^+$+1) $C_{29}H_{36}OCl$ Calcd. 451.2404, found 451.2399.

6-(4-((-((Z)-((5S,7S)-Adamantan-2-ylidene)(4-chlorophenyl)methyl)phenoxy)hexyl methanesulfonate (5)

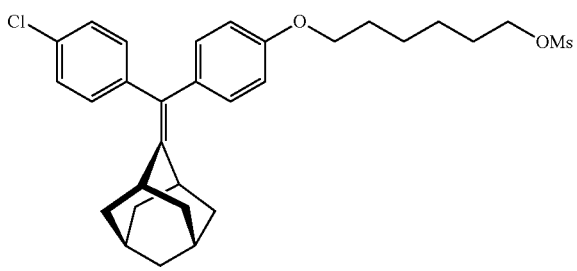

The title compound (5) was prepared from the reaction of the compound 4 (135 mg, 0.30 mmol) with methanesulfonyl chloride (51 mg, 0.45 mmol), and triethylamine (101 mg, 1.00 mmol) in 98% yield, following the same procedure described for the preparation of the compound 2.

$^1$H NMR (500 MHz, $CDCl_3$) δ 1.48-1.58 (m, 4H), 1.83 (quintet, J=7.0 Hz, 4H), 1.84-1.91 (m, 10H), 2.02 (s, 2H), 2.74 (s, 1H), 2.82 (s, 1H), 3.02 (s, 3H), 3.95 (t, J=6.5 Hz, 2H), 4.26 (t, J=6.5 Hz, 2H), 6.81 (d, J=8.5 Hz, 2H), 7.02 (d, J=8.5 Hz, 2H), 7.06 (d, J=8.5 Hz, 2H), 7.24 (d, J=8.5 Hz, 2H). $^{13}$C NMR (126 MHz, $CDCl_3$) δ 25.49, 25.87, 28.36, 29.33, 29.37, 34.66, 37.74, 37.32, 37.62, 39.80, 67.72, 70.22, 114.13, 128.33, 129.22, 130.86, 131.16, 131.90, 135.13, 141.97, 147.25, 157.66. HRMS (ESI, M$^+$+1) $C_{30}H_{38}O_4SCl$ Calcd. 529.2179, found 529.2183.

6-(4-((-((Z)-((5S,7S)-adamantan-2-ylidene)(4-chlorophenyl)methyl)phenoxy)-N,N-diethylhexan-1-amine (NB-54)

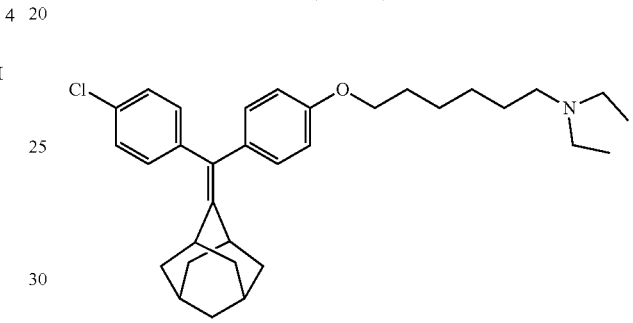

NB-54 was obtained (10 mg, sticky liquid) was obtained from the reaction of the compound 5 (12 mg, 0.022 mmol) and diethylamine (40 mg, 0.50 mmol) in 90% yield as described to prepare for NB-55.

$^1$HNMR (500 MHz, $CDCl_3$) δ 1.02 (t, J=7.0 Hz, 6H), 1.43 (quintet, J=7.0 Hz, 2H), 1.56 (quintet, J=7.0 Hz, 2H), 1.73-1.92 (m, 14H), 2.01 (brs, 2H), 2.44 (t, J=7.5 Hz, 2H), 2.55 (q, J=7.0 Hz, 4H), 2.73 (s, 1H), 2.82 (s, 1H), 3.93 (t, J=6.0 Hz, 2H), 6.80 (d, J=8.5 Hz, 2H), 7.01 (d, J=8.5 Hz, 2H), 7.05 (d, J=8.5 Hz, 2H), 7.24 (d, J=8.5 Hz, 2H).

1-(6-(4-((-((Z)-((5S,7S)-Adamantan-2-ylidene)(4-chlorophenyl)methyl)phenoxy)hexyl)pyrrolidine (NB-55)

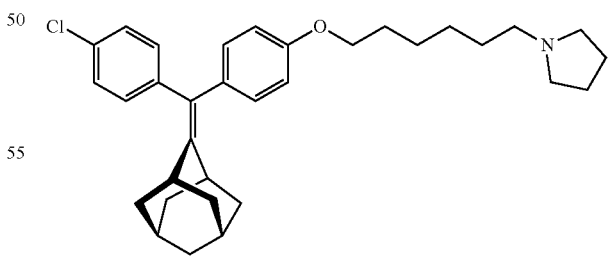

The mixture of the compound 5 (53 mg, 0.10 mmol) and pyrrolidine (28 mg, 0.40 mmol) in DMF (100 μL) was stirred at 55° C. for 3 hr. The solvent was evaporated gently using nitrogen stream. To this was added $NaHCO_3$ (40 mg) and DI water (1 mL) and extracted with EtOAc (400 μL×3). The extract was washed with brine, water, and dried over $Na_2SO_4$ to provide the sticky liquid NB-55 (48 mg).

¹H NMR (500 M Hz, CDCl₃) δ 1.41 (quintet, J=7.0 Hz, 2H), 1.48 (quintet, J=7.0 Hz, 2H), 1.56 (quintet, J=7.0 Hz, 2H), 1.76-1.81 (m, 6H), 1.82~1.92 (m, 10H), 2.01 (s, 2H), 2.44 (t, J=6.5 Hz, 2H), 2.46~2.51 (m, 4H), 2.74 (s, 1H), 2.82 (s, 1H), 3.93 (t, J=6.5 Hz, 2H), 6.81 (d, J=8.5 Hz, 2H), 7.02 (d, J=8.5 Hz, 2H), 7.06 (d, J=8.5 Hz, 2H), 7.24 (d, J=8.5 Hz, 2H). ¹³C NMR (126 MHz, CDCl₃) δ 23.62, 26.34, 27.76, 28.36, 29.27, 29.54, 34.64, 34.73, 37.32, 39.80, 54.48, 56.86, 68.01, 114.15, 128.32, 129.27, 130.83, 131.17, 131.87, 135.00, 141.99, 147.18, 157.76. FIRMS (ESI, M⁺+1) $C_{33}H_{43}ONCl$ Calcd. 504.3033, found 504.3033.

1-(6-(4-((-((Z)-((5S,7S)-Adamantan-2-ylidene)(4-chlorophenyl)methyl)phenoxy)hexyl)-1-methylpyrrolidin-1-ium iodide (NB-63)

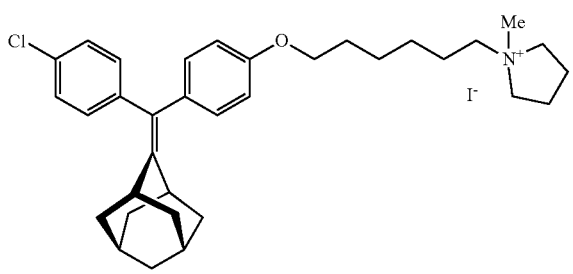

The mixed solution of NB-55 (60 mg, 0.12 mmol) and methyl iodide (200 μL) in ethyl acetate (500 μL) was heated up at 50° C. for 1 hr to form ppt. The evaporation of solvent afforded NB-63 quantitatively. This is pure enough to need no further purification.

¹H NMR (500 MHz, CDCl₃+CD₃OD) δ 1.45~1.63 (m, 4H), 1.77~1.93 (m, 14H), 2.02 (s, 2H), 2.23~2.40 (Brs, 4H), 2.73 (s, 1H), 2.80 (s, 1H), 3.28 (s, 3H), 3.69 (t, 0.1=7.0 Hz, 2H), 3.82 (brs, 4H), 3.95 (t, J=7.0 Hz, 2H), 6.82 (d, J=8.5 Hz, 2H), 7.02 (d, J=8.5 Hz, 2H), 7.07 (d, J=8.5 Hz, 2H), 7.25 (d, J=8.5 Hz, 2H).). ¹³C NMR (126 MHz, CDCl₃+CD₃OD) δ 21.97, 23.66, 24.31, 26.02, 26.28, 28.35, 29.24, 34.65, 37.13, 39.80, 53.95, 64.56, 65.06, 67.61. HRMS (ESI, M⁺) $C_{34}H_{45}ONCl$ Calcd. 518.3190, found 518.3181.

1-(6-(4-((Z)-((5S,7S)-adamantan-2-ylidene)(4-chlorophenyl)methyl)phenoxy)hexyl)-1H-imidazole (NB-60)

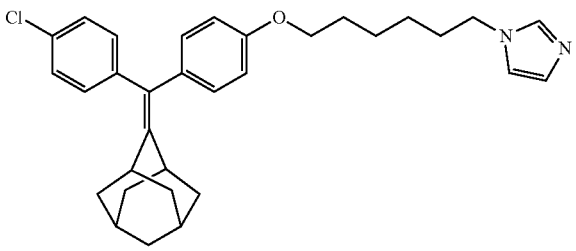 [SMILES: Clc1ccc(C(=C2C3CC4CC(C3)CC2C4)c2ccc(OCCCCCCn3ccnc3)cc2)cc1]

NB-60 was prepared from the reaction with compound 5 and imidazole in DMF at 80° C.

¹H NMR (500 MHz, Chloroform-d) δ 1.38-1.47 (m, 4H), 1.75~1.82 (m, 4H), 1.87 (s, 10H), 1.92-1.98 (m, 2H), 2.01 (s, 2H), 2.73 (s, 1H), 2.81 (s, 1H), 3.94 (t, J=6.2 Hz, 2H), 6.77-6.85 (m, 3H), 6.97-7.09 (m, 5H), 7.25 (d, J=8.0 Hz, 2H), 7.76 (brs, 1H).

1-(6-(4-((Z)-((5S,7S)-adamantan-2-ylidene)(4-chlorophenyl)methyl)phenoxy)hexyl)-3-methyl-1H-imidazol-3-ium iodide (NB-62)

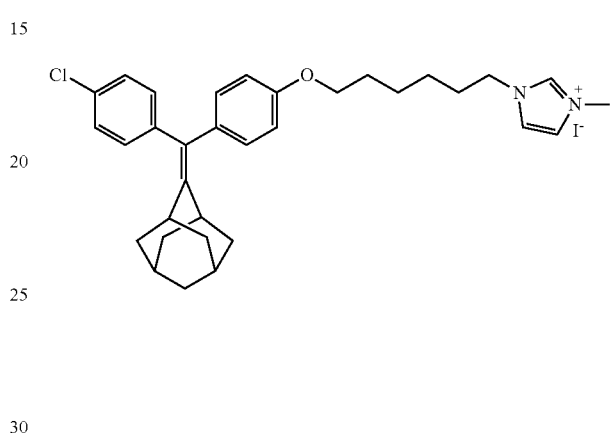

NB-62 was obtained from the reaction of NB-60 and methyl iodide in ethyl acetate solution in a sealed vial at 80° C.

¹H NMR (500 MHz, Chloroform-d) δ 1.39-1.59 (m, 4H), 1.77~1.93 (m, 12H), 2.00 (s, 4H), 2.72 (s, 1H), 2.80 (s, 1H), 3.94 (d, J=6.2 Hz, 2H), 4.10 (s, 3H), 4.37 (brs, 2H), 6.81 (d, J=8.0 Hz, 2H), 6.93-7.13 (m, 5H), 7.15-7.27 (m, 3H), 9.64 (s, 1H).

1-(6-(4-((Z)-((5S,7S)-adamantan-2-ylidene)(4-chlorophenyl)methyl)phenoxy)hexyl)-4-methylpiperazine (NB-64)

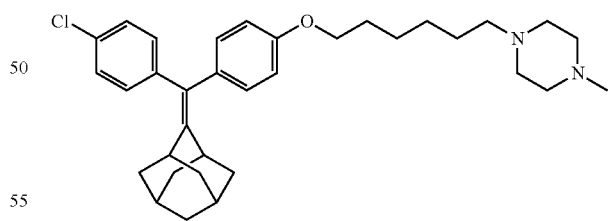

NB-64 was prepared from the substitution reaction with compound 5 and 1-methylpiperazine.

¹HNMR (500 MHz, CDCl₃) δ 1.38 (quintet, J=6.4 Hz, 2H), 1.49 (quintet, J=6.4 Hz, 2H), 1.53-1.62 (m, 2H), 1.78 (quintet, J=7.0 Hz, 2H), 1.83~1.91 (m, 10H), 2.01 (s, 2H), 2.36 (s, 3H), 2.43 (t, J=6.5 Hz, 2H), 2.46~2.71 (brs, 8H), 2.74 (s, 1H), 2.82 (s, 1H), 3.92 (t, J=6.5 Hz, 2H), 6.81 (d, J=8.5 Hz, 2H), 7.01 (d, J=8.5 Hz, 2H), 7.06 (d, J=8.5 Hz, 2H), 7.24 (d, J=8.5 Hz, 2H).

1-(6-(4-((Z)-((5S,7S)-Adamantan-2-ylidene)(4-chlorophenyl)methyl)phenoxy)hexyl)piperidine (NB-118)

1-(6-(4-((Z)-((5S,7S)-Adamantan-2-ylidene)(4-chlorophenyl)methyl)phenoxy)hexyl)azepane (NB-119)

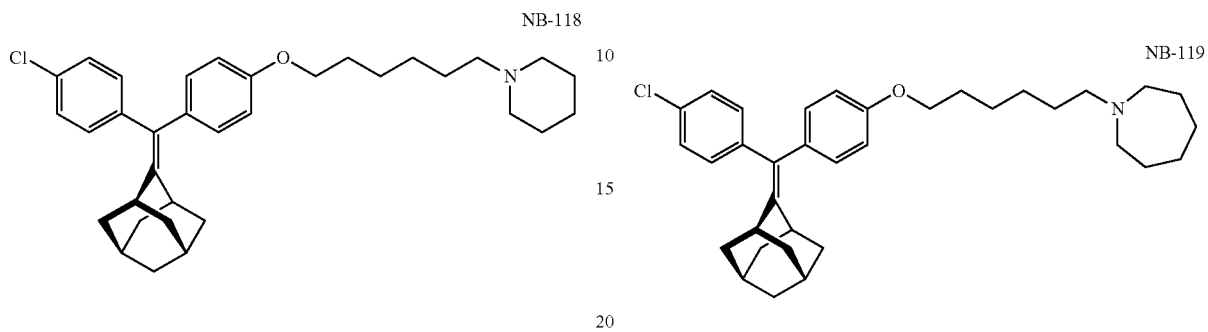

NB-118 (44 mg, sticky liquid) was obtained from the reaction of the compound 5 (50 mg, 0.095 mmol) and piperidine (45 mg, 0.53 mmol) in 89% yield as described to prepare for NB-55.

$^1$H NMR (500 MHz, CDCl$_3$) δ 1.31 (quintet, J=7.0 Hz, 2H), 1.36 (quintet, J=7.0 Hz, 2H), 1.40~1.56 (m, 4H), 1.56~1.63 (m, 4H), 1.78 (quintet, J=7.0 Hz, 2H), 1.83~1.91 (m, 10H), 2.01 (s, 2H), 2.29 (t, J=6.5 Hz, 2H), 2.32~2.44 (m, 4H), 2.74 (s, 1H), 2.82 (s, 1H), 3.92 (t, J=6.5 Hz, 2H), 6.81 (d, J=8.5 Hz, 2H), 7.01 (d, J=8.5 Hz, 2H), 7.06 (d, J=8.5 Hz, 2H), 7.24 (d, J=8.5 Hz, 2H). $^{13}$C NMR (126 MHz, CDCl$_3$) δ 24.76, 26.33, 27.78, 28.03, 28.36, 29.26, 34.64, 37.33, 39.80, 54.92, 68.01, 114.15, 128.32, 129.28, 130.82, 131.16, 131.16, 131.88, 135.00, 141.99, 147.18, 157.78. HRMS (ESI, M$^+$+1) C$_{34}$H$_{45}$ONCl Calcd. 518.3190, found 518.3192.

NB-119 (44 mg, sticky liquid) was obtained from the reaction of the compound 5 (50 mg, 0.095 mmol) and azepane (40 mg, 0.40 mmol) in 87% yield as described to prepare for NB-55.

$^1$H NMR (500 MHz, CDCl$_3$) δ 1.31 (quintet, J=7.0 Hz, 2H), 1.35 (quintet, J=7.0 Hz, 2H), 1.44~1.55 (m, 4H), 1.56~1.76 (m, 6H), 1.77 (quintet, J=7.0 Hz, 2H), 1.83~1.91 (m, 10H), 2.00 (s, 2H), 2.44 (t, J=6.5 Hz, 2H), 2.62 (t, J=6.0 Hz, 4H), 2.73 (s, 1H), 2.81 (s, 1H), 3.93 (t, J=6.5 Hz, 2H), 6.80 (d, J=8.5 Hz, 2H), 7.00 (d, J=8.5 Hz, 2H), 7.05 (d, J=8.5 Hz, 2H), 7.23 (d, J=8.5 Hz, 2H). $^{13}$C NMR (126 MHz, CDCl$_3$) δ 26.33, 27.26, 27.65, 27.75, 28.18, 28.37, 29.56, 34.64, 34.74, 37.33, 55.84, 58.51, 68.01, 114.14, 128.30, 129.27, 130.81, 131.15, 131.87, 134.98, 141.98, 147.16, 157.77. HRMS (ESI, M$^+$+1) C$_{35}$H$_{47}$ONCl Calcd. 532.3346, found 532.3347.

(S)-1-(6-(4-((Z)-((5S,7S)-adamantan-2-ylidene)(4-chlorophenyl)methyl)phenoxy)hexyl)-1-methyl-1λ$^4$-piperidin-2-ylium iodide (NB-84)

1-(6-(4-((Z)-((5S,7S)-adamantan-2-ylidene)(4-chlorophenyl)methyl)phenoxy)hexyl)-1-methylazepan-1-ium iodide (NB-85)

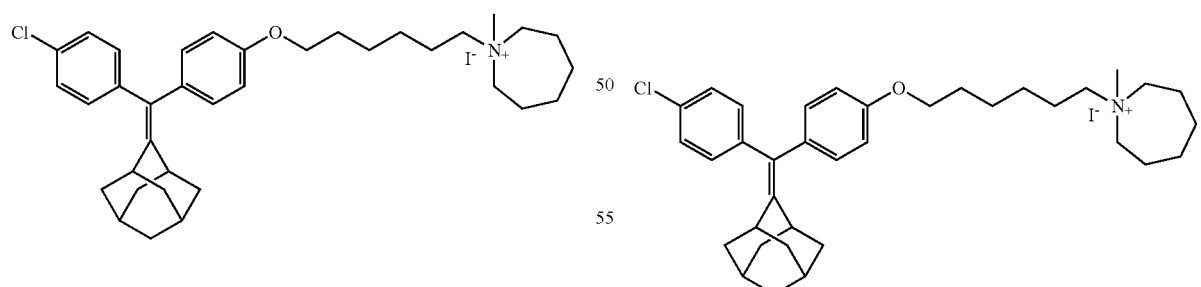

NB-84 was obtained from the reaction of NB-118 with methyl iodide in ethyl acetate solution at rt in a sealed vial.

$^1$HNMR (500 MHz, CDCl$_3$) δ 1.49 (quintet, J=7.0 Hz, 2H), 1.56 (quintet, J=7.0 Hz, 2H), 1.60~1.66 (m, 2H), 1.71~1.81 (m, 4H), 1.83~1.86 (m, 10H), 1.87-1.94 (m, 4H), 1.98 (s, 2H), 2.70 (s, 1H), 2.77 (s, 1H), 3.24 (s, 3H), 3.40 (t, J=6.5 Hz, 2H), 3.49-3.55 (m, 4H), 3.93 (t, J=6.5 Hz, 2H), 6.78 (d, J=8.5 Hz, 2H), 7.01 (d, J=8.5 Hz, 2H), 7.03 (d, J=8.5 Hz, 2H), 7.22 (d, J=8.5 Hz, 2H).

NB-85 was obtained from the reaction of NB-119 with methyl iodide in ethyl acetate solution at rt in a sealed vial.

$^1$HNMR (500 MHz, CDCl$_3$) δ 1.49~1.63 (m, 4H), 1.77~1.91 (m, 18H), 1.92~1.99 (m, 4H), 2.01 (s, 2H), 2.73 (s, 1H), 2.80 (s, 1H), 3.33 (s, 3H), 3.61-3.70 (m, 6H), 3.96 (t, J=6.5 Hz, 2H), 6.81 (d, J=8.5 Hz, 2H), 7.02 (d, J=8.5 Hz, 2H), 7.06 (d, J=8.5 Hz, 2H), 7.25 (d, J=8.5 Hz, 2H).

8,8'-(((((5r,7r)-adamantan-2-ylidene)methylene)bis(4,1-phenylene))bis(oxy))bis(octan-1-ol)

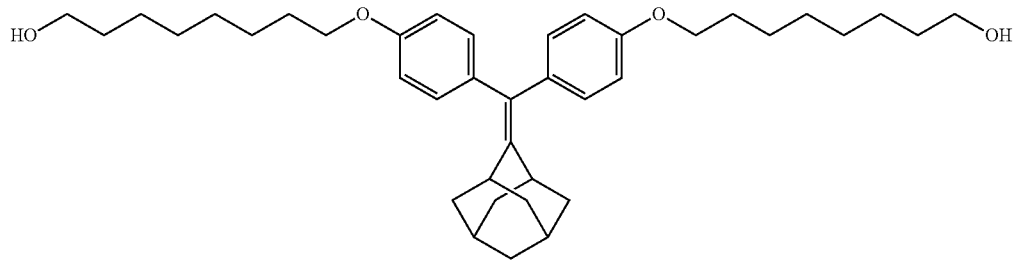 [SMILES: OCCCCCCCCOc1ccc(C(=C2C3CC4CC(C3)CC2C4)c2ccc(OCCCCCCCCO)cc2)cc1]

Compound 8,8'-(((((5r,7r)-adamantan-2-ylidene)methylene)bis(4,1-phenylene))bis(oxy))bis(octan-1-ol) was obtained from the reaction of the compound 3 with 8-bromooctane-1-ol in DMF at 50° C. in the presence of cesium carbonate. $^1$H NMR (500 MHz, Chloroform-d) δ 1.31-1.42 (m, 12H), 1.43-1.50 (m, 4H), 1.54-1.63 (m, 4H), 1.77 (quintet, J=6.4 Hz, 4H), 1.84-1.92 (m, 10H), 2.01 (s, 2H), 2.81 (s, 2H), 3.66 (t, J=6.6 Hz, 4H), 3.93 (t, J=6.5 Hz, 4H), 6.80 (d, J=8.5 Hz, 4H), 7.08 (d, J=8.5 Hz, 4H). $^{13}$C NMR (126 MHz, CDCl$_3$) δ 25.92, 26.28, 28.48, 29.50, 29.57, 29.59, 33.02, 34.67, 37.46, 39.86, 63.31, 68.01, 113.99, 129.91, 130.82, 135.88, 145.84, 157.54.

(((((5r,7r)-adamantan-2-ylidene)methylene)bis(4,1-phenylene))bis(oxy))bis(octane-8,1-diyl) dimethanesulfonate (6A)

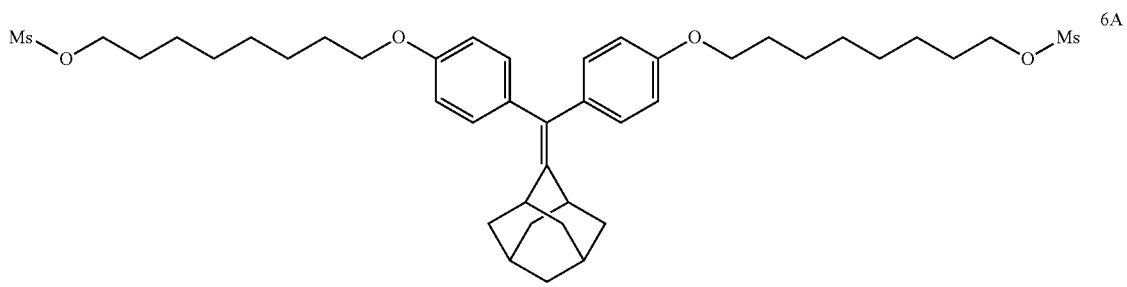 [SMILES: CS(=O)(=O)OCCCCCCCCOc1ccc(C(=C2C3CC4CC(C3)CC2C4)c2ccc(OCCCCCCCCOS(C)(=O)=O)cc2)cc1]

Compound 6A was obtained quantitatively from the similar way to make compound 2.

$^1$H NMR (500 MHz, Chloroform-d) δ 1.33-1.53 (m, 16H), 1.72-1.81 (m, 8H), 1.83-1.94 (m, 1 OH), 2.01 (s, 2H), 2.81 (s, 2H), 3.02 (s, 6H), 3.93 (t, J=6.4 Hz, 4H), 4.24 (t, J=6.5 Hz, 4H), 6.80 (d, J=8.6 Hz, 4H), 7.03 (d, J=8.6 Hz, 4H). $^{13}$C NMR (126 MHz, CDCl$_3$) δ 25.62, 26.24, 28.47, 29.21, 29.35, 29.42, 29.54, 34.67, 37.45, 37.62, 39.85, 67.94, 70.39, 113.98, 129.89, 130.82, 135.90, 145.88, 157.52.

1,1'-((((((5r,7r)-adamantan-2-ylidene)methylene)bis(4,1-phenylene))bis(oxy))bis(octane-8,1-diyl))bis(azepane) (NB-80)

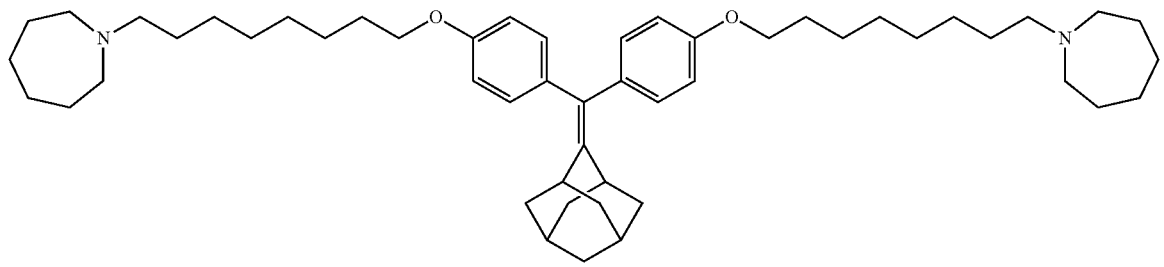 [SMILES: c1cc(C(=C2C3CC4CC(C3)CC2C4)c2ccc(OCCCCCCCCN3CCCCCC3)cc2)ccc1OCCCCCCCCN1CCCCCC1]

The reaction of compound 6A with azepane as described to make NB-72 afforded NB-80 quantitatively.

¹H NMR (500 MHz, Chloroform-d) δ 1.23-1.56 (m, 20H), 1.56-1.72 (m, 16H), 1.77 (quintet, J=6.7 Hz, 4H), 1.87 (s, 10H), 2.01 (s, 2H), 2.40-2.53 (m, 4H), 2.62-2.70 (m, 8H), 2.81 (s, 2H), 3.93 (t, J=6.5 Hz, 4H), 6.80 (d, J=8.5 Hz, 4H), 7.03 (d, J=8.5 Hz, 4H).

1,1'-(((((5r,7r)-adamantan-2-ylidene)methylene)bis(4,1-phenylene))bis(oxy))bis(octane-8,1-diyl))bis(1-methylazepan-1-ium) diiodide (NB-81)

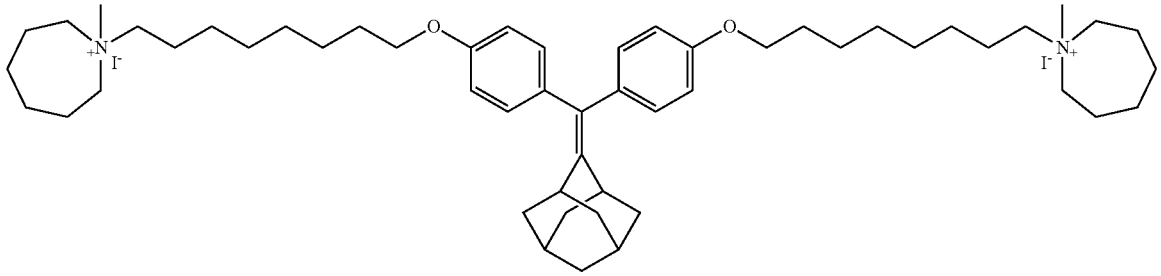 [SMILES: C[N+]1(CCCCCCCCOc2ccc(C(=C3C4CC5CC(C4)CC3C5)c3ccc(OCCCCCCCC[N+]4(C)CCCCCC4)cc3)cc2)CCCCCC1 ; [I-] ; [I-]]

NB-81 was obtained quantitatively from the reaction of NB-80 with methyl iodide as described to make NB-73.

¹H NMR (500 MHz, Chloroform-d) δ 1.24-1.45 (m, 20H), 1.62-1.73 (m, 16H), 1.74-1.80 (m, 10H), 1.81-1.89 (m, 8H), 1.91 (s, 2H), 2.69 (s, 2H), 3.07 (s, 6H), 3.24-3.37 (m, 4H), 3.44 (t, J=6.7 Hz, 4H), 3.85 (t, J=6.4 Hz, 4H), 6.71 (d, J=8.5 Hz, 4H), 6.93 (d, J=8.5 Hz, 4H).

(5r,7r)-2-(bis(4-(4-bromobutoxy)phenyl)methylene)adamantine (7)

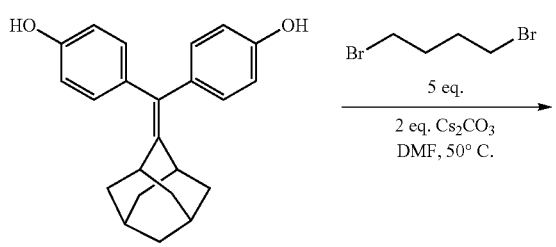

-continued

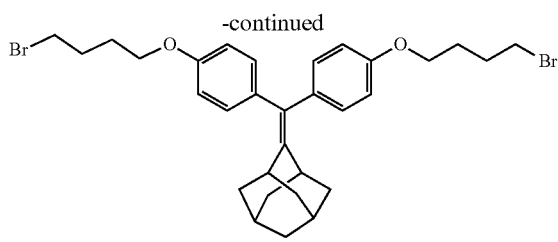

The reaction of compound 1A with 6 eq. 1,4-dibromobutane and cesium carbonate in DMF at 50° C. produced the compound 7.

¹H NMR (500 MHz, Chloroform-d) δ 1.91 (s, 10H), 1.92-1.98 (m, 4H), 2.02 (s, 2H), 2.09 (quintet, J=6.9 Hz, 4H), 2.81 (s, 2H), 3.43-3.59 (m, 4H), 3.90-4.06 (m, 4H), 6.81 (d, J=8.1 Hz, 4H), 7.04 (d, J=8.1 Hz, 4H). ¹³C NMR (126 MHz, CDCl₃) δ 28.21, 28.47, 29.77, 33.83, 34.69, 37.44, 39.87, 66.90, 114.00, 129.78, 130.87, 136.10, 146.07, 157.31.

1,1'-(((((5r,7r)-adamantan-2-ylidene)methylene)bis(4,1-phenylene))bis(oxy))bis(butane-4,1-diyl))dipiperidine (NB-120)

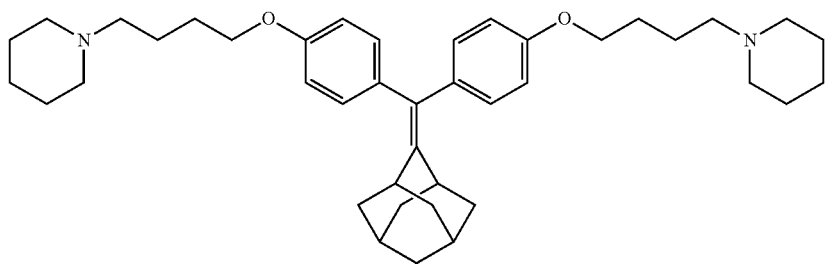 [SMILES: c1cc(C(=C2C3CC4CC(C3)CC2C4)c2ccc(OCCCCN3CCCCC3)cc2)ccc1OCCCCN1CCCCC1]

NB-120 was obtained quantitatively from the reaction of compound 7 with piperidine as described to make NB-65.

$^{1}$H NMR (500 MHz, Chloroform-d) δ 1.39-1.52 (m, 4H), 1.61 (quintet, J=5.6 Hz, 12H), 1.64-1.74 (m, 4H), 1.79 (quintet, J=6.6 Hz, 4H), 1.87 (d, J=7.6 Hz, 10H), 2.01 (s, 2H), 2.37 (t, J=7.7 Hz, 8H), 2.81 (s, 2H), 3.96 (t, J=6.4 Hz, 4H), 6.80 (d, J=8.5 Hz, 4H), 7.03 (d, J=8.5 Hz, 4H).

1-(4-(4-((E)-((5R,7R)-adamantan-2-ylidene)(4-(4-(1-metheyliumylpiperidin-1-ium-1-yl)butoxy)phenyl)methyl)phenoxy)butyl)-1-methylpiperidin-1-ium diiodide (NB-86)

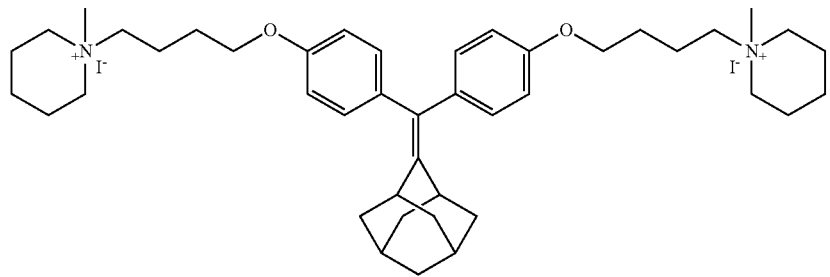 [SMILES: C[N+]1(CCCCOc2ccc(C(=C3C4CC5CC(C4)CC3C5)c3ccc(OCCCC[N+]4(C)CCCCC4)cc3)cc2)CCCCC1 ; [I-] ; [I-]]

NB-86 was obtained quantitatively from the reaction of NB-120 with methyl iodide as described to make NB-73.

$^{1}$H NMR (500 MHz, Chloroform-d) δ 1.62-2.00 (m, 28H), 2.70 (s, 2H), 2.89 (s, 4H), 3.14 (s, 6H), 3.49 (q, J=5.3 Hz, 8H), 3.55-3.64 (m, 4H), 3.99 (t, J=5.7 Hz, 4H), 6.76 (d, J=8.5 Hz, 4H), 6.96 (d, J=8.5 Hz, 4H).

1,1'-((((((5r,7r)-adamantan-2-ylidene)methylene)bis(4,1-phenylene))bis(oxy))bis(butane-4,1-diyl))bis(azepane) (NB-121)

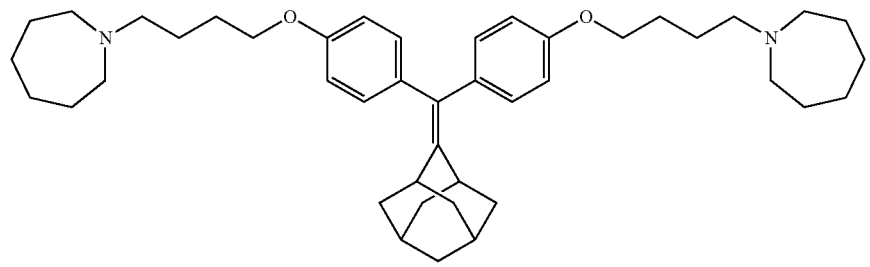 [SMILES: c1cc(C(=C2C3CC4CC(C3)CC2C4)c2ccc(OCCCCN3CCCCCC3)cc2)ccc1OCCCCN1CCCCCC1]

NB-121 was obtained quantitatively from the reaction of the compound 7 with azepane as described to make NB-65.

$^{1}$H NMR (500 MHz, Chloroform-d) δ 1.56-1.71 (m, 16H), 1.78 (quintet, J=6.7 Hz, 4H), 1.83-1.91 (m, 14H), 2.01 (s, 2H), 2.54 (t, J=6.7 Hz, 4H), 2.62-2.71 (m, 8H), 2.81 (s, 2H), 3.96 (t, J=6.4 Hz, 4H), 6.80 (d, J=8.5 Hz, 4H), 7.03 (d, J=8.5 Hz, 4H).

1,1'-((((((5r,7r)-adamantan-2-ylidene)methylene)bis(4,1-phenylene))bis(oxy))bis(butane-4,1-diyl))bis(1-methylazepan-1-ium) diiodide (NB-87)

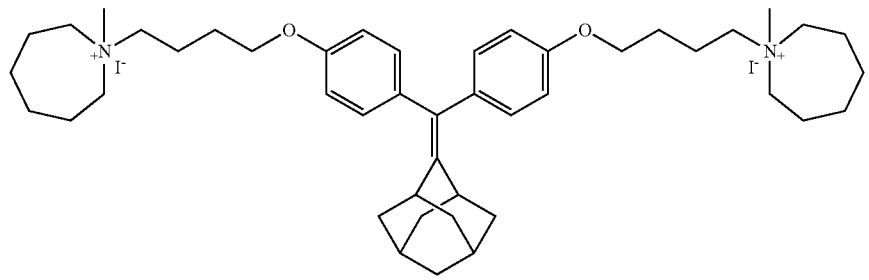 [SMILES: C[N+]1(CCCCOc2ccc(C(=C3C4CC5CC(C4)CC3C5)c3ccc(OCCCC[N+]4(C)CCCCCC4)cc3)cc2)CCCCCC1 ; [I-] ; [I-]]

NB-87 was obtained quantitatively from the reaction of NB-121 with methyl iodide as described to make NB-73.

$^1$H NMR (500 MHz, Chloroform-d) δ 1.69 (quintet, J=6.4 Hz, 8H), 1.74-1.81 (m, 8H), 1.81-1.99 (m, 20H), 2.69 (s, 2H), 3.13 (s, 6H), 3.41-3.59 (m, 12H), 3.98 (t, J=5.8 Hz, 4H), 6.75 (d, J=8.5 Hz, 4H), 6.95 (d, J=8.5 Hz, 4H).

(((((5r,7r)-adamantan-2-ylidene)methylene)bis(4,1-phenylene))bis(oxy))bis(pentane-5,1-diyl) dimethanesulfonate (8)

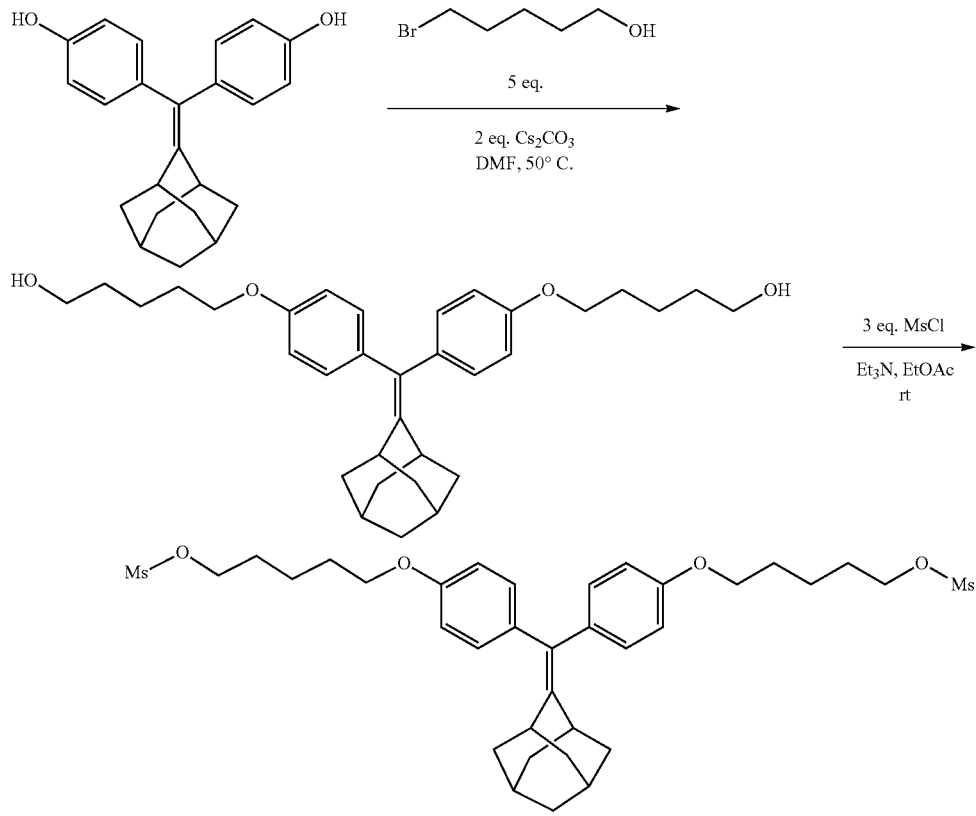

Compound 8 was prepared from the reaction of bisphenol compound 1A with 5-bromo-pentane-1-ol, followed by methanesulfonylation as described to make compound 2.

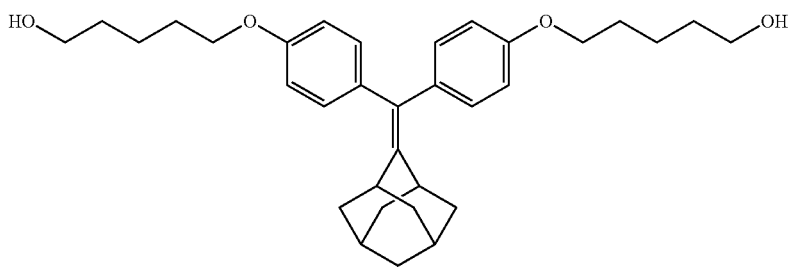 [SMILES: OCCCCCOc1ccc(C(=C2C3CC4CC(C3)CC2C4)c2ccc(OCCCCCO)cc2)cc1]

¹H NMR (500 MHz, Chloroform-d) δ 1.51-1.64 (m, 4H), 1.64-1.75 (m, 4H), 1.75-1.95 (m, 14H), 2.01 (s, 2H), 2.81 (s, 2H), 3.70 (t, J=6.5 Hz, 4H), 3.96 (t, J=6.3 Hz, 4H), 6.81 (d, J=8.4 Hz, 4H), 7.03 (d, J=8.4 Hz, 4H).

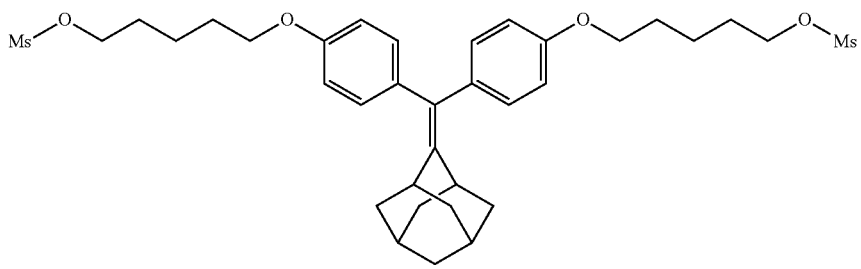 [SMILES: CS(=O)(=O)OCCCCCOc1ccc(C(=C2C3CC4CC(C3)CC2C4)c2ccc(OCCCCCOS(C)(=O)=O)cc2)cc1]

¹H NMR (500 MHz, Chloroform-d) δ 1.62 (quintet, J=6.2 Hz, 4H), 1.78-1.93 (m, 18H), 2.01 (s, 1H), 2.80 (s, 1H), 3.02 (s, 6H), 3.96 (t, J=6.2 Hz, 4H), 4.27 (t, J=6.5 Hz, 4H), 6.80 (d, J=8.4 Hz, 4H), 7.04 (d, J=8.4 Hz, 4H).

1,1'-((((((5r,7r)-adamantan-2-ylidene)methylene)bis (4,1-phenylene))bis(oxy))bis(pentane-5,1-diyl))dipiperidine (NB-122)

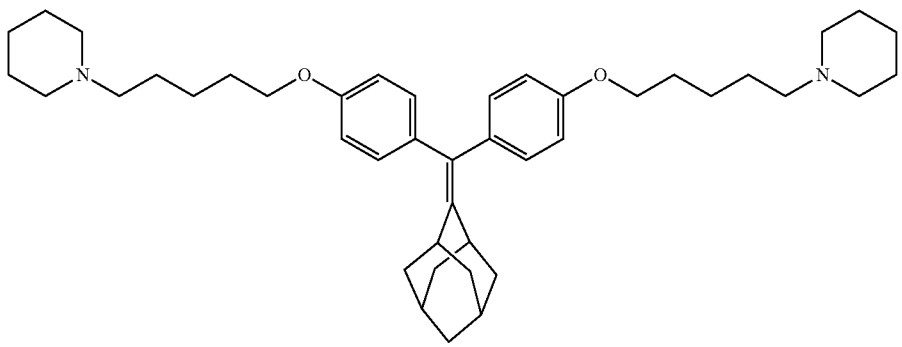

NB-122 was obtained quantitatively from the reaction of compound 8 and 5 eq. piperidine in DMF at 50° C.

¹H NMR (500 MHz, Chloroform-d) δ 1.40-1.53 (m, 8H), 1.53-1.68 (m, 12H), 1.80 (quintet, J=6.8 Hz, 4H), 1.87 (s, 10H), 2.01 (s, 2H), 2.33 (t, J=6.5 Hz, 4H), 2.39 (s, 8H), 2.81 (s, 2H), 3.94 (t, J 6.5 Hz, 4H), 6.79 (d, J=8.5 Hz, 4H), 7.02 (d, J=8.5 Hz, 4H).

1,1'-((((((5r,7r)-adamantan-2-ylidene)methylene)bis(4,1-phenylene))bis(oxy))bis(pentane-5,1-diyl))bis(1-methylpiperidin-1-ium) diiodide (NB-88)

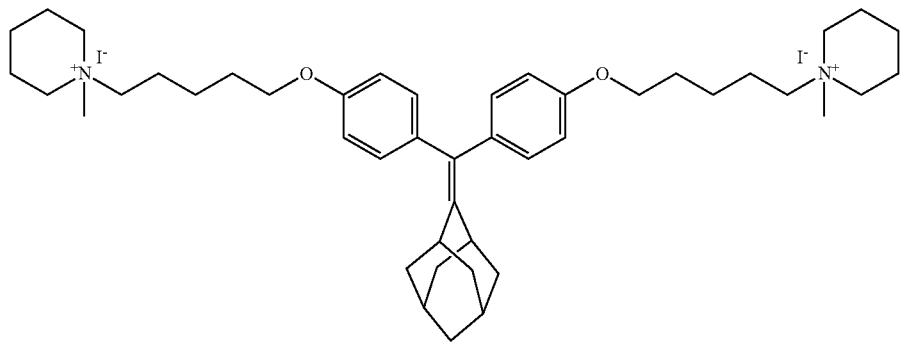 [SMILES: C[N+]1(CCCCCOc2ccc(C(=C3C4CC5CC(C4)CC3C5)c3ccc(OCCCCC[N+]4(C)CCCCC4)cc3)cc2)CCCCC1 ; [I-] ; [I-]]

NB-88 was obtained quantitatively from the methylation of NB-122 with methyl iodide in ethyl acetate at rt in a sealed vial.

$^1$H NMR (500 MHz, Chloroform-d) δ 1.47-1.61 (m, 4H), 1.65-1.74 (m, 8H), 1.74-1.91 (m, 26H), 1.94 (s, 2H), 2.70 (s, 2H), 3.13 (s, 6H), 3.38-3.59 (m, 8H), 3.92 (t, J=6.0 Hz, 4H), 6.74 (d, J=8.5 Hz, 4H), 6.96 (d, J=8.5 Hz, 4H).

1,1'-((((((5r,7r)-adamantan-2-ylidene)methylene)bis(4,1-phenylene))bis(oxy))bis(pentane-5,1-diyl))bis(azepane) (NB-123)

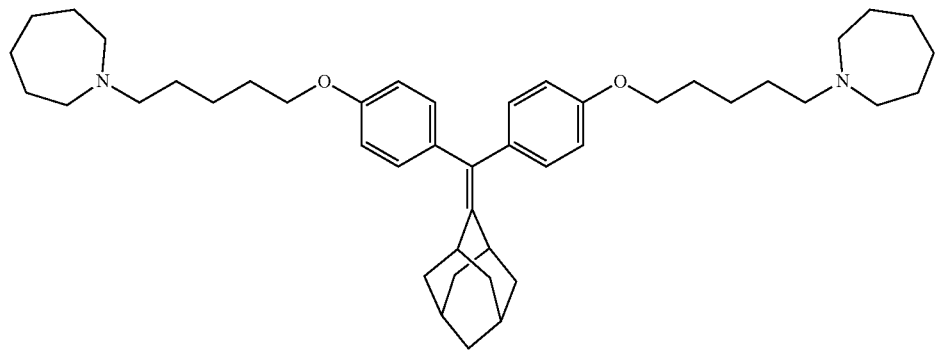 [SMILES: c1cc(C(=C2C3CC4CC(C3)CC2C4)c2ccc(OCCCCCN3CCCCCC3)cc2)ccc1OCCCCCN1CCCCCC1]

NB-123 was obtained quantitatively from the reaction of compound 8 and azepane in DMF at 50° C.

$^1$H NMR (500 MHz, Chloroform-d) δ 1.38-1.51 (m, 4H), 1.52-1.72 (m, 20H), 1.83 (t, J=6.9 Hz, 4H), 1.86 (s, 10H), 2.00 (s, 2H), 2.47-2.57 (m, 4H), 2.60-2.72 (m, 8H), 2.81 (s, 2H), 3.94 (t, J=6.5 Hz, 4H), 6.80 (d, J=8.4 Hz, 4H), 7.04 (d, J=8.4 Hz, 4H).

1,1'-((((((5r,7r)-adamantan-2-ylidene)methylene)bis(4,1-phenylene))bis(oxy))bis(pentane-5,1-diyl))bis(1-methylazepan-1-ium) diiodide (NB-89)

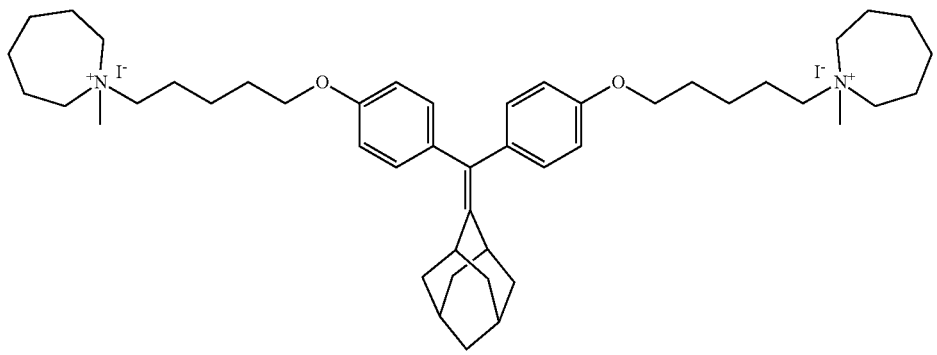 [SMILES: C[N+]1(CCCCCOc2ccc(C(=C3C4CC5CC(C4)CC3C5)c3ccc(OCCCCC[N+]4(C)CCCCCC4)cc3)cc2)CCCCCC1 ; [I-] ; [I-]]

NB-89 was obtained quantitatively from the methylation of NB-123 with methyl iodide in ethyl acetate at rt.

$^1$H NMR (500 MHz, Chloroform-d) δ 1.54 (p, J=7.8 Hz, 4H), 1.61-1.89 (m, 30H), 1.93 (s, 2H), 2.70 (s, 2H), 3.11 (s, 6H), 3.25 (brs, 4H), 3.39-3.53 (m, 12H), 3.92 (t, J=6.0 Hz, 4H), 6.73 (d, J=8.5 Hz, 4H), 6.95 (d, J=8.5 Hz, 4H).

2,2'-(((((((((5r,7r)-adamantan-2-ylidene)methylene)bis(4,1-phenylene))bis(oxy))bis(ethane-2,1-diyl))bis(oxy))bis(ethane-2,1-diyl))bis(oxy))bis(N,N-diethylethan-1-amine) (NB-53)

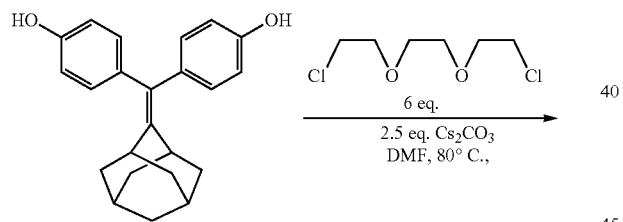

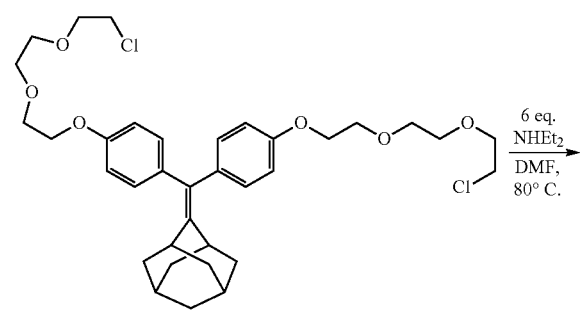

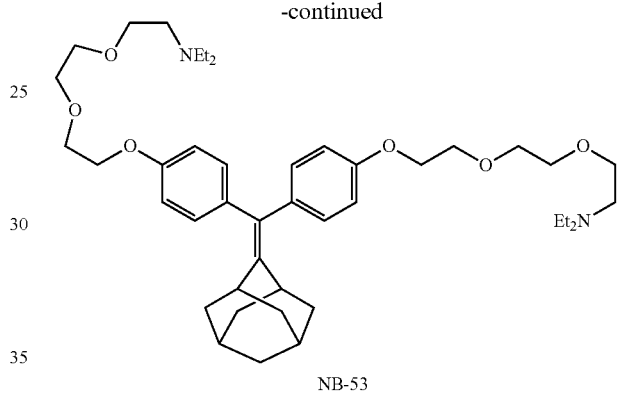

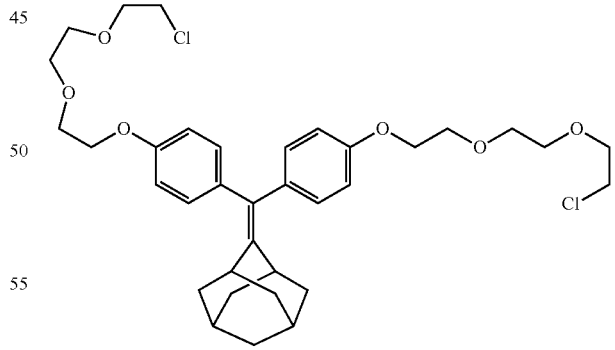

Bisphenol compound 1A afforded NB-53 through the reaction with 6 eq. 1,2-bis(2-chloroethoxy)ethane and subsequently with diethyl amine.

$^1$H NMR (500 MHz, Chloroform-d) δ 1.78-1.96 (m, 10H), 2.00 (s, 2H), 2.79 (s, 2H), 3.63 (dd, J=5.4, 3.7 Hz, 4H), 3.67-3.81 (m, 12H), 3.86 (dd, J=5.7, 3.9 Hz, 4H), 4.12 (t, J=4.8 Hz, 4H), 6.83 (d, J=8.1 Hz, 4H), 7.02 (d, 0.1=8.4 Hz, 4H).

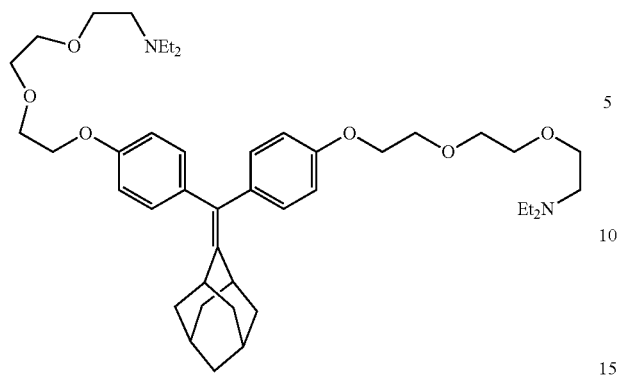

¹H NMR (500 MHz, Chloroform-d) δ 1.06 (t, J=6.8 Hz, 12H), 1.98 (s, 10H), 2.18 (s, 2H), 2.55-2.81 (m, 10H), 3.53-3.68 (m, 12H), 3.72 (s, 4H), 3.84 (s, 4H), 4.11 (s, 4H), 6.82 (s, 4H), 6.99 (q, J=8.8, 8.0 Hz, 4H).

1,1'-((((((5r,7r)-adamantan-2-ylidene)methylene)bis(4,1-phenylene))bis(oxy))bis(hexane-6,1-diyl))dipyrrolidine (NB-65)

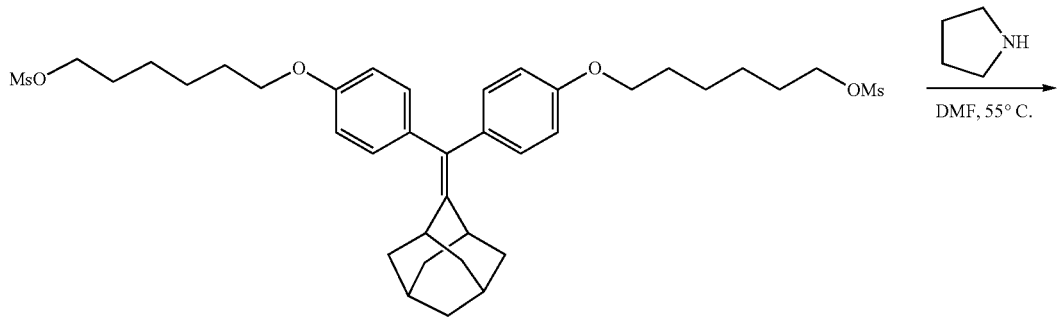

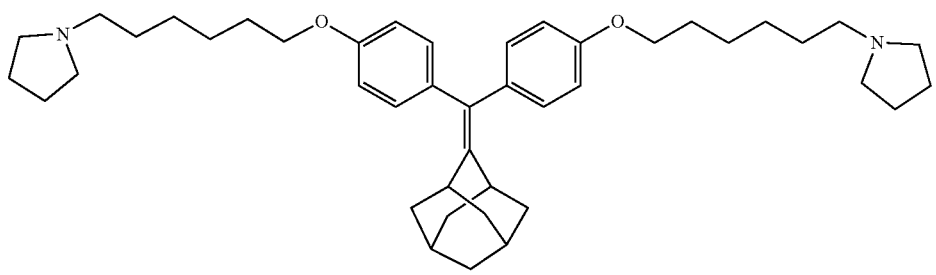

NB-65

The mixture of the compound 2 (68 mg, 0.10 mmol) and pyrrolidine (57 mg, 0.80 mmol) in DMF (200 μL) was stirred at 55° C. for 3 hr. The solvent was evaporated gently using nitrogen stream. To this was added NaHCO$_3$ (80 mg) and DI water (1 mL) and extracted with EtOAc (400 μL×3). The extract was washed with brine, water, and dried over Na$_2$SO$_4$ to provide the sticky liquid type of NB-65 (51 mg).

¹H NMR (500 MHz, CDCl$_3$) δ 1.40 (quintet, J=7.0 Hz, 4H), 1.49 (quintet, J=7.0 Hz, 4H), 1.56 (quintet, J=7.0 Hz, 4H), 1.74-1.82 (m, 12H), 1.82-1.92 (m, 10H), 2.01 (s, 2H), 2.43 (t, J=7.0 Hz, 4H), 2.47-2.55 (m, 8H), 2.81 (s, 2H), 3.93 (t, J=6.0 Hz, 4H), 6.80 (d, J=8.5 Hz, 4H), 7.03 (d, J=8.5 Hz, 4H). ¹³C NMR (126 MHz, CDCl$_3$) δ 23.66, 26.37, 27.79, 28.50, 29.35, 29.58, 34.68, 37.48, 39.87, 54.54, 56.90, 68.01, 114.01, 129.95, 130.82, 135.89, 145.83, 157.56. HRMS (ESI, M$^+$+1) C$_{43}$H$_{63}$O$_2$N$_2$ Calcd. 639.4890, found 639.4909.

1,1'-((((((5r,7r)-adamantan-2-ylidene)methylene)bis(4,1-phenylene))bis(oxy))bis(hexane-6,1-diyl))bis(1-methylpyrrolidin-1-ium) diiodide (NB-68)

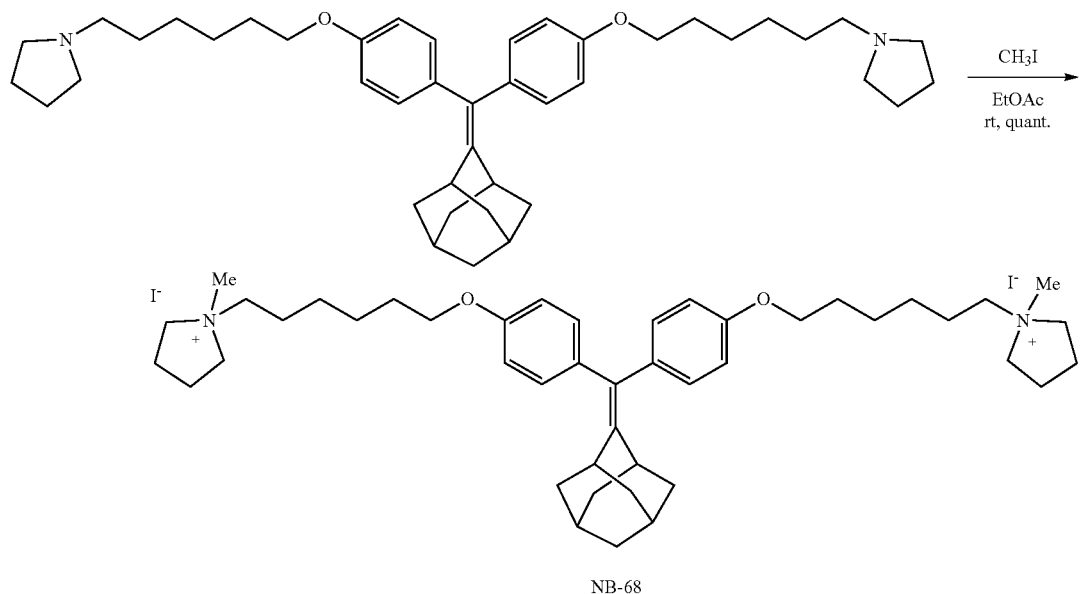

NB-68

The mixed solution of NB-65 (32 mg, 0.05 mmol) and methyl iodide (100 μL) in ethyl acetate (500 μL) was heated up at 50° C. for 1 hr to form ppt. The evaporation of solvent afforded NB-68 (45 mg) quantitatively. This is pure enough to need no further purification.

$^1$H NMR (500 MHz, CDCl$_3$+CD$_3$OD) δ 1.38 (quintet, J=7.5 Hz, 4H), 1.47 (quintet, J=7.5 Hz, 4H), 1.59-1.82 (m, 18H), 1.89 (s, 2H), 2.07-2.25 (m, 8H), 2.66 (s, 2H), 3.03 (s, 6H), 3.38 (t, J=7.5 Hz, 4H), 3.54 n (s, 8H), 3.86 (t, t, J=7.5 Hz, 4H), 6.69 (d, J=8.5 Hz, 4H), 6.91 (d, J=8.5 Hz, 4H). $^{13}$C NMR (126 MHz, CDCl$_3$+CD$_3$OD) δ 14.15, 21.77, 24.02, 25.76, 26.09, 28.31, 29.00, 34.52, 37.25, 39.67, 64.85, 67.55, 113.98, 129.58, 130.64, 135.99, 146.02, 157.17. HRMS (ESI, M$^{2+}$) C$_{45}$H$_{66}$O$_2$N$_2$ Calcd. 334.2640, found 334.2643.

1,1'-((((((5r,7r)-Adamantan-2-ylidene)methylene)bis(4,1-phenylene))bis(oxy))bis(hexane-6,1-diyl))dipiperidine (NB-70)

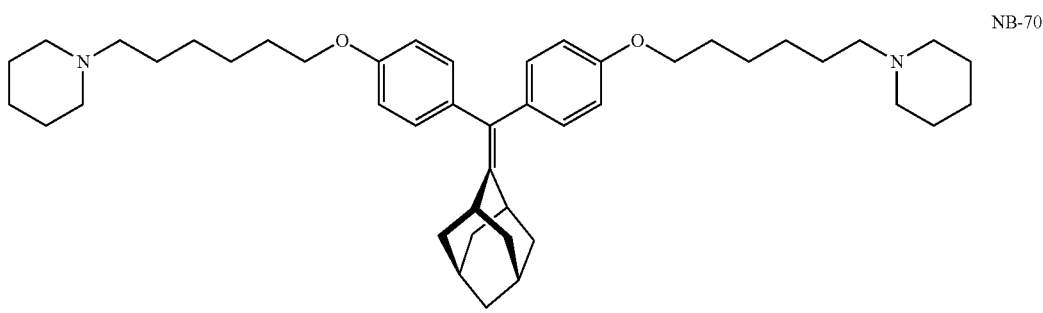

NB-70

NB-70 (36 mg, sticky liquid) was obtained from the reaction of the compound 2 (50 mg, 0.058 mmol) and piperidine (45 mg, 0.53 mmol) in 92% yield as described to prepare for NB-65.

1H NMR (500 MHz, CDCl$_3$) δ 1.36 (quintet, J=7.0 Hz, 4H), 1.40-1.58 (m, 12H), 1.59 (quintet, J=7.0 Hz, 8H), 1.78 (quintet, J=7.0 Hz, 4H), 1.82-1.92 (m, 10H), 2.00 (s, 2H), 2.30 (t, J=7.0 Hz, 4H), 2.32-2.44 (brs, 8H), 2.81 (s, 2H), 3.93 (t, J=6.5 Hz, 4H), 6.80 (d, J 8.5 Hz, 4H), 7.03 (d, J=8.5 Hz, 4H). $^{13}$C NMR (126 MHz, CDCl$_3$) δ 24.77, 26.28, 26.36, 27.18, 27.81, 28.49, 29.56, 34.66, 37.46, 39.86, 54.94, 59.85, 67.96, 113.99, 129.94, 130.81, 135.87, 145.81, 157.54. HRMS (ESI, M$^+$+1) C$_{45}$H$_{67}$O$_2$N$_2$ Calcd. 667.5203, found 667.5210.

1,1'-((((((5r,7r)-adamantan-2-ylidene)methylene)bis(4,1-phenyl ene))bis(oxy))bis(hexane-6,1-diyl))bis(1-methyl piperidin-1-ium) diodide (NB-71)

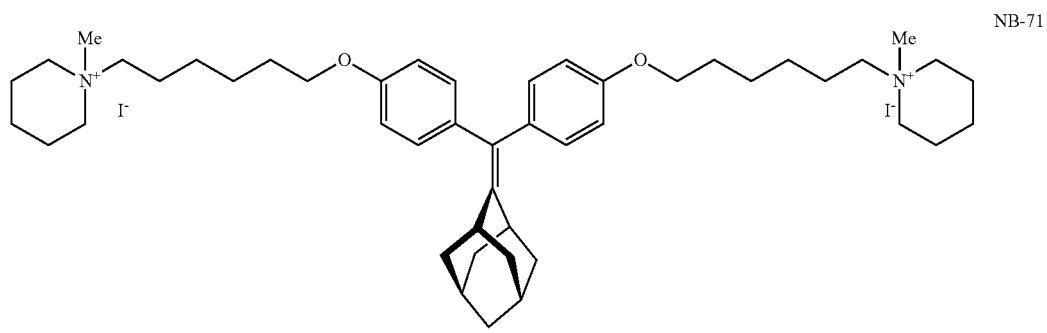

NB-71 (70 mg) was prepared from the reaction of the NB-70 (40 mg, 0.075 mmol) and methyl iodide (200 μL) quantitatively by following the procedure as described to prepare for NB-68.

$^1$H NMR (500 MHz, CDCl$_3$+CD$_3$OD) δ 1.43 (quintet, J=7.5 Hz, 4H), 1.52 (quintet, J=7.5 Hz, 4H), 1.63-1.92 (m, 30H), 1.94 (s, 2H), 2.71 (s, 2H), 3.13 (s, 6H), 3.43-3.54 (m, 12H), 3.91 (t, J=7.5 Hz, 4H), 6.75 (d, J=8.5 Hz, 4H), 6.96 (d, J=8.5 Hz, 4H). $^{13}$C NMR (126 MHz, CDCl$_3$+CD$_3$OD) δ 20.29, 20.87, 22.10, 25.84, 26.11, 28.36, 29.08, 34.57, 37.33, 39.74, 48.50, 61.47, 63.89, 67.61, 114.06, 129.60, 130.70, 136.02, 146.08, 157.23. HRMS (ESI, M$^{2+}$) C$_{47}$H$_{70}$O$_2$N$_2$ Calcd. 348.2797, found 348.2798.

1,1'-((((((5r,7r)-Adamantan-2-ylidene)methylene)bis(4,1-phenyl ene))bis(oxy))bis(hexane-6,1-diyl))bis(azepane) (NB-72)

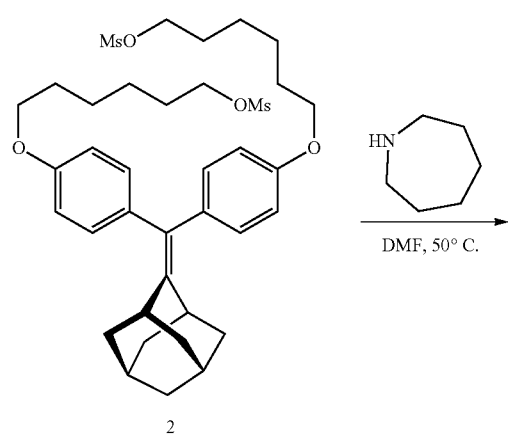

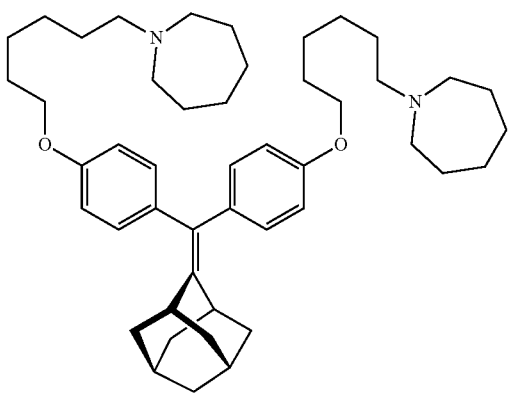

NB-72 (37 mg, sticky liquid) was obtained from the reaction of the compound 2 (50 mg, 0.058 mmol) and azepane (55 mg, 0.55 mmol) in 91% yield following the procedure as described to prepare for NB-65.

$^1$H NMR (500 MHz, CDCl$_3$) δ 1.35 (quintet, J=7.5 Hz, 4H), 1.49 (quintet, J=7.5 Hz, 4H), 1.51 (quintet, J=7.5 Hz, 4H), 1.61 (brs, 8H), 1.65 (brs, 8H), 1.77 (quintet, J=7.5 Hz, 4H), 1.86 (brs, 10H), 2.01 (s, 2H), 2.47 (t, J=7.5 Hz, 4H), 2.63 (t, J=6.0 Hz, 8H), 2.81 (s, 2H), 3.93 t, J=6.0 Hz, 4H), 6.80 (d, J=8.5 Hz, 4H), 7.03 (d, J=8.5 Hz, 4H). $^{13}$C NMR (126 MHz, CDCl$_3$) δ 26.35, 27.26, 27.66, 27.76, 28.21, 28.48, 29.59, 34.66, 37.46, 39.86, 55.85, 58.53, 67.99, 113.98, 125.22, 130.82, 135.87, 145.82, 157.55. HRMS (ESI, M$^+$+1) C$_{47}$H$_{71}$O$_2$N$_2$ Calcd. 695.5516, found 695.5529.

1,1'-((((((5r,7r)-adamantan-2-ylidene)methylene)bis (4,1-phenylene))bis(oxy))bis(hexane-6,1-diyl))bis(1-methylazepan-1-ium) diiodide (NB-73)

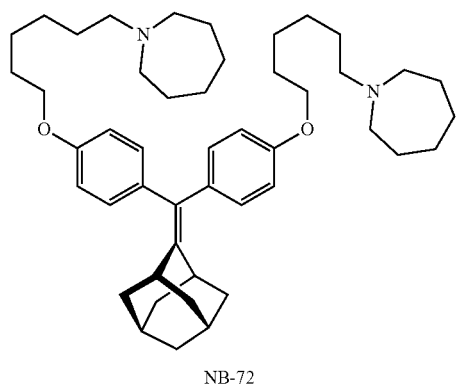

NB-72

CH$_3$I / EtOAc →

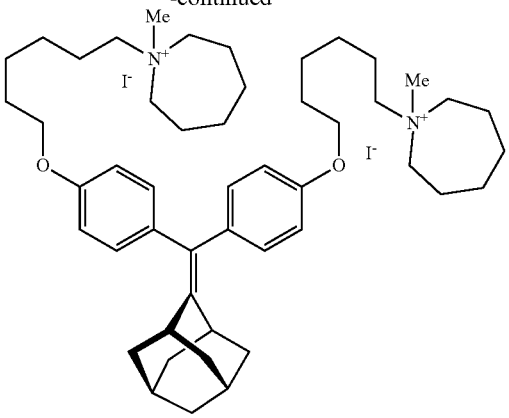

NB-73

NB-73 (47 mg) was prepared from the reaction of the NB-72 (35 mg, 0.05 mmol) and methyl iodide (100 μL) quantitatively by following the procedure as described to prepare for NB-68.

$^1$H NMR (500 MHz, CDCl$_3$+CD$_3$OD) δ 1.43 (quintet, J=7.5 Hz, 4H), 1.55 (quintet, J=7.5 Hz, 4H), 1.71 (brs, 8H), 1.73-1.92 (m, 26H), 1.95 (s, 2H), 2.73 (s, 2H), 3.07 (s, 6H), 3.27-3.50 (m, 12H), 3.94 (t, J=7.5 Hz, 4H), 6.76 (d, J=8.5 Hz, 4H), 6.98 (d, J=8.5 Hz, 4H). $^{13}$C NMR (126 MHz, CDCl$_3$+CD$_3$OD) δ 21.84, 22.69, 25.83, 26.20, 27.74, 28.40, 29.12, 34.58, 37.26, 39.65, 50.45, 64.76, 65.44, 67.58. 113.94, 129.88, 130.62, 135.94, 145.87, 157.36. HRMS (ESI, M$^{2+}$) C$_{49}$H$_{76}$O$_2$N$_2$ Calcd. 363.3032, found 363.2957.

6,6'-(((((5r,7r)-adamantan-2-ylidene)methylene)bis (4,1-phenylene))bis(oxy))bis(N,N-diethylhexan-1-amine) (NB-51)

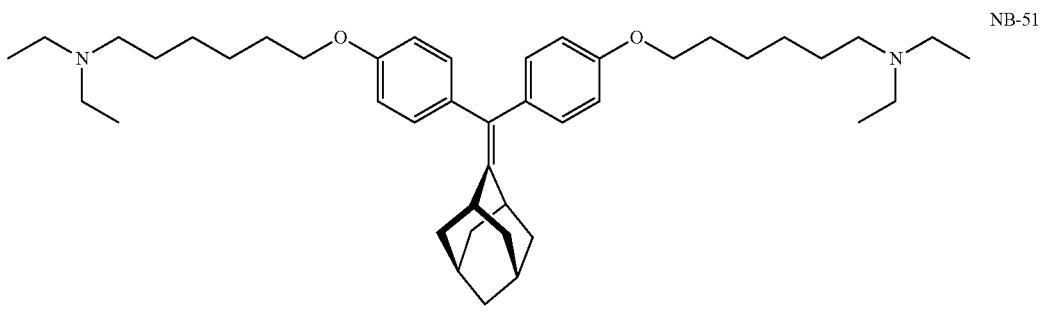

NB-51

NB-51 (33 mg) was obtained from the reaction of the compound 2 (50 mg, 0.058 mmol) and diethyl amine (50 mg, 0.68 mmol) in 89% yield following the procedure as described to prepare for NB-65.

$^1$H NMR (500 MHz, CDCl$_3$) δ 1.03 (t, J=7.0 Hz, 12H), 1.37 (quintet, J=7.0 Hz, 4H), 1.42-1.52 (m, 8H), 1.79 (quintet, J=7.0 Hz, 4H), 1.82-1.92 (m, 10H), 2.00 (brs, 2H), 2.43 (t, J=7.5 Hz, 4H), 2.53 (q, J=7.0 Hz, 8H), 2.81 (bes, 2H), 3.93 (t, J=6.0 Hz, 2H), 6.80 (d, J=8.5 Hz, 4H), 7.02 (d, J=8.5 Hz, 4H). $^{13}$C NMR (126 MHz, CDCl$_3$) δ 11.91, 26.36, 27.18, 27.75, 28.48, 29.60, 34.66, 37.46, 39.85, 47.13, 53.12, 67.97, 113.98, 129.93, 130.81, 135.87, 145.82, 157.54. FIRMS (ESI, M$^+$) C$_{43}$H$_{67}$O$_2$N$_2$ Calcd. 643.5203, found 643.5225.

6-(4-(((5r,7r)-adamantan-2-ylidene)(4-((6-(diethyl (methyl)-λ⁴-azaneyl)hexyl)oxy)phenyl)methyl)phenoxy)-N,N-diethyl-N-methylhexan-1-aminium diiodide (NB-115)

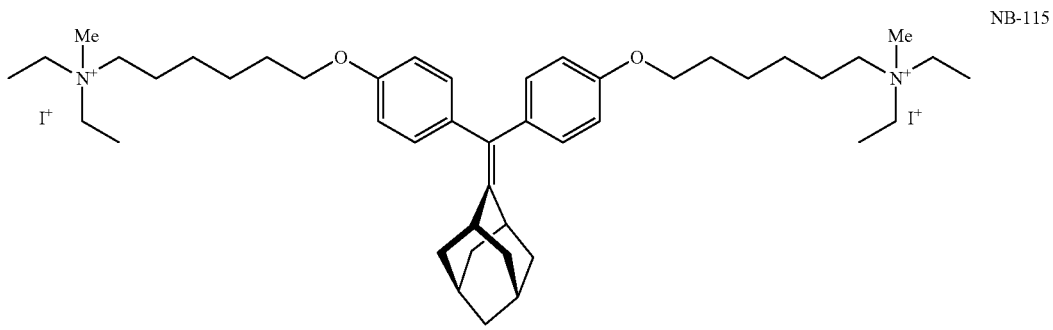

NB-115

NB-115 (45 mg) was prepared from the reaction of the NB-51 (32 mg, 0.05 mmol) and methyl iodide (100 μL) quantitatively by following the procedure as described to prepare for NB-68.

$^1$H NMR (500 MHz, CDCl$_3$) δ 1.32 (t, J=7.0 Hz, 12H), 1.45 (quintet, J=7.0 Hz, 4H), 1.53 (quintet, J=7.0 Hz, 4H), 1.64-1.76 (m, 8H), 1.76-1.85 (m, 10H), 1.96 (brs, 2H), 2.73 (brs, 2H), 3.08 (s, 6H), 3.33 (t, J=7.0 Hz, 4H), 3.42 (q, J=7.0 Hz, 8H), 3.93 (t, J=6.0 Hz, 2H), 6.74 (d, J=8.5 Hz, 4H), 6.99 (d, J=8.5 Hz, 4H). $^{13}$C NMR (126 MHz, CDCl$_3$) δ 8.49, 22.51, 25.86, 26.16, 28.37, 29.11, 34.58, 37.34, 39.76, 57.03, 61.00, 67.59, 114.06, 129.63, 130.73, 136.03, 146.09, 157.26. HRMS (ESI, M$^{2+}$) C$_{45}$H$_{72}$O$_2$N$_2$ Calcd. 336.2804, found 336.2797.

4,4'-((((((5r,7r)-adamantan-2-ylidene)methylene)bis (4,1-phenylene))bis(oxy))bis(hexane-6,1-diyl))bis(1-methylpiperazine) (NB-66)

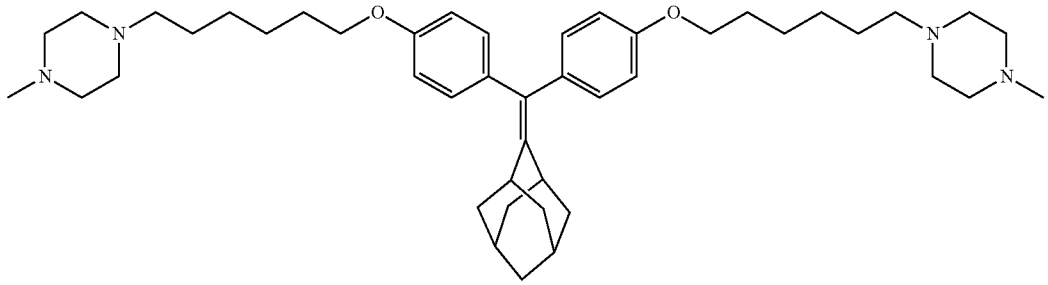

NB-66 was obtained from the reaction of compound 2 and 1-methylpiperazine in DMF at 55° C. quantitatively as described to make NB-65.

$^1$H NMR (500 MHz, Chloroform-d) δ 1.38 (quintet, J=6.4 Hz, 4H), 1.48 (quintet, J=6.4 Hz, 4H), 1.58 (quintet, J=6.4 Hz, 4H), 1.77 (quintet, J=6.4 Hz, 4H), 1.82-1.90 (m, 10H), 2.00 (s, 2H), 2.31 (s, 6H), 2.36 (t, J=6.3 Hz, 4H), 2.40-2.68 (brs, 8H), 2.80 (s, 2H), 3.93 (t, J=6.4 Hz, 4H), 6.80 (d, J=8.5 Hz, 4H), 7.02 (d, J=8.5 Hz, 4H).

1,1'-((((((5r,7r)-adamantan-2-ylidene)methylene)bis
(4,1-phenylene))bis(oxy))bis(hexane-6,1-diyl))bis(1,
4-dimethylpiperazin-1-ium) dimethanesulfonate
(NB-69)

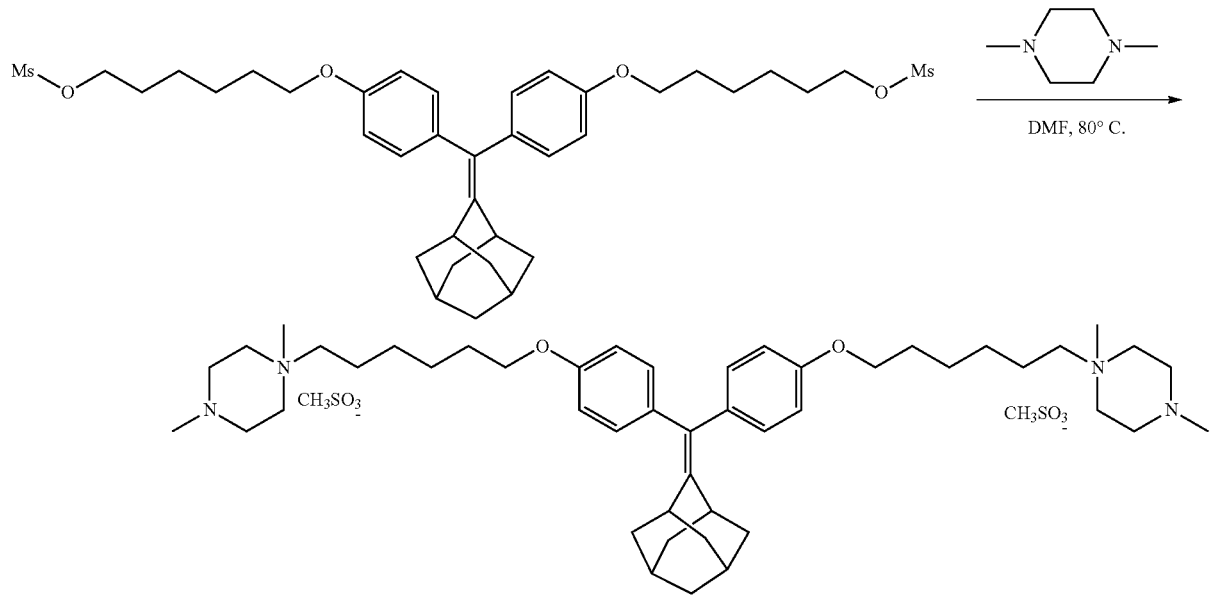

NB-69 was obtained from the reaction of compound 2 with 1,4-dimethylpiperazine in DMF at 80° C. quantitatively as described to prepare for NB-73.

$^1$HNMR (500 MHz, Methanol-$d_4$) δ 1.47-1.58 (m, 8H), 1.76-1.83 (m, 8H), 1.84 (s, 10H), 1.96 (s, 2H), 2.39 (s, 4H), 2.69 (s, 6H), 2.74-2.84 (m, 8H), 3.09 (s, 6H), 3.31 (s, 6H), 3.35-3.48 (m, 8H), 3.97 (t, J=6.1 Hz, 4H), 6.80 (d, J=8.1 Hz, 4H), 6.98 (d, J=8.1 Hz, 4H).

1,1'-((((((5r,7r)-adamantan-2-ylidene)methylene)bis
(4,1-phenylene))bis(oxy))bis(hexane-6,1-diyl))bis
(1H-imidazole) (NB-61)

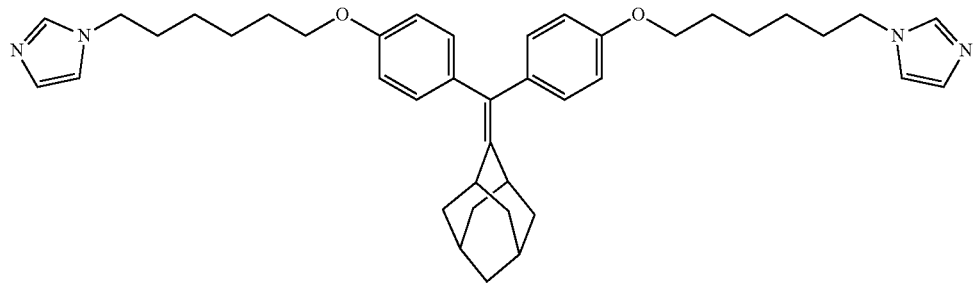 [SMILES: c1cn(CCCCCCOc2ccc(C(=C3C4CC5CC(C4)CC3C5)c3ccc(OCCCCCCn4ccnc4)cc3)cc2)cn1]

NB-61 was obtained from the reaction of compound 2 with imidazole in DMF at 80° C. in 88% yield as describe to prepare for NB-65.

$^1$H NMR (500 MHz, Chloroform-d) δ 1.29-1.42 (m, 4H), 1.42-1.54 (m, 4H), 1.74 (quintet, J=6.4 Hz, 4H), 1.82 (s, 10H), 1.97 (s, 2H), 2.55-2.68 (m, 8H), 2.75 (s, 2H), 3.80-3.92 (m, 4H), 6.75 (d, J=8.2 Hz, 4H), 6.94 (s, 1H), 6.99 (d, J=8.2 Hz, 4H), 7.06 (s, 1H), 7.71 (s, 1H).

2,2'-((((((5r,7r)-adamantan-2-ylidene)methylene)bis(4,1-phenylene))bis(oxy))bis(hexane-6,1-diyl))bis(ethylazanediyl))bis(ethan-1-ol) (NB-130)

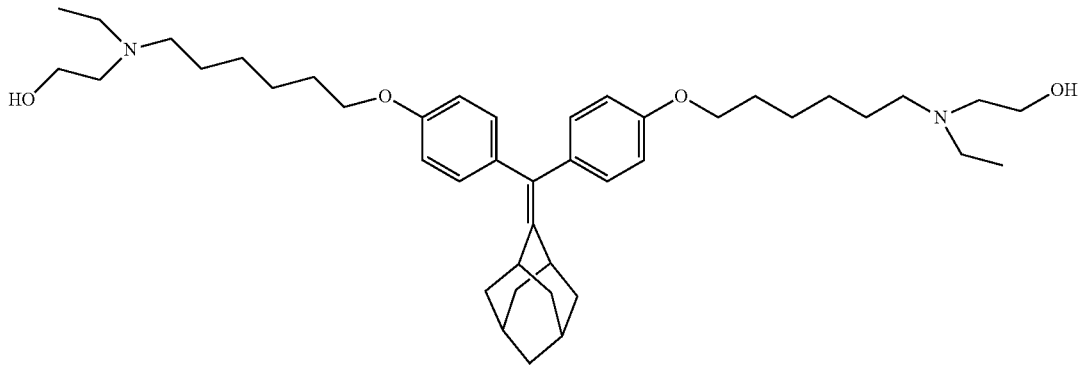 [SMILES: CCN(CCO)CCCCCCOc1ccc(C(=C2C3CC4CC(C3)CC2C4)c2ccc(OCCCCCCN(CC)CCO)cc2)cc1]

NB-130 (30 mg) was obtained from the reaction of the compound 2 (35 mg, 0.051 mmol) and 2-(ethylamino)ethanol (50 mg, 0.56 mmol) in 87% yield following the procedure as described to prepare for NB-65.

$^1$H NMR (500 MHz, Chloroform-d) δ 1.04 (t, J=7.1 Hz, 6H), 1.31-1.44 (m, 4H), 1.45-1.53 (m, 8H), 1.71-1.82 (m, 4H), 1.82-1.93 (m, 10H), 2.01 (s, 2H), 2.42-2.52 (m, 4H), 2.52-2.65 (m, 8H), 2.81 (s, 2H), 3.55 (t, J=5.5 Hz, 4H), 3.93 (t, J=6.4 Hz, 4H), 6.80 (d, J=8.5 Hz, 4H), 7.03 (d, J=8.5 Hz, 4H). $^{13}$C NMR (126 MHz, CDCl$_3$) δ 12.10, 26.31, 27.43, 27.45, 28.48, 29.58, 34.67, 37.46, 39.86, 47.42, 53.33, 55.10, 58.55, 67.92, 113.99, 129.94, 130.81, 135.89, 145.84, 157.53. HRMS (ESI, M$^+$+1) C$_{43}$H$_{67}$O$_4$N$_2$ Calcd. 675.510, found 675.5093.

6,6'-(((((5r,7r)-adamantan-2-ylidene)methylene)bis(4,1-phenylene))bis(oxy))bis(N-ethyl-N-(2-hydroxyethyl)-N-methylhexan-1-aminium) diiodide (NB134)

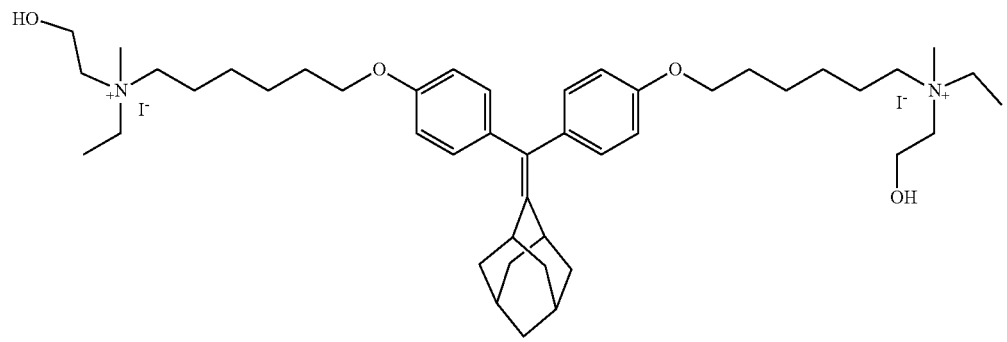 [SMILES: CC[N+](C)(CCO)CCCCCCOc1ccc(C(=C2C3CC4CC(C3)CC2C4)c2ccc(OCCCCCC[N+](C)(CC)CCO)cc2)cc1 ; [I-] ; [I-]]

NB-134 (21 mg) was prepared from the reaction of the NB-130 (15 mg, 0.022 mmol) and methyl iodide (100 μL) following the procedure as described to prepare for NB-68.

$^1$H NMR (500 MHz, Chloroform-d+methanol-d$_4$) δ 1.32 (t, J=7.1 Hz, 4H), 1.41 (quintet, J=7.5 Hz, 4H), 1.51 ((quintet, J=7.5 Hz, 4H), 1.63-1.85 (m, 18H), 1.95 (s, 2H), 2.72 (s, 2H), 3.12 (s, 6H), 3.30-3.42 (m, 4H), 3.43-3.59 (m, 8H), 3.90 (t, J=6.2 Hz, 4H), 3.99 (t, J=4.8 Hz, 4H), 6.75 (d, J=8.5 Hz, 4H), 6.97 (d, J=8.5 Hz, 4H). HRMS (ESI, M$^{2+}$) C$_{45}$H$_{70}$O$_4$N$_2$ Calcd. 352.2746, found 352.2715.

2,2',2'',2'''-((((((5r,7r)-adamantan-2-ylidene)methylene)bis(4,1-phenylene))bis(oxy))bis(hexane-6,1-diyl))bis(azanetriyl))tetrakis(ethan-1-ol) (NB-131)

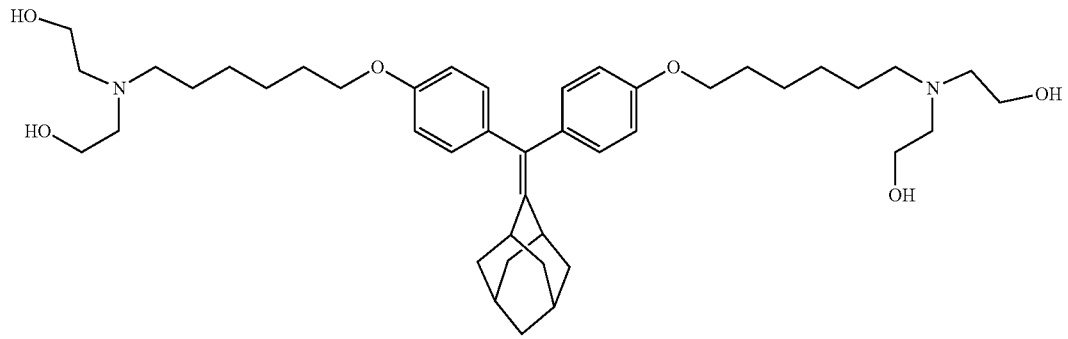 [SMILES: OCCN(CCO)CCCCCCOc1ccc(C(=C2C3CC4CC(C3)CC2C4)c2ccc(OCCCCCCN(CCO)CCO)cc2)cc1]

NB-131 (24 mg) was obtained from the reaction of the compound 2 (26 mg, 0.038 mmol) and diethanolamine (105 mg, 1.00 mmol) in 90% yield following the procedure as described to prepare for NB-65.

$^1$H NMR (500 MHz, Chloroform-d) δ 1.37 (q, J=7.9 Hz, 4H), 1.41-1.55 (m, 8H), 1.70-1.80 (m, 4H), 1.80-1.94 (m, 10H), 2.00 (s, 2H), 2.55 (t, J 6.4 Hz, 4H), 2.66 (t, J 5.3 Hz, 8H), 2.80 (s, 2H), 3.62 (t, J=5.4 Hz, 8H), 3.93 (t, J=6.4 Hz, 4H), 6.80 (d, J=8.5 Hz, 4H), 7.03 (d, J=8.5 Hz, 4H). $^{13}$C NMR (126 MHz, CDCl$_3$) δ 26.27, 27.17, 27.33, 28.47, 29.53, 34.66, 37.45, 39.85, 54.93, 56.27, 59.89, 67.88, 114.01, 129.89, 130.81, 135.92, 145.87, 157.49. HRMS (ESI, M$^+$+1) C$_{43}$H$_{67}$O$_6$N$_2$ Calcd. 707.4999, found 707.4995.

6,6'-(((((5r,7r)-adamantan-2-ylidene)methylene)bis(4,1-phenylene))bis(oxy))bis(N,N-bis(2-hydroxyethyl)-N-methylhexan-1-aminium) diiodide (NB-135)

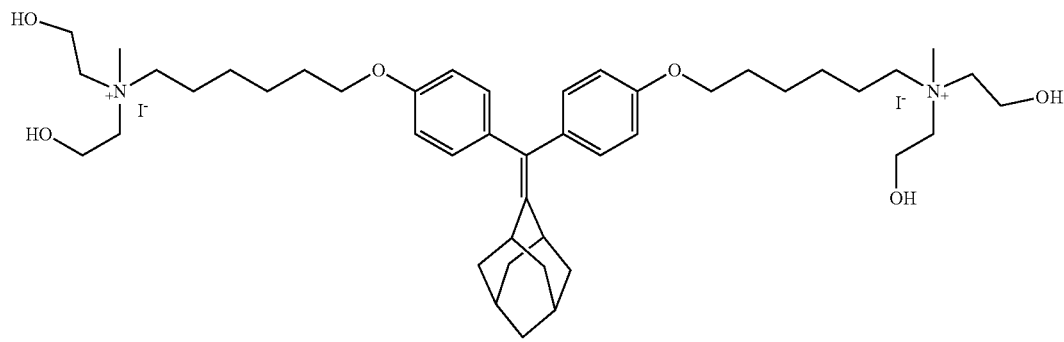 [SMILES: C[N+](CCO)(CCO)CCCCCCOc1ccc(C(=C2C3CC4CC(C3)CC2C4)c2ccc(OCCCCCC[N+](C)(CCO)CCO)cc2)cc1 ; [I-] ; [I-]]

NB-135 (21 mg) was prepared from the reaction of the NB-131 (15 mg, 0.021 mmol) and methyl iodide (100 μL) quantitatively by following the procedure as described to prepare for NB-68.

$^1$H NMR (500 MHz, Chloroform-d+methanol-d$_4$) δ 1.37 (q, J=7.7 Hz, 4H), 1.48 (h, J=7.4 Hz, 4H), 1.62-1.84 (m, 18H), 1.91 (s, 2H), 2.69 (s, 2H), 3.15 (s, 6H), 3.39-3.48 (m, 4H), 3.50-3.62 (m, 8H), 3.87 (t, J=6.2 Hz, 4H), 3.90-3.99 (m, 8H), 6.71 (d, J=8.2 Hz, 4H), 6.94 (d, J=8.2 Hz, 4H). HRMS (ESI, M$^2$) C$_{45}$H$_{70}$O$_6$N$_2$ Calcd. 368.2695, found 368.2664.

1,1'-((((((5r,7r)-adamantan-2-ylidene)methylene)bis(4,1-phenylene))bis(oxy))bis(hexane-6,1-diyl))bis(azetidine) (NB-133)

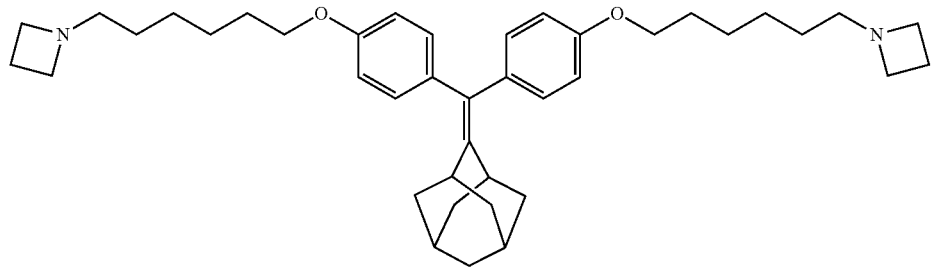 [SMILES: c1cc(C(=C2C3CC4CC(C3)CC2C4)c2ccc(OCCCCCCN3CCC3)cc2)ccc1OCCCCCCN1CCC1]

NB-133 (20 mg) was obtained from the reaction of the compound 2 (25 mg, 0.036 mmol) and azetidine (80 mg, 1.40 mmol) in 91% yield following the procedure as described to prepare for NB-65.

$^1$H NMR (500 MHz, Chloroform-d) δ 1.35 (q, J=3.6 Hz, 4H), 1.41-1.56 (m, 4H), 1.63-1.71 (m, 4H), 1.72-1.80 (m, 4H), 1.81-1.91 (m, 10H), 2.00 (s, 2H), 2.32 (t, J=7.5 Hz, 4H), 2.65 (t, J=6.5 Hz, 4H), 2.80 (s, 2H), 3.16 (t, J=7.0 Hz, 8H), 3.92 (t, J=6.5 Hz, 4H), 6.79 (d, J=8.3 Hz, 4H), 7.02 (d, J=8.3 Hz, 4H). $^{13}$C NMR (126 MHz, CDCl$_3$) δ 17.94, 26.35, 28.48, 29.56, 34.66, 37.45, 39.85, 45.79, 55.47, 58.33, 60.22, 67.97, 113.99, 129.93, 130.80, 135.87, 145.83, 157.53. HRMS (ESI, M$^+$+1) C$_{41}$H$_{59}$O$_2$N$_2$ Calcd. 611.4577, found 611.4572.

1,1'-((((((5r,7r)-adamantan-2-ylidene)methylene)bis(4,1-phenylene))bis(oxy))bis(hexane-6,1-diyl))bis(1-methylazetidin-1-ium) diiodide (NB-137)

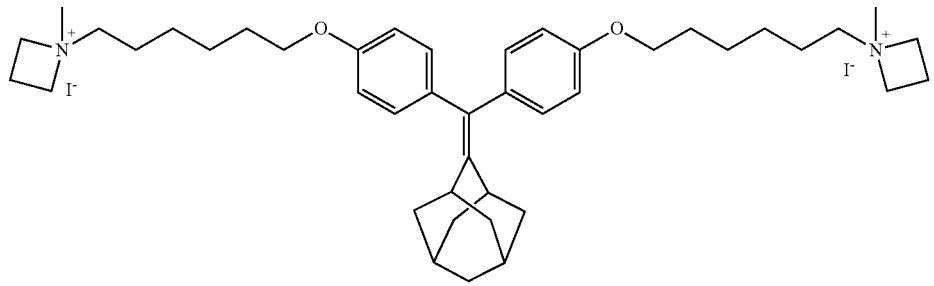

NB-137 (10 mg) was prepared from the reaction of the NB-133 (8.0 mg, 0.021 mmol) and methyl iodide (100 μL) by following the procedure as described to prepare for NB-68.

$^1$H NMR (500 MHz, Chloroform-d+methanol-d$_4$) δ 1.33 (s, 8H), 1.58-1.77 (m, 18H), 1.83 (s, 2H), 2.07-2.43 (m, 4H), 2.61 (s, 2H), 2.90-3.72 (m, 18H), 3.80 (t, J=6.5 Hz, 4H), 6.64 (d, J=8.1 Hz, 4H), 6.86 (d, J=8.0 Hz, 4H). HRMS (ESI, M$^{2+}$) C$_{43}$H$_{64}$N$_2$O$_2$ Calcd. 320.2484, found 320.2451.

1,1'-((((((5r,7r)-adamantan-2-ylidene)methylene)bis(4,1-phenylene))bis(oxy))bis(hexane-6,1-diyl))bis(azetidin-3-ol) (NB-145)

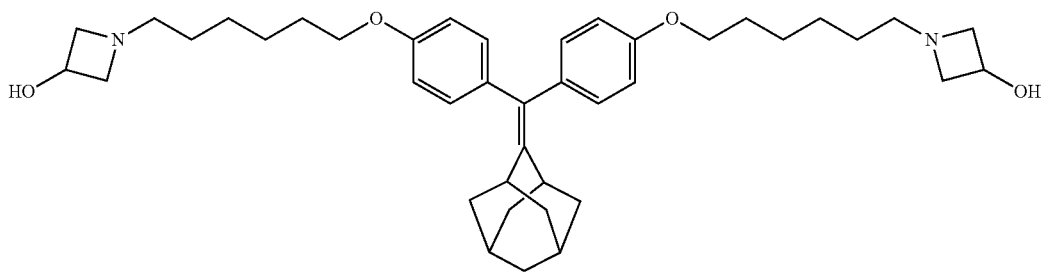 [SMILES: OC1CN(CCCCCCOc2ccc(C(=C3C4CC5CC(C4)CC3C5)c3ccc(OCCCCCCN4CC(O)C4)cc3)cc2)C1]

NB-145 (20 mg) was obtained from the reaction of the compound 2 (25 mg, 0.036 mmol) and 3-hydroxyazetidine (90 mg, 1.23 mmol) in 86% yield following the procedure as described to prepare for NB-65.

$^1$H NMR (500 MHz, Chloroform-d) δ 0.79-0.97 (m, 4H), 1.32-1.42 (m, 4H), 1.42-1.53 (m, 4H), 1.67-1.81 (m, 4H), 1.81-1.91 (m, 10H), 2.00 (s, 2H), 2.29 (t, J=7.3 Hz, 4H), 2.48 (t, J=6.5 Hz, 4H), 2.80 (s, 2H), 2.93 (t, J=5.9 Hz, 4H), 3.66 (t, J=6.4 Hz, 4H), 4.44 (q, J=5.9 Hz, 2H), 6.80 (d, J=8.2 Hz, 4H), 7.03 (d, J=8.2 Hz, 4H). HRMS (ESI, M$^+$+1) $C_{41}H_{59}O_4N_2$ Calcd. 643.4475, found 643.4457.

1,1'-((((((5r,7r)-adamantan-2-ylidene)methylene)bis(4,1-phenylene))bis(oxy))bis(hexane-6,1-diyl))bis(3-methylazetidin-3-ol) (NB-143)

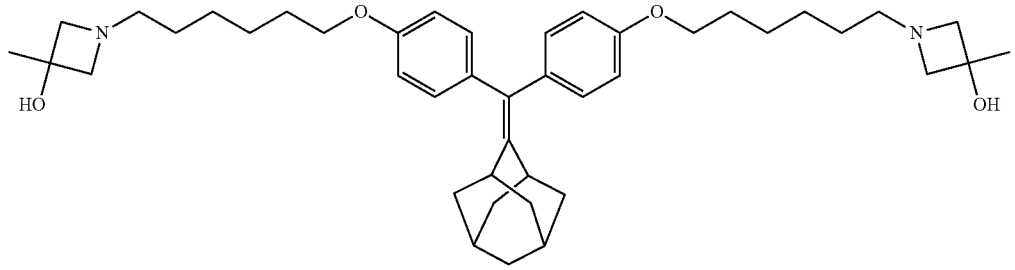

NB-143 (21 mg) was obtained from the reaction of the compound 2 (25 mg, 0.036 mmol) and 3-methyl-3-hydroxyazetidine (90 mg, 1.03 mmol) in 88% yield following the procedure as described to prepare for NB-65.

$^1$H NMR (500 MHz, Chloroform-d) δ 0.83-0.90 (m, 4H), 1.27 (s, 6H), 1.34-1.52 (m, 8H), 1.7-1.84 (m, 4H), 1.84-1.95 (m, 10H), 2.00 (s, 2H), 2.52 (t, J=6.5 Hz, 4H), 2.80 (s, 2H), 3.13 (d, J=8.0 Hz, 4H), 3.34 (d, J=8.0 Hz, 4H), 3.93 (t, J=6.4 Hz, 4H), 6.79 (d, J=8.2 Hz, 4H), 7.03 (d, J=8.2 Hz, 4H). HRMS (ESI, M$^+$+1) $C_{43}H_{63}O_4N_2$ Calcd. 671.4788, found 671.4801.

1,1'-((((((5r,7r)-adamantan-2-ylidene)methyl ene)bis(4,1-phenylene))bis(oxy))bis(hexane-6,1-diyl))bis(3-hydroxy-1,3-dimethylazetidin-1-ium) diiodide (NB-144)

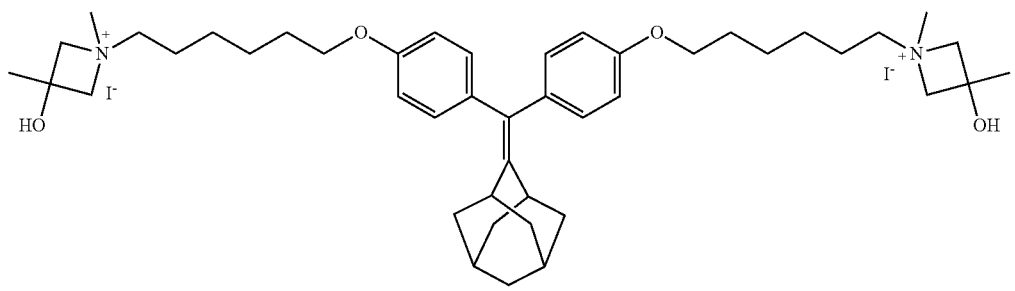

NB-144 (11 mg) was prepared from the reaction of the NB-143 (9.0 mg, 0.013 mmol) and methyl iodide (100 μL) by following the procedure as described to prepare for NB-68.

$^1$H NMR (500 MHz, Chloroform-d+methanol-d$_4$) δ 1.35-1.45 (m, 4H), 1.45-1.2 (m, 4H), 1.53 (s, 6H), 1.56-1.65 (m, 4H), 1.68-1.85 (d, J=31.7 Hz, 14H), 1.93 (s, 2H), 2.70 (s, 2H), 3.17 (d, J=6.8 Hz, 6H), 3.27-3.37 (m, 4H), 3.46 (m, 4H), 3.89 (t, J=6.2 Hz, 4H), 4.09-4.40 (m, 8H), 6.72 (d, J=8.2 Hz, 4H), 6.95 (d, J=8.2 Hz, 4H). HRMS (ESI, M$^{2+}$) $C_{45}H_{68}O_4N_2$ Calcd. 350.2587, found 350.2543.

((2S,2'S)-((((((5r,7r)-adamantan-2-ylidene)methylene)bis(4,1-phenylene))bis(oxy))bis(hexane-6,1-diyl))bis(pyrrolidine-1,2-diyl))dimethanol (NB-138)

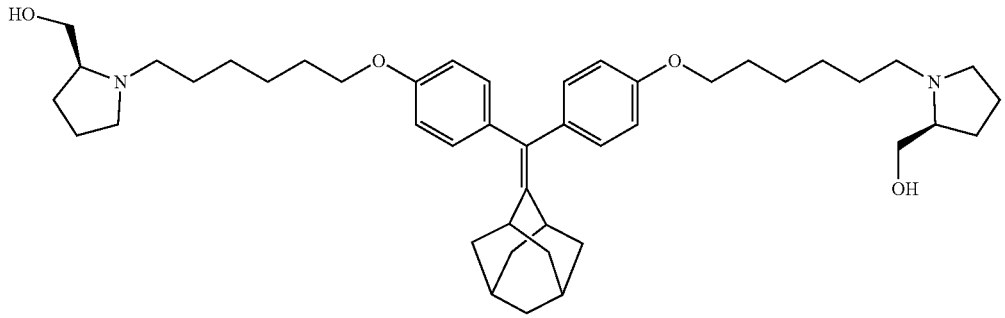 [SMILES: OC[C@@H]1CCCN1CCCCCCOc1ccc(C(=C2C3CC4CC(C3)CC2C4)c2ccc(OCCCCCCN3CCC[C@H]3CO)cc2)cc1]

NB-138 (23 mg) was obtained from the reaction of the compound 2 (28 mg, 0.041 mmol) and (S)-pyrrolidin-2-ylmethanol (101 mg, 1.00 mmol) in 81% yield following the procedure as described to prepare for NB-65.

$^1$H NMR (500 MHz, Chloroform-d) δ 1.32-1.57 (m, 8H), 1.57-1.96 (m, 26H), 2.01 (s, 2H), 2.41-2.58 (m, 4H), 2.80 (s, 2H), 2.85-2.99 (m, 4H), 3.37-3.48 (m, 2H), 3.53-3.64 (m, 2H), 3.73-3.81 (m, 2H), 3.94 (t, J=6.3 Hz, 4H), 6.80 (d, J=8.2 Hz, 4H), 7.03 (d, J=8.2 Hz, 4H). HRMS (ESI, M$^+$+1) $C_{45}H_{67}O_4N_2$ Calcd. 699.5101, found 699.5121.

(1R,1'R,2S,2'S)-1,1'-((((((5r,7r)-adamantan-2-ylidene)methylene)bis(4,1-phenylene))bis(oxy))bis(hexane-6,1-diyl))bis(2-(hydroxymethyl)-1-methylpyrrolidin-1-ium) diiodide (NB-139)

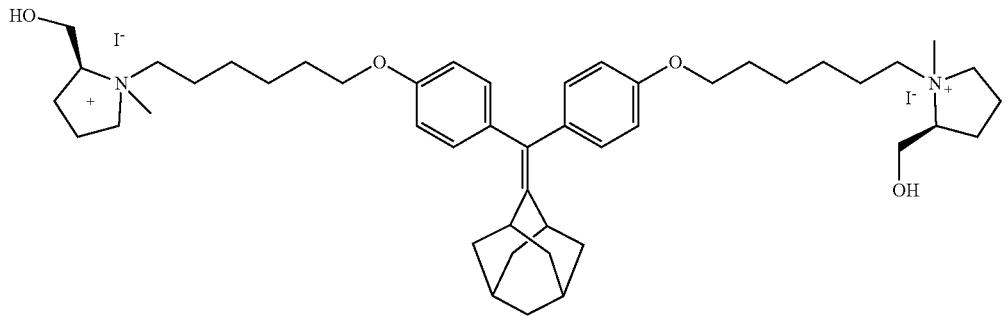

NB-139 (13 mg) was prepared from the reaction of the NB-138 (10.0 mg, 0.014 mmol) and methyl iodide (100 μL) by following the procedure as described to prepare for NB-68.

$^1$H NMR (500 MHz, Chloroform-d+methanol-d$_4$) δ 1.29-1.56 (m, 8H), 1.62-1.87 (m, 20H), 1.92 (s, 2H), 1.96-2.44 (m, 6H), 2.70 (s, 2H), 2.95 (s, 6H), 3.30-3.44 (m, 2H), 3.44-3.56 (m, 4H), 3.57-3.68 (m, 2H), 3.71-4.03 (m, 10H), 6.72 (d, J=8.1 Hz, 4H), 6.95 (d, J=8.1 Hz, 4H). HRMS (ESI, M$^{2+}$) $C_{47}H_{70}O_4N_2$ Calcd. 364.2746, found 364.2713.

1,1'-((((((5r,7r)-adamantan-2-ylidene)methylene)bis(4,1-phenylene))bis(oxy))bis(hexane-6,1-diyl))bis(piperidin-4-ol) (NB-132)

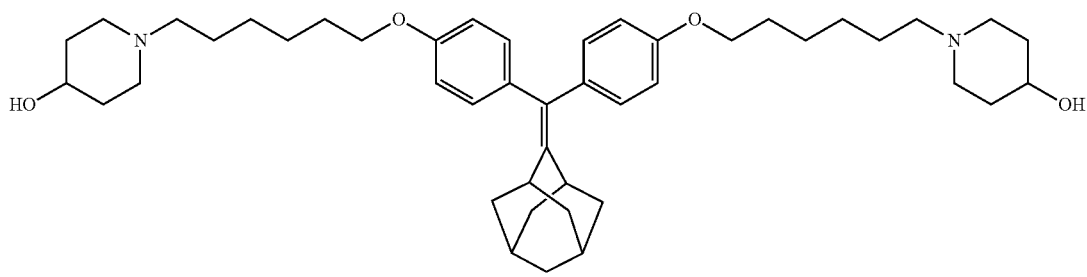 [SMILES: OC1CCN(CCCCCCOc2ccc(C(=C3C4CC5CC(C4)CC3C5)c3ccc(OCCCCCCN4CCC(O)CC4)cc3)cc2)CC1]

NB-132 (24 mg) was obtained from the reaction of the compound 2 (28 mg, 0.041 mmol) and 4-hydroxypiperidine (101 mg, 1.00 mmol) in 84% yield following the procedure as described to prepare for NB-65.

$^1$H NMR (500 MHz, Chloroform-d) δ 1.27-1.68 (m, 16H), 1.78 (q, J=7.6, 7.1 Hz, 4H), 1.82-1.95 (m, 14H), 2.00 (s, 2H), 2.12 (t, J=10.7 Hz, 6H), 2.27-2.41 (m, 4H), 2.79 (t, J=7.5 Hz, 4H), 3.69 (t, J=4.3 Hz, 2H), 3.93 (t, J=6.5 Hz, 4H), 6.79 (d, J=8.5 Hz, 4H), 7.02 (d, J=8.5 Hz, 4H). $^{13}$C NMR (126 MHz, CDCl$_3$) δ 26.31, 27.32, 27.68, 28.47, 29.53, 29.94, 34.66, 34.70, 37.45, 39.85, 51.43, 58.85, 67.94, 114.01, 129.91, 130.80, 135.90, 145.86, 157.51. HRMS (ESI, M$^+$+1) C$_{45}$H$_{67}$O$_4$N$_2$ Calcd. 699.5101, found 699.5099.

1,1'-((((((5r,7r)-adamantan-2-ylidene)methylene)bis(4,1-phenylene))bis(oxy))bis(hexane-6,1-diyl))bis(4-hydroxy-1-methylpiperidin-1-ium) diiodide (NB-136)

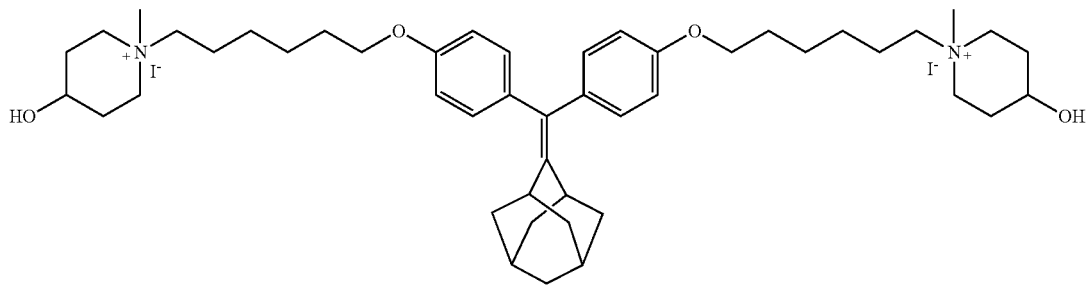

NB-136 (13 mg) was prepared from the reaction of the NB-132 (10.0 mg, 0.014 mmol) and methyl iodide (100 μL) by following the procedure as described to prepare for NB-68.

$^1$H NMR (500 MHz, Chloroform-d+methanol-d$_4$) δ 1.40 (t, 0.1=7.1 Hz, 4H), 1.49 (q, J=7.4 Hz, 4H), 1.59-1.95 (m, 20H), 1.95-2.12 (m, 4H), 2.67 (s, 2H), 3.04 (s, 6H), 3.27-3.56 (m, 14H), 3.83-4.05 (m, 8H), 6.70 (d, J=8.2 Hz, 4H), 6.93 (d, J=8.2 Hz, 4H). HRMS (ESI, M$^{2+}$) C$_{47}$H$_{70}$O$_4$N$_2$ Calcd. 364.2753, found 364.2636.

1,1'-((((((5r,7r)-adamantan-2-ylidene)methylene)bis(4,1-phenylene))bis(oxy))bis(hexane-6,1-diyl))bis(1-(2-hydroxyethyl)pyrrolidin-1-ium) diiodide (NB-140)

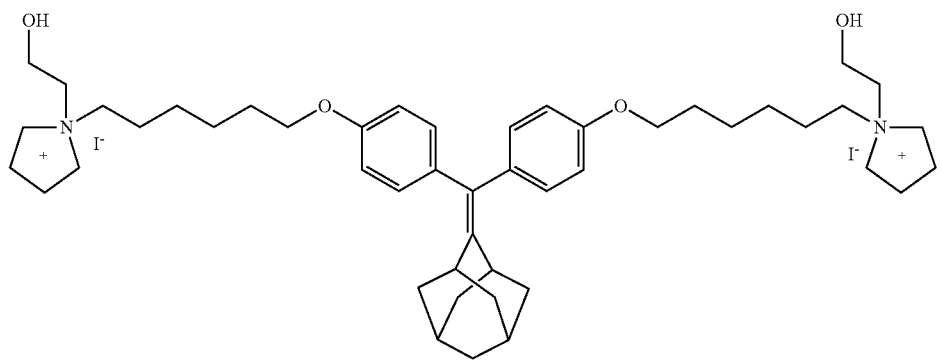

NB-140 (13 mg) was prepared from the reaction of the NB-65 (10.0 mg, 0.016 mmol) and 2-iodoethanol (100 μL) by following the procedure as described to prepare for NB-68.

$^1$H NMR (500 MHz, Chloroform-d+methanol-d$_4$) δ 1.36 (d, J=7.9 Hz, 4H), 1.45 (t, J=7.8 Hz, 4H), 1.62-1.79 (m, 18H), 1.86 (s, 2H), 2.06-2.24 (m, 8H), 2.64 (s, 2H), 3.27-3.34 (m, 4H), 3.34-3.42 (m, 4H), 3.44-3.53 (m, 4H), 3.60-3.68 (m, 4H), 3.81-3.89 (m, 8H), 6.67 (d, J=8.2 Hz, 4H), 6.89 (d, J=8.2 Hz, 4H). HRMS (ESI, M$^{2+}$) C$_{47}$H$_{70}$O$_4$N$_2$ Calcd. 364.2753, found 364.2746.

1,1'-((((((5r,7r)-adamantan-2-ylidene)methylene)bis (4,1-phenylene))bis(oxy))bis(hexane-6,1-diyl))bis(1-(2-hydroxyethyl)piperidin-1-ium) diiodide (NB-141)

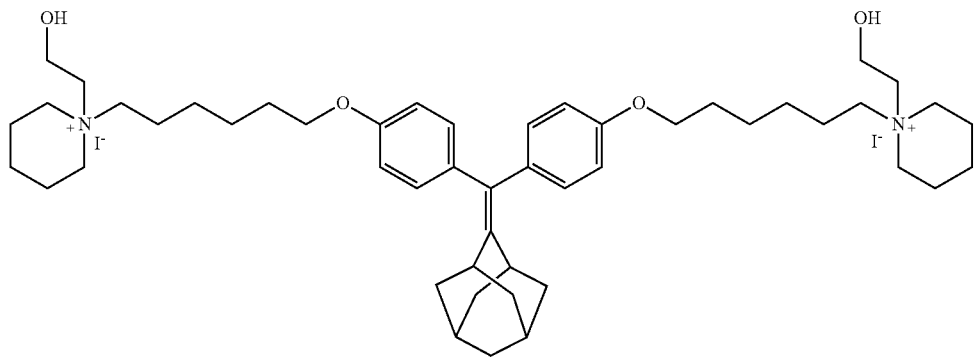

NB-141 (14 mg) was prepared from the reaction of the NB-70 (10.0 mg, 0.015 mmol) and 2-iodoethanol (100 μL) by following the procedure as described to prepare for NB-71.

$^1$H NMR (500 MHz, Chloroform-d+methanol-$d_4$) δ 1.31-1.41 (m, 4H), 1.41-1.51 (m, 4H), 1.60-1.76 (m, 22H), 1.76-1.88 (m, 10H), 2.63 (s, 2H), 3.20-3.51 (m, 16H), 3.80-3.90 (m, 8H), 6.67 (d, J=8.4 Hz, 4H), 6.88 (d, J=8.2 Hz, 4H). HRMS (ESI, M$^{2+}$) $C_{49}H_{74}O_4N_2$ Calcd. 378.2903, found 378.2879.

1,1'-((((((5r,7r)-adamantan-2-ylidene)methylene)bis (4,1-phenylene))bis(oxy))bis(hexane-6,1-diyl))bis(1-(2-hydroxyethyl)azepan-1-ium) diiodide (NB-142)

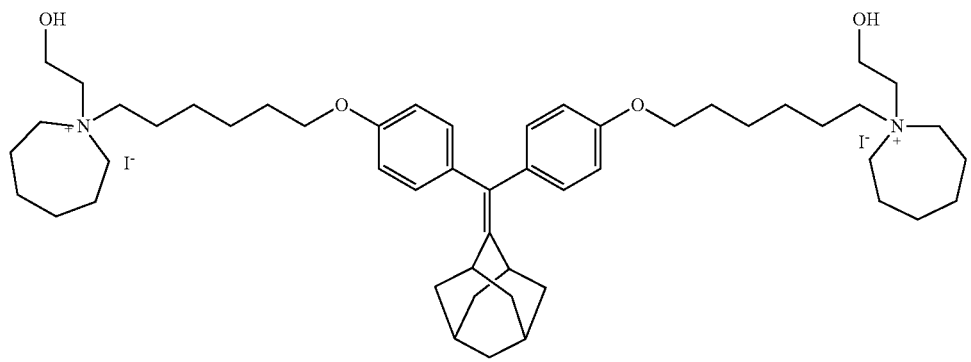

NB-142 (14 mg) was prepared from the reaction of the NB-72 (10.0 mg, 0.014 mmol) and 2-iodoethanol (100 μL) by following the procedure as described to prepare for NB-73.

$^1$H NMR (500 MHz, Chloroform-d+methanol-$d_4$) δ 1.35-1.46 (m, 4H), 1.47-1.56 (m, 4H), 1.61-1.84 (m, 26H), 1.90 (s, 10H), 2.68 (s, 2H), 3.25-3.48 (m, 12H), 3.57 (d, J=30.8 Hz, 4H), 3.90 (t, J=6.1 Hz, 4H), 3.93-4.00 (m, 4H), 6.73 (d, J=8.2 Hz, 4H), 6.94 (d, J=8.0 Hz, 4H). HRMS (ESI, M$^{2+}$) $C_{51}H_{78}O_4N_2$ Calcd. 392.3059, found 392.3055.

6-(4-(((E)-((5R,7R)-Adamantan-2-ylidene)(4-((6-azidohexyl)oxy)phenyl)methyl)phenoxy)hexyl methanesulfonate (6)

1-(6-(4-(((Z)-((5r,7r)-adamantan-2-ylidene)(4-((6-azidohexyl)oxy)phenyl)methyl)phenoxy)hexyl) azepane (N₃-NB-72)

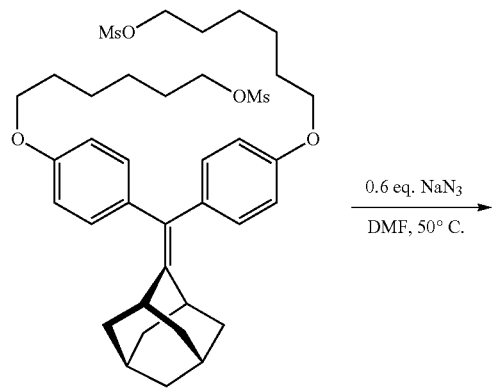

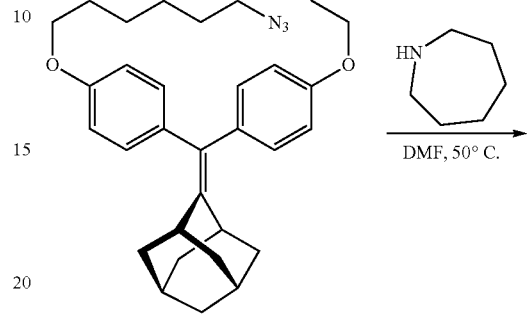

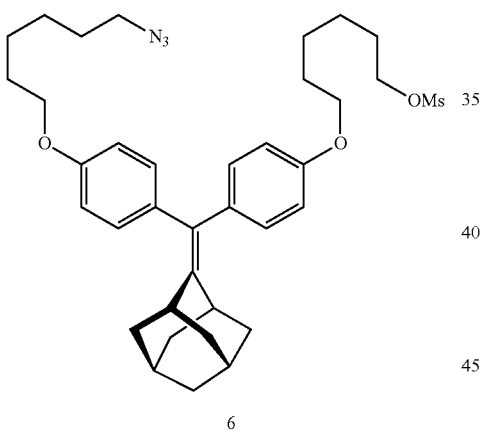

The mixture of the compound 2 (34 mg, 0.05 mmol) and NaN₃ (2.0 mg, 0.03 mmol) in DMF (100 μL) was stirred for 1 hr at 50° C. The solvent was removed with gentle stream of nitrogen, flowed by redissolving it into EtOAc (200 μL) to load a SiO₂ Preparative TLC (20×20 cm) to collect the title compound 6 (20 mg) (film type solid) with 10% EtOAc/n-Hexane.

$^1$H NMR (500 MHz, CDCl₃) δ 1.42-1.57 (m, 8H), 1.65 (quintet, J=7.5 Hz, 2H), 1.76-1.92 (m, 14H), 2.01 (brs, 2H), 2.81 (Brs, 2H), 3.01 (s, 3H), 3.30 (t, J=7.0 Hz, 2H), 3.95 (t, J=6.0 Hz, 4H), 4.26 (t, J=7.0 Hz, 2H), 6.79 (d, J=8.5 Hz, 2H), 6.80 (d, J=8.5 Hz, 2H), 7.03 (d, J=8.5 Hz, 4H). $^{13}$C NMR (126 MHz, CDCl₃) δ 25.49, 25.87, 25.99, 26.77, 28.47, 29.06, 29.33, 29.38, 29.46, 34.67, 37.44, 37.62, 39.85, 51.65, 67.69, 67.78, 70.23, 113.98, 129.85, 130.84, 135.94, 135.99, 145.94, 157.44, 157.48. FIRMS (ESI, M$^+$+1) C₃₆H₅₀O₅N₃S Calcd. 636.3471, found 636.3451.

N₃-NB-72 (12 mg) was obtained from the reaction of the compound 6 (15 mg, 0.024 mmol) and azepane (20 mg, 0.02 mmol) following the procedure as described to prepare for NB-65.

$^1$H NMR (500 MHz, CDCl₃) δ 1.37 (quintet, J=7.0 Hz, 2H), 1.44-1.57 (m, 8H), 1.59-1.70 (m, 10H), 1.76-1.84 (m, 4H), 1.84-1.93 (m, 10H), 2.02 (brs, 2H), 2.49 (t, J=7.5 Hz, 2H), 2.64 (t, J=6.0 Hz, 4H), 2.82 (Brs, 2H), 3.31 (t, J=7.0 Hz, 2H), 3.95 (q, J=6.0 Hz, 4H), 6.81 (d, J=8.5 Hz, 4H), 7.03 (d, J=8.5 Hz, 2H), 7.04 (d, J=8.5 Hz, 2H). $^{13}$C NMR (126 MHz, CDCl₃) δ 25.99, 26.33, 27.26, 27.65, 27.67, 28.08, 28.48, 29.06, 29.46, 29.59, 34.67, 37.46, 39.86, 51.65, 55.82, 58.50, 67.77, 67.99, 113.98, 113.99, 129.90, 130.81, 130.84, 135.85, 135.97, 145.87, 157.46, 157.56. FIRMS (ESI, M$^+$+1) C₄₁H₅₉O₂N₄ Calcd. 639.4638, found 639.4639.

97

6-(4-((E)-((5r,7r)-adamantan-2-ylidene)(4-((6-(azepan-1-yl)hexyl)oxy)phenyl)methyl)phenoxy)hexan-1-amine (NH$_2$-NB-72)

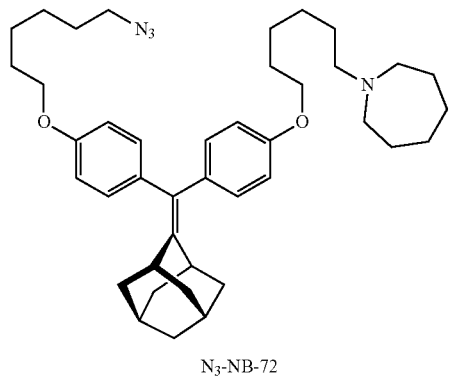

N$_3$-NB-72

LAH
───→
Et$_2$O, r.t.

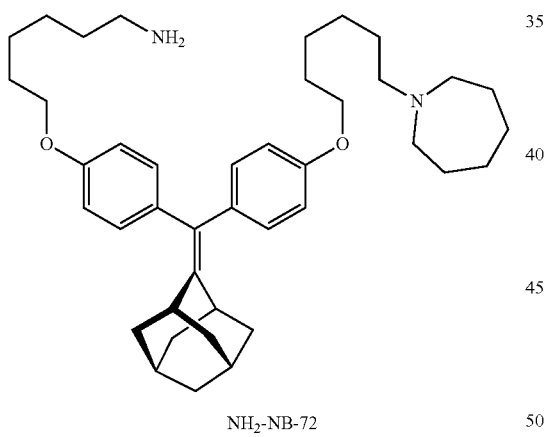

NH$_2$-NB-72

LAH (lithium aluminum hydride, 8 mg, 0.21 mmol) was added to the solution N$_3$-NB-72 (10 mg, 0.016 mmol) in diethyl ether (500 μL) and left the reaction solution in inert atmosphere environment for 1 hr at rt. To this added 10% NaOH aqueous solvent, extracted with dichloromethane (200 μL×4), washed with a deionized water, dried over Na$_2$SO$_4$, and evaporation afforded NH$_2$—NB-72 (5 mg) as a film type solid. This was used without further purification.

$^1$H NMR (500 MHz, CDCl$_3$) δ 1.30-1.43 (m, 4H), 1.45-1.58 (m, 8H), 1.59-1.69 (m, 8H), 1.76~1.84 (m, 4H), 1.84-1.94 (m, 10H), 2.02 (brs, 2H), 2.48 (t, J=7.5 Hz, 2H), 2.64 (t, J=6.0 Hz, 4H), 2.71 (t, J=7.5 Hz, 2H), 2.82 (Brs, 2H), 3.95 (q, J=6.0 Hz, 4H), 6.80 (d, J=8.5 Hz, 4H), 7.04 (d, J=8.5 Hz, 4H). ESI (m/z, (M+2H)$^{2+}$) 307.6.

98

5-((6-(4-((L')-((5r,7r)-adamantan-2-ylidene)(4-((6-(azepan-1-yl)hexyl)oxy)phenyl)methyl)phenoxy)hexyl)carbamoyl)-2-(6-hydroxy-3-oxo-3H-xanthen-9-yl)benzoic acid (Fluorescein-NB-72)

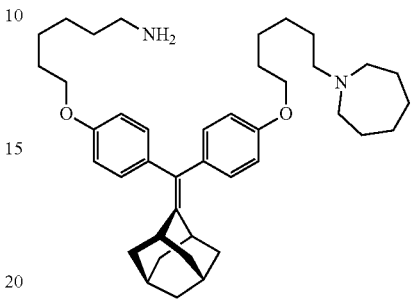

NH$_2$-NB-72

5-FAM
────→
DMF, Et$_3$N, r.t.

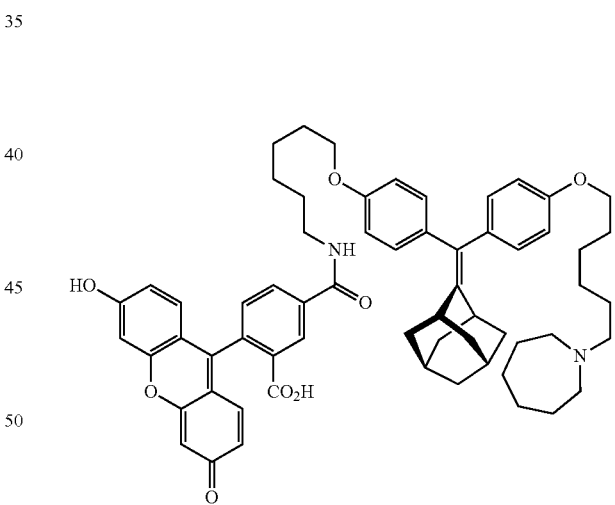

Fluorescein-NB-72

To the mixture of NH$_2$—NB-72 (3 mg, 4.90 μmol) and 5-FAM (3.4 mg, 7.40 μmol) in DMF (100 μL) was added (11 mg, 0.11 mmol) at rt and reacted for 1 hr at rt. After the solvent was evaporated using a nitrogen stream, the title compound (Fluorescein-NB-72, 1.4 mg) was separated on SiO$_2$ PLC using 10% MeOH/DCM (v/v). ESI (m/z) 971.9 (M$^+$+1), 487.6 (M/Z$^{2+2H}$).

1-(6-(4-(((1r,3r,5r,7r)-adamantan-2-ylidene)(4-((6-aminohexyl)oxy)phenyl)methyl)phenoxy)hexyl)-1-methylazepan-1-ium iodide (N₃-NB-73)

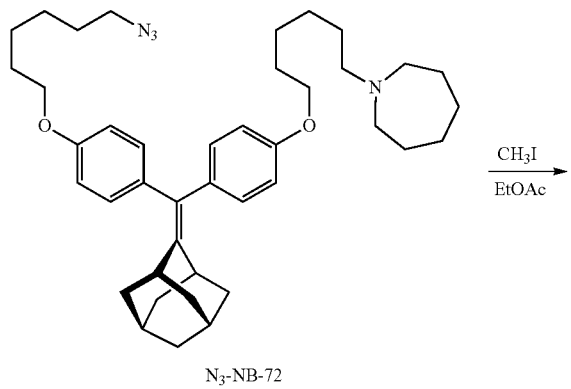

N₃-NB-72

¹H NMR (500 MHz, CDCl₃) δ 1.49-1.51 (m, 8H), 1.65 (quintet, J=7.0 Hz, 2H), 1.72-1.92 (m, 20H), 1.92-2.05 (m, 6H), 2.79 (Brs, 2H), 3.29 (t, J=7.0 Hz, 2H), 3.33 (s, 3H), 3.60-3.70 (m, 6H), 3.94 (t, J=6.0 Hz, 2H), 3.95 (t, J=6.0 Hz, 2H), 6.80 (d, J=8.5 Hz, 4H), 7.03 (d, J=8.5 Hz, 2H), 7.04 (d, J=8.5 Hz, 2H). ¹³C NMR (126 MHz, CDCl₃) δ 22.39, 23.14, 25.98, 26.02, 26.25, 26.76, 27.64, 28.46, 29.05, 29.28, 29.46, 34.67, 37.44, 39.86, 51.64, 65.21, 65.30, 67.63, 67.83, 114.03, 114.06, 129.82, 130.79, 130.82, 135.95, 136.02, 146.03, 157.40, 157.50. HRMS (ESI, M⁺) $C_{42}H_{61}O_2N_4$ Calcd. 653.4795, found 653.4780.

1-(6-(4-((Z)-((5r,7r)-adamantan-2-ylidene)(4-((6-(4-((3-carboxy-4-(6-hydroxy-3-oxo-3H-xanthen-9-yl)benzamido)methyl)-1H-1,2,3-triazol-1-yl)hexyl)oxy)phenyl)methyl)phenoxy)hexyl)-1-methylazepan-1-ium iodide (Fl-NB-73)

Fl-NB-73

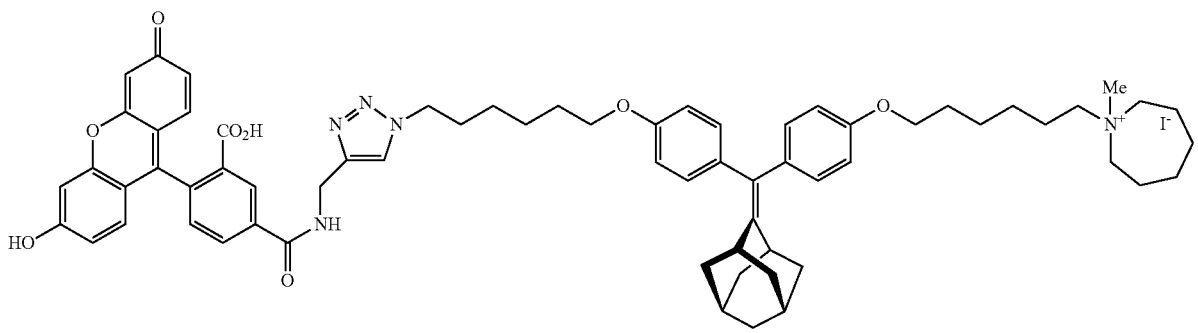

-continued

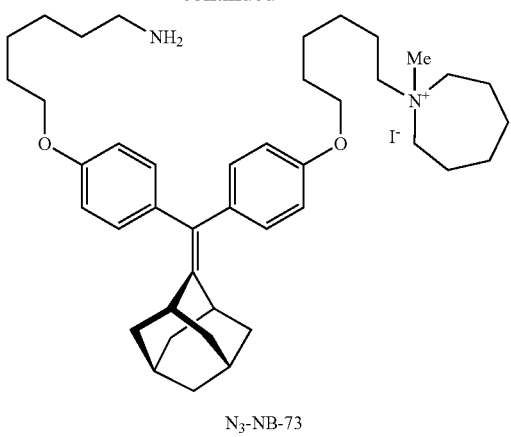

N₃-NB-73

N₃-NB-73 (3.7 mg) was obtained from the reaction of the N₃-NB-72 (3 mg, 4.89 μmol) and methyl iodide (100 μL) in ethyl acetate solvent (100 μL) by following the procedure as described to prepare for NB-68.

The mixture of the N₃-NB-73 (3 mg, 3.8 μmol) and fluorescein-propargyl amide (3 mg, 7.2 μmol) in the presence of 0.2 mol % CuI in a 1:1 mixture of DIEA:AcOH (20 μL) in DCM (200 μL) was stirred for 2 hr at rt. The reaction mixture was loaded on a SiO₂ TLC plate (20×20 cm) directly. Developing with 25% MeOH/DCM (v/v) provided the title compound Fl-NB-73 (2.1 mg, Rf=0.15). FIRMS (ESI, M⁺) $C_{66}H_{76}O_8N_5$ Calcd. 1066.5694, found 1066.5677.

Example 2. Structure-Activity Analysis of FOXM1 Inhibitors

Using a high throughput fluorescence-resonance energy transfer assay to screen for inhibitors of the binding of full length FOXM1 to a FOXM1 DNA response element, ~170,000 compounds were evaluated consisting of libraries from Cambridge Inc., in-house University of Illinois research samples, and an NCI inventory. Only 47 molecules were found to be substantive hits, and of these only three remained after further filtering for pan-assay interference (PAIN) and promiscuous-type compounds (see below). The potency of these three compounds as inhibitors of the proliferation of several breast cancer cell lines was modest, ca. 15-25 μM. Prominent, common features of these compounds were: 1) an acid function, and 2) a lipophilic core, potentially with an adamantane moiety.

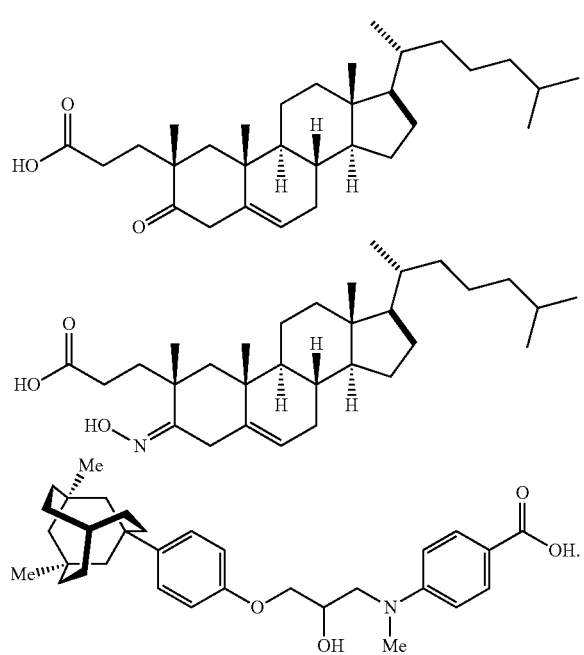

Diaryl Alkylidine Monoamines and their Methiodide Salts After further studies of various lipophilic acid compounds that proved unfruitful, and without being limited to any particular theory, it was hypothesized that the combination of a lipophilic core with an amine function might produce more potent FOXM1 inhibitors. Based on this hypothesis, as shown in Table 1, members of the adamantane-2-methylidene-(2-chlorophenyl-2-phenoxyalkyl-tertiary amine) system (NB-41, 54, 55, 60, 62, 63, 64, 84, 85, 118, and 119) were prepared, which have a mono hexamethylene linker, and evaluated in breast cancer cell proliferation assays. These compounds have a core consisting of a diaryl alkylidine system connected to an adamantyl unit. The sole phenolic compound NB-41 showed very good anti-proliferative activity against both MCF-7 and DT-22 cells ($IC_{50}$=1.5-2.0 μM), being two fold more potent than FDI6 ($IC_{50}$=3.1 μM for MCF-7, 4.8 μM for DT-22, and 4.5 μM for MDA-MB-231) and almost equivalent to thiostrepton ($IC_{50}$=1.4 μM for MCF-7, 3.6 μM for DT-22), both known FOXM1 inhibitors. The phenolic OH in NB-41, however, gives this compound high binding affinity to the estrogen receptor α (ERα) and antiestrogenic activity. To reduce its ERα binding affinity and thereby mitigate its action through ERα, the phenolic OH was converted to a chloride; this change reduced the relative binding affinity (RBA) of the phenol NB-41 for ERα from 82 to 1.2 for the chloro compound NB-54 (the RBA for estradiol is 100). Most of the chlorine-substituted compounds (NB-54, 55, 60, 62, 63, 64, 84, 85, 118, and 119) that were tested had very low RBAs for ERα, in the range of 0.1 to 0.3; only NB-54 was somewhat greater (1.2). The low level of ERα binding of these compounds should ensure that their antiproliferative activity in ERα-positive breast cancer cells (e.g., MCF-7 cells) involves action through FOXM1 and is minimally affected by interaction with ERα; their action on ERα-negative DT-22 and MDA-MB-231 cells cannot involve ERα.

TABLE 1

Mono linear alkyl linked amines and their methiodide salt derivatives.

| Code # | Structure | RBA* ERα | $IC_{50}$ (μM) MCF7 | $IC_{50}$ (μM) DT-22 | $IC_{50}$ (μM) MDA-MB-231 | PK (40 mg/kg) s.c. ($AUC_{0-48}$(μM*hr), $t_{1/2}$ (hr)) | PK (40 mg/kg) p.o. ($AUC_{0-48}$(μM*hr), $t_{1/2}$ (hr)) |
|---|---|---|---|---|---|---|---|
| NB-41 | 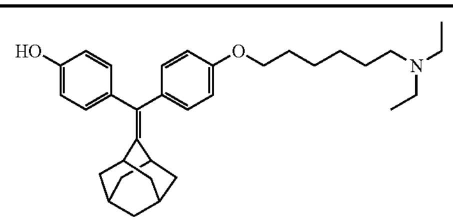 | 82.0 | 1.5 | 2.0 | n.a | 13.3, 22.5 | 5.6, 15.1 |
| NB-54 | 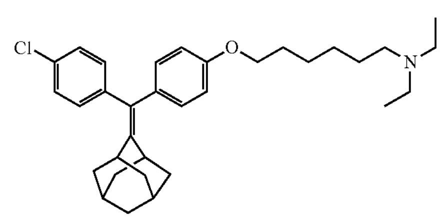 | 1.17 | 4.0 | n.a | 4.0 | n.a | n.a |
| NB-55 | 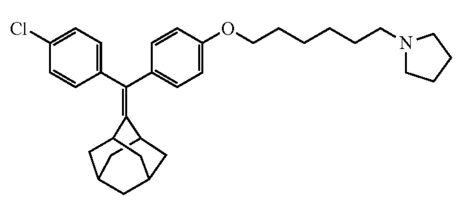 [SMILES: Clc1ccc(C(=C2C3CC4CC(C3)CC2C4)c2ccc(OCCCCCCN3CCCC3)cc2)cc1] | 0.34 | 3.0 | 6.0 | 10 | 34.7, 26.7 | 35.7, 16.6 |

TABLE 1-continued
Mono linear alkyl linked amines and their methiodide salt derivatives.
| Code # | Structure | RBA* ERα | IC$_{50}$ (μM) | | | PK (40 mg/kg) | |
| --- | --- | --- | --- | --- | --- | --- | --- |
| | | | MCF7 | DT-22 | MDA-MB-231 | s.c. (AUC$_{0-48}$(μM*hr), t$_{1/2}$ (hr)) | p.o. |
| NB-63 | 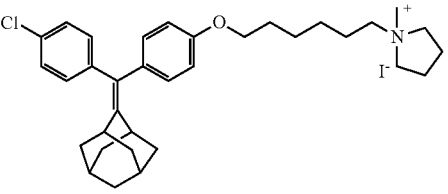 | 0.15 | 5.5 | 6.0 | n.a | 159.7, 31.5 | too low to measure |
| NB-60 | 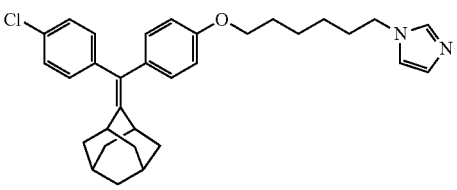 [SMILES: Clc1ccc(C(=C2C3CC4CC(C3)CC2C4)c2ccc(OCCCCCCn3ccnc3)cc2)cc1] | n.a. | 16 | n.a | n.a | n.a | n.a |
| NB-62 | 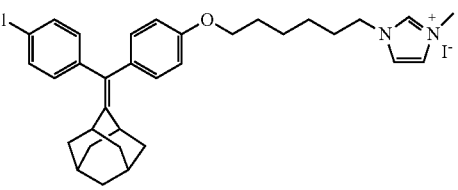 | 0.16 | 5.5 | n.a | n.a | 150.3, 36.8 | too low to measure |
| NB-64 | 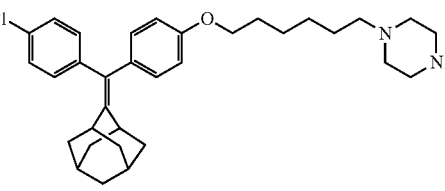 | 0.12 | 3.0 | n.a | n.a | n.a | n.a |
| NB-118 | 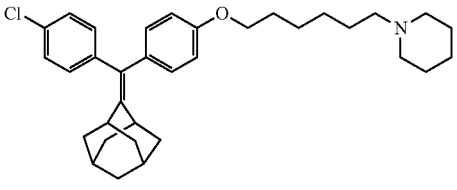 [SMILES: Clc1ccc(C(=C2C3CC4CC(C3)CC2C4)c2ccc(OCCCCCCN3CCCCC3)cc2)cc1] | n.a. | 4.4 | n.a | n.a | n.a | n.a |
| NB-84 | 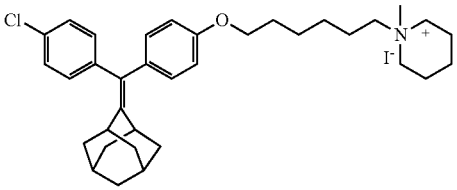 | n.a. | 6.0 | n.a | n.a | n.a | n.a |
| NB-119 | 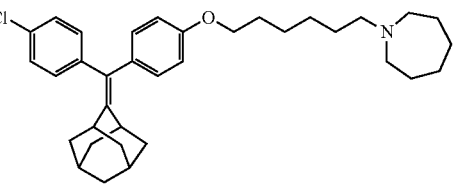 | n.a. | 4.2 | n.a | n.a | n.a | n.a |

TABLE 1-continued

Mono linear alkyl linked amines and their methiodide salt derivatives.

| Code # | Structure | RBA* ERα | MCF7 | IC₅₀ (μM) DT-22 | MDA-MB-231 | s.c. | PK (40 mg/kg) p.o. (AUC₀₋₄₈(μM*hr), $t_{1/2}$ (hr)) |
|---|---|---|---|---|---|---|---|
| NB-85 |  | n.a. | 9.8 | n.a | n.a | n.a | n.a | s.c.:DMSO:Corn oil (1:10) 100 μL injection; p.o.: PEG400:PVP:Tween 80:CMC (9:0.5:0.5:90) 200 μL adm.
*:RBA was evaluated based on 100 binding affinity of estradiol to estrogen receptor.

Although the activity of these compounds was somewhat less compared to NB-41, compounds NB-55, 64, 118, and 119 had more potent anti-proliferative effects against MCF-7 cells than that of the known small molecule FOXM1 inhibitor, FDI6. For further study, the methiodide salts were prepared from some of these amines. Comparisons of the anti proliferative potencies of the amines vs. their methiodide salts showed that in three cases, the amines had higher potencies (NB-55 vs. NB-63, NB-118 vs. NB-84, and NB-119 vs. NB-85). In contrast, the imidazolylium methiodide (NB-62) had a three-fold greater anti-proliferative potency compared to its parent compound (NB-60). The activity of these compounds on the activity of genes known to be regulated by FOXM1 was investigated, and it was found that NB-55 reversed the effect of FOXM1 on genes that were both upregulated and downregulated by this transcription factor, consistent with effects expected for FOXM1 inhibition by a small molecule (FIGS. 15A-15B and FIGS. 16A-16F).

In pharmacokinetic studies, NB-55 demonstrated a relatively good profile of blood levels, sufficient to reach therapeutic levels in blood when 80 mg/kg was administered, either through subcutaneous (s.c.) or oral (p.o.) routes. Moreover, it is worthwhile to note that although the methiodide salt NB-63 had somewhat reduced anti-proliferative activity compared to its parent compound (NB-55), the area under the curve measure [AUC (μM*h)] after s.c. administration of NB-63 was approximately 3 fold greater and its $t_{1/2}$ was somewhat extended compared to NB-55. The PK profile for the methiodide salt NB-63 after p.o. administration, however, was less good than for the amine NB-55. Under these conditions, the results show that the methiodide salt forms have poorer PK activity p.o. than the parent compounds, but often superior PK profiles s.c.

Diaryl Alkylidine Diamines and Their Methiodide Salts
Next, the related diamines, adamantane-2-methylidene-(2, 2-bis(phenoxy-alkyl-tertiary amine)) systems were investigated to determine whether replacing the chloro group with a second alkoxy-tertiary amine group would improve their cellular anti-proliferative activity as well as reduce their ERα binding affinity compared to those of the mono amine series. The results are shown in Tables 2 and 3. The bis(diethylaminohexyl) linker system (NB-51) showed ~5 fold improvement in anti-proliferative activity (IC₅₀=0.7 μM) in MCF-7 cells compared to the corresponding mono-amine NB-54 (IC₅₀=4.0 μM). Unlike the compounds with mono-(tertiary amine)hexyl linkers and their methiodide salts shown in Table 1, it is noteworthy that the bismethiodide salt (NB-115) exhibited a two-fold improvement (IC₅₀=0.8 μM) in suppressing proliferation of the ERα-negative breast cancer cell line DT-22 compared to that of its parent diamine compound NB-51 (IC₅₀=1.5 μM), while its activity on MCF-7 cells was relatively unchanged. Despite its good cellular activity, NB-51 did not show a sufficiently good PK profile (by either s.c. or p.o. routes) for further in vivo study. In contrast to the diamine NB-51, its methiodide salt (NB-115) showed a vastly improved PK profile after s.c. administration in terms of AUC (746 μM*h) with preservation of a favorable clearance time $t_{1/2}$ (38.6 hr). This profile was sufficiently favorable for an in vivo study using a low dose of NB-115.

TABLE 2

Bis linear C4, C5, and C8 linked amine derivatives and their methiodide salts.

| Code # | Structure | RBA ERα | MCF7 | IC₅₀ (μM) DT-22 | MDA-MB-231 | s.c. | PK (40 mg/kg) p.o. (AUC₀₋₄₈(μM*hr), $t_{1/2}$ (hr)) |
|---|---|---|---|---|---|---|---|
| NB-120 | 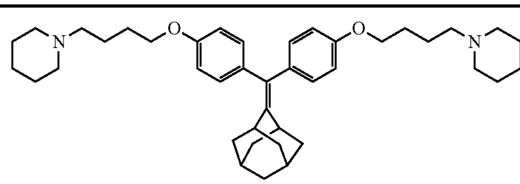 | n.a | 0.9 | n.a | n.a | n.a | n.a |

TABLE 2-continued

Bis linear C4, C5, and C8 linked amine derivatives and their methiodide salts.

| Code # | Structure | RBA ERα | IC$_{50}$ (μM) | | | PK (40 mg/kg) | |
|---|---|---|---|---|---|---|---|
| | | | MCF7 | DT-22 | MDA-MB-231 | s.c. (AUC$_{0-48}$(μM*hr), t$_{1/2}$ (hr)) | p.o. |
| NB-86 | 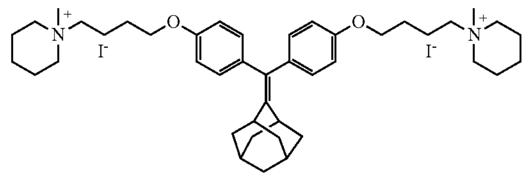 | n.a | 1.4 | 1.9 | 1.1 | n.a | n.a |
| NB-121 | 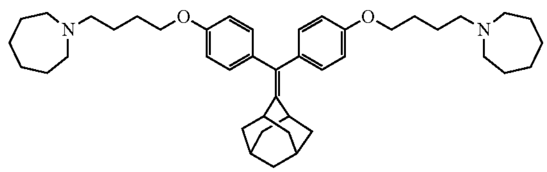 [SMILES: c1cc(C(=C2C3CC4CC(C3)CC2C4)c2ccc(OCCCCN3CCCCCC3)cc2)ccc1OCCCCN1CCCCCC1] | n.a | 1.6 | n.a | n.a | n.a | n.a |
| NB-87 | 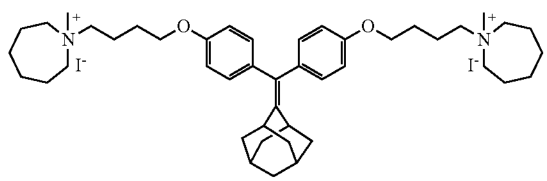 | n.a | 1.7 | 1.5 | 0.9 | n.a | n.a |
| NB-122 | 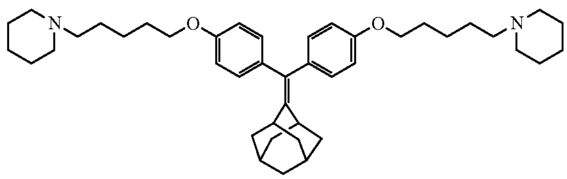 [SMILES: c1cc(C(=C2C3CC4CC(C3)CC2C4)c2ccc(OCCCCCN3CCCCC3)cc2)ccc1OCCCCCN1CCCCC1] | n.a | 1.2 | n.a | n.a | n.a | n.a |
| NB-88 | 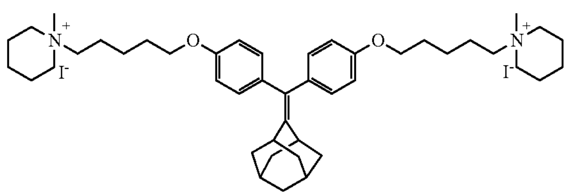 | n.a | 1.7 | 1.2 | 0.7 | n.a | n.a |
| NB-123 | 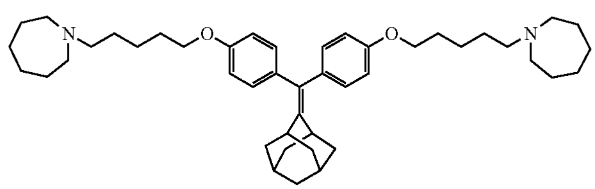 [SMILES: c1cc(C(=C2C3CC4CC(C3)CC2C4)c2ccc(OCCCCCN3CCCCCC3)cc2)ccc1OCCCCCN1CCCCCC1] | n.a | 1.0 | n.a | n.a | n.a | n.a |
| NB-89 | 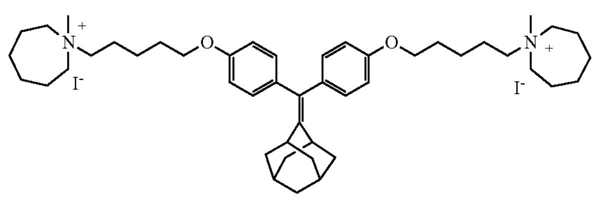 | n.a | 0.7 | 1.1 | 0.5 | n.a | n.a |
| NB-80 | 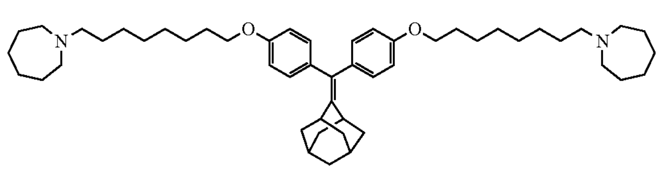 [SMILES: c1cc(C(=C2C3CC4CC(C3)CC2C4)c2ccc(OCCCCCCCCN3CCCCCC3)cc2)ccc1OCCCCCCCCN1CCCCCC1] | n.a | 2.7 | 3.4 | n.a | n.a | n.a |

TABLE 2-continued

Bis linear C4, C5, and C8 linked amine derivatives and their methiodide salts.

| Code # | Structure | RBA ERα | IC$_{50}$ (μM) MCF7 | DT-22 | MDA-MB-231 | PK (40 mg/kg) s.c. p.o. (AUC$_{0-48}$(μM*hr), t$_{1/2}$ (hr)) |
|---|---|---|---|---|---|---|
| NB-81 | 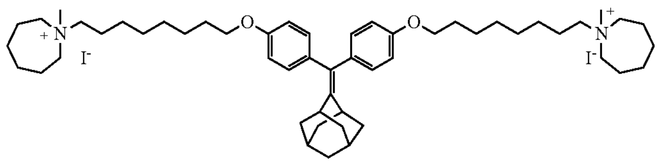 | n.a | 0.6 | 1.6 | n.a | Died at 40 mg/kg s.c adm. |

TABLE 3

Bishexamethylene linked amines, their methiodide salt derivatives.

| Code # | Structure | RBA ERα | IC$_{50}$ (μM) MCF7 | DT-22 | MDA-MB-231 | PK (60 mg/kg) s.c. p.o. (AUC$_{0-48}$(μM*hr), t$_{1/2}$ (hr)) |
|---|---|---|---|---|---|---|
| NB-51 | 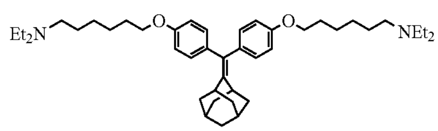 | 0.21 | 0.7 | 1.5 | n.a. | 4.7, 61.8* 1.8, 20.1* |
| NB-115 | 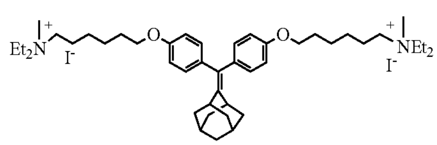 | n.a. | 1.1 | 0.8 | n.a. | 746.2, 38.6# too low to measure |
| NB-53 | 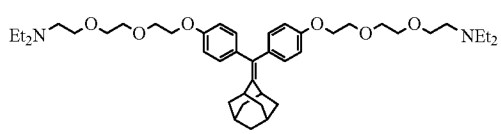 | 0.15 | 3.5 | n.a. | <5 | n.a. n.a. |
| NB-133 | 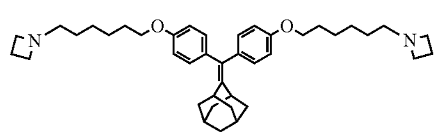 [SMILES: c1cc(C(=C2C3CC4CC(C3)CC2C4)c2ccc(OCCCCCCN3CCC3)cc2)ccc1OCCCCCCN1CCC1] | n.a | 0.8 | n.a | n.a. | n.a n.a |
| NB-137 | 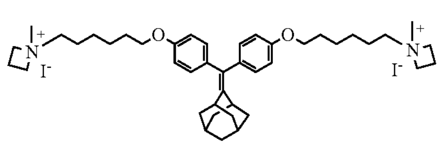 | n.a | 2.3 | n.a | n.a. | n.a. n.a |
| NB-65 | 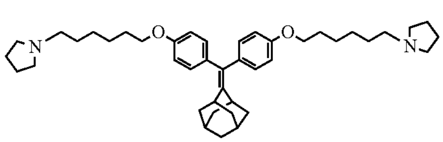 [SMILES: c1cc(C(=C2C3CC4CC(C3)CC2C4)c2ccc(OCCCCCCN3CCCC3)cc2)ccc1OCCCCCCN1CCCC1] | 0.05 | 0.8 | 1.0 | n.a. | 14.76, 48.6 too low to measure |

TABLE 3-continued

Bishexamethylene linked amines, their methiodide salt derivatives.

| Code # | Structure | RBA ERα | IC$_{50}$ (μM) MCF7 | DT-22 | MDA-MB-231 | PK (60 mg/kg) s.c. (AUC$_{0-48}$(μM*hr), t$_{1/2}$ (hr)) | p.o. |
|---|---|---|---|---|---|---|---|
| NB-68 | 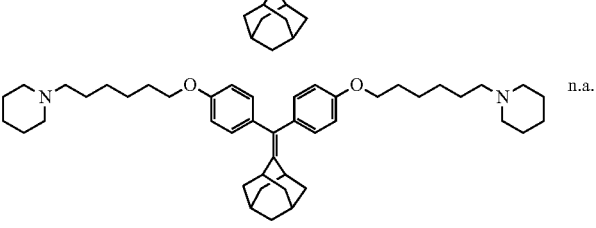 | 0.05 | 0.8 | 0.7 | 1.7 | 289.4, 109.3 | 0.18, 18.5 |
| NB-70 | 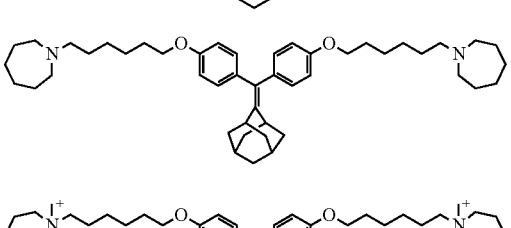 | n.a. | 0.7 | n.a. | 0.9 | 10.2, 221.5 | 6.0, 90.9 |
| NB-71 | 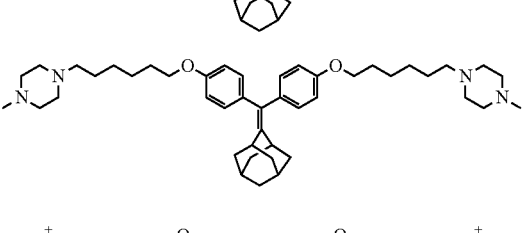 | n.a. | 1.1 | 0.8 | 0.5 | 364.3, 119.2 | n.a. |
| NB-72 | 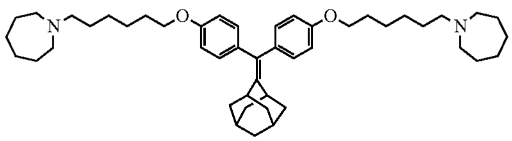 [SMILES: c1cc(C(=C2C3CC4CC(C3)CC2C4)c2ccc(OCCCCCCN3CCCCCC3)cc2)ccc1OCCCCCCN1CCCCCC1] | n.a. | 0.7 | 0.7 | n.a. | n.a. | n.a. |
| NB-73 | 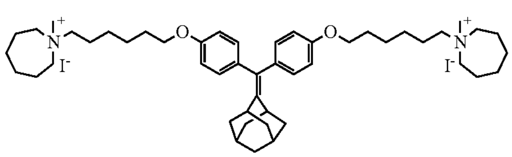 | n.a. | 0.7 | 0.5 | 0.3 | 190.5, 170.0 | too low to measure |
| NB-66 | 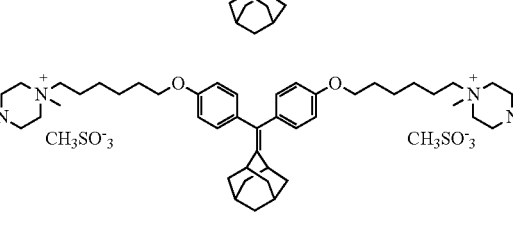 | 0.05 | 0.8 | n.a. | n.a. | 6.1, 45.6 | too low to measure |
| NB-69 | 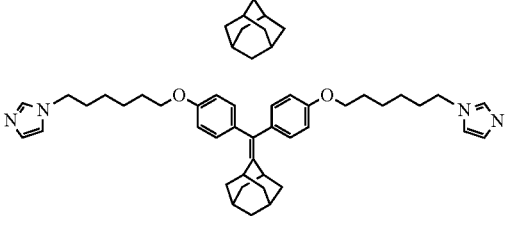 | n.a. | 6.0 | n.a. | n.a. | n.a. | n.a. |
| NB-61 | 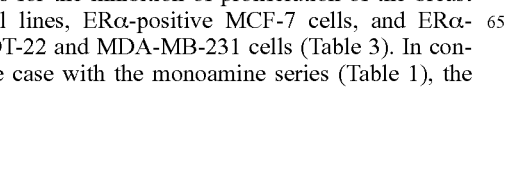 | n.a. | 7.5 | n.a. | n.a. | n.a. | n.a. |

*20 mg/kg administration. #40 mg/Kg.

It is notable that most of the bis(phenoxy-alkyl-tertiary amine systems (NB-65, 66, 70, and 72) had submicromolar IC$_{50}$ values for the inhibition of proliferation of the breast cancer cell lines, ERα-positive MCF-7 cells, and ERα-negative DT-22 and MDA-MB-231 cells (Table 3). In contrast to the case with the monoamine series (Table 1), the methiodide salts of most of these diamines had antiproliferative potencies very similar to those of the corresponding diamines (NB-68 vs. NB-65; NB-71 vs. NB-70; NB-73 vs. NB-72). Only the piperazinyl-based compound (NB-66) as the methanesulfonate salt (NB-69) had markedly reduced potency (IC$_{50}$=6.0 μM for the salt vs. IC$_{50}$=0.8 μM for the diamine). The imidazolyl-terminated system (NB-61, $IC_{50}$=7.5 µM) also showed a poorer activity compared to other alkyl based bis(tertiary amine) systems. When the ring size of the terminal amine is changed from open chain (diethylamine, NB-51), to 5-membered cyclic (pyrrolidine, NB-65), 6-membered cyclic (piperidine, NB-70), of 7-membered cyclic (azepane, NB-72) amines, the $IC_{50}$ values for inhibition of MCF-7, DT-22, and MDA-MB-231 cells showed essentially no change. It is also notable that—where assayed—both the diamines and their methiodide salts had very low binding affinities for the ERα. Many of these compound have inhibitory effects on FOXM1-regulated genes (as shown in FIGS. 15A-15B and FIGS. 16A-16F). The PK properties of NB-65, NB-68, NB-70, NB-71, NB-73 and NB-66 indicate that, where comparisons can be made, the bismethiodide salts are superior to the bisamines after s.c. administration, but less good after p.o. administration.

NB-73, which has a 7-membered amine ring and is the methiodide salt of NB-72, showed submicromolar potency in suppressing proliferation ($IC_{50}$=0.7 µM for MCF-7, 0.5 µM for DT-22, and 0.3 µM for MDA-MB-231 cells), as well as a good gene regulatory activity. Unlike the bishexyl linker of most of the compounds, the bis(triethyleneglycol) linker in NB-53 does not show any benefit in increasing antiproliferative potency compared to other bishexyl linked compounds, as shown in Table 3.

The effect of the length of the linear alkyl linker was investigated (Table 2). The bisbutyl systems (NB-120 and NB-121) and their methiodide salts (NB-86 and NB-87), the bispentyl systems (NB-122 and NB-123) and their methiodide salts (NB-88 and NB-89), and the bisoctyl system and its salt (NB-80 and NB-81) were synthesized and evaluated for their antiproliferative potencies on MCF-7, DT-22, and MDA-MB-231 cells, as shown in Table 2. In general, most compounds had $IC_{50}$ values of 1.0-2.0 µM for MCF-7 cells, except for NB-89, the methiodide salt of NB-123 linked with pentyl group; its $IC_{50}$ values were 0.6 µM, 1.1 µM, and 0.5 µM on MCF-7, DT-22, and MDA-MB-231 cells, respectively. Overall, compared to other alkyl linkers, linking the terminal tertiary amine group to the core system with a hexyl group appeared to be preferred for FOXM1 to have an anti-proliferative effect on breast cancer cells.

Results from additional compounds that have hydroxyl-substituted his-amine and bisammonium groups on the side chains, are provided in Table 4. Their $IC_{50}$ values for inhibition of MCF7 cell proliferation are similar to those of other bisamine and bisammonium compounds (Tables 2-3), being in the single digit micromolar to submicromolar range.

TABLE 4

Bishexamethylene linked hydroxylamines and their methiodide salt derivatives.

| Code # | Structure | RBA ERα | IC$_{50}$ (µM) MCF7 | DT-22 | MDA-MB-231 | PK (40 mg/kg) s.c. p.o. (AUC$_{0-48}$(µM*hr), t$_{1/2}$ (hr)) |
|---|---|---|---|---|---|---|
| NB-130 | [structure] | n.a | 1.2 | n.a | n.a. | n.a / too low to measure |
| NB-134 | [structure] | n.a | 1.1 | 1.5 | n.a. | n.a / n.a |
| NB-131 | [structure] | n.a. | 0.9 | n.a | n.a. | n.a / too low to measure |
| NB-135 | [structure] | n.a. | 2.1 | n.a | n.a. | n.a / n.a |

TABLE 4-continued

Bishexamethylene linked hydroxylamines and their methiodide salt derivatives.

| Code # | Structure | RBA ERα | IC$_{50}$ (µM) MCF7 | DT-22 | MDA-MB-231 | PK (40 mg/kg) s.c. (AUC$_{0-48}$(µM*hr), t$_{1/2}$ (hr)) | p.o. |
|---|---|---|---|---|---|---|---|
| NB-145 | 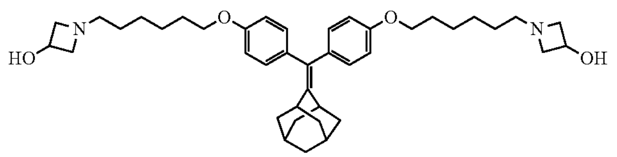 [SMILES: OC1CN(CCCCCCOc2ccc(C(=C3C4CC5CC(C4)CC3C5)c3ccc(OCCCCCCN4CC(O)C4)cc3)cc2)C1] | n.a. | 0.9 | n.a | n.a. | n.a | too low to measure |
| NB-143 | 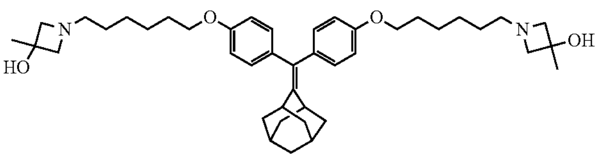 [SMILES: CC1(O)CN(CCCCCCOc2ccc(C(=C3C4CC5CC(C4)CC3C5)c3ccc(OCCCCCCN4CC(C)(O)C4)cc3)cc2)C1] | n.a. | 1.1 | n.a | n.a. | n.a | n.a |
| NB-144 | 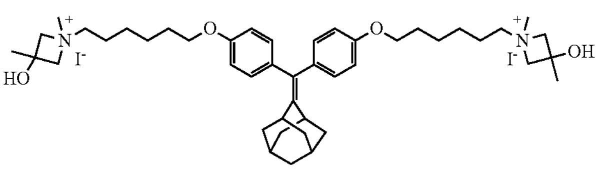 | n.a. | 1.8 | n.a. | n.a. | n.a | n.a |
| NB-138 | 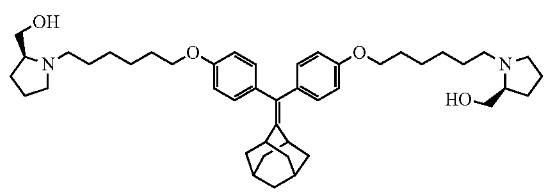 [SMILES: OC[C@@H]1CCCN1CCCCCCOc1ccc(C(=C2C3CC4CC(C3)CC2C4)c2ccc(OCCCCCCN3CCC[C@H]3CO)cc2)cc1] | n.a. | 0.7 | n.a | n.a. | n.a | 1.84, 25.0 |
| NB-139 | 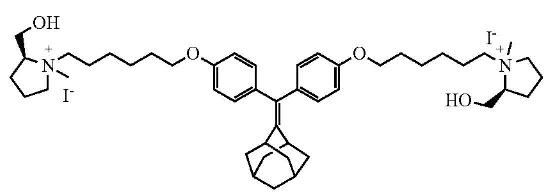 | n.a. | 0.9 | n.a | n.a. | n.a | n.a |
| NB-132 | 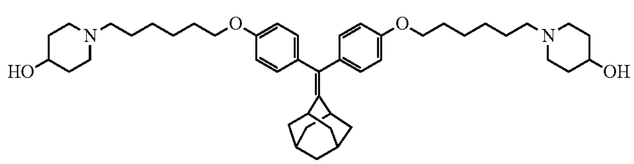 [SMILES: OC1CCN(CCCCCCOc2ccc(C(=C3C4CC5CC(C4)CC3C5)c3ccc(OCCCCCCN4CCC(O)CC4)cc3)cc2)CC1] | n.a | 1.6 | n.a. | n.a | n.a. | n.a. |
| NB-136 | 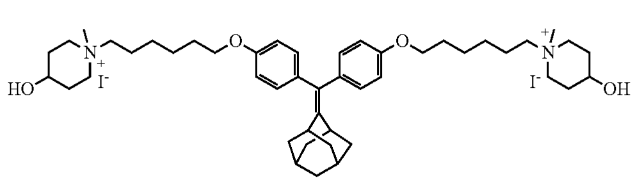 | n.a | 1.0 | n.a. | n.a. | n.a. | n.a. |
| NB-140 | 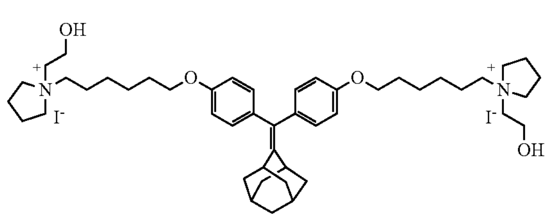 | n.a | 1.6 | n.a | n.a | n.a | n.a |

TABLE 4-continued

Bishexamethylene linked hydroxylamines and their methiodide salt derivatives.

| Code # | Structure | RBA ERα | MCF7 | IC$_{50}$ (μM) DT-22 | MDA-MB-231 | PK (40 mg/kg) s.c. p.o. (AUC$_{0-48}$(μM*hr), t$_{1/2}$ (hr)) |
|---|---|---|---|---|---|---|
| NB-141 | 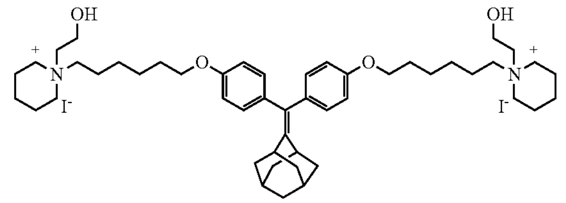 | n.a. | 3.6 | n.a | n.a | n.a n.a |
| NB-142 | 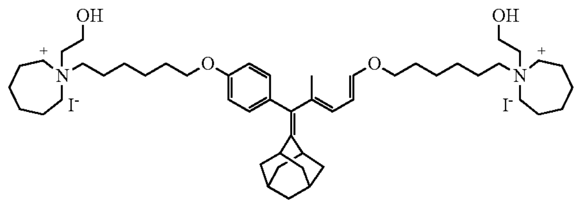 | n.a. | 2.4 | n.a | n.a | n.a n.a |

In view of the structure-activity relationships that arose from the studies herein of these series of monoamines, diamines, and their methiodide salts, a subset of compounds were selected for more detailed studies. Based on their cellular potencies and PK properties, a total of 10 compounds, 5 amines and their corresponding methiodide salts, were selected, all of which had hexamethylene linkers. One set was the monoamine NB-55 and its methiodide salt NB-63. The other 4 sets were the diamines NB-65, NB-70, NB-72, and NB-51, and their corresponding methiodide salts, NB-68, NB-71, NB-73, and NB-115.

Figure 2A:
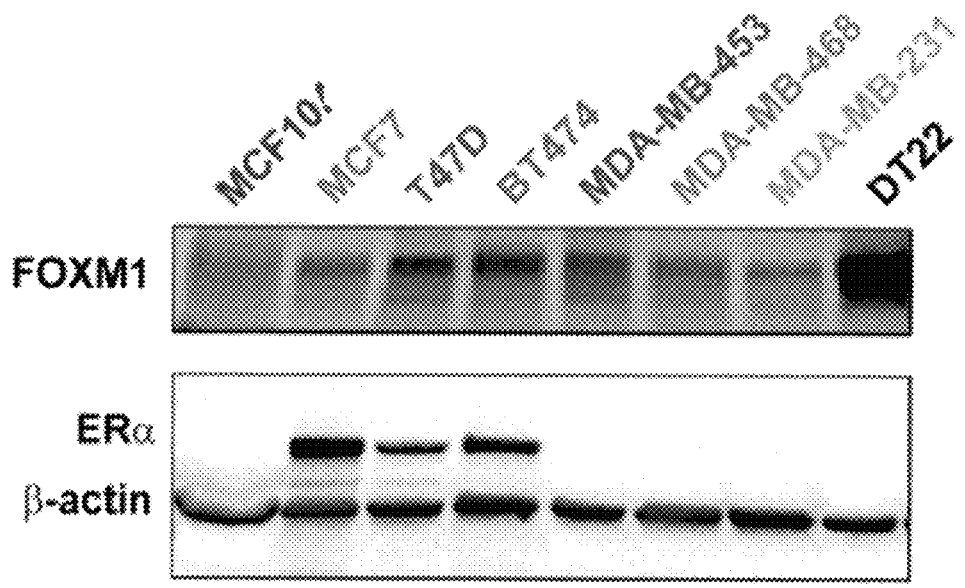
FIGS. 2A and 2B shows representative results of the panel of breast cancer cell lines used for initial FOXM1 inhibitor screening.
Figure 2B:
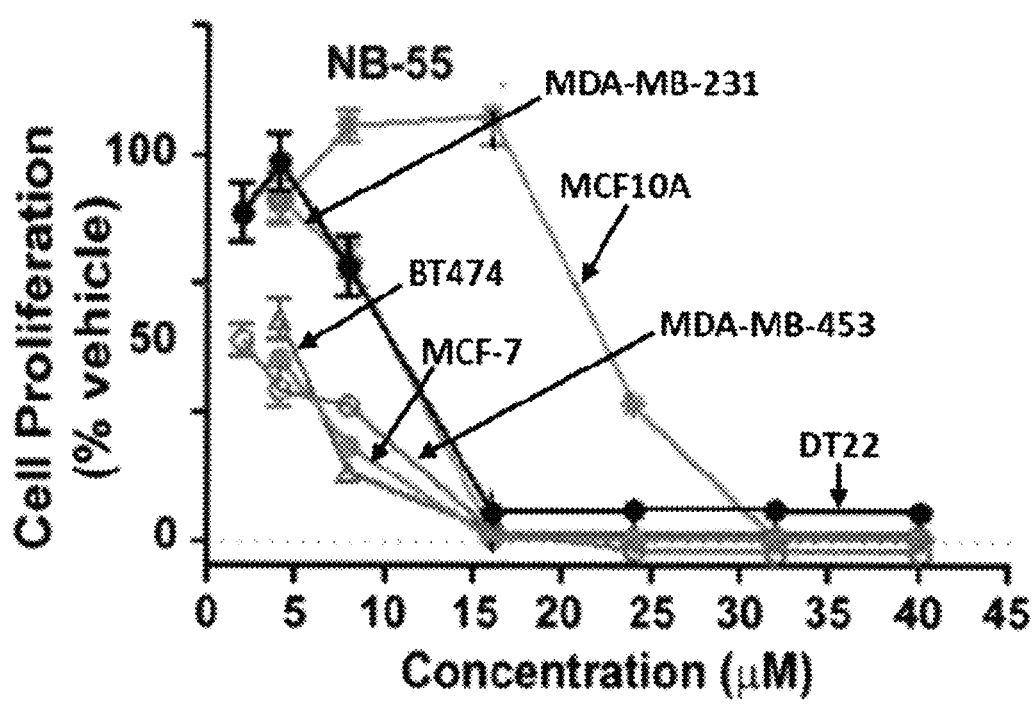
Figure 8:
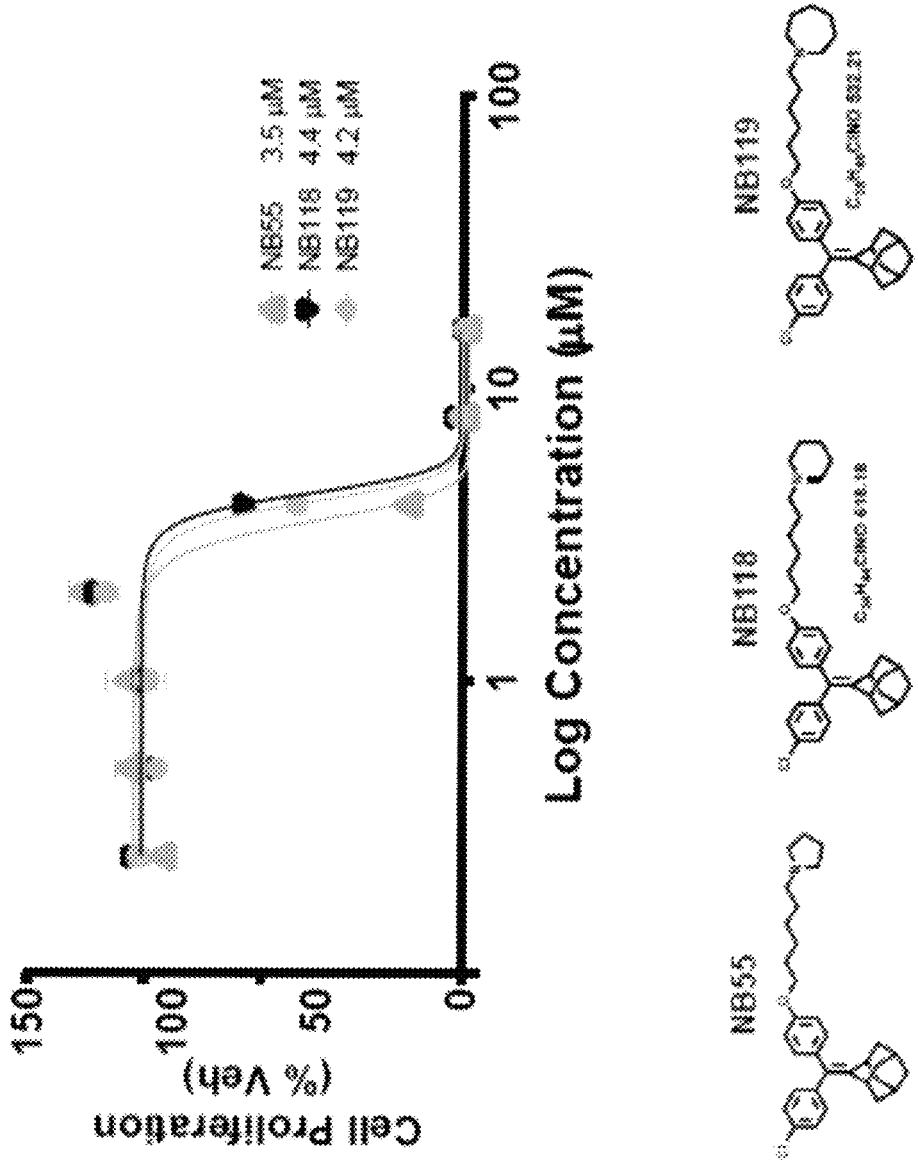
FIG. 8 shows representative results of examination of the effects of ring size on efficacy of the monoamine compound NB-55. Dose-response effects of NB-55 (5-membered ring), NB-118 (6-membered ring), and NB-119 (7-membered ring) on proliferation of MCF7 cells are provided. Cells were treated with compounds or control vehicle (0.1% ethanol) for 3 days and cell number was determined by WST-1 assay. Values are mean±SEM from triplicate samples.

Example 3. Effects of Compounds on Proliferation of a Panel of Breast Cancer Cells Differing in their FOXM1 Expression A panel of human breast cancer cell lines that differed in their FOXM1 protein content (high, DT22 cells; moderate, MCF7, T47D, BT474, MDA-MB-453, MDA-MB-468, and MDA-MB-231 cells; and low, MCF10A cells) were studied to examine the effects of potential FOXM1 inhibitor compounds on cell proliferation. All cell lines are ER-negative except for MCF7, T47D and BT474 cells (FIG. 2A). As shown in FIG. 2B, where the effects of the earliest lead FOXM1 inhibitor (the monoamine NB-55) on cell proliferation were monitored, it was found that cells with high and intermediate levels of FOXM1 protein showed relatively similar dose-responses for inhibition of cell proliferation, whereas MCF10A, with a low level of FOXM1, showed a reduced sensitivity to NB-55, requiring a concentration of NB-55 five times higher to achieve equal 50% suppression of proliferation. Because NB-55 has a 5-membered ring amine group (FIG. 1), further studies were carried out to investigate whether ring size might improve compound potency. Thus, compounds with 6- and 7-membered ring sizes (NB-118 and NB-119) were tested, but it was found that these changes in ring size did not affect inhibitory efficacy or potency (FIG. 8).

Figure 3A:
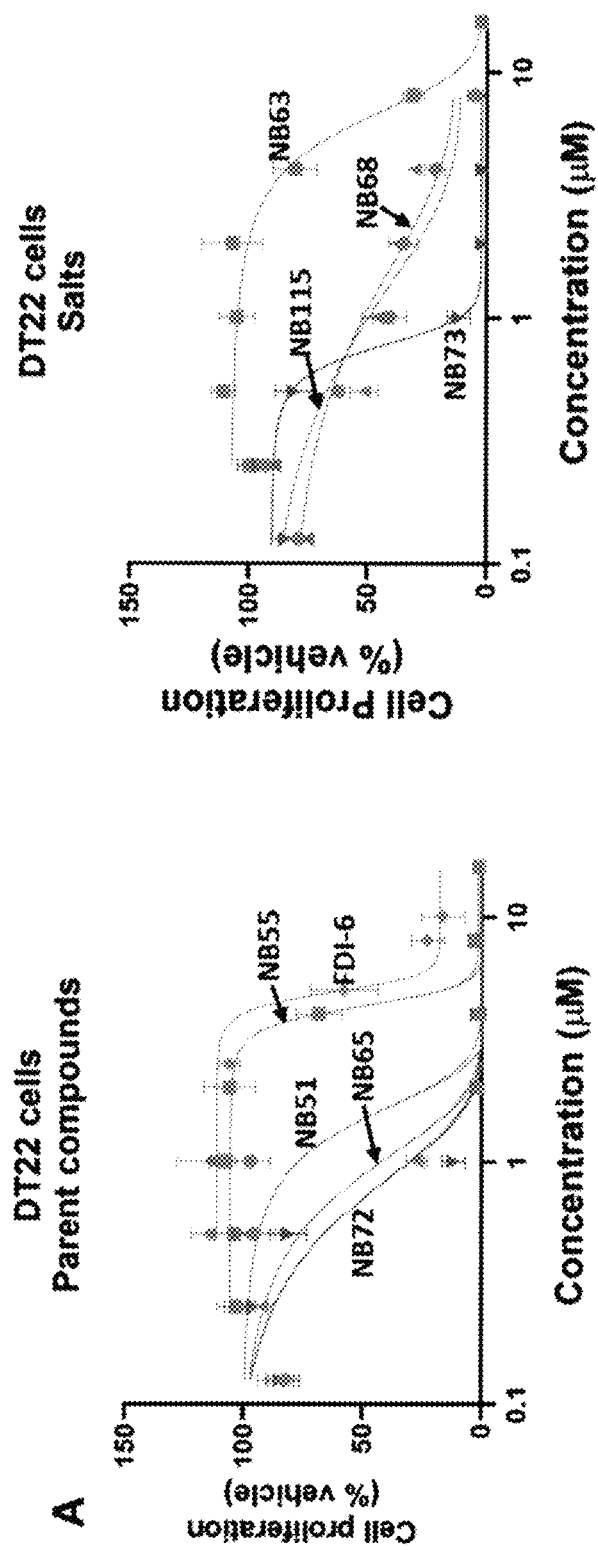
FIGS. 3A and 3B shows representative results of inhibition of cell proliferation by parent amine and their methiodide salt compounds. DT22 (FIG. 3A) or MCF7 (FIG. 3B) cells were incubated for 3 days with the indicated concentrations of each compound or with FDI-6 for comparison. Assays were run in triplicate. Values are mean±SEM.
Figure 3B:
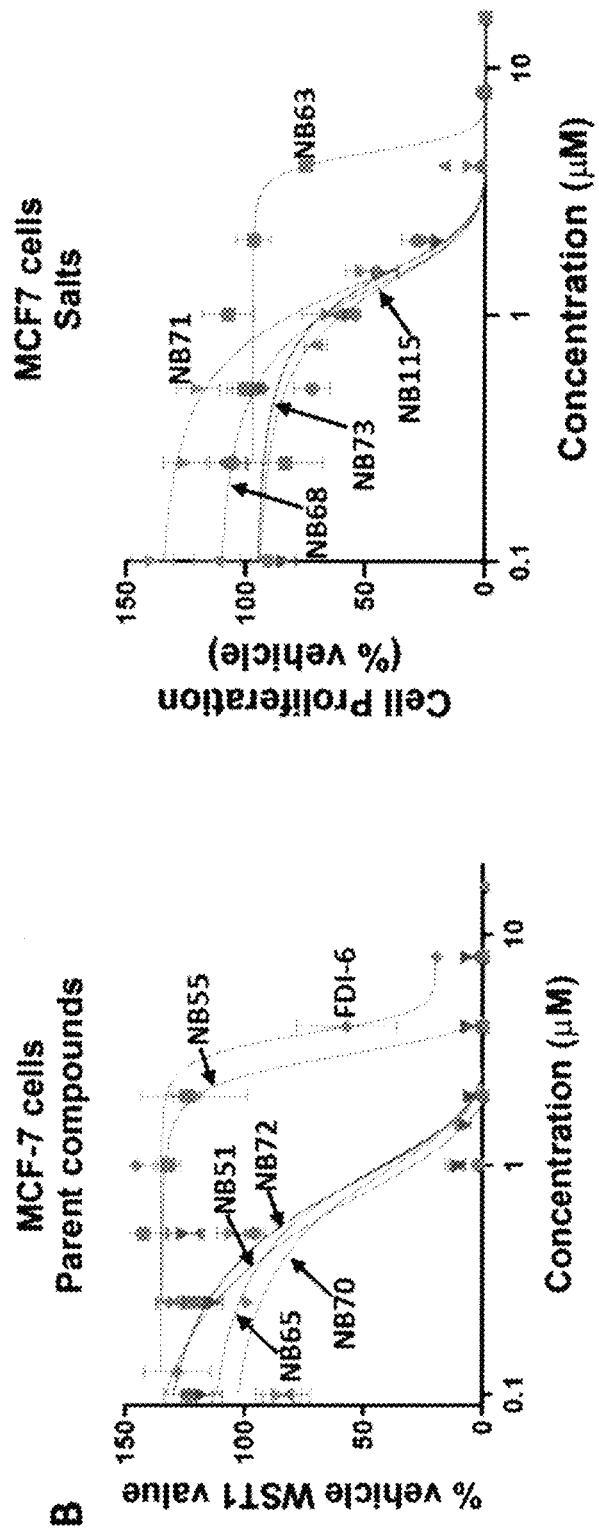

Because the IC$_{50}$ for inhibition of proliferation by the monoamine NB-55 was only ca. 2-10 μM in the breast cancer cell lines, NB-55 was compared with some members of the diamine series (NB-51, 55, 65, 70, 72), as well as with their methiodide salts (NB-63, 68, 71, 73, 115), for possible improved potency. In these studies, several reported FOXM1 inhibitors were also used as comparator compounds (FIGS. 3A-3B). These included FDI-6, a recently reported small molecule inhibitor (Gormally, et al., Nature communications, 2014; 5:5165) and the microbial compound thiostrepton (Bhat et al., PLoS ONE, 2009; 4:e5592). Notably, all of the diamines were markedly more potent than the monoamine NB-55 and also FDI-6 and thiostrepton in suppressing cell proliferation in both ER-positive MCF7 and ER-negative DT22 cells. In these cell assays, the methiodide salts, whether of the monoamine (NB-63) or the diamines (NB-68, 71, 73, 115), had potencies very similar to that of their parent amine compounds. Thus, in terms of antiproliferative activity in these breast cancer cell lines, the diamines were considerably more potent than the monoamine, but in no case did formation of the corresponding methiodide salts have a substantial effect on their cellular potencies.

Dose-response antiproliferative studies in additional cell lines beyond the ER-positive MCF7 and the basal/claudin low triple negative DT22 cells gave similar findings. Thus, in triple negative MDA-MB-231 and MDA-MB-453 breast cancer cells, IC$_{50}$ values for the monoamine NB-55 were 3-5 μM, whereas the diamines and their methiodide salts gave IC$_{50}$ values of 0.6±0.14 μM, very similar to those observed with MCF7 and DT22 cells for suppression of cell proliferation.

Figure 9:
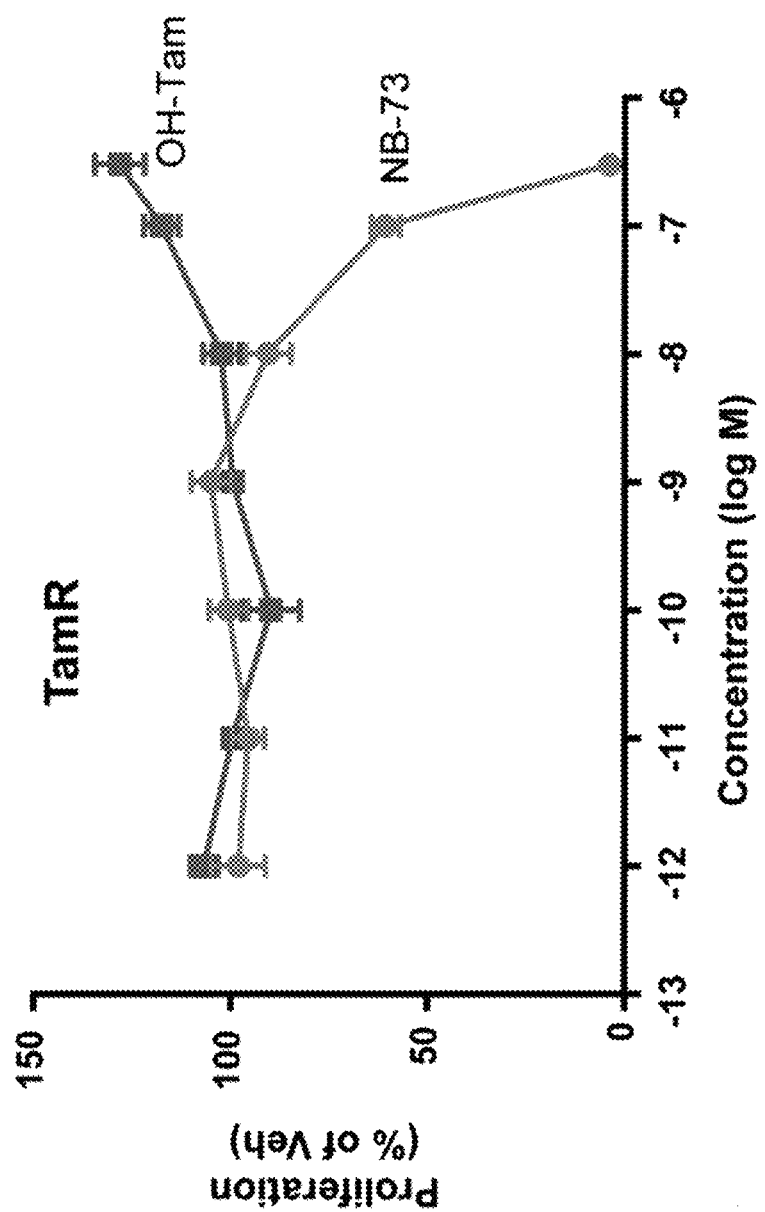
FIG. 9 shows that compound NB-73 inhibits the proliferation of Tamoxifen-resistant MCF7 cells. Cells were treated with NB-73 or trans-hydroxytamoxifen (HOT) for 6 days and cell numbers were monitored. Values are mean±SD of three separate assays.

Of interest, the diamine salt tested, NB-73, also effectively suppressed the proliferation of tamoxifen-resistant MCF7 breast cancer cells, whose growth was weakly stimulated rather than suppressed by trans-hydroxytamoxifen (FIG. 9).

Example 4. Effects of Compounds on FOXM1 Target Gene Expression

Figure 4A:
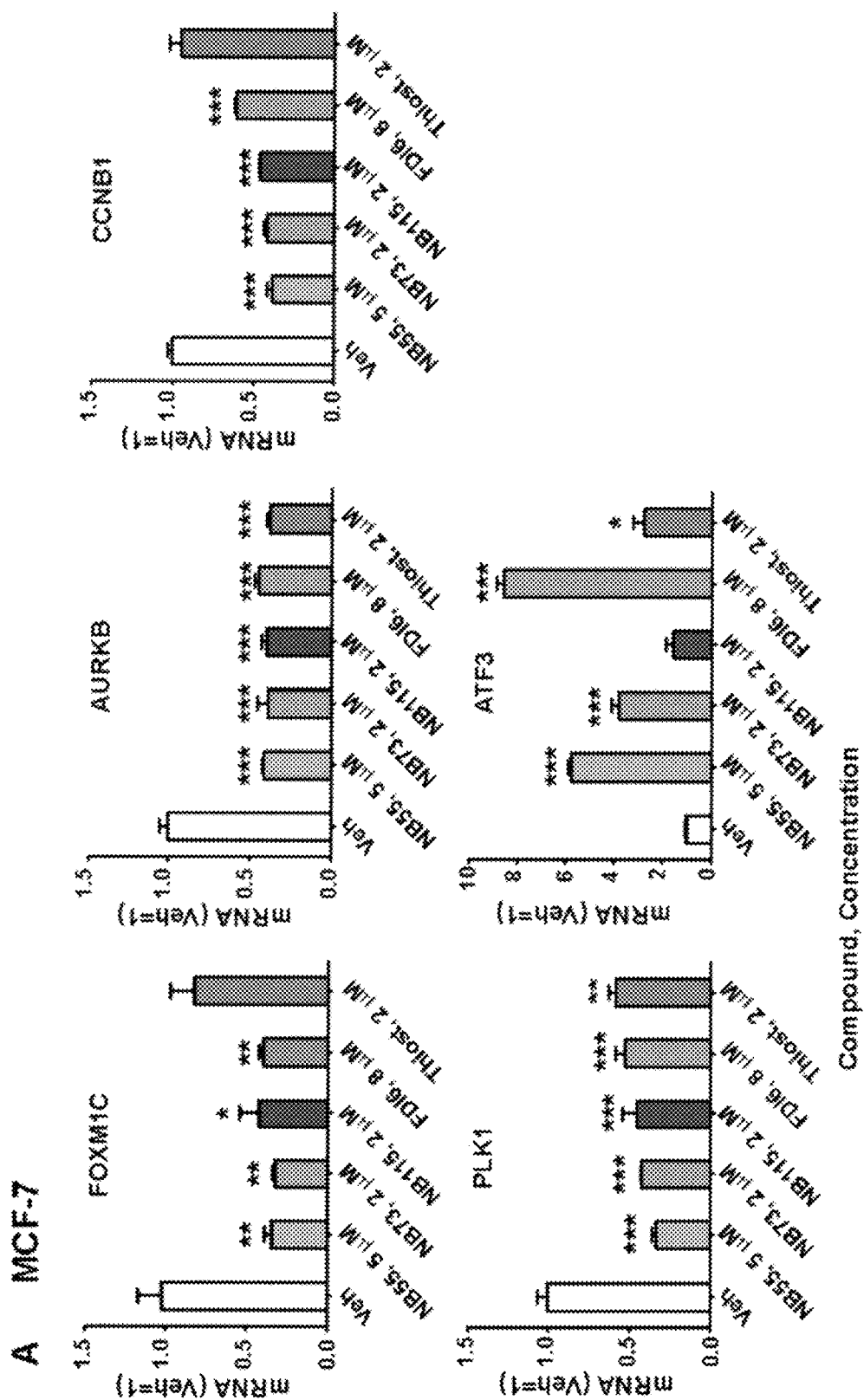
FIG. 4A shows representative results of inhibition of FOXM1 target gene expression by parent amine and methiodide salt compounds. Inhibition of the expression of FOXM1 upregulated genes (FORMIC, AURKB, CCNB1, PLK1) and reversal of FOXM1 downregulation of ATF3 in MCF7 cells. MCF7 cells were incubated for 24 h with each compound or with FDI-6 or thiostrepton at the indicated $IC_{50}$ concentration for each compound based on cell proliferation assays. RNA was extracted from cells and expression of different genes was monitored by qRT-PCR. Assays were run in triplicate. Values are mean±SEM. *, $p<0.05$; , $p<0.01$; *, $p<0.001$.
Figure 4B:
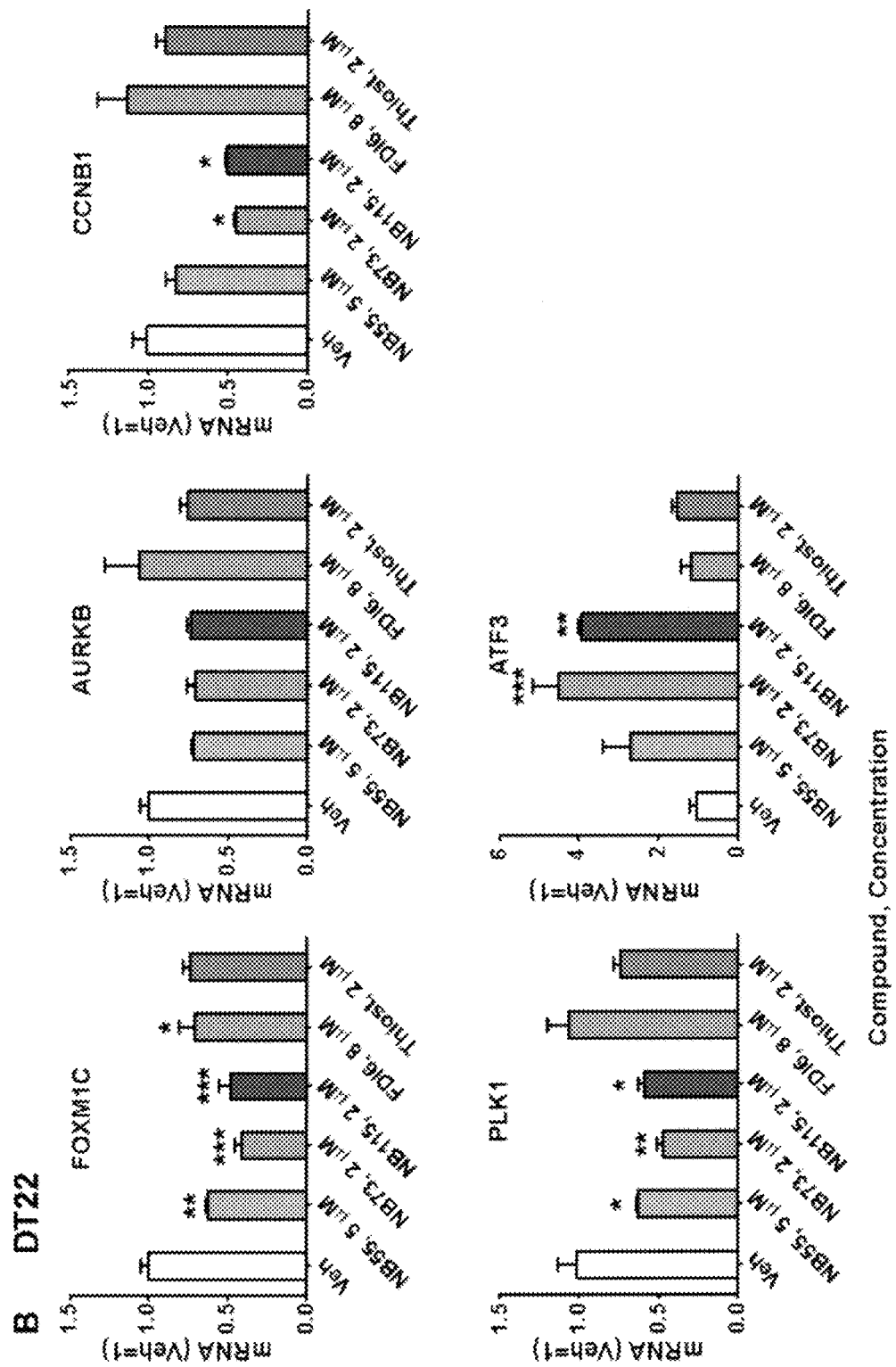
FIG. 4B shows representative results of inhibition of FOXM1 target gene expression by parent amine and methiodide salt compounds. Inhibition of the expression of FOXM1 upregulated genes (FORM1C, AURKB, CCNB1, PLK1) and reversal of FOXM1 downregulation of ATF3 in DT22 cells. DT22 cells were incubated for 24 h with each compound or with FDI-6 or thiostrepton at the indicated $IC_{50}$ concentration for each compound based on cell proliferation assays. RNA was extracted from cells and expression of different genes was monitored by qRT-PCR. Assays were run in triplicate. Values are mean±SEM. *, $p<0.05$; , $p<0.01$; *, $p<0.001$.

Further experiments were carried out to examine the ability of these compounds to inhibit expression of classic FOXM1 target genes, genes normally up-regulated by FOXM1 (CCNB1, PLK1, AURKB and FOXM1C), and also to reverse downregulation of the FOXM1 target gene ATF3 (FIGS. 4A-4B). These are genes found to be regulated by FOXM1 based on our siFOXM1 microarray studies (Bergamaschi et al., Breast Cancer Res., 2014; 16:436) as well as thiostrepton gene microarray (Sanders et al., Genome Biology, 2015, 16:130) and FDI-6 RNA-seq studies in MCF7 cells by others (Gormally et al., Nature communications, 2014, 5:5165).

Analysis of gene expression using three FOXM1 inhibitors at their $IC_{50}$ concentration for suppression of cell proliferation, showed that NB-55, NB-73 and NB-115 significantly reduced the expression of all FOXM1 stimulated target genes (FOXM1C, AURKB, CCNB1 and PLK1) and increased expression of ATF3, a gene suppressed by FOXM1 in both ER-positive MCF7 and ER-negative DT22 cells (FIGS. 4A-4B). NB-55, NB-73 and NB-115 were as effective as FDI-6 at its $IC_{50}$ concentration (8 μM) and were generally more effective than thiostrepton at its $IC_{50}$ concentration (2 μM).

Figure 5A:
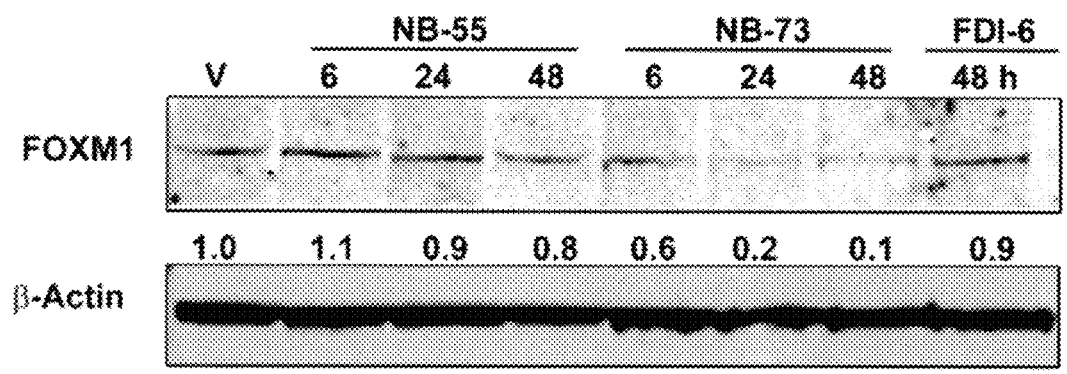
FIG. 5A shows representative results of treatment of MDA-MB-231 cells with NB-55 (5 μM), NB-73 (1.5 μM), NB-115 (4 μM) or FDI-6 (8 μM) on FOXM1 level.
Figure 5B:
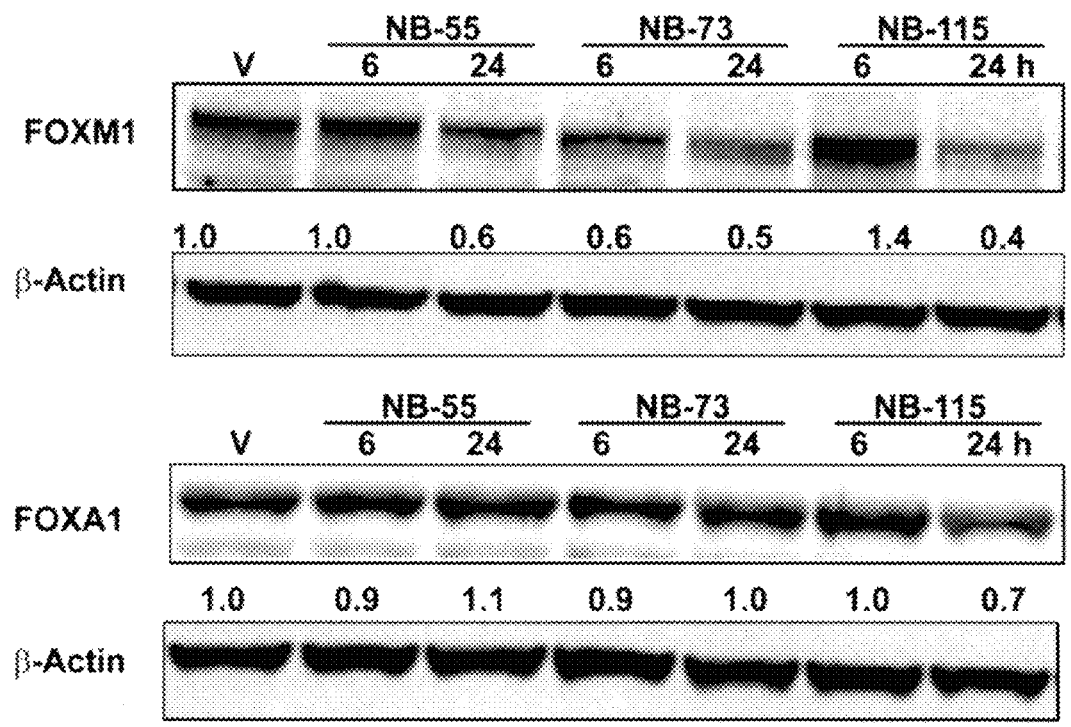
FIG. 5B shows representative results of treatment of MCF7 cells with NB-55 (8 μM), NB-73 (4 μM), NB-115 (4 μM) or FDI-6 (20 μM) on the cellular level of FOXM1 or FOXA1 protein monitored by Western blot over time.

Because of the known interrelationships between FOXM1 and ERα, with FOXM1 and ERα being FOXM1 target genes (Bergamaschi et al., Breast Cancer Res., 2014; 16:436; Millour et al., Oncogene, 2010, 29:2983-95; Sanders et al., Genome biology, 2013, 14:R6), it was examined and found herein that the FOXM1 inhibitor disclosed herein downregulated cellular FOXM1 and ERα proteins in a time-dependent manner, as did thiostrepton and FDI-6 (FIG. 5A). They also all decreased the cellular level of FOXM1 and ERα mRNAs (FIG. 5B).

Example 5. Direct Binding of Inhibitors to FOXM1 and Increased Sensitivity to Proteolysis Upon Inhibitor Binding to FOXM1

Figure 10A:
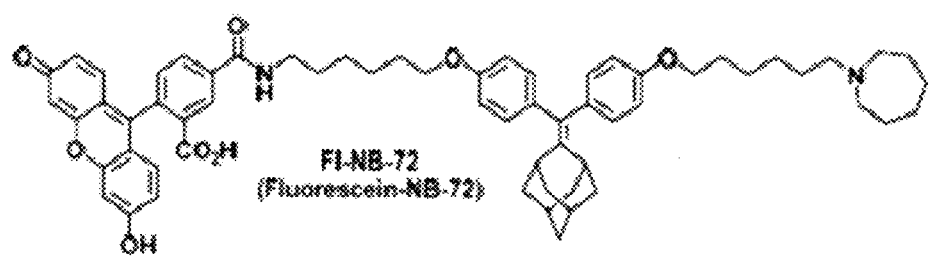
FIGS. 10A-10C shows representative results of fluorescence assays of binding of FOXM1 inhibitors to FOXM1 protein.
Figure 10B:
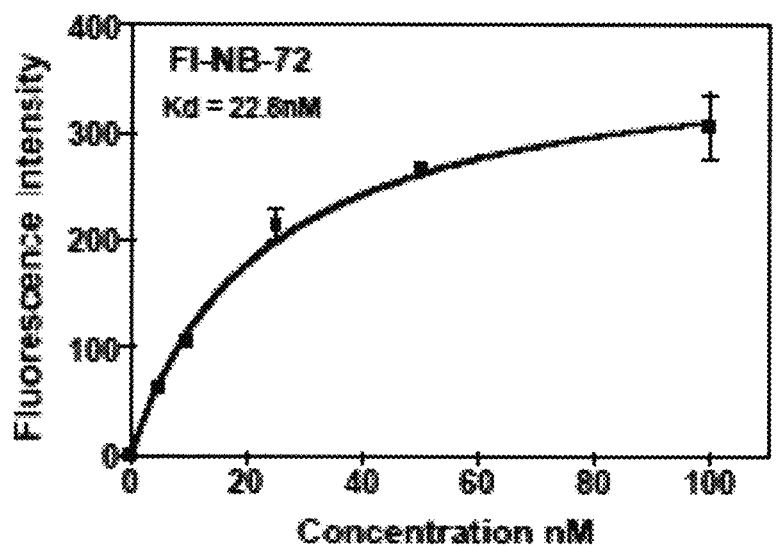
Figure 10C:
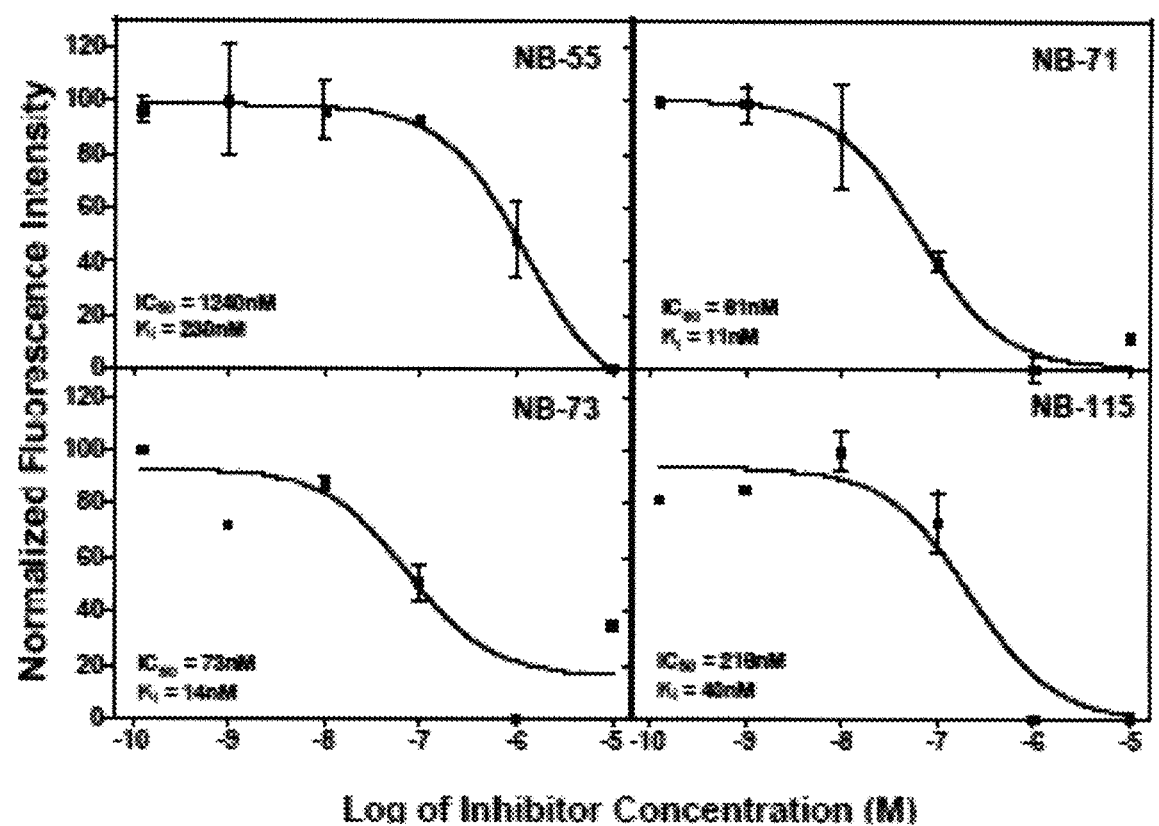

To ascertain whether the compounds herein inhibit FOXM1 directly, a tr-FRET assay was developed for FOXM1 binding. An acceptor fluorophore Fl-NB-72 was created by replacing one amine appendage of diamine compound NB-72 with fluorescein (FIG. 10A), and a terbium donor was attached to purified full length FOXM1 through a streptavidin-biotin linker. FOXM1 titrations showed that Fl-NB-72 bound to the FOXM1 protein with a $K_d$ of 23 nM (FIG. 10B). The interaction of ten compounds we studied with FOXM1 were assessed by a competition assay, monitoring the decrease in FRET signal as a fixed concentration of Fl-NB-72 was displaced by the inhibitor. Representative examples are shown in FIG. 10C. The $K_i$ values, calculated from the $IC_{50}$ values, are given in Table 5.

TABLE 5

Affinity of FOXM1 inhibitors and FDI-6 for binding to FOXM1 protein

| Compound | [Cpd No.] $K_i$ (μM)$^a$ | |
|---|---|---|
| | Amine | Methiodide Salt |
| Monoamine | | |
| Cl & 5-ring | [NB-55] 0.23 | [NB-63] 0.076 |
| Diamines | | |
| 5-ring | [NB-65] 0.19 | [NB-68] 0.051 |
| 6-ring | [NB-70] 0.10 | [NB-71] 0.011 |

TABLE 5-continued

Affinity of FOXM1 inhibitors and FDI-6 for binding to FOXM1 protein

| Compound | [Cpd No.] $K_i$ (μM)$^a$ | |
|---|---|---|
| | Amine | Methiodide Salt |
| 7-ring | [NB-72] 0.065 | [NB-73] 0.014 |
| Et$_2$ amine | [NB-51] 0.13 | [NB-115] 0.040 |
| FDI-6 | | 0.143 |

$^a K_i$ values are calculated from $IC_{50}$ values.

The mono and diamines and their methiodide salts have high binding affinity for FOXM1, with $K_i$ values in the submicromolar range. The methiodide salts of the diamines bind with higher affinity than the diamines themselves, and overall, the $K_i$ values for FOXM1 binding are somewhat less than the $IC_{50}$ values for inhibition of cell proliferation. The latter likely reflects the fact that the available concentrations of compound in cell studies may be reduced due to association with proteins in tissue culture media containing serum and by other factors affecting cell uptake.

Figure 11:
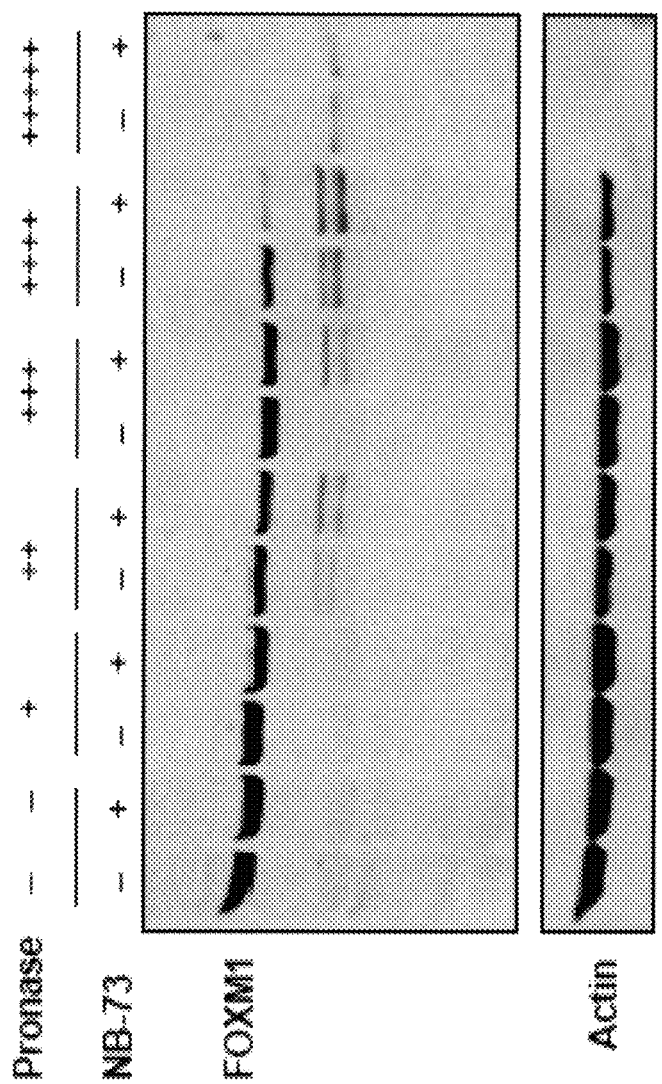
FIG. 11 shows representative effect of the compound NB-73 on sensitivity of FOXM1 protein to proteolysis by exogenous protease. DT22 cell lysates were incubated without or with 10 μM NB-73 for 1 h and then with varying concentrations of pronase (none, $1:10^3$; 1:10⁴; $1:10^5$; and $1:10^6$) in the continued absence or presence of NB-73 for an additional 30 min at room temperature as described in Methods. Proteins were then separated on a 4-20% SDS- PAGE gel and gels were exposed to FOXM1 antibody (Abcam rabbit polyclonal 1:750) and β-actin antibody (1:500, mouse monoclonal).

Of interest, it was observed that treatment with FOXM1 inhibitor rendered the FOXM1 protein more readily proteolyzed by pronase (FIG. 11), suggesting that binding of the compound (NB-73) to FOXM1 perturbs the protein structure so as to destabilize FOXM1 by increasing its ability to be degraded by pronase. Without being limited by any theory, this finding implies that the reduced intracellular level of FOXM1 after treatment of cells with compound may, at least in part, reflect an increased susceptibility to proteolysis of FOXM1 upon inhibitor binding.

Example 6. Pharmacokinetics of FOXM1 Inhibitors

Figure 6A:
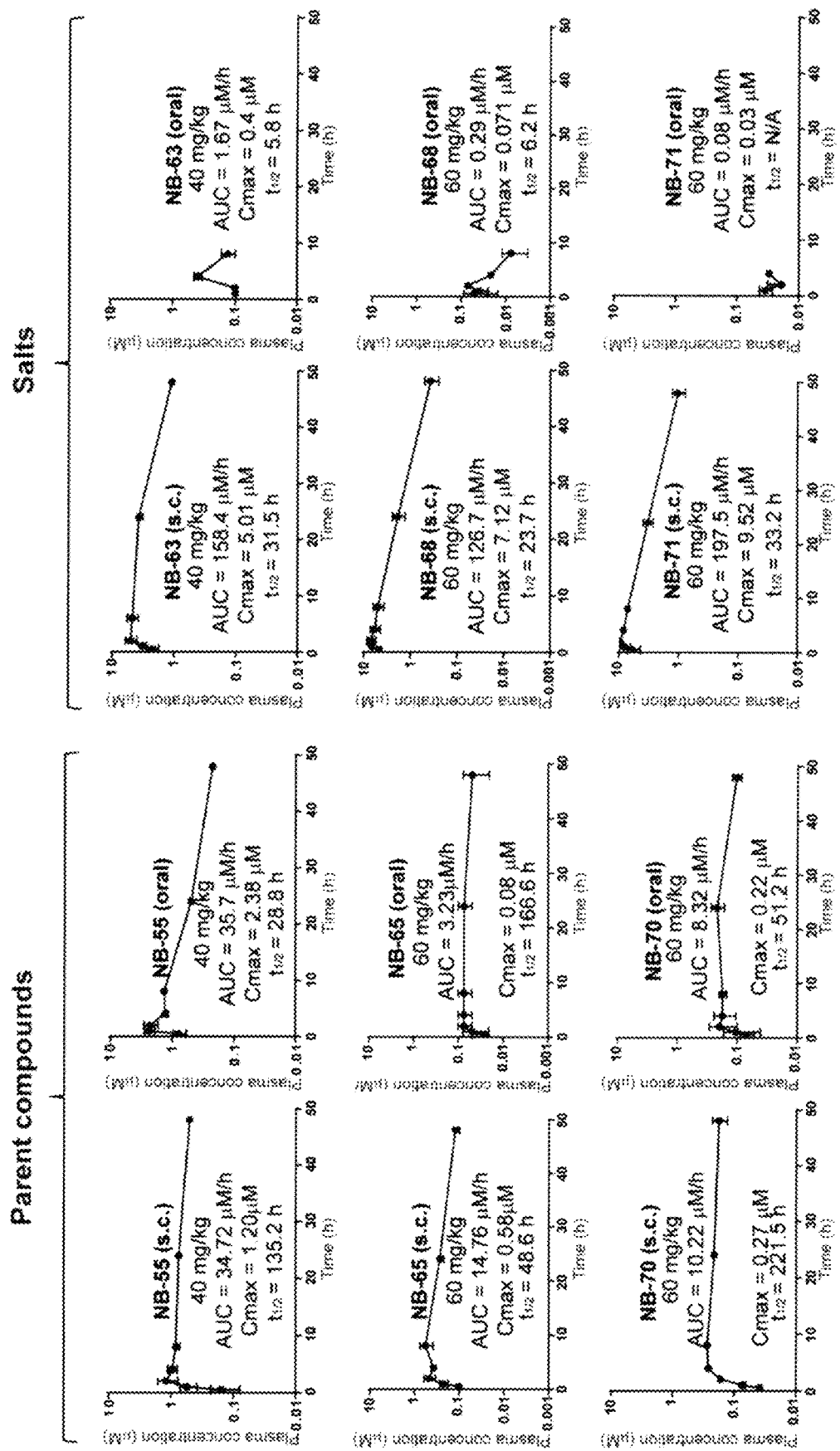
FIGS. 6A-6B shows pharmacokinetics and half-lives of compounds in mice after s.c. or oral administration. Pharmacokinetics (PK) of amine compounds and their respective methiodide salt compound.
Figure 6B:
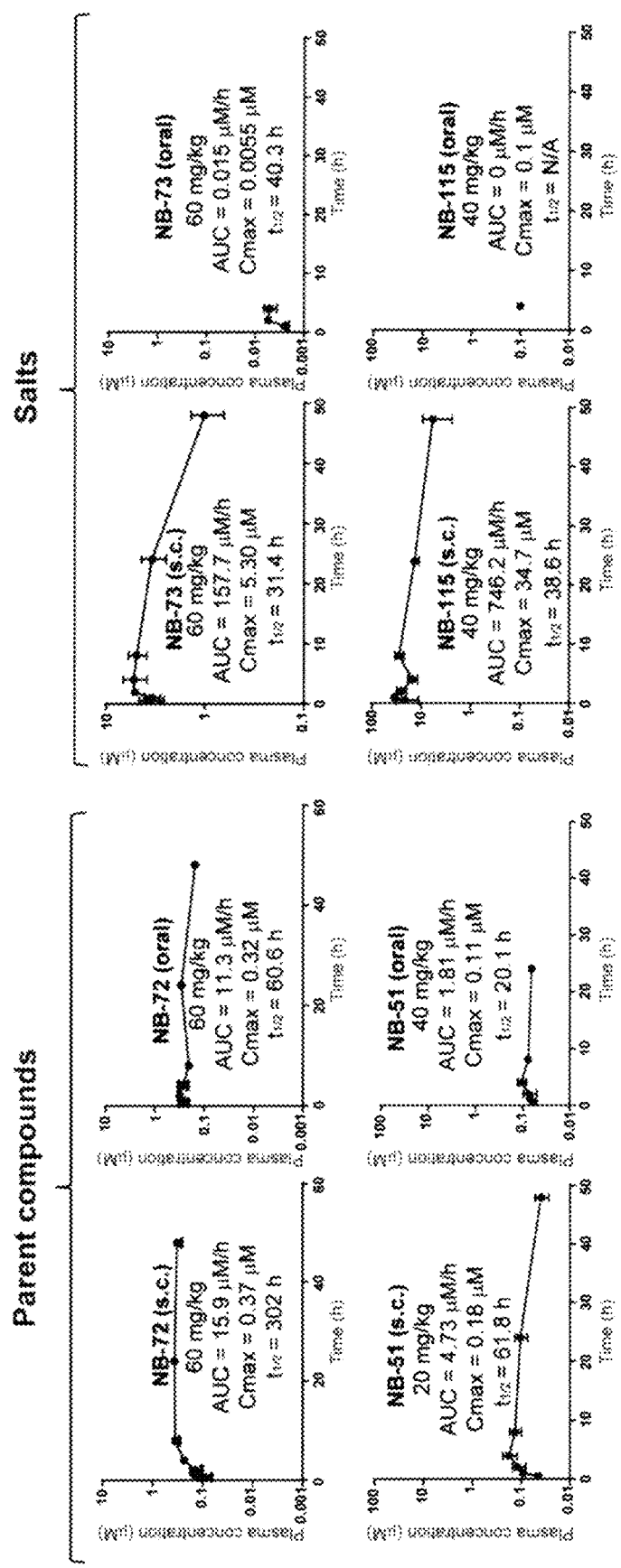

In pharmacokinetic (PK) studies with several of the most promising FOXM1 inhibitor compounds in mice, it was found that some monoamines and diamines showed very good subcutaneous and oral bioavailability (FIGS. 6A-6B). Hence, as seen in FIGS. 6A-6B, examination of compound half-lives and accumulation in plasma after a single subcutaneous injection or single oral administration of the parent mono- and diamines (NB-55, 65, 70, 72, and 51) revealed the good and rather equivalent PK by either route of administration. It is striking that the PK properties of the monoamine NB-55, particularly after oral dosing, were markedly superior to those of the diamines; this stands in contrast to the lower potency of the monoamine compared to the diamines in terms of antiproliferative potency in cells in culture (FIGS. 3A-3B).

Figure 12:
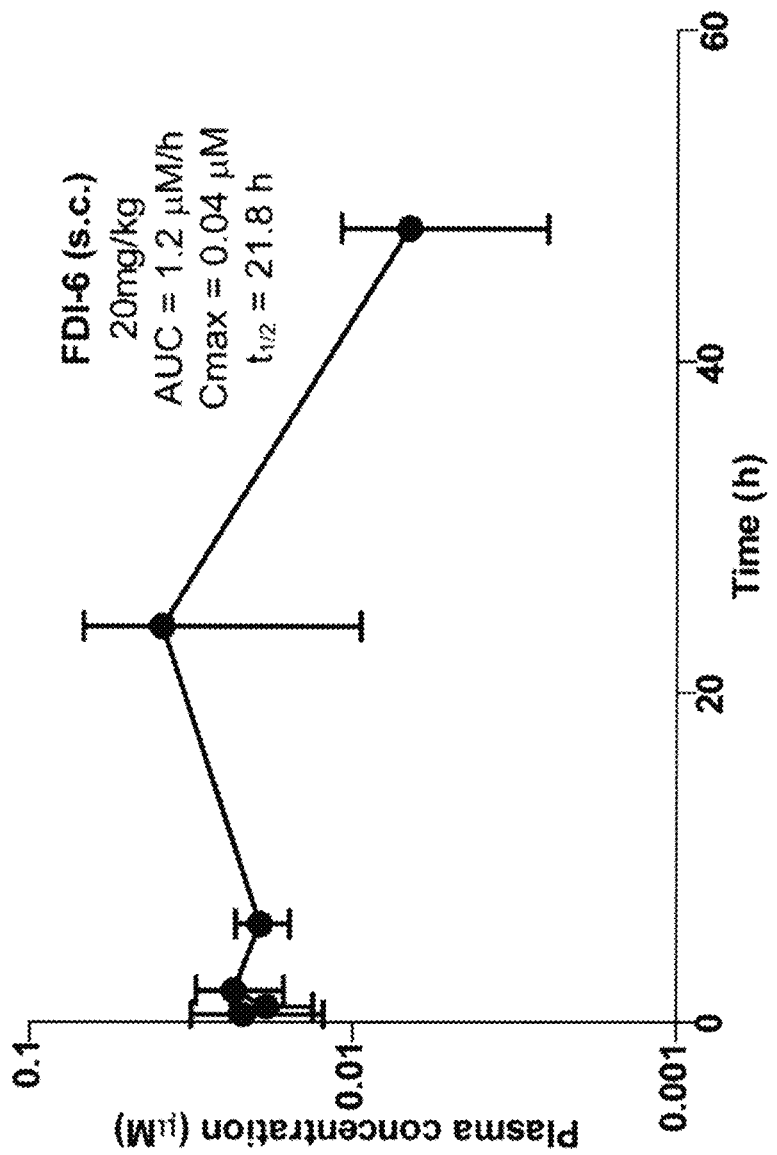
FIG. 12 shows representative pharmacokinetics and half-life of FDI-6 in mice after s.c. or oral administration. PK was studied after single dose administration via s.c. injection at 20 mg/kg or oral gavage at 40 mg/kg. Multiple plasma samples were collected from each mouse (n=4 for each experiment) over the course of 48 h after compound was administered at time zero. Compound was quantified using LC-MS/MS. The data were fitted to a non-compartment PK model. FDI 6 was not detectable in blood after oral administration; therefore, only data from s.c. administration is presented.

While conversion of the mono- and diamines to their methiodide salts did not have a beneficial effect on their cellular potencies (FIGS. 3A-3B), it did improve their subcutaneous PK behavior; the oral bioavailability of these salts, however, was diminished (FIGS. 6A-6B). Hence, after s.c. injection of NB-63, NB-68, NB-71, NB-73 and NB-115, very high blood levels of compound were observed, followed by long half-lives (from approximately 25 h to 40 h, FIGS. 6A-6B), whereas only very low levels were found after oral administration. In striking contrast, the FOXM1 inhibitor FDI-6 achieved only very low blood levels after s.c. administration at 20 mg/kg, and was undetectable after oral administration at 40 mg/kg (FIG. 12).

Figure 7A:
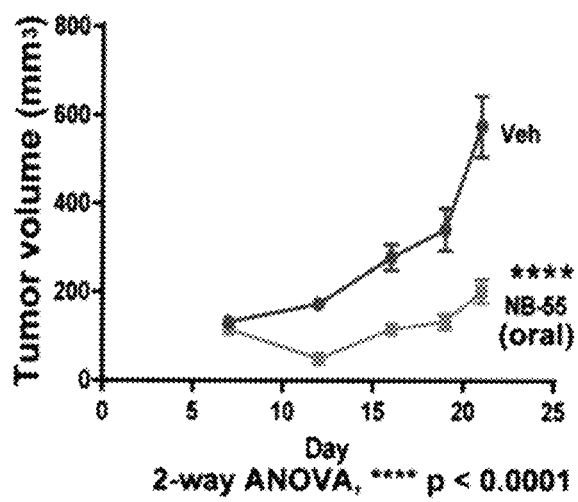
FIGS. 7A-7D show that compounds NB-55, NB-68, NB-71, and NB-73 suppress breast tumor xenograft growth and the expression of FOXM1-regulated genes. Triple negative human breast cancer DT22 cells were injected into the mammary fat pad of intact 7 week old NSG mice, and mice bearing DT22 tumors were dosed with the compounds.
Figure 7B:
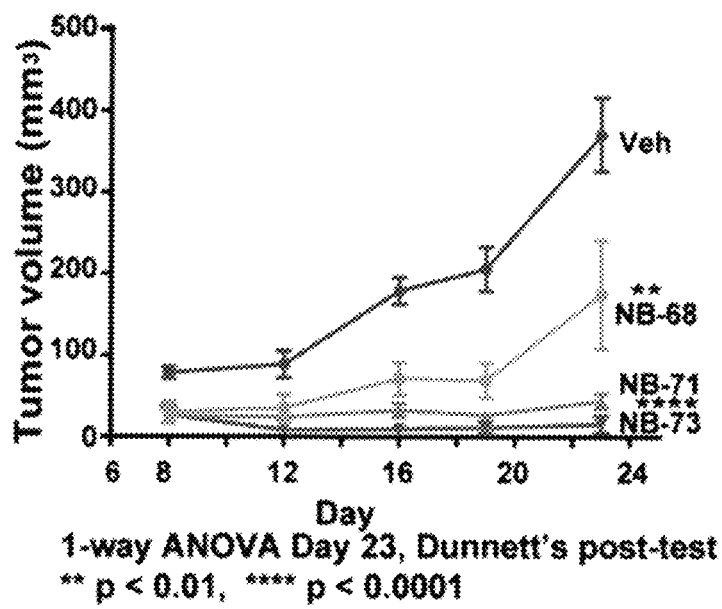
Figure 7C:
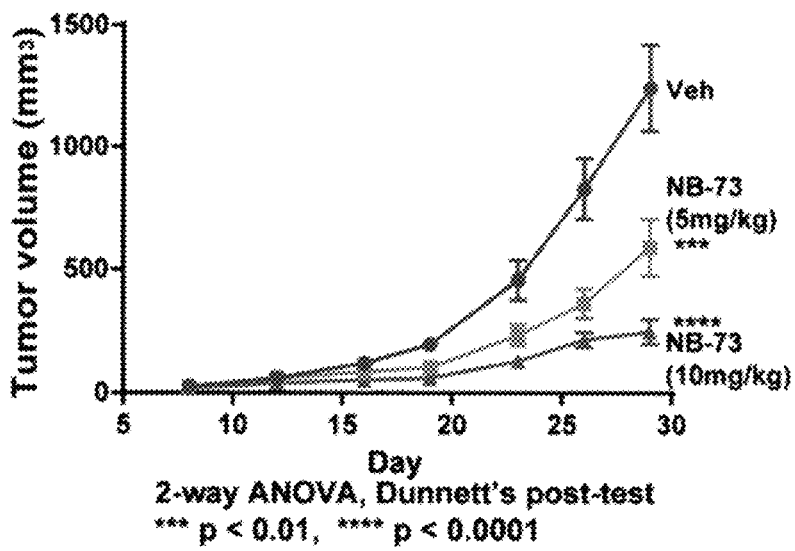
Figure 7D:
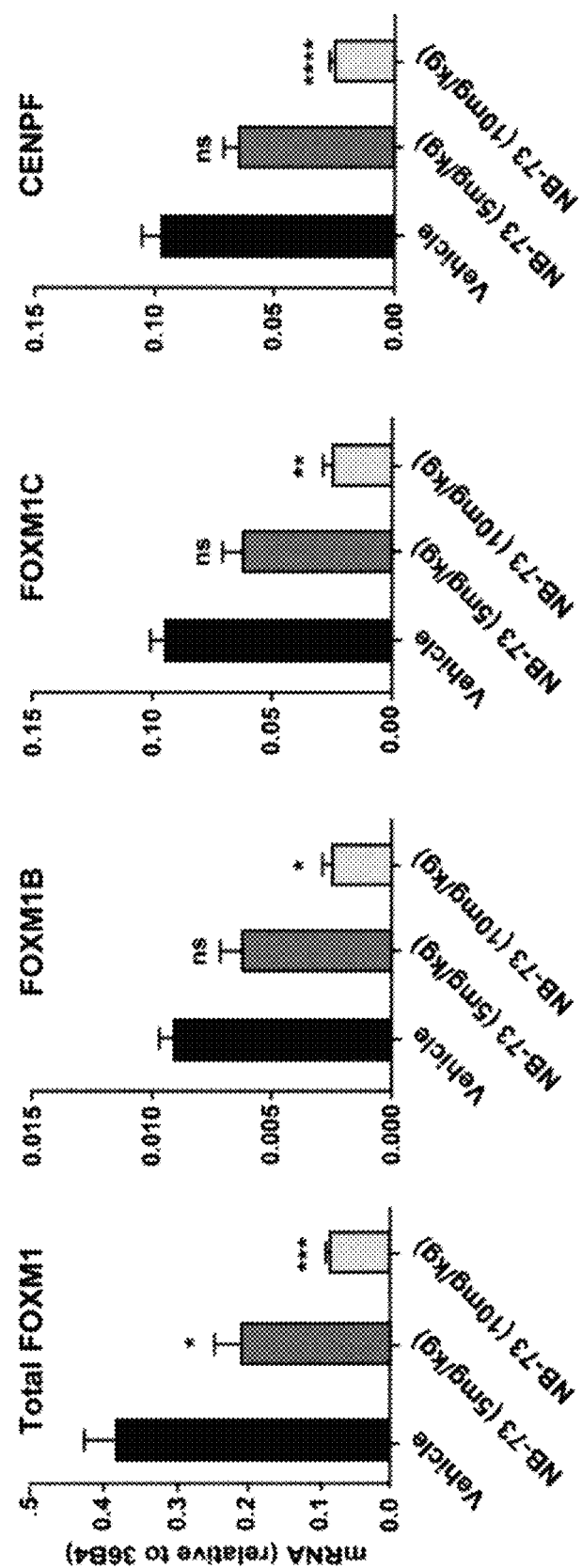
Figure 13:
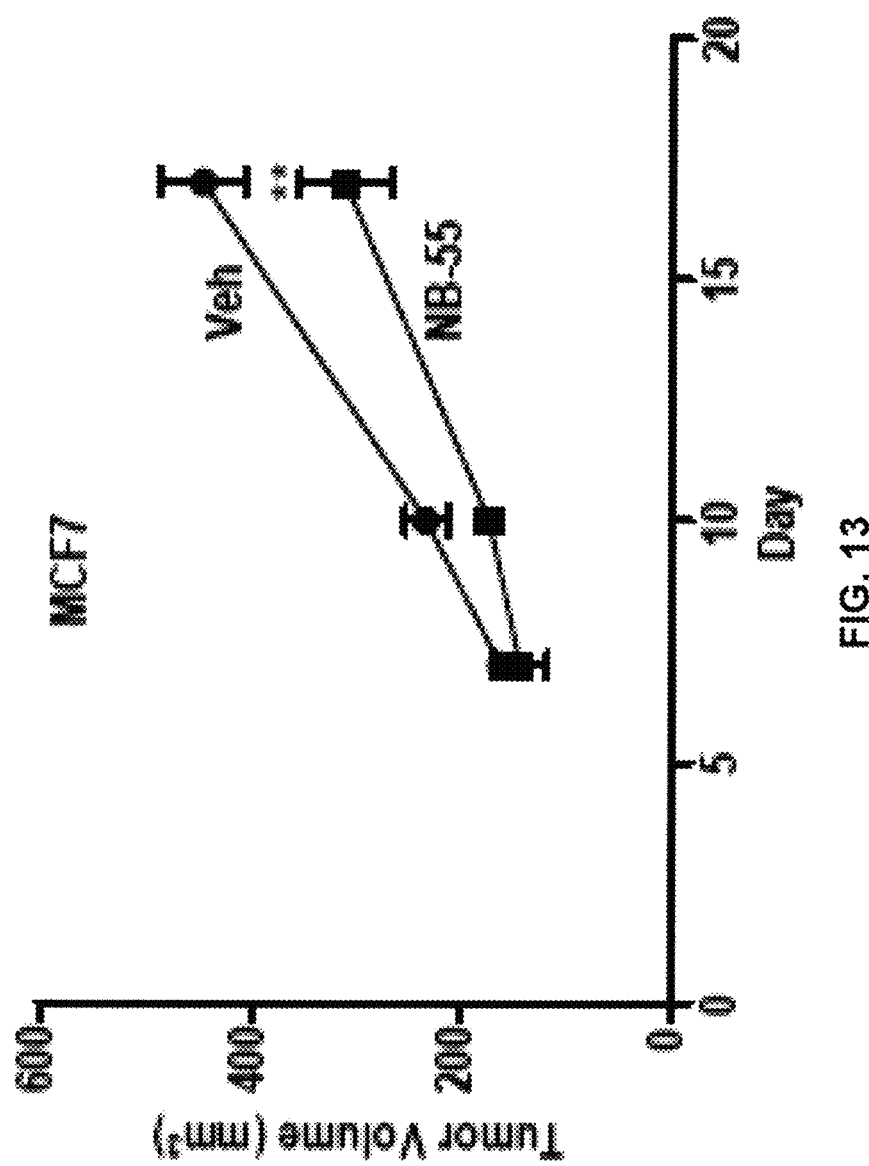
FIG. 13 shows that compound NB-55 reduces MCF7 breast cancer xenograft growth. MCF7 cells were injected into the mammary fat pad of 7-week-old ovariectomized NSG mice and allowed to grow in the presence of an E2 pellet (0.36 mg E2, Innovative Research) for 3 weeks. When tumors reached ca. 150 mm$^3$ in size, animals received vehicle or NB-55 (100 mg/kg) s.c. daily and tumor growth was monitored. (2-way ANOVA, Bonferroni post-test; **, $p<0.01$, n=8 per group).

Example 7. Efficacy of FOXM1 Inhibitors in Suppressing the Growth of Human Breast Tumor Xenografts and FOXM1-Regulated Gene Expression in Tumors Studies in female NOD/SCID-gamma (NSG) mice showed that monoamine NB-55, when given s.c. or orally daily, very effectively suppressed the growth of DT22 triple negative human breast tumor xenografts that express high levels of FOXM1 (FIG. 7A). Daily treatment with NB-55 also reduced the growth of established MCF7 E2-treated tumors (FIG. 13), but growth suppression was more pronounced in DT22 tumors that have higher levels of FOXM1 protein. Lower doses of the diammonium salts NB-68, NB-71 and NB-73 were also tested as tumor suppressive agents, since these compounds had higher inherent cellular potencies and achieved higher blood levels after s.c. dosing than did NB-55. At 20 mg/kg every other day for the first 10 days and then 10 mg/kg every other day subsequently, NB-68, NB-71 and NB-73 were found to greatly suppress tumor growth (FIG. 7B). Because of their effectiveness, animals were then treated with 5 and 10 mg/kg of NB-73 s.c. daily and then every other day starting on day 21. As seen in FIG. 7C, NB-73 reduced tumor growth at 5 mg/kg and even more markedly suppressed growth at 10 mg/kg. Accompanying this suppression of tumor growth by low doses of NB-73, the expression of FOXM1-regulated genes, including FOXM1 itself, was reduced in tumors in a dose-dependent manner, with all gene expressions being greatly reduced upon treatment with 10 mg/kg NB-73 and tumors treated with 5 mg/kg NB-73 also showing significant reduction in several FOXM1-regulated genes (FIG. 7D).

Figure 14A:
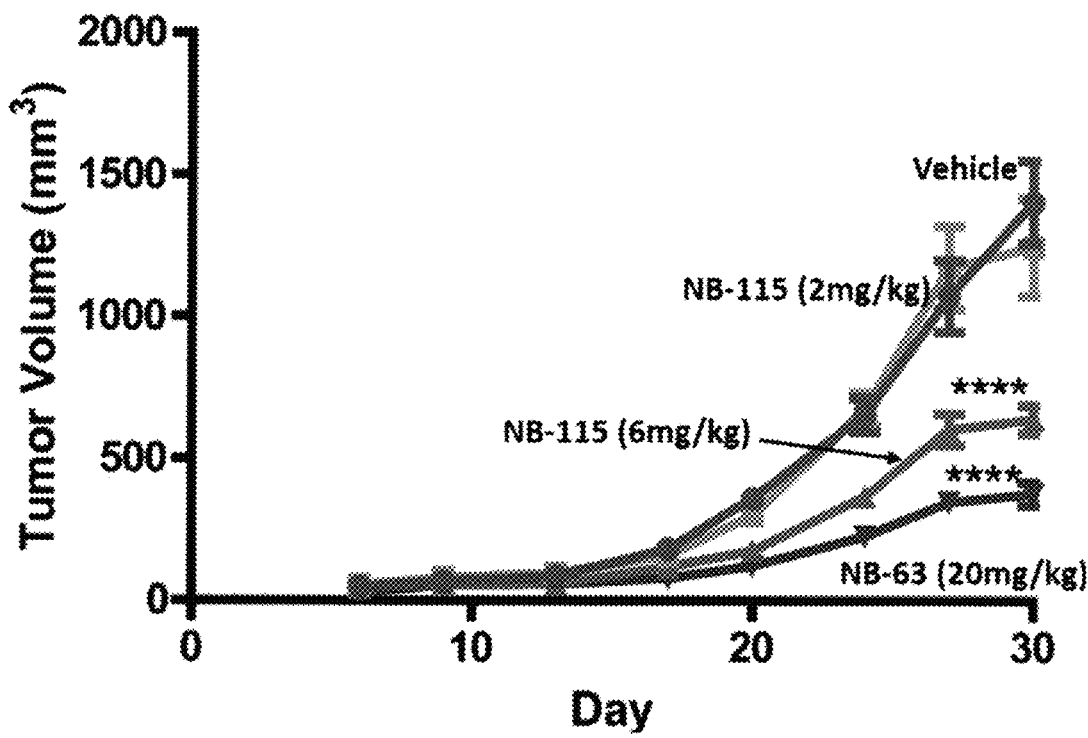
FIG. 14A shows that low doses of the compounds NB-63 (methiodide salt of NB-55) and NB-115 (methiodide salt of NB-51) suppress the growth of DT22-Luc xenograft tumors. Female NSG animals (8 weeks of age) received 1×10$^6$ DT22-Luc cells injected orthotopically into the thoracic mammary gland. NB-115 was injected s.c. daily at 2 mg/kg or 6 mg/kg, and NB-63 was injected s.c. daily at 20 mg/kg until day 20 and thereafter at 10 mg/kg every other day. Effect on tumor volume is shown. (2-way ANOVA, Dunnett's post-test; ****$p<0.0001$, n=8 per group).
Figure 14B:
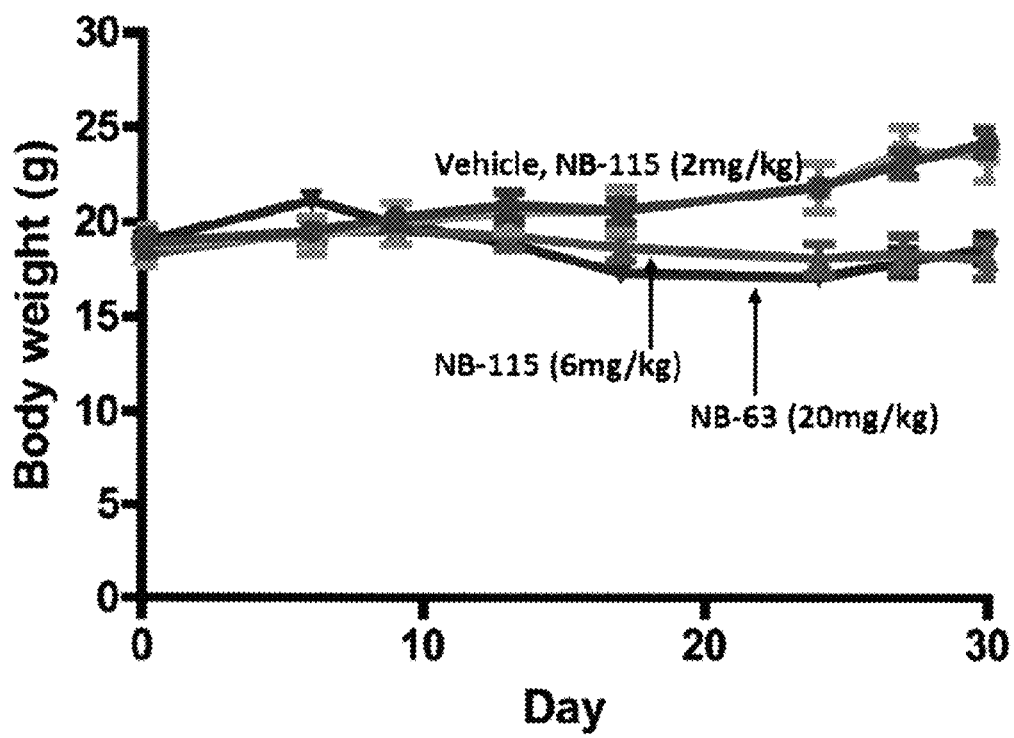
FIG. 14B shows that low doses of the compounds NB-63 (methiodide salt of NB-55) and NB-115 (methiodide salt of NB-51) that suppress the growth of DT22-Luc xenograft tumors do not affect animal body weights. Female NSG animals (8 weeks of age) received 1×10$^6$ DT22-Luc cells injected orthotopically into the thoracic mammary gland. NB-115 was injected s.c. daily at 2 mg/kg or 6 mg/kg, and NB-63 was injected s.c. daily at 20 mg/kg until day 20 and thereafter at 10 mg/kg every other day. Animal body weights were monitored. (2-way ANOVA, Dunnett's post-test; ****, $p<0.0001$, n=8 per group).
Figure 15A:
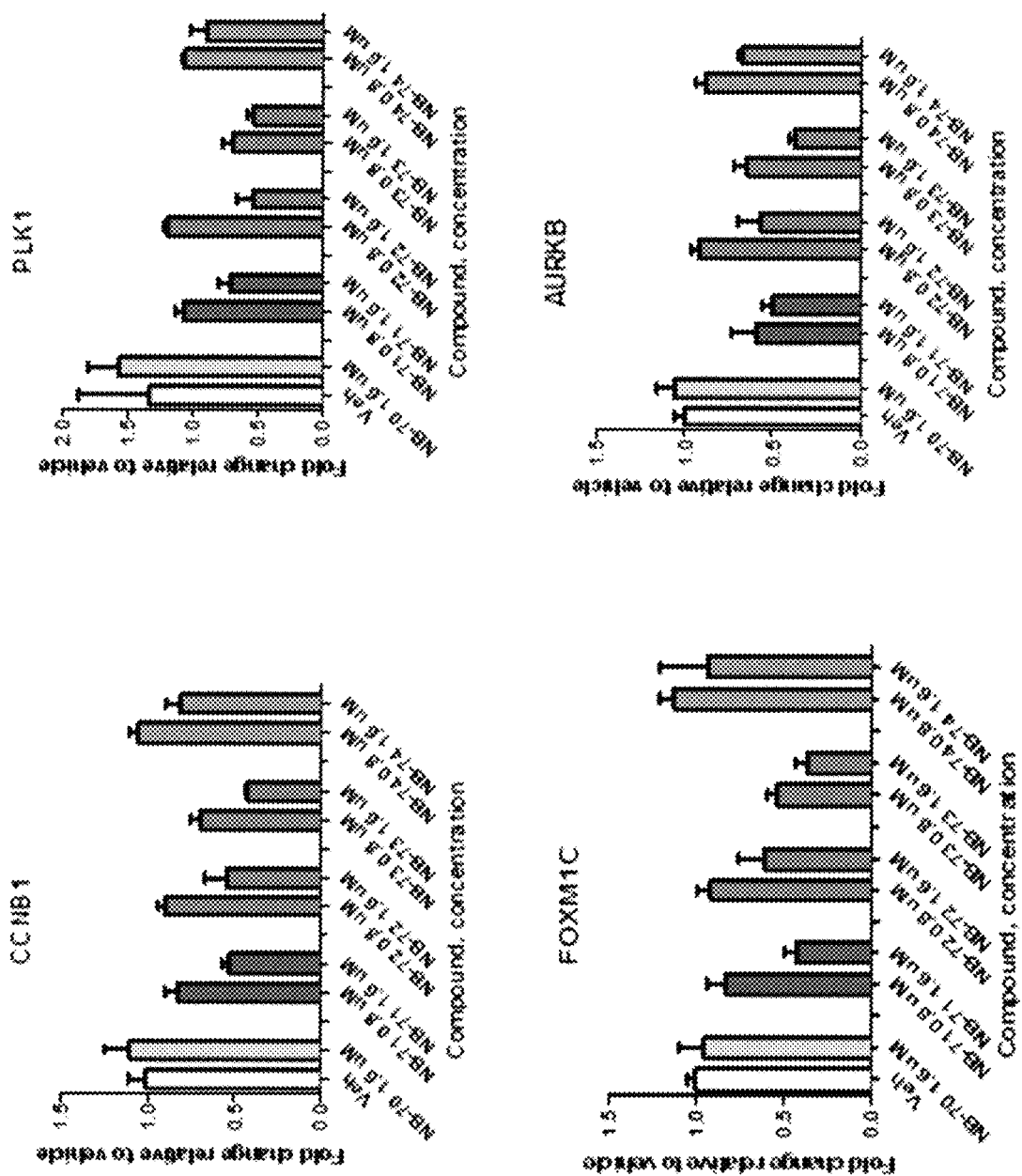
FIG. 15A shows representative results of assays of FOXM1-specific gene regulation by compounds in MCF-7 cells. Genes normally up-regulated by FOXM1 that are decreased by FOXM1 inhibitors. Cells were seeded in 6-well plates and grown to ~50% confluency. They were then treated with inhibitors for 24 hours before Trizol harvest. RNA was isolated, cDNA was prepared, and RNA levels measured by RT-PCR.
Figure 15B:
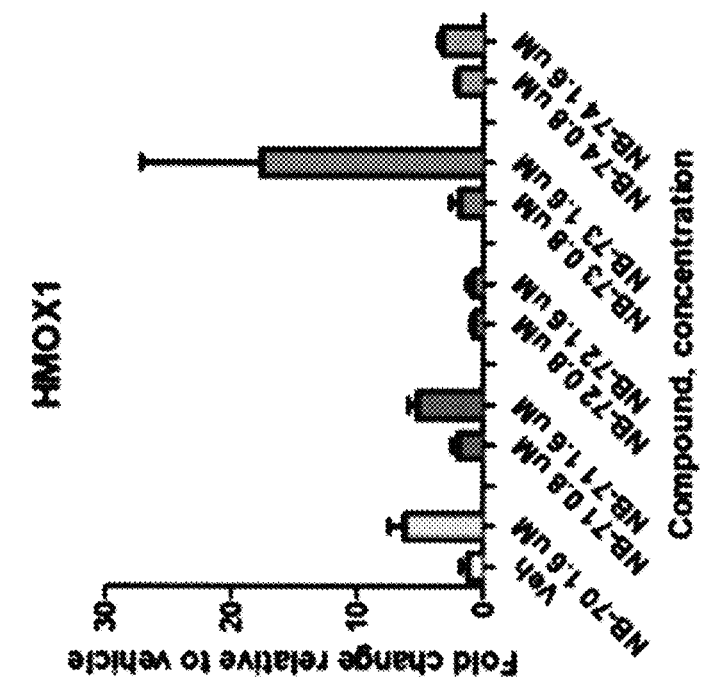
FIG. 15B shows representative results of assays of FOXM1-specific gene regulation by compounds in MCF-7 cells. Genes normally down-regulated by FOXM1 that are increased by FOXM1 inhibitors.
Figure 15B:
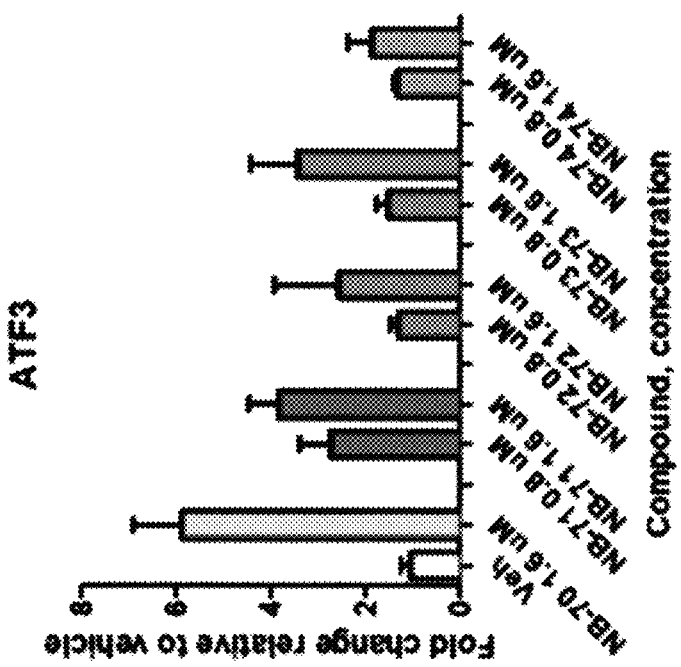
Figure 16A:
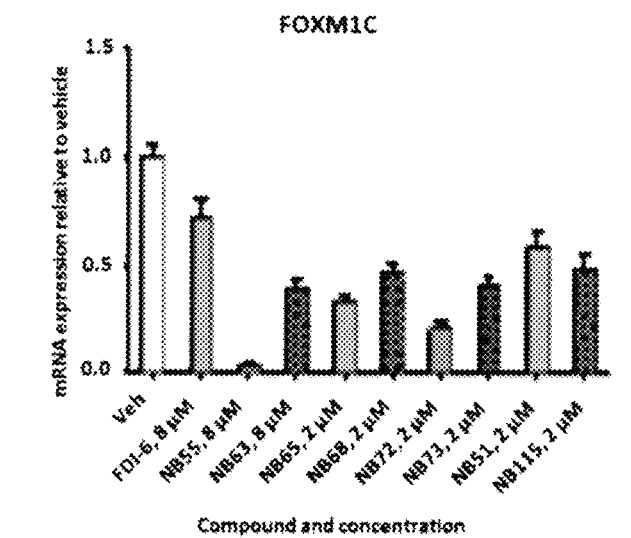
FIGS. 16A-16E shows representative results of assays of FOXM1-specific gene regulation by compounds in DT-22 cells. Genes normally up-regulated by FOXM1 that are decreased by FOXM1 inhibitors. Cells were seeded in 6-well plates and grown to ~50% confluency. They were then treated with inhibitors for 24 hours before Trizol harvest. RNA was isolated, cDNA was prepared, and RNA levels measured by RT-PCR.
Figure 16B:
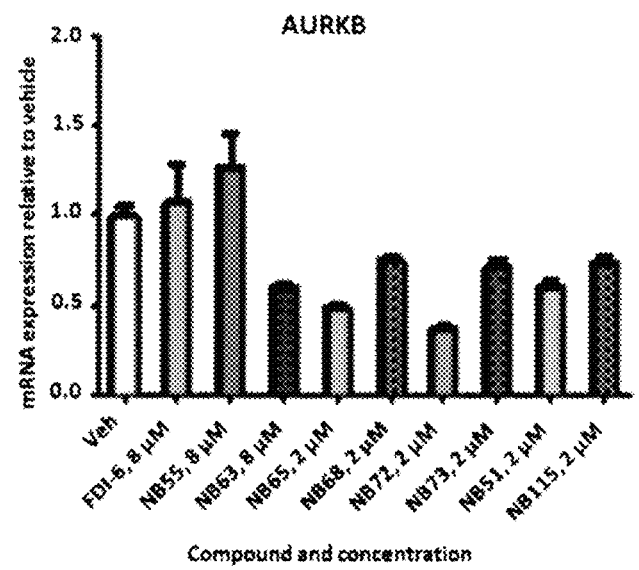
Figure 16C:
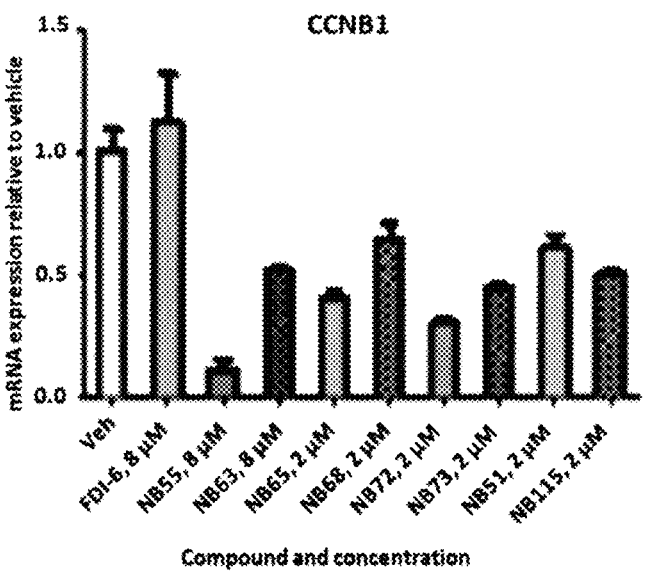
Figure 16D:
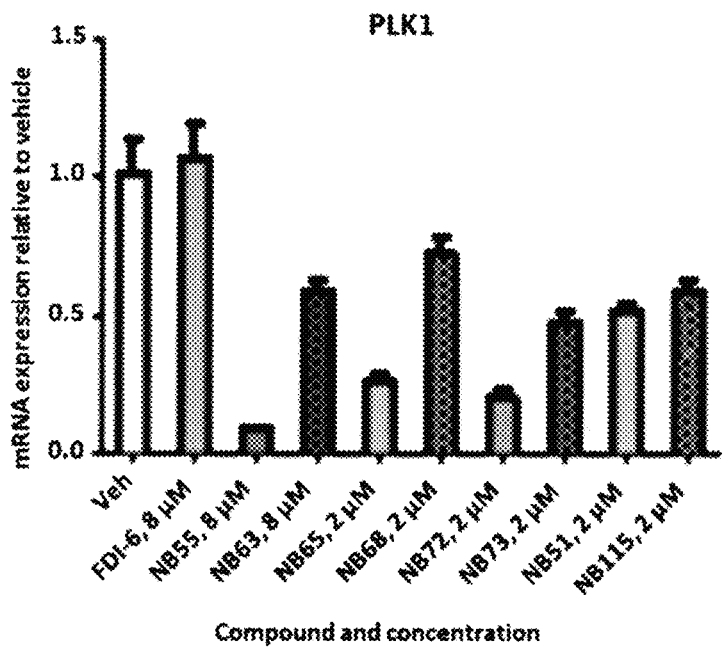
Figure 16E:
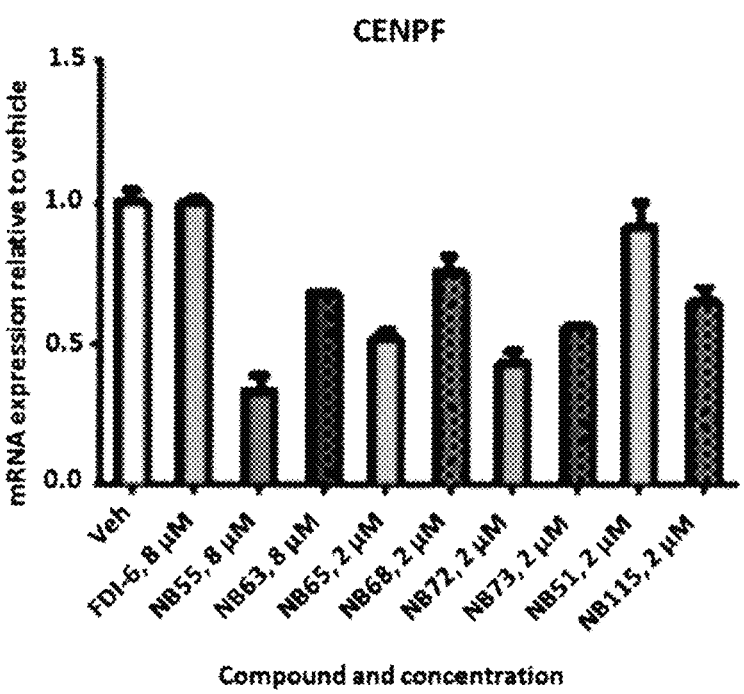
Figure 16F:
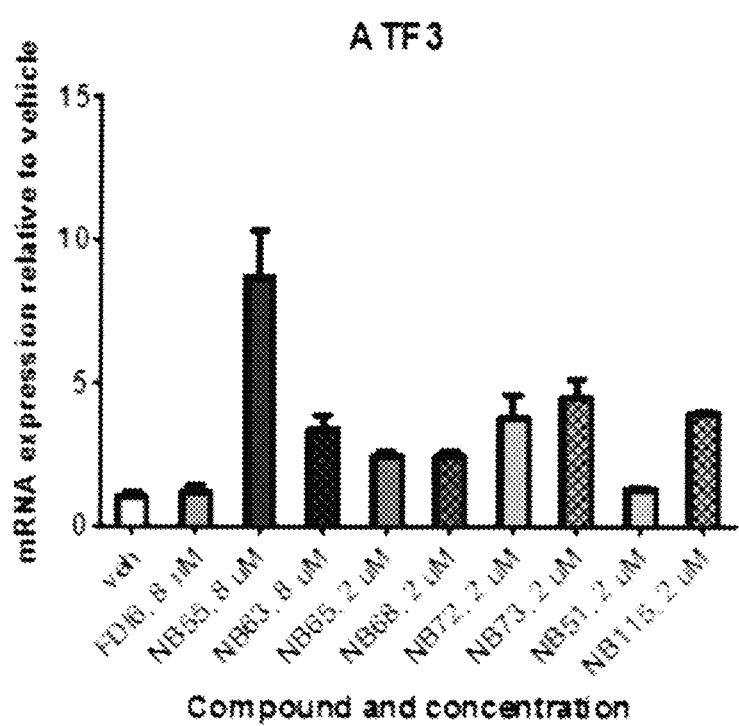
FIG. 16F shows representative results of assays of FOXM1-specific gene regulation by compounds in DT-22 cells. Gene normally down-regulated by FOXM1 that are increased by FOXM1 inhibitors.

Low doses of the compounds NB-63 and NB-115, that showed good PK properties with high blood levels and long half-lives, were also effective in suppressing the growth of DT22 xenograft tumors (FIGS. 14A-14B), and had little impact on animal body weight.

Example 8. Fluorescence Assays with FOXM1

Competitive binding assays of FOXM1 inhibitor binding to FOXM1 by tr-FRET were conducted. All tr-FRET experiments used FRET buffer (20 mM Tris, pH 7.5, 50 mM NaCl, 0.01% NP-40 detergent, 10% glycerol) with 0.3 mg/ml ovalbumin and 0.1 mM butylated hydroxy-anisole added fresh daily. Solutions of the protein, fluorescent probe and inhibitor dilutions were prepared at 3× the final concentrations, the final dilution taking place as they were mixed together on the microtiter plate.

A stock solution of Biotin-FOXM1 was prepared and stored at 5.6 µM at −80° C. After thawing, it was diluted to be 5 nM final concentration in the assay, with 1.25 nM tetravalent streptavidin-terbium (SaTb). The inhibitors were prepared at 7×10-4M in DMF (dimethylformamide) and then serially diluted into FRET buffer plus 2% DMF to ensure solubility. Final concentrations were 10-5M to 10-9M, with the last point being buffer only, no inhibitor. Fluorescein-NB-72 (Fl-NB-72) was prepared at 1 mM in DMF and stored at −20° C. It was diluted into plain FRET buffer to give 100 nM in the assay.

Incubations were done in duplicate on black Molecular Devices 96-well microtiter plates. 5 µL of Fl-NB-72 and 5 µL of the FOXM1-SaTh solution were mixed and allowed to incubate 15 min at room temperature, in the dark. To this were added 5 µL of the inhibitor dilutions, mixed and incubated, in the dark, at room temperature, for 1 h. Time-resolved Forster resonance energy transfer (tr-FRET) measurements were performed with a Victor X5 plate reader (Perkin Elmer, Shelton, CT) with an excitation filter at 340/10 nm and emission filters for terbium and fluorescein at 495/20 and 520/25 nm, respectively, with a 100 µs delay. Diffusion-enhanced FRET was determined by a parallel incubation without biotin-FOXM1 and subtracted as a background signal. Graphs were prepared using Graph Pad/Prism 4. The $K_i$ for each compound was calculated from the $IC_{50}$ value using the Cheng-Prusoff equation:

$$K_i^{compound} = IC_{50}^{compound}/(1+T_0/K_d^{Fl-NB-72})$$

in which $T_0$ is the concentration and $K_d^{Fl-NB-72}$ is the binding affinity of Fl-NB-72.

Direct binding experiments for determination of $K_d$ for Fl-NB-72. For measuring the $K_d$ of the Fl-NB-72, the ligand was diluted into FRET buffer+2% DMF, to give concentrations 3× of final. The Biotin-FOXM1 was diluted to a concentration of 3×(5 nM+1.25 nM SaTb). 5 µL of each of these were mixed on a black Molecular Devices microtiter plate with 5 µL of FRET buffer, so that each component was diluted 3×. Each point was prepared in duplicate, mixed, and incubated for 1 h at room temperature, in the dark. tr-FRET was measured on a Victor X5 microtiter plate reader with settings as given above.

Figure 17A:
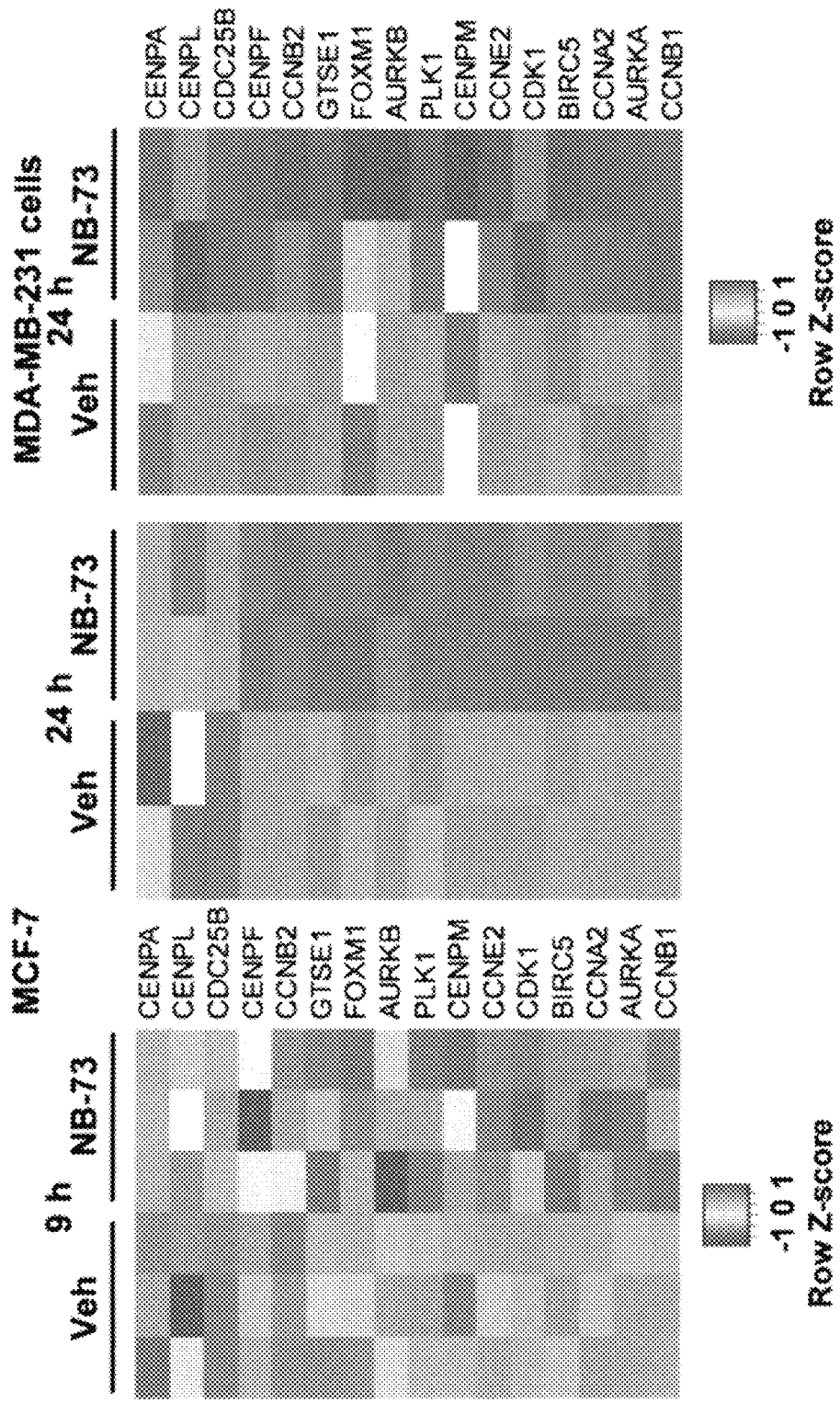
FIGS. 17A-17C shows representative results of RNA-Seq analysis of the effects of compounds on gene expression in breast cancer cells.
Figure 17B:
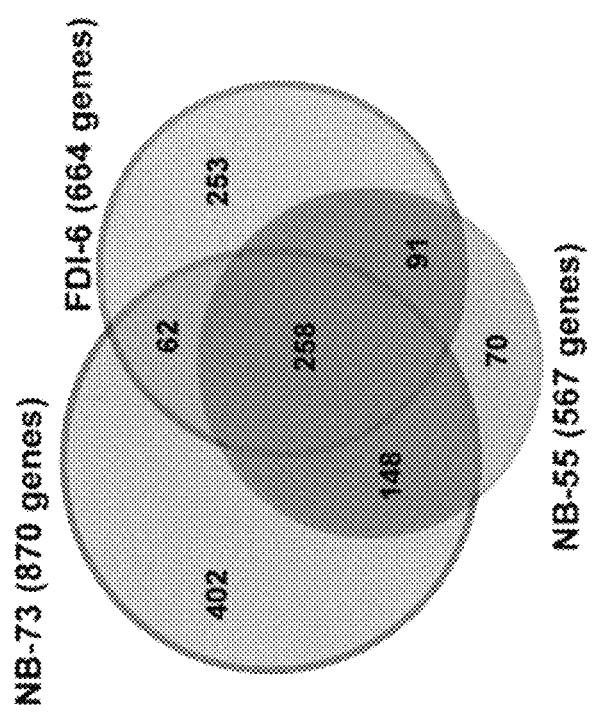
Figure 17C:
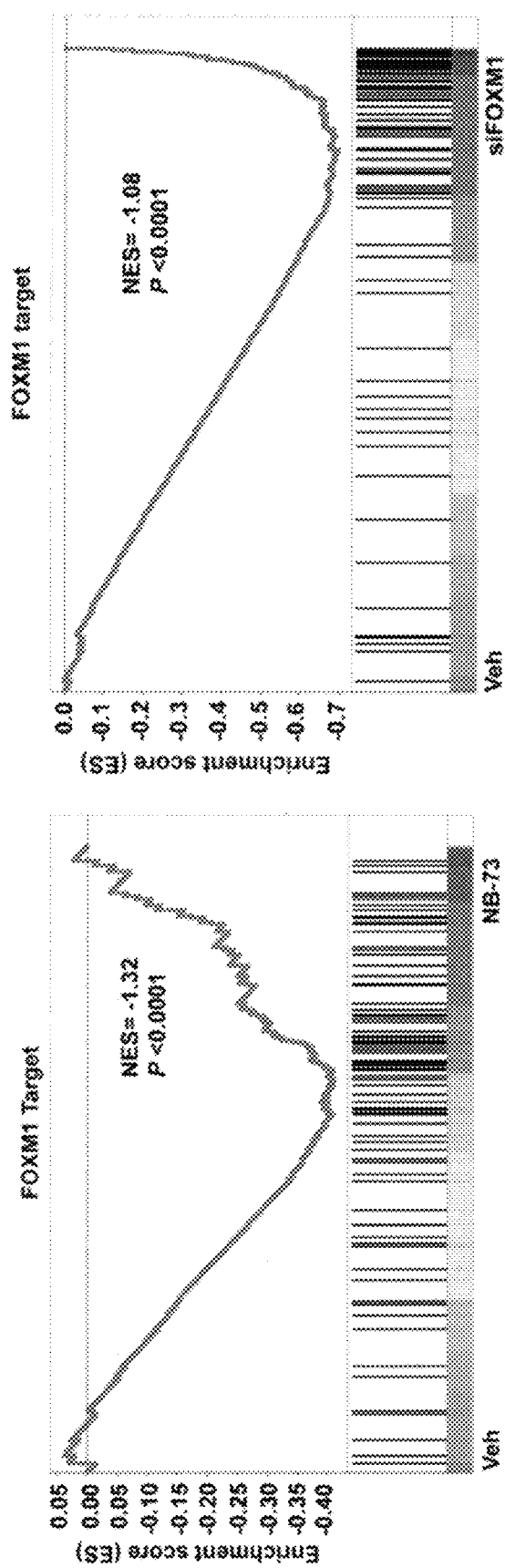

Example 9. RNA-Seq Analysis of the Effects of Compounds and of siFOXM1 on Global FOXM1 Gene Regulation RNA-Seq was used to examine the effects of these compounds on gene regulation globally. Because full FOXM1 depletion results in mitotic catastrophe and cell death, concentrations of compounds that suppressed cell proliferation by about 60% were used. As seen in the heat maps in FIG. 17A, NB-73 regulated FOXM1 RNA-signature genes at 9 h and even more strongly at 24 h in MCF7 and MDA-MB-231 cells. Further, as shown in the Venn diagram (FIG. 17B), there was extensive overlap in the genes regulated more than 2-fold and with FDRs <0.05 by NB-73, NB-55 and FDI-6. Notably, 72% of genes regulated by NB-55 and 48% of genes regulated by FDI-6 overlapped with NB-73 regulated genes, indicating that these compounds regulated many similar genes. Gene Set Enrichment Analyses (GSEA) and Enrichment Scores for gene regulations by NB-73 or siFOXM1 treatment of cells are shown in FIG. 17C. These analyses testing the differential gene expression data against gene sets consisting of FOXM1 target genes revealed negative enrichment scores, indicating that NB-73 and siFOXM1 downregulate expression of genes in the FOXM1 cistrome. The major categories of gene regulations, identified by Gene Ontology analysis, included proliferation, G2/M transition of mitotic cell cycle, apoptosis, regulation of transcription, DNA replication and DNA repair, activities well known to be under FOXM1 regulation. The results from RNA-seq and gene set enrichment analyses indicate that the compounds decrease expression of FOXM1-regulated genes and suppress gene ontologies under FOXM1 regulation.

For reasons of completeness, various aspects of the invention are set out in the following numbered clauses:

Clause 1. A compound of formula (I), or a pharmaceutically acceptable salt thereof,

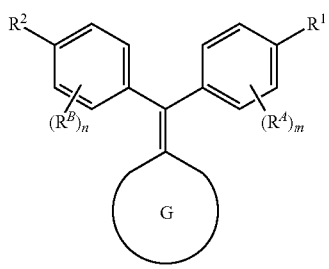

(I)

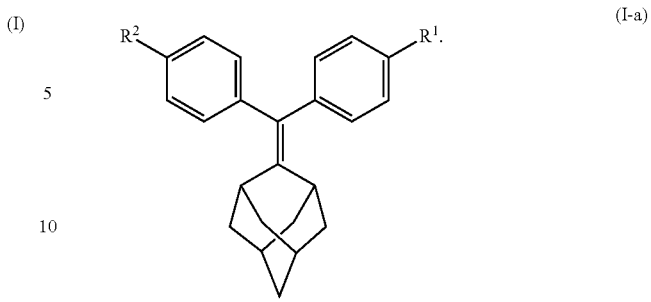

(I-a)

wherein

G is an optionally substituted polycycloalkylidene;

$R^A$ and $R^B$ at each occurrence are independently halogen, $C_{1-4}$alkyl, or $C_{1-4}$halolakyl;

$R^1$ and $R^2$ are independently —OH, halogen, —CN, —$OC_{2-8}$alkylene-L-T, or —$OR^3$, and at least one of $R^1$ and $R^2$ is —$OR^3$;

L is a linker;

T is a fluorescence acceptor or a fluorescence donor;

$R^3$ is —$(CH_2CH_2O)_p$—$C_{2-8}$alkylene-$NR^xR^y$;

$R^x$ and $R^y$ at each occurrence are independently hydrogen, $C_{1-4}$alkyl, —$C_{2-4}$alkylene-OH, or $R^x$ and $R^y$ together with the nitrogen to which they are attached form a 4- to 8-membered heterocycle or heteroaryl, wherein the heterocycle and heteroaryl are optionally substituted with 1, 2, 3, or 4 substituents independently selected from the group consisting of $C_{1-4}$alkyl, halogen, —OH, $C_{1-4}$halolakyl, and —$C_{1-4}$alkylene-OH;

m is 0, 1, 2, 3, or 4;

n is 0, 1, 2, 3, or 4; and p is 0, 1, 2, 3, 4, or 5.

Clause 2. The compound of clause 1, or a pharmaceutically acceptable salt thereof, wherein G is

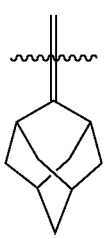

Clause 3. The compound of any one of clauses 1-2, or a pharmaceutically acceptable salt thereof, wherein m is 0, or n is 0, or both m and n are 0.

Clause 4. The compound of any one of clauses 1-3, or a pharmaceutically acceptable salt thereof, wherein the compound is of formula (I-a)

Clause 5. The compound of any one of clauses 1-4, or a pharmaceutically acceptable salt thereof, wherein one of $R^1$ and $R^2$ is —OH, halogen, or —CN, and the other is —$OR^3$.

Clause 6. The compound of any one of clauses 1-4, or a pharmaceutically acceptable salt thereof, wherein one of $R^1$ and $R^2$ is —$OC_{2-8}$alkylene-L-T, and the other is —$OR^3$.

Clause 7. The compound of any one of clauses 1-6, or a pharmaceutically acceptable salt thereof, wherein p is 0, 1, or 2.

Clause 8. The compound of any one of clauses 1-7, or a pharmaceutically acceptable salt thereof, wherein $R^3$ is —$C_{4-8}$alkylene-$NR^xR^y$.

Clause 9. The compound of any one of clauses 1-8, or a pharmaceutically acceptable salt thereof, wherein $R^x$ and $R^y$ at each occurrence are independently $C_{1-4}$alkyl or —$C_{2-4}$alkylene-OH.

Clause 10. The compound of any one of clauses 1-8, or a pharmaceutically acceptable salt thereof, wherein $R^x$ and $R^y$ together with the nitrogen to which they are attached form 4- to 8-membered heterocycle or heteroaryl, wherein the heterocycle and heteroaryl are optionally substituted with 1, 2, 3, or 4 substituents independently selected from the group consisting of $C_{1-4}$alkyl, halogen, —OH, $C_{1-4}$halolakyl, and —$C_{1-4}$alkylene-OH.

Clause 11. The compound of any one of clauses 1-8 and 10, or a pharmaceutically acceptable salt thereof, wherein —$NR^xR^y$ is

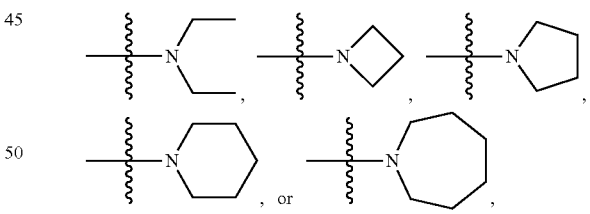

each of which is optionally substituted with 1, 2, 3, or 4 substituents independently selected from the group consisting of $C_{1-4}$alkyl, halogen, —OH, $C_{1-4}$halolakyl, and —$C_{1-4}$alkylene-OH.

Clause 12. A pharmaceutically acceptable salt of the compound of any one of clauses 1-8, wherein $R^3$ is —$(CH_2CH_2O)_p$—$C_{2-8}$alkylene-$[NR^xR^yR^z]^+·X^-$;

$R^x$ and $R^y$ at each occurrence are independently $C_{1-4}$alkyl or —$C_{2-4}$alkylene-OH, or $R^x$ and $R^y$ together with the nitrogen to which they are attached form a 4- to 8-membered heterocycle or heteroaryl, wherein the heterocycle and heteroaryl are optionally substituted with 1, 2, 3, or 4 substituents independently selected from the group consisting of $C_{1-4}$alkyl, halogen, —OH, $C_{1-4}$halolakyl, and —$C_{1-4}$alkylene-OH;

$R^x$ is $C_{1-4}$alkyl or —$C_{2-4}$alkylene-OH; and $X^-$ is a counterion.

Clause 13. The salt of clause 12, wherein $R^x$ and $R^y$ at each occurrence are independently $C_{1-4}$alkyl or —$C_{2-4}$alkylene-OH.

Clause 14. The salt of clause 12, wherein $R^x$ and $R^y$ together with the nitrogen to which they are attached form 4- to 8-membered heterocycle or heteroaryl, wherein the heterocycle and heteroaryl are optionally substituted with 1, 2, 3, or 4 substituents independently selected from the group consisting of $C_{1-4}$alkyl, halogen, —OH, $C_{1-4}$halolakyl, and —$C_{1-4}$alkylene-OH.

Clause 15. The salt of any one of clauses 12 and 14, wherein the —$[NR^xR^yR^z]^+ \cdot X^-$ group is

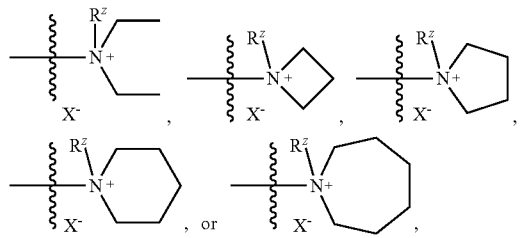

each of which is optionally substituted with 1, 2, 3, or 4 substituents independently selected from the group consisting of $C_{1-4}$alkyl, halogen, —OH, $C_{1-4}$halolakyl, and —$C_{1-4}$alkylene-OH.

Clause 16. The salt of any one of clauses 12-15, wherein $R^z$ is methyl or hydroxyethyl.

Clause 17. The salt of any one of clauses 12-16, wherein $X^-$ is halides, sulfonate, phosphonate, acetate, oxalate, fumarate, tartarate, or lactate salts.

Clause 18. The salt of any one of clauses 12-17, or a pharmaceutically acceptable salt thereof, wherein $X^-$ is $I^-$ or $CH_3SO_3^-$.

Clause 19. The compound of any one of clauses 1-4 and 6-11, or a pharmaceutically acceptable salt thereof, wherein -L-T is

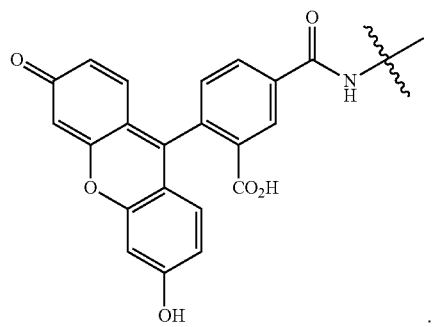 [SMILES: *NC(=O)c1ccc(-c2c3ccc(=O)cc-3oc3cc(O)ccc23)c(C(=O)O)c1]

Clause 20. The compound of clause 1, selected from the group consisting of 1-(6-(4-((Z)-((5S,7S)-adamantan-2-ylidene)(4-chlorophenyl)methyl)phenoxy)hexyl)pyrrolidine;

1-(6-(4-((Z)-((5S,7S)-Adamantan-2-ylidene)(4-chlorophenyl)methyl)phenoxy)hexyl)piperidine;

1-(6-(4-((Z)-((5S,7S)-adamantan-2-ylidene)(4-chlorophenyl)methyl)phenoxy)hexyl)azepane;

1,1'-((((((5r,7r)-adamantan-2-ylidene)methylene)bis(4,1-phenylene))bis(oxy))bis(hexane-6,1-diyl))dipyrrolidine;

1,1'-((((((5r,7r)-Adamantan-2-ylidene)methylene)bis(4,1-phenylene))bis(oxy))bis(hexane-6,1-diyl))dipiperidine;

1,1'-((((((5r,7r)-Adamantan-2-ylidene)methylene)bis(4,1-phenylene))bis(oxy))bis(hexane-6,1-diyl))bis(azepane);

6,6'-((((((5r,7r)-adamantan-2-ylidene)methyl ene)bis(4,1-phenylene))bis(oxy))bis(N, N-diethylhexan-1-amine);

2,2'-(((((((5r,7r)-adamantan-2-ylidene)methylene)bis(4,1-phenylene))bis(oxy))bis(hexane-6,1-diyl))bis(ethylazanediyl))bis(ethan-1-ol);

2,2',2'',2'''-(((((((5r,7r)-adamantan-2-ylidene)methylene)bis(4,1-phenylene))bis(oxy))bis(hexane-6,1-diyl))bis(azanetriyl))tetrakis(ethan-1-ol);

1,1'-((((((5r,7r)-adamantan-2-ylidene)methylene)bis(4,1-phenylene))bis(oxy))bis(hexane-6,1-diyl))bis(azetidine);

1,1'-((((((5r,7r)-adamantan-2-ylidene)methylene)bis(4,1-phenylene))bis(oxy))bis(hexane-6,1-diyl))bis(azetidin-3-ol);

1,1'-((((((5r,7r)-adamantan-2-ylidene)methylene)bis(4,1-phenyl ene))bis(oxy))bis(hexane-6,1-diyl))bis(3-methylazetidin-3-ol);

((2S,2'S)-((((((5r,7r)-adamantan-2-ylidene)methylene)bis(4,1-phenylene))bis(oxy))bis(hexane-6,1-diyl))bis(pyrrolidine-1,2-diyl))dimethanol;

1,1'-((((((5r,7r)-adamantan-2-ylidene)methylene)bis(4,1-phenylene))bis(oxy))bis(hexane-6,1-diyl))bis(piperidin-4-ol);

5-((6-(4-((E)-((5r,7r)-adamantan-2-ylidene)(4-((6-(azepan-1-yl)hexyl)oxy)phenyl)methyl)phenoxy)hexyl)carbamoyl)-2-(6-hydroxy-3-oxo-3H-xanthen-9-yl)benzoic acid;

1-(6-(4-((Z)-((5r,7r)-adamantan-2-ylidene)(4-((6-(4-((3-carboxy-4-(6-hydroxy-3-oxo-3H-xanthen-9-yl)benzamido)methyl)-1H-1,2,3-triazol-1-yl)hexyl)oxy)phenyl)methyl)phenoxy)hexyl)-1-methylazepan-1-ium iodide;

4-((E)-((5R,7R)-adamantan-2-ylidene)(4-((6-(diethylamino)hexyl)oxy)phenyl)methyl)phenol;

6-(4-((Z)-((5S,7S)-adamantan-2-ylidene)(4-chlorophenyl)methyl)phenoxy)-N,N-diethylhexan-1-amine;

1-(6-(4-((Z)-((5S,7S)-adamantan-2-ylidene)(4-chlorophenyl)methyl)phenoxy)hexyl)-1H-imidazole;

1-(6-(4-((Z)-((5S,7S)-adamantan-2-ylidene)(4-chlorophenyl)methyl)phenoxy)hexyl)-4-methylpiperazine;

1,1'-((((((5r,7r)-adamantan-2-ylidene)methyl ene)bis(4,1-phenyl ene))bis(oxy))bis(butane-4,1-diyl))dipiperidine;

1,1'-((((((5r,7r)-adamantan-2-ylidene)methyl ene)bis(4,1-phenylene))bis(oxy))bis(butane-4,1-diyl))bis(azepane);

1,1'-((((((5r,7r)-adamantan-2-ylidene)methyl ene)bis(4,1-phenylene))bis(oxy))bis(pentane-5,1-diyl))dipiperidine;

1,1'-((((((5r,7r)-adamantan-2-ylidene)methylene)bis(4,1-phenylene))bis(oxy))bis(pentane-5,1-diyl))bis(azepane);

1,1'-((((((5r,7r)-adamantan-2-ylidene)methylene)bis(4,1-phenylene))bis(oxy))bis(octane-8,1-diyl))bis(azepane);

2,2'-(((((((((5r,7r)-adamantan-2-ylidene)methylene)bis(4,1-phenylene))bis(oxy))bis(ethane-2,1-diyl))bis(oxy))bis(ethane-2,1-diyl))bis(oxy))bis(N,N-diethylethan-1-amine);

4,4'-((((((5r,7r)-adamantan-2-ylidene)methylene)bis(4,1-phenylene))bis(oxy))bis(hexane-6,1-diyl))bis(1-methylpiperazine); and 1,1'-((((((5r,7r)-adamantan-2-ylidene)methylene)bis(4,1-phenylene))bis(oxy))bis(hexane-6,1-diyl))bis(1H-imidazole), or a pharmaceutically acceptable salt thereof.

Clause 21. The salt of clause 12, selected from the group consisting of 1-(6-(4-((Z)-((5S,7S)-adamantan-2-ylidene)(4-chlorophenyl)methyl)phenoxy)hexyl)-1-methylpyrrolidin-1-ium iodide;

1,1'-((((((5r,7r)-adamantan-2-ylidene)methylene)bis(4,1-phenylene))bis(oxy))bis(hexane-6,1-diyl))bis(1-methylpyrrolidin-1-ium) diiodide;

1,1'-((((((5r,7r)-adamantan-2-ylidene)methylene)bis(4,1-phenylene))bis(oxy))bis(hexane-6,1-diyl))bis(1-methylpiperidin-1-ium) diodide;

1,1'-((((((5r,7r)-adamantan-2-ylidene)methylene)bis(4,1-phenylene))bis(oxy))bis(hexane-6,1-diyl))bis(1-methylazepan-1-ium) diiodide;

6-(4-(((5r,7r)-adamantan-2-ylidene)(4-((6-(diethyl(methyl)-$\lambda^4$-azaneyl)hexyl)oxy)phenyl)methyl)phenoxy)-N,N-diethyl-N-methylhexan-1-aminium diiodide;

6,6'-(((((5r,7r)-adamantan-2-ylidene)methylene)bis(4,1-phenylene))bis(oxy))bis(N-ethyl-N-(2-hydroxyethyl)-N-methylhexan-1-aminium) diiodide;

6,6'-(((((5r,7r)-adamantan-2-ylidene)methyl ene)bis(4,1-phenyl ene))bis(oxy))bis(N,N-bis(2-hydroxyethyl)-N-methylhexan-1-aminium) diiodide;

1,1'-((((((5r,7r)-adamantan-2-ylidene)methylene)bis(4,1-phenylene))bis(oxy))bis(hexane-6,1-diyl))bis(1-methylazetidin-1-ium) diiodide;

1,1'-((((((5r,7r)-adamantan-2-ylidene)methyl ene)bis(4,1-phenyl ene))bis(oxy))bis(hexane-6,1-diyl))bis(3-hydroxy-1,3-dimethylazetidin-1-ium) diiodide;

(1R,1'R,2S,2'S)-1,1'-((((((5r,7r)-adamantan-2-ylidene) methylene)bis(4,1-phenylene))bis(oxy))bis(hexane-6,1-diyl))bis(2-(hydroxymethyl)-1-methylpyrrolidin-1-ium) diiodide;

1,1'-((((((5r,7r)-adamantan-2-ylidene)methylene)bis(4,1-phenylene))bis(oxy))bis(hexane-6,1-diyl))bis(4-hydroxy-1-methylpiperidin-1-ium) diiodide;

1,1'-((((((5r,7r)-adamantan-2-ylidene)methylene)bis(4,1-phenylene))bis(oxy))bis(hexane-6,1-diyl))bis(1-(2-hydroxyethyl)pyrrolidin-1-ium) diiodide;

1,1'-((((((5r,7r)-adamantan-2-ylidene)methylene)bis(4,1-phenylene))bis(oxy))bis(hexane-6,1-diyl))bis(1-(2-hydroxyethyl)piperidin-1-ium) diiodide;

1,1'-((((((5r,7r)-adamantan-2-ylidene)methylene)bis(4,1-phenylene))bis(oxy))bis(hexane-6,1-diyl))bis(1-(2-hydroxyethyl)azepan-1-ium) diiodide;

1-(6-(4-((Z)-((5S,7S)-adamantan-2-ylidene)(4-chlorophenyl)methyl)phenoxy)hexyl)-3-methyl-1H-imidazol-3-ium iodide;

(S)-1-(6-(4-((Z)-((5S,7S)-adamantan-2-ylidene)(4-chlorophenyl)methyl)phenoxy)hexyl)-1-methyl-1$\lambda^4$-piperidin-2-ylium iodide;

1-(6-(4-((Z)-((5 S,7S)-adamantan-2-ylidene)(4-chlorophenyl)methyl)phenoxy)hexyl)-1-methylazepan-1-ium iodide;

1-(4-(4-((E)-((5R,7R)-adamantan-2-ylidene)(4-(4-(1-metheyliumylpiperidin-1-ium-1-yl)butoxy)phenyl) methyl)phenoxy)butyl)-1-methylpiperidin-1-ium diiodide;

1,1'-((((((5r,7r)-adamantan-2-ylidene)methylene)bis(4,1-phenylene))bis(oxy))bis(butane-4,1-diyl))bis(1-methylazepan-1-ium) diiodide;

1,1'-((((((5r,7r)-adamantan-2-ylidene)methylene)bis(4,1-phenylene))bis(oxy))bis(pentane-5,1-diyl))bis(1-methylpiperidin-1-ium) diiodide;

1,1'-((((((5r,7r)-adamantan-2-ylidene)methylene)bis(4,1-phenylene))bis(oxy))bis(pentane-5,1-diyl))bis(1-methylazepan-1-ium) diiodide;

1,1'-((((((5r,7r)-adamantan-2-ylidene)methylene)bis(4,1-phenyl ene))bis(oxy))bis(octane-8,1-diyl))bis(1-methylazepan-1-ium) diiodide; and 1,1'-((((((5r,7r)-adamantan-2-ylidene)methylene)bis(4,1-phenylene))bis(oxy))bis(hexane-6,1-diyl))bis(1,4-dimethylpiperazin-1-ium) dimethanesulfonate.

Clause 22. A pharmaceutical composition comprising a therapeutically effective amount of a compound of any one of clauses 1-11 and 20, or a pharmaceutically acceptable salt thereof, and a pharmaceutically acceptable carrier.

Clause 23. A pharmaceutical composition comprising a therapeutically effective amount of a pharmaceutically acceptable salt of any one of clauses 12-18 and 21, and a pharmaceutically acceptable carrier.

Clause 24. The pharmaceutical composition of any one of clauses 22 and 23, further comprising a therapeutically effective amount of at least one additional anti-cancer therapeutic agent.

Clause 25. A method of inhibiting FOXM1 comprising administering to a subject in need thereof a therapeutically effective amount of a compound of any one of clauses 1-11 and 20, or a pharmaceutically acceptable salt thereof, or the pharmaceutical composition of clause 22.

Clause 26. A method of inhibiting FOXM1 comprising administering to a subject in need thereof a therapeutically effective amount of a pharmaceutically acceptable salt of any one of clauses 12-18 and 21, or the pharmaceutical composition of clause 23.

Clause 27. A method of inhibiting cancer growth comprising administering to a subject in need thereof a therapeutically effective amount of a compound of any one of clauses 1-11 and 20, or a pharmaceutically acceptable salt thereof, or the pharmaceutical composition of clause 22.

Clause 28. A method of inhibiting cancer growth comprising administering to a subject in need thereof a therapeutically effective amount of a pharmaceutically acceptable salt of any one of clauses 12-18 and 21, or the pharmaceutical composition of clause 23.

Clause 29. A method of treating cancer comprising administering to a subject in need thereof a therapeutically effective amount of a compound of any one of clauses 1-11 and 20, or a pharmaceutically acceptable salt thereof, or the pharmaceutical composition of clause 22.

Clause 30. A method of treating cancer comprising administering to a subject in need thereof a therapeutically effective amount of a pharmaceutically acceptable salt of any one of clauses 12-18 and 21, or the pharmaceutical composition of clause 23.

Clause 31. The method of any one of clauses 27-30, wherein the cancer is breast cancer, prostate cancer, glioblastoma, ovarian cancer, gastrointestinal cancer, non-small cell lung cancer, pancreatic ductal adenocarcinoma, or a combination thereof.

Clause 32. The method of clause 31, wherein the breast cancer is hormone receptor-positive breast cancer, ER-positive breast cancer, HER2-positive breast cancer, triple negative breast cancer, tamoxifen-resistant breast cancer, or a combination thereof.

Clause 33 The method of any one of clauses 25-32, further comprising administering a therapeutically effective amount of at least one additional cancer treatment.

Clause 34. The method of any one of clauses 29 and 30, wherein the method is a method of therapeutically treating cancer.

Claus 35. An assay method of screening for a substance that may be acting as a FOXM1 inhibitor, the method comprising the steps of:

incubating
  i) a FOXM1 that is fused with an amino acid sequence that allows covalent attachment of biotin,
  ii) a streptavidin that is labeled with a fluorescent donor moiety or a fluorescent acceptor moiety, and
  iii) a compound of claim 6, or a salt thereof, wherein T is a fluorescent acceptor moiety if the streptavidin is labeled with a fluorescent donor moiety, or wherein T is a fluorescent donor moiety if the streptavidin is labeled with a fluorescent acceptor moiety in a reaction mixture in either the presence or absence of the substance;
exposing the reaction mixture to light that allows fluorescence resonance energy transfer to take place; and
measuring fluorescence emission from the reaction mixture;
wherein if the fluorescence emission measurement from the reaction mixture in the presence of the substance is different than the fluorescent emission measurement from the mixture in the absence of the substance, the substance is acting as a FOXM1 inhibitor.

Clause 36. The method of clause 35, further comprising providing a compound of claim 6, or a salt thereof, wherein T is a fluorescent acceptor moiety if the streptavidin is labeled with a fluorescent donor moiety, or wherein T is a fluorescent donor moiety if the streptavidin is labeled with a fluorescent acceptor moiety.

Clause 37. The method of clause 36, further comprising providing a streptavidin that is labeled with a fluorescent donor moiety or a fluorescent acceptor moiety.

Clause 38. The method of clause 37, further comprising providing a FOXM1 that is fused with an amino acid sequence that allows covalent attachment of biotin.

Clause 39. A kit for the screening a substance that may be acting a FOXM1 inhibitor, the kit comprising:
  a first solution comprising FOXM1 fused at C-terminus with an amino acid sequence that allows covalent attachment of biotin,
  a second solution comprising streptavidin labeled with a fluorescent donor moiety or a fluorescent acceptor moiety,
  a third solution comprising a compound of clause 6, or a pharmaceutically acceptable salt thereof, wherein T is a fluorescence donor moiety if the streptavidin is labeled with a fluorescence acceptor moiety, or wherein T is a fluorescence acceptor if the streptavidin is labeled with a fluorescence donor moiety, and at least one buffer.

Some aspects of the invention are set out in the following numbered clauses:

Clause A1. A composition comprising the structure:

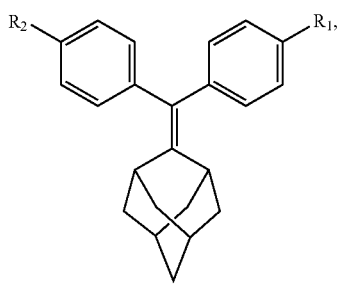

wherein $R_1$ is selected from OH, Cl or $R_2$, and
$R_2$ is selected from

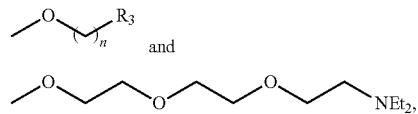

wherein n is about 4-8 and
$R_3$ is selected from:

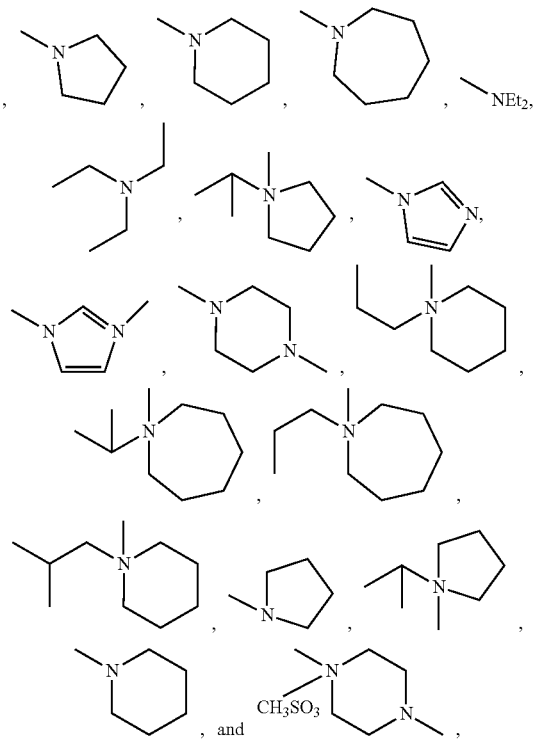

and stereoisomers and pharmaceutically acceptable salts thereof.

Clause A2. The composition of clause A1, wherein $R_1$ is the same as $R_2$.

Clause A3. The composition of clause A1, wherein the pharmaceutically acceptable salts is selected from methiodide, methylammnoium halides, sulfonate, phosphonate, acetate, oxalate, fumarate, tartarate, and lactate salts.

Clause A4. The composition of clause A1, wherein the pharmaceutically acceptable salts is selected from:

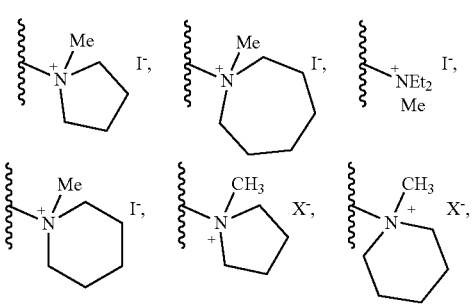

-continued

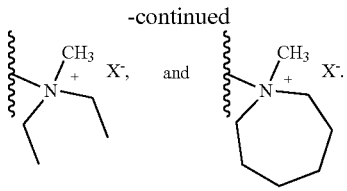

Clause A5. A method of inhibiting FOXM1 in a subject, the method comprising administering to a subject a therapeutically effective amount of composition of any of clauses A1-A4.

Clause A6. A method of inhibiting cancer growth in a subject, the method comprising administering to a subject having or suspected of having cancer a therapeutically effective amount of a composition of any of clauses A1-A4.

Clause A7. A method of treating cancer in a subject, the method comprising administering to a subject having or suspected of having cancer a therapeutically effective amount of a composition of any of clauses A1-A4.

Clause A8. The method of any of clauses A5-A7, wherein the cancer is selected from breast cancer, prostate cancer, glioblastoma, ovarian cancer, gastrointestinal cancer, non-small cell lung cancer, and pancreatic ductal adenocarcinoma.

Clause A9. The method of any of clauses A5-A8, wherein the breast cancer is selected from hormone receptor-positive breast cancers, ER-positive breast cancers, HER2-positive breast cancers, triple negative breast cancers, and tamoxifen-resistant breast cancers.

Clause A10. The method of any of clauses A5-A9, further comprising administering a therapeutically effective amount of at least one additional cancer treatment.

Clause A11. A composition of clause A1, where one amine appendage of the diamine compound is replaced with a fluorescence donor or a fluorescence acceptor.

Clause A12. A composition comprising the structure:

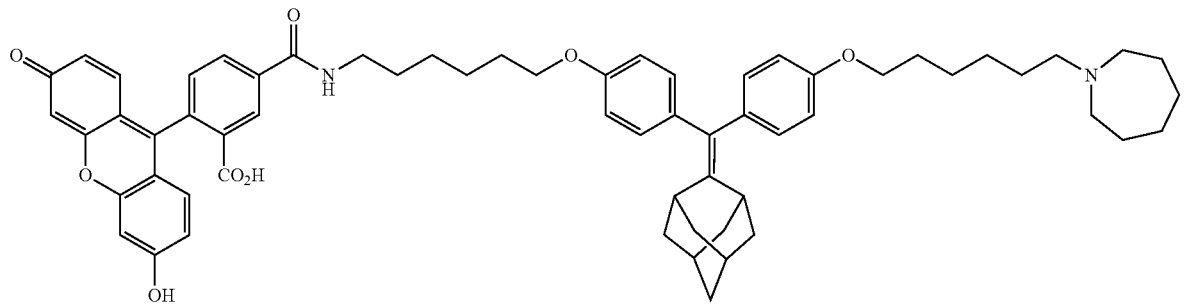 [SMILES: O=C(NCCCCCCOc1ccc(C(=C2C3CC4CC(C3)CC2C4)c2ccc(OCCCCCCN3CCCCCC3)cc2)cc1)c1ccc(-c2c3ccc(=O)cc-3oc3cc(O)ccc23)c(C(=O)O)c1]

Clause A13. A method of screening for a substance that may be acting as a FOXM1 inhibitor, the method comprising the steps of:
a) providing a FOXM1 that is fused with an amino acid sequence that allows covalent attachment of biotin;
b) providing streptavidin that is labeled with a fluorescent donor moiety or a fluorescent acceptor moiety;
c) providing a composition of clause A11 or A12, wherein the composition is labeled with a fluorescent acceptor moiety if the streptavidin in step b) is labeled with a fluorescent donor moiety, and wherein the composition of clause A11 or A12 is labeled with a fluorescent donor moiety if said streptavidin in step b) is labeled with a fluorescent acceptor moiety;
d) incubating the FOXM1, the streptavidin and the composition of clause A11 or clause A12 in a reaction mixture in either the presence or absence of the substance;
e) exposing the reaction mixture to light that allows fluorescence resonance energy transfer to take place and measuring fluorescence emission from the reaction mixture; wherein if the fluorescence emission measurement from the reaction mixture in the presence of the substance is different than the fluorescent emission measurement from the mixture in the absence of the substance, the substance is acting as a FOXM1 inhibitor.

Clause A14. A kit for the screening a substance that may be acting a FOXM1 inhibitor, the kit comprising:
a solution comprising FOXM1 that is fused at its C-terminus with an amino acid sequence that allows covalent attachment of biotin,
a solution comprising streptavidin that is labeled with a fluorescent donor moiety or a fluorescent acceptor moiety,
a solution comprising a composition of clause A11 or A12 labeled with a fluorescence donor moiety or a fluorescent acceptor moiety, and
at least one buffer.

The invention claimed is:
1. A compound of formula (I), or a pharmaceutically acceptable salt thereof,

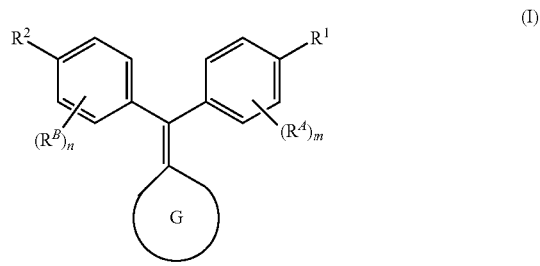

wherein
G is an optionally substituted polycycloalkylidene;
$R^A$ and $R^B$ at each occurrence are independently halogen, $C_{1-4}$alkyl, or $C_{1-4}$haloalkyl;
$R^1$ and $R^2$ are independently —OH, halogen, —CN, —OC$_{2-8}$alkylene-L-T, or —OR$^3$, and at least one of $R^1$ and $R^2$ is —OR$^3$;
L is a linker;
T is a fluorescence acceptor or a fluorescence donor;

R³ is —C₄₋₈alkylene-NRˣRʸ, —CH₂CH₂O—CH₂CH₂—NRˣRʸ, or —(CH₂CH₂O)₂—CH₂CH₂—NRˣRʸ;

Rˣ and Rʸ at each occurrence are independently C₁₋₄alkyl or —C₂₋₄alkylene-OH, or Rˣ and Rʸ together with the nitrogen to which they are attached form a 4- to 8-membered heterocycle or heteroaryl, wherein the heterocycle and heteroaryl are optionally substituted with 1, 2, 3, or 4 substituents independently selected from the group consisting of C₁₋₄alkyl, halogen, —OH, C₁₋₄haloalkyl, and —C₁₋₄alkylene-OH;

m is 0, 1, 2, 3, or 4; and n is 0, 1, 2, 3, or 4.

2. The compound of claim 1, or a pharmaceutically acceptable salt thereof, wherein G is

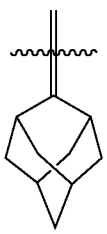

3. The compound of claim 1, or a pharmaceutically acceptable salt thereof, wherein m is 0, or n is 0, or both m and n are 0.

4. The compound of claim 1, or a pharmaceutically acceptable salt thereof, wherein the compound is of formula (I-a)

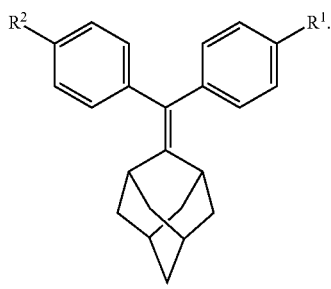

5. The compound of claim 1, or a pharmaceutically acceptable salt thereof, wherein one of R¹ and R² is —OH, halogen, or —CN, and the other is —OR³.

6. The compound of claim 1, or a pharmaceutically acceptable salt thereof, wherein one of R¹ and R² is —OC₂₋₈alkylene-L-T, and the other is —OR³.

7. The compound of claim 1, or a pharmaceutically acceptable salt thereof, wherein R³ is —C₄₋₈alkylene-NRˣRʸ.

8. The compound of claim 1, or a pharmaceutically acceptable salt thereof, wherein Rˣ and Rʸ together with the nitrogen to which they are attached form 4- to 8-membered heterocycle or heteroaryl, wherein the heterocycle and heteroaryl are optionally substituted with 1, 2, 3, or 4 substituents independently selected from the group consisting of C₁₋₄alkyl, halogen, —OH, C₁₋₄haloalkyl, and —C₁₋₄alkylene-OH.

9. The compound of claim 1, or a pharmaceutically acceptable salt thereof, wherein —NRˣRʸ is

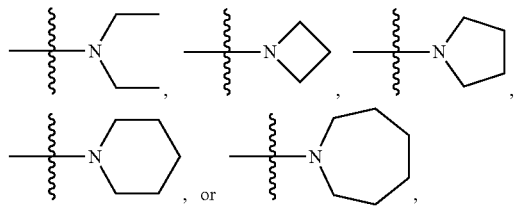

each of which is optionally substituted with 1, 2, 3, or 4 substituents independently selected from the group consisting of C₁₋₄alkyl, halogen, —OH, C₁₋₄haloalkyl, and —C₁₋₄alkylene-OH.

10. A pharmaceutically acceptable salt of a compound of Formula (I),

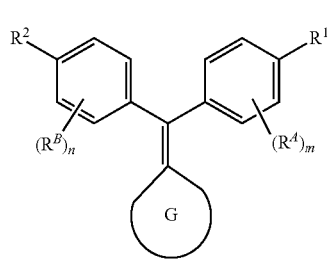

Wherein

G is an optionally substituted polycycloalkylidene;

Rᴬ and Rᴮ at each occurrence are independently halogen, C₁₋₄alkyl, or C₁₋₄haloalkyl;

R¹ and R² are independently —OH, halogen, —CN, —OC₂₋₈alkylene-L-T, or —OR³, and at least one of R¹ and R² is —OR³;

L is a linker;

T is a fluorescence acceptor or a fluorescence donor;

R³ is —(CH₂CH₂O)ₚ—C₂₋₈alkylene-[NRˣRʸRᶻ]⁺·X⁻;

Rˣ and Rʸ at each occurrence are independently C₁₋₄alkyl or —C₂₋₄alkylene-OH, or Rˣ and Rʸ together with the nitrogen to which they are attached form a 4- to 8-membered heterocycle or heteroaryl, wherein the heterocycle and heteroaryl are optionally substituted with 1, 2, 3, or 4 substituents independently selected from the group consisting of C₁₋₄alkyl, halogen, —OH, C₁₋₄haloalkyl, and —C₁₋₄alkylene-OH;

Rᶻ is C₁₋₄alkyl or C₂₋₄alkylene-OH;

m is 0, 1, 2, 3, or 4;

n is 0, 1, 2, 3, or 4;

p is 0, 1, 2, 3, 4, or 5; and

X⁻ is a counterion.

11. The salt of claim 10, wherein Rˣ and Rʸ at each occurrence are independently C₁₋₄alkyl or —C₂₋₄alkylene-OH.

12. The salt of claim 10, wherein Rˣ and Rʸ together with the nitrogen to which they are attached form 4- to 8-membered heterocycle or heteroaryl, wherein the heterocycle and heteroaryl are optionally substituted with 1, 2, 3, or 4 substituents independently selected from the group consisting of C₁₋₄alkyl, halogen, —OH, C₁₋₄haloalkyl, and —C₁₋₄alkylene-OH.

13. The salt of claim 10, wherein the —[NR^xR^yR^z]^+·X^− group is

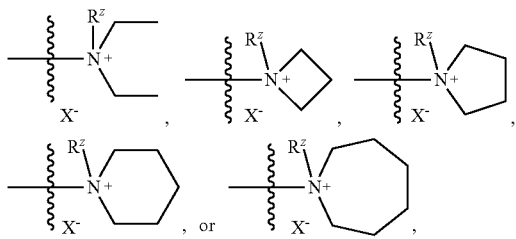

each of which is optionally substituted with 1, 2, 3, or 4 substituents independently selected from the group consisting of $C_{1-4}$alkyl, halogen, —OH, $C_{1-4}$haloalkyl, and —$C_{1-4}$alkylene-OH.

14. The salt of claim 10, wherein $R^z$ is methyl or hydroxyethyl.

15. The salt of claim 10, wherein X^− is halides, sulfonate, phosphonate, acetate, oxalate, fumarate, tartrate, or lactate salts.

16. The salt of claim 10, or a pharmaceutically acceptable salt thereof, wherein X^− is I^− or $CH_3SO_3^−$.

17. The compound of claim 1, or a pharmaceutically acceptable salt thereof, wherein -L-T is

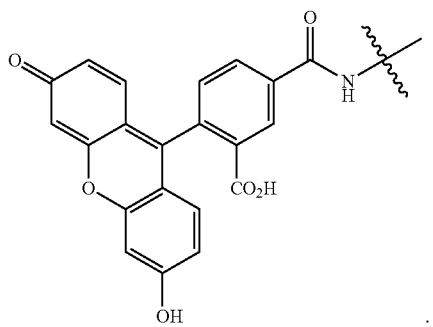 [SMILES: *NC(=O)c1ccc(-c2c3ccc(=O)cc-3oc3cc(O)ccc23)c(C(=O)O)c1]

18. The compound of claim 1, selected from the group consisting of 1-(6-(4-((Z)-((5S,7S)-adamantan-2-ylidene)(4-chlorophenyl)methyl)phenoxy)hexyl)pyrrolidine;
1-(6-(4-((Z)-((5S,7S)-Adamantan-2-ylidene)(4-chlorophenyl)methyl)phenoxy)hexyl)piperidine;
1-(6-(4-((Z)-((5S,7S)-adamantan-2-ylidene)(4-chlorophenyl)methyl)phenoxy)hexyl)azepane;
1,1'-((((((5r,7r)-adamantan-2-ylidene)methylene)bis(4,1-phenylene))bis(oxy))bis(hexane-6,1-diyl))dipyrrolidine;
1,1'-((((((5r,7r)-Adamantan-2-ylidene)methylene)bis(4,1-phenylene))bis(oxy))bis(hexane-6,1-diyl))dipiperidine;
1,1'-((((((5r,7r)-Adamantan-2-ylidene)methylene)bis(4,1-phenylene))bis(oxy))bis(hexane-6,1-diyl))bis(azepane);
6,6'-(((((5r,7r)-adamantan-2-ylidene)methylene)bis(4,1-phenylene))bis(oxy))bis(N,N-diethylhexan-1-amine);
2,2'-((((((5r,7r)-adamantan-2-ylidene)methylene)bis(4,1-phenylene))bis(oxy))bis(hexane-6,1-diyl))bis(ethylazanediyl))bis(ethan-1-ol);
2,2',2'',2'''-(((((((5r,7r)-adamantan-2-ylidene)methylene)bis(4,1-phenylene))bis(oxy))bis(hexane-6,1-diyl))bis(azanetriyl))tetrakis(ethan-1-ol);
1,1'-((((((5r,7r)-adamantan-2-ylidene)methylene)bis(4,1-phenylene))bis(oxy))bis(hexane-6,1-diyl))bis(azetidine);
1,1'-((((((5r,7r)-adamantan-2-ylidene)methylene)bis(4,1-phenylene))bis(oxy))bis(hexane-6,1-diyl))bis(azetidin-3-ol);
1,1'-((((((5r,7r)-adamantan-2-ylidene)methylene)bis(4,1-phenylene))bis(oxy))bis(hexane-6,1-diyl))bis(3-methylazetidin-3-ol);
((2S,2'S)-((((((5r,7r)-adamantan-2-ylidene)methylene)bis(4,1-phenylene))bis(oxy))bis(hexane-6,1-diyl))bis(pyrrolidine-1,2-diyl))dimethanol;
1,1'-((((((5r,7r)-adamantan-2-ylidene)methylene)bis(4,1-phenylene))bis(oxy))bis(hexane-6,1-diyl))bis(piperidin-4-ol);
5-((6-(4-((E)-((5r,7r)-adamantan-2-ylidene)(4-((6-(azepan-1-yl)hexyl)oxy)phenyl)methyl)phenoxy)hexyl)carbamoyl)-2-(6-hydroxy-3-oxo-3H-xanthen-9-yl)benzoic acid;
1-(6-(4-((Z)-((5r,7r)-adamantan-2-ylidene)(4-((6-(4-((3-carboxy-4-(6-hydroxy-3-oxo-3H-xanthen-9-yl)benzamido)methyl)-1H-1,2,3-triazol-1-yl)hexyl)oxy)phenyl)methyl)phenoxy)hexyl)-1-methylazepan-1-ium iodide;
4-((E)-((5R,7R)-adamantan-2-ylidene)(4-((6-(diethylamino)hexyl)oxy)phenyl)methyl)phenol;
6-(4-((Z)-((5S,7S)-adamantan-2-ylidene)(4-chlorophenyl)methyl)phenoxy)-N,N-diethylhexan-1-amine;
1-(6-(4-((Z)-((5S,7S)-adamantan-2-ylidene)(4-chlorophenyl)methyl)phenoxy)hexyl)-1H-imidazole;
1-(6-(4-((Z)-((5S,7S)-adamantan-2-ylidene)(4-chlorophenyl)methyl)phenoxy)hexyl)-4-methylpiperazine;
1,1'-((((((5r,7r)-adamantan-2-ylidene)methylene)bis(4,1-phenylene))bis(oxy))bis(butane-4,1-diyl))dipiperidine;
1,1'-((((((5r,7r)-adamantan-2-ylidene)methylene)bis(4,1-phenylene))bis(oxy))bis(butane-4,1-diyl))bis(azepane);
1,1'-((((((5r,7r)-adamantan-2-ylidene)methylene)bis(4,1-phenylene))bis(oxy))bis(pentane-5,1-diyl))dipiperidine;
1,1'-((((((5r,7r)-adamantan-2-ylidene)methylene)bis(4,1-phenylene))bis(oxy))bis(pentane-5,1-diyl))bis(azepane);
1,1'-((((((5r,7r)-adamantan-2-ylidene)methylene)bis(4,1-phenylene))bis(oxy))bis(octane-8,1-diyl))bis(azepane);
2,2'-(((((((5r,7r)-adamantan-2-ylidene)methylene)bis(4,1-phenylene))bis(oxy))bis(ethane-2,1-diyl))bis(oxy))bis(ethane-2,1-diyl))bis(oxy))bis(N,N-diethylethan-1-amine);
4,4'-((((((5r,7r)-adamantan-2-ylidene)methylene)bis(4,1-phenylene))bis(oxy))bis(hexane-6,1-diyl))bis(1-methylpiperazine); and
1,1'-((((((5r,7r)-adamantan-2-ylidene)methylene)bis(4,1-phenylene))bis(oxy))bis(hexane-6,1-diyl))bis(1H-imidazole),
or a pharmaceutically acceptable salt thereof.

19. The salt of claim 10, selected from the group consisting of 1-(6-(4-((Z)-((5S,7S)-adamantan-2-ylidene)(4-chlorophenyl)methyl)phenoxy)hexyl)-1-methylpyrrolidin-1-ium iodide;
1,1'-((((((5r,7r)-adamantan-2-ylidene)methylene)bis(4,1-phenylene))bis(oxy))bis(hexane-6,1-diyl))bis(1-methylpyrrolidin-1-ium) diiodide;

1,1'-((((((5r,7r)-adamantan-2-ylidene)methylene)bis(4,1-phenylene))bis(oxy))bis(hexane-6,1-diyl))bis(1-methylpiperidin-1-ium) diodide;

1,1'-((((((5r,7r)-adamantan-2-ylidene)methylene)bis(4,1-phenylene))bis(oxy))bis(hexane-6,1-diyl))bis(1-methylazepan-1-ium) diiodide;

6-(4-(((5r,7r)-adamantan-2-ylidene)(4-((6-(diethyl(methyl)-λ$^4$-azaneyl)hexyl)oxy)phenyl)methyl)phenoxy)-N,N-diethyl-N-methylhexan-1-aminium diiodide;

6,6'-(((((5r,7r)-adamantan-2-ylidene)methylene)bis(4,1-phenylene))bis(oxy))bis(N-ethyl-N-(2-hydroxyethyl)-N-methylhexan-1-aminium) diiodide;

6,6'-(((((5r,7r)-adamantan-2-ylidene)methylene)bis(4,1-phenylene))bis(oxy))bis(N,N-bis(2-hydroxyethyl)-N-methylhexan-1-aminium) diiodide;

1,1'-((((((5r,7r)-adamantan-2-ylidene)methylene)bis(4,1-phenylene))bis(oxy))bis(hexane-6,1-diyl))bis(1-methylazetidin-1-ium) diiodide;

1,1'-((((((5r,7r)-adamantan-2-ylidene)methylene)bis(4,1-phenylene))bis(oxy))bis(hexane-6,1-diyl))bis(3-hydroxy-1,3-dimethylazetidin-1-ium) diiodide;

(1R,1'R,2S,2'S)-1,1'-((((((5r,7r)-adamantan-2-ylidene)methylene)bis(4,1-phenylene))bis(oxy))bis(hexane-6,1-diyl))bis(2-(hydroxymethyl)-1-methylpyrrolidin-1-ium) diiodide;

1,1'-((((((5r,7r)-adamantan-2-ylidene)methylene)bis(4,1-phenylene))bis(oxy))bis(hexane-6,1-diyl))bis(4-hydroxy-1-methylpiperidin-1-ium) diiodide;

1,1'-((((((5r,7r)-adamantan-2-ylidene)methylene)bis(4,1-phenylene))bis(oxy))bis(hexane-6,1-diyl))bis(1-(2-hydroxyethyl)pyrrolidin-1-ium) diiodide;

1,1'-((((((5r,7r)-adamantan-2-ylidene)methylene)bis(4,1-phenylene))bis(oxy))bis(hexane-6,1-diyl))bis(1-(2-hydroxyethyl)piperidin-1-ium) diiodide;

1,1'-((((((5r,7r)-adamantan-2-ylidene)methylene)bis(4,1-phenylene))bis(oxy))bis(hexane-6,1-diyl))bis(1-(2-hydroxyethyl)azepan-1-ium) diiodide;

1-(6-(4-((Z)-((5S,7S)-adamantan-2-ylidene)(4-chlorophenyl)methyl)phenoxy)hexyl)-3-methyl-1H-imidazol-3-ium iodide;

(S)-1-(6-(4-((Z)-((5S,7S)-adamantan-2-ylidene)(4-chlorophenyl)methyl)phenoxy)hexyl)-1-methyl-1λ$^4$-piperidin-2-ylium iodide;

1-(6-(4-((Z)-((5 S,7S)-adamantan-2-ylidene)(4-chlorophenyl)methyl)phenoxy)hexyl)-1-methylazepan-1-ium iodide;

1-(4-(4-((E)-((5R,7R)-adamantan-2-ylidene)(4-(4-(1-metheyliumylpiperidin-1-ium-1-yl)butoxy)phenyl)methyl)phenoxy)butyl)-1-methylpiperidin-1-ium diiodide;

1,1'-((((((5r,7r)-adamantan-2-ylidene)methylene)bis(4,1-phenylene))bis(oxy))bis(butane-4,1-diyl))bis(1-methylazepan-1-ium) diiodide;

1,1'-((((((5r,7r)-adamantan-2-ylidene)methylene)bis(4,1-phenylene))bis(oxy))bis(pentane-5,1-diyl))bis(1-methylpiperidin-1-ium) diiodide;

1,1'-((((((5r,7r)-adamantan-2-ylidene)methylene)bis(4,1-phenylene))bis(oxy))bis(pentane-5,1-diyl))bis(1-methylazepan-1-ium) diiodide;

1,1'-((((((5r,7r)-adamantan-2-ylidene)methylene)bis(4,1-phenylene))bis(oxy))bis(octane-8,1-diyl))bis(1-methylazepan-1-ium) diiodide; and 1,1'-((((((5r,7r)-adamantan-2-ylidene)methylene)bis(4,1-phenylene))bis(oxy))bis(hexane-6,1-diyl))bis(1,4-dimethylpiperazin-1-ium) dimethanesulfonate.

20. A pharmaceutical composition comprising a therapeutically effective amount of a compound of claim 1, or a pharmaceutically acceptable salt thereof, and a pharmaceutically acceptable carrier.

21. A pharmaceutical composition comprising a therapeutically effective amount of a pharmaceutically acceptable salt of claim 10, and a pharmaceutically acceptable carrier.

22. The pharmaceutical composition of claim 20, further comprising a therapeutically effective amount of at least one additional anti-cancer therapeutic agent.

23. A method of inhibiting FOXM1 comprising administering to a subject in need thereof a therapeutically effective amount of a compound of claim 1, or a pharmaceutically acceptable salt thereof.

24. A method of inhibiting FOXM1 comprising administering to a subject in need thereof a therapeutically effective amount of a pharmaceutically acceptable salt of claim 10.

25. A method of inhibiting cancer growth comprising administering to a subject in need thereof a therapeutically effective amount of a compound of claim 1, or a pharmaceutically acceptable salt thereof.

26. A method of inhibiting cancer growth comprising administering to a subject in need thereof a therapeutically effective amount of a pharmaceutically acceptable salt of claim 10.

27. A method of treating cancer comprising administering to a subject in need thereof a therapeutically effective amount of a compound of claim 1, or a pharmaceutically acceptable salt thereof.

28. A method of treating cancer comprising administering to a subject in need thereof a therapeutically effective amount of a pharmaceutically acceptable salt of claim 10.

29. The method of claim 27, wherein the cancer is breast cancer, prostate cancer, glioblastoma, ovarian cancer, gastrointestinal cancer, non-small cell lung cancer, pancreatic ductal adenocarcinoma, or a combination thereof.

30. The method of claim 29, wherein the breast cancer is hormone receptor-positive breast cancer, ER-positive breast cancer, HER2-positive breast cancer, triple negative breast cancer, tamoxifen-resistant breast cancer, or a combination thereof.

31. The method of claim 27, further comprising administering a therapeutically effective amount of at least one additional cancer treatment.

32. The method of claim 27, wherein the method is a method of therapeutically treating cancer.

33. An assay method, comprising
incubating
 i) a FOXM1 that is fused with an amino acid sequence that allows covalent attachment of biotin,
 ii) a streptavidin that is labeled with a fluorescent donor moiety or a fluorescent acceptor moiety, and
 iii) a compound of claim 6, or a salt thereof, wherein T is a fluorescent acceptor moiety if the streptavidin is labeled with a fluorescent donor moiety, or wherein T is a fluorescent donor moiety if the streptavidin is labeled with a fluorescent acceptor moiety in a reaction mixture in either the presence or absence of the substance;
exposing the reaction mixture to light that allows fluorescence resonance energy transfer to take place; and
measuring fluorescence emission from the reaction mixture;
wherein if the fluorescence emission measurement from the reaction mixture in the presence of the substance is different than the fluorescent emission measurement from the mixture in the absence of the substance, the substance is acting as a FOXM1 inhibitor.

34. The method of claim 33, further comprising providing a compound of claim 6, or a salt thereof, wherein T is a fluorescent acceptor moiety if the streptavidin is labeled with a fluorescent donor moiety, or wherein T is a fluorescent donor moiety if the streptavidin is labeled with a fluorescent acceptor moiety.

35. The method of claim 34, further comprising providing a streptavidin that is labeled with a fluorescent donor moiety or a fluorescent acceptor moiety.

36. The method of claim 35, further comprising providing a FOXM1 that is fused with an amino acid sequence that allows covalent attachment of biotin.

37. A kit, comprising:
a first solution comprising FOXM1 fused at C-terminus with an amino acid sequence that allows covalent attachment of biotin,
a second solution comprising streptavidin labeled with a fluorescent donor moiety or a fluorescent acceptor moiety,
a third solution comprising a compound of claim 6, or a pharmaceutically acceptable salt thereof, wherein T is a fluorescence donor moiety if the streptavidin is labeled with a fluorescence acceptor moiety, or wherein T is a fluorescence acceptor if the streptavidin is labeled with a fluorescence donor moiety, and
at least one buffer.

* * * * *